United States Patent
Shi et al.

(10) Patent No.: US 9,745,384 B2
(45) Date of Patent: Aug. 29, 2017

(54) PEPTIDES USEFUL FOR MODULATING HISTONE DEMETHYLASE FUNCTION

(71) Applicant: The Brigham and Women's Hospital, Inc., Boston, MA (US)

(72) Inventors: Yujiang Geno Shi, Chestnut Hill, MA (US); Rui Fang, West Hartford, CT (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 14/653,915

(22) PCT Filed: Dec. 20, 2013

(86) PCT No.: PCT/US2013/076903
§ 371 (c)(1),
(2) Date: Jun. 19, 2015

(87) PCT Pub. No.: WO2014/100578
PCT Pub. Date: Jun. 26, 2014

(65) Prior Publication Data
US 2015/0329644 A1 Nov. 19, 2015

Related U.S. Application Data

(60) Provisional application No. 61/740,181, filed on Dec. 20, 2012.

(51) Int. Cl.
| | |
|---|---|
| *C07K 7/08* | (2006.01) |
| *C12N 15/12* | (2006.01) |
| *C12N 15/00* | (2006.01) |
| *C07K 16/40* | (2006.01) |
| *C12N 15/113* | (2010.01) |
| *C07K 16/18* | (2006.01) |
| *C12N 9/04* | (2006.01) |
| *C07K 14/47* | (2006.01) |
| *A61K 38/00* | (2006.01) |

(52) U.S. Cl.
CPC ........... *C07K 16/40* (2013.01); *C07K 7/08* (2013.01); *C07K 14/4702* (2013.01); *C07K 16/18* (2013.01); *C12N 9/0006* (2013.01); *C12N 15/1137* (2013.01); *A61K 38/00* (2013.01); *C07K 2317/34* (2013.01); *C07K 2317/76* (2013.01); *C12N 2310/14* (2013.01); *C12N 2310/531* (2013.01)

(58) Field of Classification Search
None
See application file for complete search history.

(56) References Cited

U.S. PATENT DOCUMENTS

2010/0256044 A1 10/2010 Roth-Chiarello

OTHER PUBLICATIONS

Lu et al., The AAPS Journal 2006, 8(3): E466-E478.*
Mendoza et al., Arch. Immunol. Ther. Exp., vol. 53, p. 47-60, 2005.*
Database NCBI: XP_003224800.1, Mar. 30, 2011. Retrieved from the internet:<URL:http://www.ncbi.nlm.nih.gov/protein/32728011?report=genbank&log$=protalign&blast_rank=100&RID=J3APB5JH01R>.
Databse EBI Dbfetch: Q49A26, Apr. 12, 2007. Retrieved from the internet<URL:http://www.ebi.ac.uk/Tools/dbfetch/dbfetch?db=SP;id=Q49A26;format=default>.
Forneris et al., "Structural Basis of LSD1-CoREST Selectivity in Histone H3 Recognition", J Biol Chem, 282(28): 20070-20074 (2007).
Lee et al., "An essential role for CoREST in nucleosomal histone 3 lysine 4 demethylation", Nature, 437(7057): 432-435 (2005).
Shi et al., "Regulation of LSD1 Histone Demethylase Activity by Its Associated Factors", Mol Cell,19(6): 857-864 (2005).
Yang et al., "Structural Basis for CoREST-Dependent Demethylation of Nucleosomes by the Human LSD1 Histone Demethylase", Mol Cell, 23(3): 377-387 (2006).

* cited by examiner

*Primary Examiner* — Hong Sang
(74) *Attorney, Agent, or Firm* — Nixon Peabody LLP; David S. Resnick; Nicole D. King

(57) ABSTRACT

We described peptides and peptide fragments that can be used to inhibit cyclin D1 and cyclin E1, function of both of which is involved in malignant growth. Methods of treatment of cancer by inhibiting interaction between NPAC and LSD2 are also provided.

7 Claims, 57 Drawing Sheets

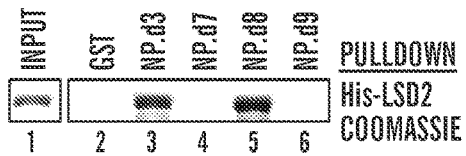
FIG. 5E
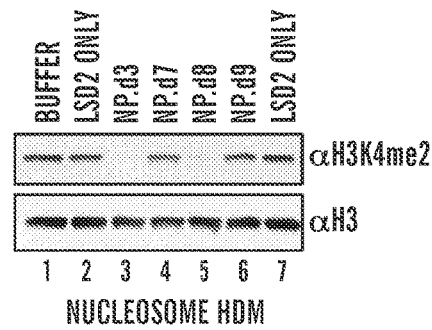
FIG. 5F
```
             219   223
              ▼     ▼
WT:  DPHFHHFLLSQT
M1:  DPHFH A FLL A QT
M2:  DPHFHH AAA SQT
M3:  DPHFH------QT
```
FIG. 5G
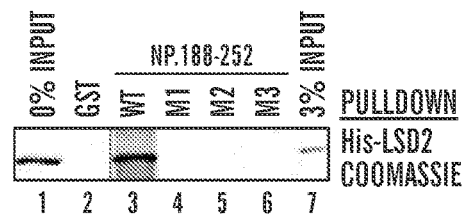
FIG. 5H
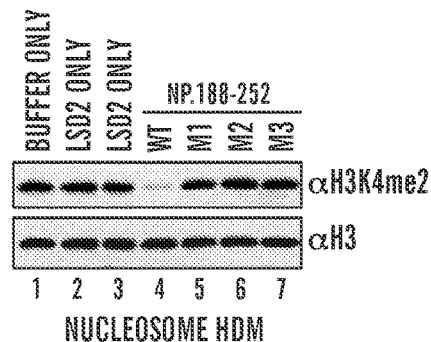
FIG. 5I

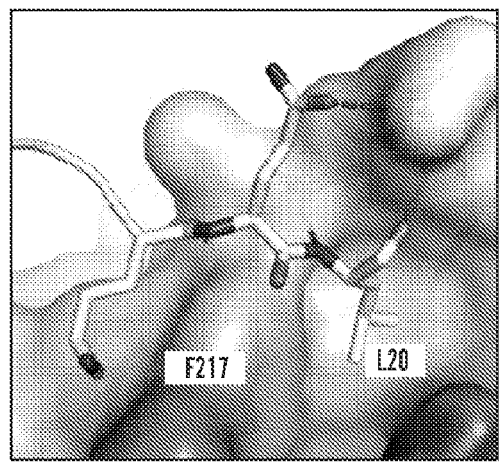
FIG. 6C
```
           214 216,217
            ▼   ▼
WT:  DPHFHHFLLSQT
M4:  APHFHHFLLSQT
M5:  DPAFHHFLLSQT
M6:  DPHAHHFLLSQT
```
FIG. 6D
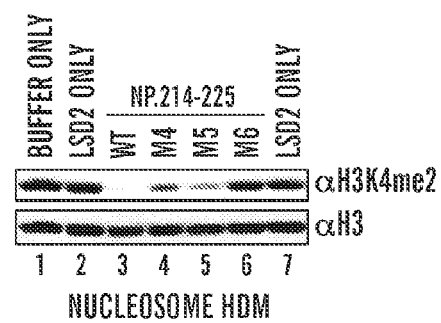
FIG. 6E

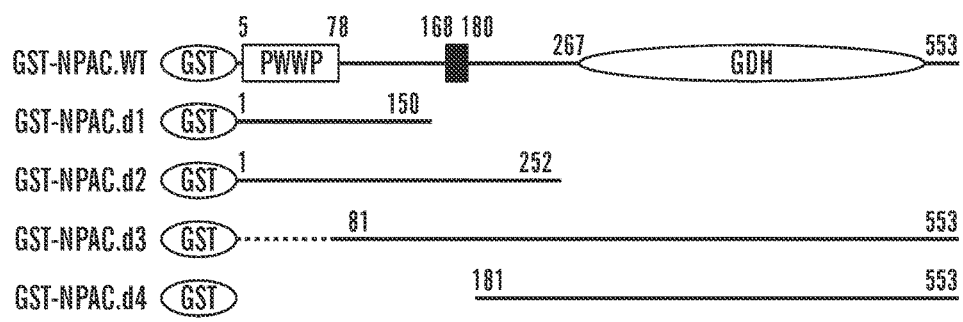
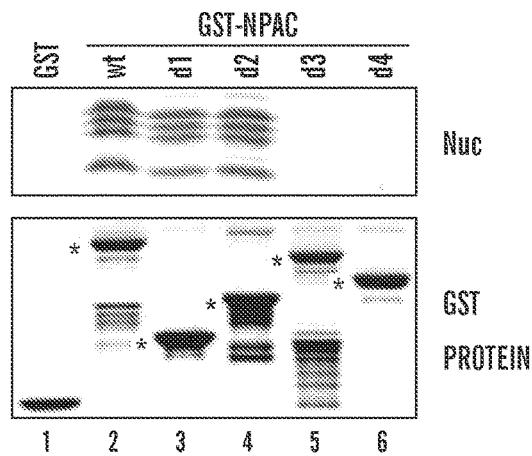
FIG. 14B

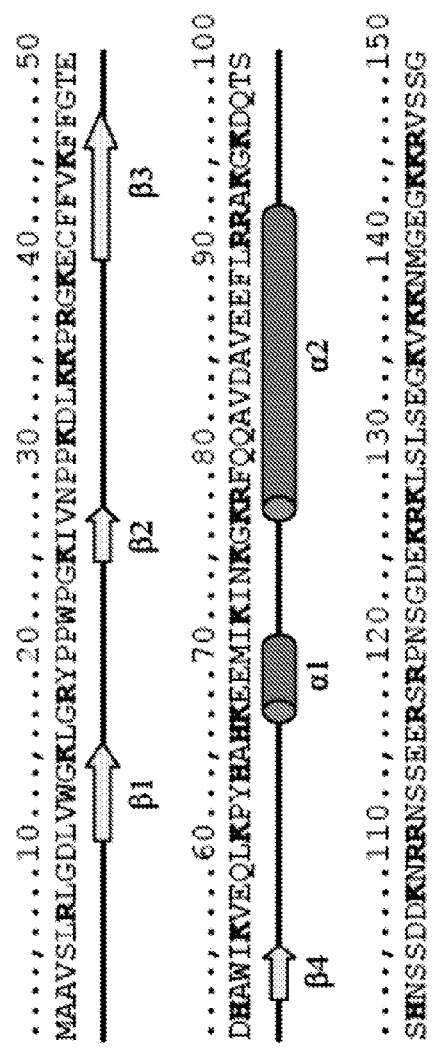
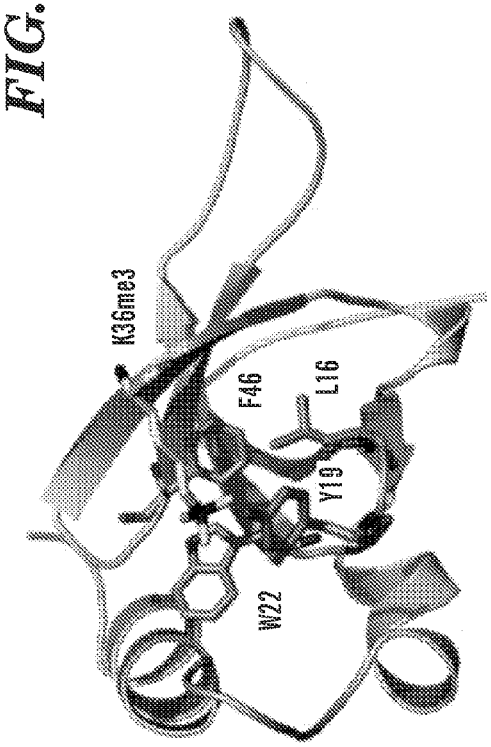
FIG. 15A
FIG. 15B
FIG. 15C

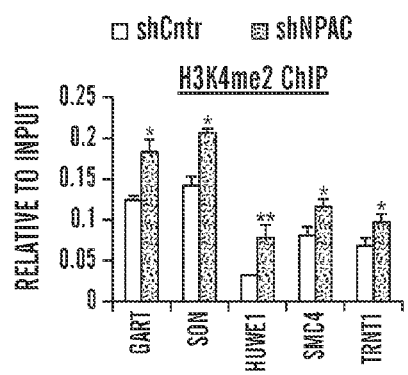 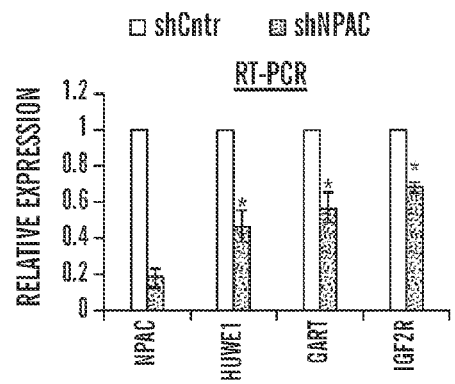
*FIG. 17G*  *FIG. 17H*
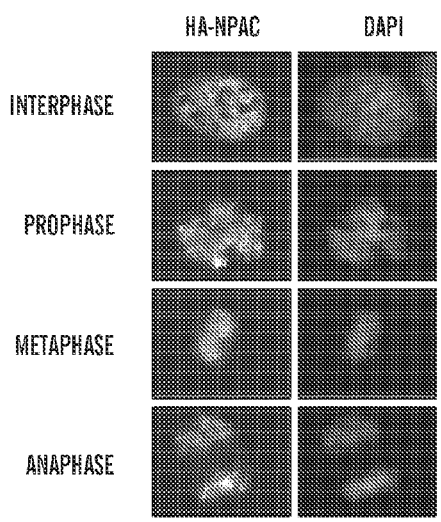 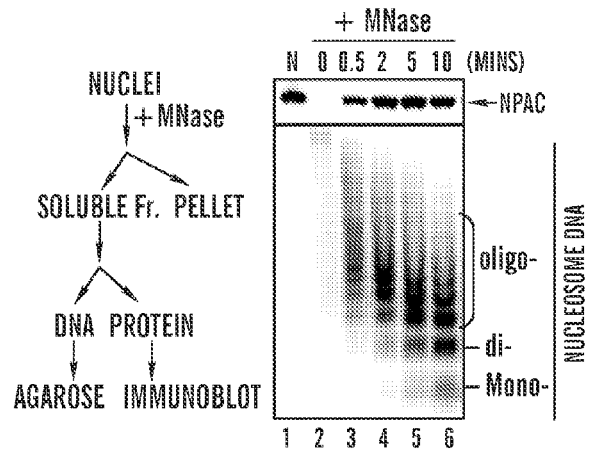
*FIG. 18A*  *FIG. 18B*

*, p, 0.05; , p<0.01; *, p<0.001

SEQUENCE LISTING

<160> NUMBER OF SEQ ID NOS: 91

<210> SEQ ID NO 1
<211> LENGTH: 12
<212> TYPE: PRT
<213> ORGANISM: Homo sapiens

<400> SEQUENCE: 1

Asp Pro His Phe His His Phe Leu Leu Ser Gln Thr
1               5                   10

<210> SEQ ID NO 2
<211> LENGTH: 7
<212> TYPE: PRT
<213> ORGANISM: Homo sapiens

<400> SEQUENCE: 2

Phe His His Phe Leu Leu Ser
1               5

<210> SEQ ID NO 3
<211> LENGTH: 16
<212> TYPE: PRT
<213> ORGANISM: Homo sapiens

<400> SEQUENCE: 3

Asp Ala Asp Pro His Phe His His Phe Leu Leu Ser Gln Thr Glu Lys
1               5                   10                  15

<210> SEQ ID NO 4
<211> LENGTH: 15
<212> TYPE: PRT
<213> ORGANISM: Homo sapiens

<400> SEQUENCE: 4

Asp Ala Asp Pro His Phe His His Phe Leu Leu Ser Gln Thr Glu
1               5                   10                  15

<210> SEQ ID NO 5
<211> LENGTH: 14
<212> TYPE: PRT
<213> ORGANISM: Homo sapiens

<400> SEQUENCE: 5

Asp Ala Asp Pro His Phe His His Phe Leu Leu Ser Gln Thr
1               5                   10

<210> SEQ ID NO 6
<211> LENGTH: 13
<212> TYPE: PRT
<213> ORGANISM: Homo sapiens

<400> SEQUENCE: 6

Asp Ala Asp Pro His Phe His His Phe Leu Leu Ser Gln
1               5                   10

<210> SEQ ID NO 7
<211> LENGTH: 12
<212> TYPE: PRT
<213> ORGANISM: Homo sapiens

<400> SEQUENCE: 7

Asp Ala Asp Pro His Phe His His Phe Leu Leu Ser
1               5                   10

<210> SEQ ID NO 8
<211> LENGTH: 15
<212> TYPE: PRT
<213> ORGANISM: Homo sapiens

<400> SEQUENCE: 8

Ala Asp Pro His Phe His His Phe Leu Leu Ser Gln Thr Glu Lys
1               5                   10                  15

<210> SEQ ID NO 9
<211> LENGTH: 14
<212> TYPE: PRT
<213> ORGANISM: Homo sapiens

<400> SEQUENCE: 9

Ala Asp Pro His Phe His His Phe Leu Leu Ser Gln Thr Glu
1               5                   10

<210> SEQ ID NO 10
<211> LENGTH: 12
<212> TYPE: PRT
<213> ORGANISM: Homo sapiens

<400> SEQUENCE: 10

Ala Asp Pro His Phe His His Phe Leu Leu Ser Gln
1               5                   10

<210> SEQ ID NO 11
<211> LENGTH: 11
<212> TYPE: PRT
<213> ORGANISM: Homo sapiens

<400> SEQUENCE: 11

Ala Asp Pro His Phe His His Phe Leu Leu Ser
1               5                   10

<210> SEQ ID NO 12
<211> LENGTH: 14
<212> TYPE: PRT
<213> ORGANISM: Homo sapiens

<400> SEQUENCE: 12

Asp Pro His Phe His His Phe Leu Leu Ser Gln Thr Glu Lys
1               5                   10

<210> SEQ ID NO 13
<211> LENGTH: 13
<212> TYPE: PRT
<213> ORGANISM: Homo sapiens

<400> SEQUENCE: 13

Asp Pro His Phe His His Phe Leu Leu Ser Gln Thr Glu
1               5                   10

<210> SEQ ID NO 14
<211> LENGTH: 12
<212> TYPE: PRT
<213> ORGANISM: Homo sapiens

<400> SEQUENCE: 14

Asp Pro His Phe His His Phe Leu Leu Ser Gln Thr
1               5                   10

<210> SEQ ID NO 15
<211> LENGTH: 11
<212> TYPE: PRT
<213> ORGANISM: Homo sapiens

<400> SEQUENCE: 15

Asp Pro His Phe His His Phe Leu Leu Ser Gln

```
1               5                   10
```

<210> SEQ ID NO 16
<211> LENGTH: 10
<212> TYPE: PRT
<213> ORGANISM: Homo sapiens

<400> SEQUENCE: 16

```
Asp Pro His Phe His His Phe Leu Leu Ser
1               5                   10
```

<210> SEQ ID NO 17
<211> LENGTH: 13
<212> TYPE: PRT
<213> ORGANISM: Homo sapiens

<400> SEQUENCE: 17

```
Pro His Phe His His Phe Leu Leu Ser Gln Thr Glu Lys
1               5                   10
```

<210> SEQ ID NO 18
<211> LENGTH: 12
<212> TYPE: PRT
<213> ORGANISM: Homo sapiens

<400> SEQUENCE: 18

```
Pro His Phe His His Phe Leu Leu Ser Gln Thr Glu
1               5                   10
```

<210> SEQ ID NO 19
<211> LENGTH: 11
<212> TYPE: PRT
<213> ORGANISM: Homo sapiens

<400> SEQUENCE: 19

```
Pro His Phe His His Phe Leu Leu Ser Gln Thr
1               5                   10
```

<210> SEQ ID NO 20
<211> LENGTH: 10
<212> TYPE: PRT
<213> ORGANISM: Homo sapiens

<400> SEQUENCE: 20

```
Pro His Phe His His Phe Leu Leu Ser Gln
1               5                   10
```

<210> SEQ ID NO 21
<211> LENGTH: 9
<212> TYPE: PRT
<213> ORGANISM: Homo sapiens

<400> SEQUENCE: 21

```
Pro His Phe His His Phe Leu Leu Ser
1               5
```

<210> SEQ ID NO 22
<211> LENGTH: 12
<212> TYPE: PRT
<213> ORGANISM: Homo sapiens

<400> SEQUENCE: 22

```
His Phe His His Phe Leu Leu Ser Gln Thr Glu Lys
1               5                   10
```

<210> SEQ ID NO 23
<211> LENGTH: 11
<212> TYPE: PRT
<213> ORGANISM: Homo sapiens

<400> SEQUENCE: 23

His Phe His His Phe Leu Leu Ser Gln Thr Glu
1               5                   10

<210> SEQ ID NO 24
<211> LENGTH: 10
<212> TYPE: PRT
<213> ORGANISM: Homo sapiens

<400> SEQUENCE: 24

His Phe His His Phe Leu Leu Ser Gln Thr
1               5                   10

<210> SEQ ID NO 25
<211> LENGTH: 9
<212> TYPE: PRT
<213> ORGANISM: Homo sapiens

<400> SEQUENCE: 25

His Phe His His Phe Leu Leu Ser Gln
1               5

<210> SEQ ID NO 26
<211> LENGTH: 8
<212> TYPE: PRT
<213> ORGANISM: Homo sapiens

<400> SEQUENCE: 26

His Phe His His Phe Leu Leu Ser
1               5

<210> SEQ ID NO 27
<211> LENGTH: 11
<212> TYPE: PRT
<213> ORGANISM: Homo sapiens

<400> SEQUENCE: 27

Phe His His Phe Leu Leu Ser Gln Thr Glu Lys
1               5                   10

<210> SEQ ID NO 28
<211> LENGTH: 10
<212> TYPE: PRT
<213> ORGANISM: Homo sapiens

<400> SEQUENCE: 28

Phe His His Phe Leu Leu Ser Gln Thr Glu
1               5                   10

<210> SEQ ID NO 29
<211> LENGTH: 9
<212> TYPE: PRT
<213> ORGANISM: Homo sapiens

<400> SEQUENCE: 29

Phe His His Phe Leu Leu Ser Gln Thr
1               5

<210> SEQ ID NO 30

```
<211> LENGTH: 8
<212> TYPE: PRT
<213> ORGANISM: Homo sapiens

<400> SEQUENCE: 30

Phe His His Phe Leu Leu Ser Gln
1               5

<210> SEQ ID NO 31
<211> LENGTH: 16
<212> TYPE: PRT
<213> ORGANISM: Homo sapiens

<400> SEQUENCE: 31

Asp Ala Asp Pro His Phe His His Phe Leu Leu Ser Gln Thr Glu Lys
1               5                   10                  15

<210> SEQ ID NO 32
<211> LENGTH: 15
<212> TYPE: PRT
<213> ORGANISM: Homo sapiens

<400> SEQUENCE: 32

Ala Asp Pro His Phe His His Phe Leu Leu Ser Gln Thr Glu Lys
1               5                   10                  15

<210> SEQ ID NO 33
<211> LENGTH: 14
<212> TYPE: PRT
<213> ORGANISM: Homo sapiens

<400> SEQUENCE: 33

Asp Pro His Phe His His Phe Leu Leu Ser Gln Thr Glu Lys
1               5                   10

<210> SEQ ID NO 34
<211> LENGTH: 13
<212> TYPE: PRT
<213> ORGANISM: Homo sapiens

<400> SEQUENCE: 34

Pro His Phe His His Phe Leu Leu Ser Gln Thr Glu Lys
1               5                   10

<210> SEQ ID NO 35
<211> LENGTH: 12
<212> TYPE: PRT
<213> ORGANISM: Homo sapiens

<400> SEQUENCE: 35

His Phe His His Phe Leu Leu Ser Gln Thr Glu Lys
1               5                   10

<210> SEQ ID NO 36
<211> LENGTH: 11
<212> TYPE: PRT
<213> ORGANISM: Homo sapiens

<400> SEQUENCE: 36

Phe His His Phe Leu Leu Ser Gln Thr Glu Lys
1               5                   10

<210> SEQ ID NO 37
<211> LENGTH: 15
<212> TYPE: PRT
```

<213> ORGANISM: Homo sapiens

<400> SEQUENCE: 37

Asp Ala Asp Pro His Phe His His Phe Leu Leu Ser Gln Thr Glu
1               5                   10                  15

<210> SEQ ID NO 38
<211> LENGTH: 14
<212> TYPE: PRT
<213> ORGANISM: Homo sapiens

<400> SEQUENCE: 38

Ala Asp Pro His Phe His His Phe Leu Leu Ser Gln Thr Glu
1               5                   10

<210> SEQ ID NO 39
<211> LENGTH: 13
<212> TYPE: PRT
<213> ORGANISM: Homo sapiens

<400> SEQUENCE: 39

Asp Pro His Phe His His Phe Leu Leu Ser Gln Thr Glu
1               5                   10

<210> SEQ ID NO 40
<211> LENGTH: 12
<212> TYPE: PRT
<213> ORGANISM: Homo sapiens

<400> SEQUENCE: 40

Pro His Phe His His Phe Leu Leu Ser Gln Thr Glu
1               5                   10

<210> SEQ ID NO 41
<211> LENGTH: 11
<212> TYPE: PRT
<213> ORGANISM: Homo sapiens

<400> SEQUENCE: 41

His Phe His His Phe Leu Leu Ser Gln Thr Glu
1               5                   10

<210> SEQ ID NO 42
<211> LENGTH: 10
<212> TYPE: PRT
<213> ORGANISM: Homo sapiens

<400> SEQUENCE: 42

Phe His His Phe Leu Leu Ser Gln Thr Glu
1               5                   10

<210> SEQ ID NO 43
<211> LENGTH: 14
<212> TYPE: PRT
<213> ORGANISM: Homo sapiens

<400> SEQUENCE: 43

Asp Ala Asp Pro His Phe His His Phe Leu Leu Ser Gln Thr
1               5                   10

<210> SEQ ID NO 44
<211> LENGTH: 13
<212> TYPE: PRT
<213> ORGANISM: Homo sapiens

<400> SEQUENCE: 44

Ala Asp Pro His Phe His His Phe Leu Leu Ser Gln Thr
1               5                   10

<210> SEQ ID NO 45
<211> LENGTH: 12
<212> TYPE: PRT
<213> ORGANISM: Homo sapiens

<400> SEQUENCE: 45

Asp Pro His Phe His His Phe Leu Leu Ser Gln Thr
1               5                   10

<210> SEQ ID NO 46
<211> LENGTH: 11
<212> TYPE: PRT
<213> ORGANISM: Homo sapiens

<400> SEQUENCE: 46

Pro His Phe His His Phe Leu Leu Ser Gln Thr
1               5                   10

<210> SEQ ID NO 47
<211> LENGTH: 10
<212> TYPE: PRT
<213> ORGANISM: Homo sapiens

<400> SEQUENCE: 47

His Phe His His Phe Leu Leu Ser Gln Thr
1               5                   10

<210> SEQ ID NO 48
<211> LENGTH: 9
<212> TYPE: PRT
<213> ORGANISM: Homo sapiens

<400> SEQUENCE: 48

Phe His His Phe Leu Leu Ser Gln Thr
1               5

<210> SEQ ID NO 49
<211> LENGTH: 13
<212> TYPE: PRT
<213> ORGANISM: Homo sapiens

<400> SEQUENCE: 49

Asp Ala Asp Pro His Phe His His Phe Leu Leu Ser Gln
1               5                   10

<210> SEQ ID NO 50
<211> LENGTH: 12
<212> TYPE: PRT
<213> ORGANISM: Homo sapiens

<400> SEQUENCE: 50

Ala Asp Pro His Phe His His Phe Leu Leu Ser Gln
1               5                   10

<210> SEQ ID NO 51
<211> LENGTH: 11
<212> TYPE: PRT
<213> ORGANISM: Homo sapiens

<400> SEQUENCE: 51

Asp Pro His Phe His His Phe Leu Leu Ser Gln
1               5                   10

<210> SEQ ID NO 52
<211> LENGTH: 10
<212> TYPE: PRT
<213> ORGANISM: Homo sapiens

<400> SEQUENCE: 52

Pro His Phe His His Phe Leu Leu Ser Gln
1               5                   10

<210> SEQ ID NO 53
<211> LENGTH: 9
<212> TYPE: PRT
<213> ORGANISM: Homo sapiens

<400> SEQUENCE: 53

His Phe His His Phe Leu Leu Ser Gln
1               5

<210> SEQ ID NO 54
<211> LENGTH: 8
<212> TYPE: PRT
<213> ORGANISM: Homo sapiens

<400> SEQUENCE: 54

Phe His His Phe Leu Leu Ser Gln
1               5

<210> SEQ ID NO 55
<211> LENGTH: 12
<212> TYPE: PRT
<213> ORGANISM: Homo sapiens

<400> SEQUENCE: 55

Asp Ala Asp Pro His Phe His His Phe Leu Leu Ser
1               5                   10

<210> SEQ ID NO 56
<211> LENGTH: 11
<212> TYPE: PRT
<213> ORGANISM: Homo sapiens

<400> SEQUENCE: 56

Ala Asp Pro His Phe His His Phe Leu Leu Ser
1               5                   10

<210> SEQ ID NO 57
<211> LENGTH: 10
<212> TYPE: PRT
<213> ORGANISM: Homo sapiens

<400> SEQUENCE: 57

Asp Pro His Phe His His Phe Leu Leu Ser
1               5                   10

<210> SEQ ID NO 58
<211> LENGTH: 9
<212> TYPE: PRT
<213> ORGANISM: Homo sapiens

<400> SEQUENCE: 58

Pro His Phe His His Phe Leu Leu Ser
1               5

<210> SEQ ID NO 59
<211> LENGTH: 8
<212> TYPE: PRT
<213> ORGANISM: Homo sapiens

<400> SEQUENCE: 59

His Phe His His Phe Leu Leu Ser
1               5

<210> SEQ ID NO 60
<211> LENGTH: 9
<212> TYPE: PRT
<213> ORGANISM: Human immunodeficiency virus

<400> SEQUENCE: 60

Arg Lys Lys Arg Arg Gln Arg Arg Arg
1               5

<210> SEQ ID NO 61
<211> LENGTH: 553
<212> TYPE: PRT
<213> ORGANISM: Homo sapiens

<400> SEQUENCE: 61

Met Ala Ala Val Ser Leu Arg Leu Gly Asp Leu Val Trp Gly Lys Leu
1               5                   10                  15

Gly Arg Tyr Pro Pro Trp Pro Gly Lys Ile Val Asn Pro Pro Lys Asp
            20                  25                  30

Leu Lys Lys Pro Arg Gly Lys Lys Cys Phe Phe Val Lys Phe Phe Gly
        35                  40                  45

Thr Glu Asp His Ala Trp Ile Lys Val Glu Gln Leu Lys Pro Tyr His
    50                  55                  60

Ala His Lys Glu Glu Met Ile Lys Ile Asn Lys Gly Lys Arg Phe Gln
65                  70                  75                  80

Gln Ala Val Asp Ala Val Glu Phe Leu Arg Arg Ala Lys Gly Lys
                85                  90                  95

Asp Gln Thr Ser Ser His Asn Ser Ser Asp Asp Lys Asn Arg Arg Asn
            100                 105                 110

Ser Ser Glu Glu Arg Ser Arg Pro Asn Ser Gly Asp Glu Lys Arg Lys
        115                 120                 125

Leu Ser Leu Ser Glu Gly Lys Val Lys Asn Met Gly Glu Gly Lys
    130                 135                 140

Lys Arg Val Ser Ser Gly Ser Ser Glu Arg Gly Ser Lys Ser Pro Leu
145                 150                 155                 160

Lys Arg Ala Gln Glu Gln Ser Pro Arg Lys Arg Gly Arg Pro Pro Lys
                165                 170                 175

Asp Glu Lys Asp Leu Thr Ile Pro Glu Ser Ser Thr Val Lys Gly Met
            180                 185                 190

Met Ala Gly Pro Met Ala Ala Phe Lys Trp Gln Pro Thr Ala Ser Glu
        195                 200                 205

Pro Val Lys Asp Ala Asp Pro His Phe His His Phe Leu Leu Ser Gln
    210                 215                 220

Thr Glu Lys Pro Ala Val Cys Tyr Gln Ala Ile Thr Lys Lys Leu Lys
225                 230                 235                 240

Ile Cys Glu Glu Glu Thr Gly Ser Thr Ser Ile Gln Ala Ala Asp Ser
                245                 250                 255

-continued

```
Thr Ala Val Asn Gly Ser Ile Thr Pro Thr Asp Lys Lys Ile Gly Phe
            260                 265                 270

Leu Gly Leu Gly Leu Met Gly Ser Gly Ile Val Ser Asn Leu Leu Lys
        275                 280                 285

Met Gly His Thr Val Thr Val Trp Asn Arg Thr Ala Glu Lys Cys Asp
    290                 295                 300

Leu Phe Ile Gln Glu Gly Ala Arg Leu Gly Arg Thr Pro Ala Glu Val
305                 310                 315                 320

Val Ser Thr Cys Asp Ile Thr Phe Ala Cys Val Ser Asp Pro Lys Ala
                325                 330                 335

Ala Lys Asp Leu Val Leu Gly Pro Ser Gly Val Leu Gln Gly Ile Arg
            340                 345                 350

Pro Gly Lys Cys Tyr Val Asp Met Ser Thr Val Asp Ala Asp Thr Val
        355                 360                 365

Thr Glu Leu Ala Gln Val Ile Val Ser Arg Gly Gly Arg Phe Leu Glu
    370                 375                 380

Ala Pro Val Ser Gly Asn Gln Gln Leu Ser Asn Asp Gly Met Leu Val
385                 390                 395                 400

Ile Leu Ala Ala Gly Asp Arg Gly Leu Tyr Glu Asp Cys Ser Ser Cys
                405                 410                 415

Phe Gln Ala Met Gly Lys Thr Ser Phe Phe Leu Gly Glu Val Gly Asn
            420                 425                 430

Ala Ala Lys Met Met Leu Ile Val Asn Met Val Gln Gly Ser Phe Met
        435                 440                 445

Ala Thr Ile Ala Glu Gly Leu Thr Leu Ala His Val Thr Gly Gln Ser
    450                 455                 460

Gln Gln Thr Leu Leu Asp Ile Leu Asn Gln Gly Gln Leu Ala Ser Ile
465                 470                 475                 480

Phe Leu Asp Gln Lys Cys Gln Asn Ile Leu Gln Gly Asn Phe Lys Pro
                485                 490                 495

Asp Phe Tyr Leu Lys Tyr Ile Gln Lys Asp Leu Arg Leu Ala Ile Ala
            500                 505                 510

Leu Gly Asp Ala Val Asn His Pro Thr Pro Met Ala Ala Ala Ala Asn
        515                 520                 525

Glu Val Tyr Lys Arg Ala Lys Ala Leu Asp Gln Ser Asp Asn Asp Met
    530                 535                 540

Ser Ala Val Tyr Arg Ala Tyr Ile His
545                 550

<210> SEQ ID NO 62
<211> LENGTH: 822
<212> TYPE: PRT
<213> ORGANISM: Homo sapiens

<400> SEQUENCE: 62

Met Ala Thr Pro Arg Gly Arg Thr Lys Lys Lys Ala Ser Phe Asp His
1               5                   10                  15

Ser Pro Asp Ser Leu Pro Leu Arg Ser Ser Gly Arg Gln Ala Lys Lys
            20                  25                  30

Lys Ala Thr Glu Thr Thr Asp Glu Asp Glu Asp Gly Gly Ser Glu Lys
        35                  40                  45

Lys Tyr Arg Lys Cys Glu Lys Ala Gly Cys Thr Ala Thr Cys Pro Val
    50                  55                  60

Cys Phe Ala Ser Ala Ser Glu Arg Cys Ala Lys Asn Gly Tyr Thr Ser
65                  70                  75                  80
```

```
Arg Trp Tyr His Leu Ser Cys Gly Glu His Phe Cys Asn Glu Cys Phe
            85              90              95
Asp His Tyr Tyr Arg Ser His Lys Asp Gly Tyr Asp Lys Tyr Thr Thr
            100             105             110
Trp Lys Lys Ile Trp Thr Ser Asn Gly Lys Thr Glu Pro Ser Pro Lys
            115             120             125
Ala Phe Met Ala Asp Gln Gln Leu Pro Tyr Trp Val Gln Cys Thr Lys
        130             135             140
Pro Glu Cys Arg Lys Trp Arg Gln Leu Thr Lys Glu Ile Gln Leu Thr
145             150             155             160
Pro Gln Ile Ala Lys Thr Tyr Arg Cys Gly Met Lys Pro Asn Thr Ala
            165             170             175
Ile Lys Pro Glu Thr Ser Asp His Cys Ser Leu Pro Glu Asp Leu Arg
            180             185             190
Val Leu Glu Val Ser Asn His Trp Trp Tyr Ser Met Leu Ile Leu Pro
            195             200             205
Pro Leu Leu Lys Asp Ser Val Ala Ala Pro Leu Leu Ser Ala Tyr Tyr
        210             215             220
Pro Asp Cys Val Gly Met Ser Pro Ser Cys Thr Ser Thr Asn Arg Ala
225             230             235             240
Ala Ala Thr Gly Asn Ala Ser Pro Gly Lys Leu Glu His Ser Lys Ala
            245             250             255
Ala Leu Ser Val His Val Pro Gly Met Asn Arg Tyr Phe Gln Pro Phe
            260             265             270
Tyr Gln Pro Asn Glu Cys Gly Lys Ala Leu Cys Val Arg Pro Asp Val
            275             280             285
Met Glu Leu Asp Glu Leu Tyr Glu Phe Pro Gly Tyr Ser Arg Asp Pro
        290             295             300
Thr Met Tyr Leu Ala Leu Arg Asn Leu Ile Leu Ala Leu Trp Tyr Thr
305             310             315             320
Asn Cys Lys Glu Ala Leu Thr Pro Gln Lys Cys Ile Pro His Ile Ile
            325             330             335
Val Arg Gly Leu Val Arg Ile Arg Cys Val Gln Glu Val Glu Arg Ile
            340             345             350
Leu Tyr Phe Met Thr Arg Lys Gly Leu Ile Asn Thr Gly Val Leu Ser
            355             360             365
Val Gly Ala Asp Gln Tyr Leu Leu Pro Lys Asp Tyr His Asn Lys Ser
            370             375             380
Val Ile Ile Ile Gly Ala Gly Pro Ala Gly Leu Ala Ala Ala Arg Gln
385             390             395             400
Leu His Asn Phe Gly Ile Lys Val Thr Val Leu Glu Ala Lys Asp Arg
            405             410             415
Ile Gly Gly Arg Val Trp Asp Asp Lys Ser Phe Lys Gly Val Thr Val
            420             425             430
Gly Arg Gly Ala Gln Ile Val Asn Gly Cys Ile Asn Asn Pro Val Ala
            435             440             445
Leu Met Cys Glu Gln Leu Gly Ile Ser Met His Lys Phe Gly Glu Arg
        450             455             460
Cys Asp Leu Ile Gln Glu Gly Gly Arg Ile Thr Asp Pro Thr Ile Asp
465             470             475             480
Lys Arg Met Asp Phe His Phe Asn Ala Leu Leu Asp Val Val Ser Glu
            485             490             495
```

```
Trp Arg Lys Asp Lys Thr Gln Leu Gln Asp Val Pro Leu Gly Glu Lys
            500                 505                 510

Ile Glu Glu Ile Tyr Lys Ala Phe Ile Lys Glu Ser Gly Ile Gln Phe
        515                 520                 525

Ser Glu Leu Glu Gly Gln Val Leu Gln Phe His Leu Ser Asn Leu Glu
    530                 535                 540

Tyr Ala Cys Gly Ser Asn Leu His Gln Val Ser Ala Arg Ser Trp Asp
545                 550                 555                 560

His Asn Glu Phe Phe Ala Gln Phe Ala Gly Asp His Thr Leu Leu Thr
                565                 570                 575

Pro Gly Tyr Ser Val Ile Ile Glu Lys Leu Ala Glu Gly Leu Asp Ile
            580                 585                 590

Gln Leu Lys Ser Pro Val Gln Cys Ile Asp Tyr Ser Gly Asp Glu Val
        595                 600                 605

Gln Val Thr Thr Thr Asp Gly Thr Gly Tyr Ser Ala Gln Lys Val Leu
    610                 615                 620

Val Thr Val Pro Leu Ala Leu Leu Gln Lys Gly Ala Ile Gln Phe Asn
625                 630                 635                 640

Pro Pro Leu Ser Glu Lys Lys Met Lys Ala Ile Asn Ser Leu Gly Ala
                645                 650                 655

Gly Ile Ile Glu Lys Ile Ala Leu Gln Phe Pro Tyr Arg Phe Trp Asp
            660                 665                 670

Ser Lys Val Gln Gly Ala Asp Phe Phe Gly His Val Pro Pro Ser Ala
        675                 680                 685

Ser Lys Arg Gly Leu Phe Ala Val Phe Tyr Asp Met Asp Pro Gln Lys
    690                 695                 700

Lys His Ser Val Leu Met Ser Val Ile Ala Gly Glu Ala Val Ala Ser
705                 710                 715                 720

Val Arg Thr Leu Asp Asp Lys Gln Val Leu Gln Gln Cys Met Ala Thr
                725                 730                 735

Leu Arg Glu Leu Phe Lys Glu Gln Glu Val Pro Asp Pro Thr Lys Tyr
            740                 745                 750

Phe Val Thr Arg Trp Ser Thr Asp Pro Trp Ile Gln Met Ala Tyr Ser
        755                 760                 765

Phe Val Lys Thr Gly Gly Ser Gly Glu Ala Tyr Asp Ile Ile Ala Glu
    770                 775                 780

Asp Ile Gln Gly Thr Val Phe Phe Ala Gly Glu Ala Thr Asn Arg His
785                 790                 795                 800

Phe Pro Gln Thr Val Thr Gly Ala Tyr Leu Ser Gly Val Arg Glu Ala
                805                 810                 815

Ser Lys Ile Ala Ala Phe
            820

<210> SEQ ID NO 63
<211> LENGTH: 4
<212> TYPE: PRT
<213> ORGANISM: Homo sapiens

<400> SEQUENCE: 63

Pro Trp Trp Pro
1

<210> SEQ ID NO 64
<211> LENGTH: 6
<212> TYPE: PRT
<213> ORGANISM: Homo sapiens
```

-continued

```
<400> SEQUENCE: 64

Tyr Gln Pro Asn Glu Cys
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Ser Gly Ser Gly Ser
1               5

<210> SEQ ID NO 66
<211> LENGTH: 7
<212> TYPE: PRT
<213> ORGANISM: Unknown
<220> FEATURE:
<223> OTHER INFORMATION: Description of Unknown: SV40 large
      T-antigen NLS peptide

<400> SEQUENCE: 66

Pro Lys Lys Lys Arg Lys Val
1               5

<210> SEQ ID NO 67
<211> LENGTH: 16
<212> TYPE: PRT
<213> ORGANISM: Unknown
<220> FEATURE:
<223> OTHER INFORMATION: Description of Unknown: Nucleoplasmin
      NLS peptide

<400> SEQUENCE: 67

Lys Arg Pro Ala Ala Thr Lys Lys Ala Gly Gln Ala Lys Lys Lys Lys
1               5                   10                  15

<210> SEQ ID NO 68
<211> LENGTH: 18
<212> TYPE: PRT
<213> ORGANISM: Homo sapiens

<400> SEQUENCE: 68

Met Lys Trp Val Thr Phe Ile Ser Leu Leu Phe Leu Phe Ser Ser Ala
1               5                   10                  15

Tyr Ser

<210> SEQ ID NO 69
<211> LENGTH: 18
<212> TYPE: PRT
<213> ORGANISM: Homo sapiens

<400> SEQUENCE: 69

Met Ala Phe Leu Trp Leu Leu Ser Cys Trp Ala Leu Leu Gly Thr Thr
1               5                   10                  15

Gly Phe

<210> SEQ ID NO 70
<211> LENGTH: 14
<212> TYPE: PRT
<213> ORGANISM: Homo sapiens
```

```
<400> SEQUENCE: 70

Met Gln Leu Leu Ser Cys Ile Ala Leu Ile Leu Ala Leu Val
1               5                   10

<210> SEQ ID NO 71
<211> LENGTH: 15
<212> TYPE: PRT
<213> ORGANISM: Homo sapiens

<400> SEQUENCE: 71

Met Asn Leu Leu Leu Ile Leu Thr Phe Val Ala Ala Ala Val Ala
1               5                   10                  15

<210> SEQ ID NO 72
<211> LENGTH: 12
<212> TYPE: PRT
<213> ORGANISM: Homo sapiens

<400> SEQUENCE: 72

Pro Leu Gly Ser Glu Phe Lys Gly Leu Arg Arg Arg
1               5                   10

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Pro Gly Ser
1

<210> SEQ ID NO 74
<211> LENGTH: 21
<212> TYPE: PRT
<213> ORGANISM: Homo sapiens

<400> SEQUENCE: 74

Ala Arg Thr Met Gln Thr Ala Arg Lys Ser Thr Gly Gly Lys Ala Pro
1               5                   10                  15

Arg Lys Gln Leu Ala
            20

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 75

His His His His His His
1               5

<210> SEQ ID NO 76
<211> LENGTH: 9
<212> TYPE: PRT
<213> ORGANISM: Homo sapiens

<400> SEQUENCE: 76

Asp Pro His Phe His His Phe Leu Leu
```

-continued

```
<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Pro His Phe His Ala Phe Leu Leu Ala Gln Thr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Pro His Phe His His Ala Ala Ala Ser Gln Thr
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Pro His Phe His Gln Thr
1               5

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Pro His Phe His His Phe Leu Leu Ser Gln Thr
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Pro Ala Phe His His Phe Leu Leu Ser Gln Thr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 82

Asp Pro His Ala His His Phe Leu Leu Ser Gln Thr
1               5                   10

<210> SEQ ID NO 83
<211> LENGTH: 20
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Lys or Met

<400> SEQUENCE: 83

Ala Arg Thr Xaa Gln Thr Ala Arg Lys Ser Thr Gly Gly Lys Ala Pro
1               5                   10                  15

Arg Lys Gln Leu
            20

<210> SEQ ID NO 84
<211> LENGTH: 8
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Lys or Met

<400> SEQUENCE: 84

Ala Arg Thr Xaa Gln Thr Ala Arg
1               5

<210> SEQ ID NO 85
<211> LENGTH: 772
<212> TYPE: PRT
<213> ORGANISM: Homo sapiens

<400> SEQUENCE: 85

Arg Lys Cys Glu Lys Ala Gly Cys Thr Ala Thr Cys Pro Val Cys Phe
1               5                   10                  15

Ala Ser Ala Ser Glu Arg Cys Ala Lys Asn Gly Tyr Thr Ser Arg Trp
                20                  25                  30

Tyr His Leu Ser Cys Gly Glu His Phe Cys Asn Glu Cys Phe Asp His
                35                  40                  45

Tyr Tyr Arg Ser His Lys Asp Gly Tyr Asp Lys Tyr Thr Thr Trp Lys
50                  55                  60

Lys Ile Trp Thr Ser Asn Gly Lys Thr Glu Pro Ser Pro Lys Ala Phe
65                  70                  75                  80

Met Ala Asp Gln Gln Leu Pro Tyr Trp Val Gln Cys Thr Lys Pro Glu
                85                  90                  95

Cys Arg Lys Trp Arg Gln Leu Thr Lys Glu Ile Gln Leu Thr Pro Gln
                100                 105                 110

Ile Ala Lys Thr Tyr Arg Cys Gly Met Lys Pro Asn Thr Ala Ile Lys
                115                 120                 125

Pro Glu Thr Ser Asp His Cys Ser Leu Pro Glu Asp Leu Arg Val Leu
                130                 135                 140

Glu Val Ser Asn His Trp Trp Tyr Ser Met Leu Ile Leu Pro Pro Leu
145                 150                 155                 160

Leu Lys Asp Ser Val Ala Ala Pro Leu Leu Ser Ala Tyr Tyr Pro Asp

```
            165                 170                 175
Cys Val Gly Met Ser Pro Ser Cys Thr Ser Thr Asn Arg Ala Ala Ala
            180                 185                 190

Thr Gly Asn Ala Ser Pro Gly Lys Leu Glu His Ser Lys Ala Ala Leu
            195                 200                 205

Ser Val His Val Pro Gly Met Asn Arg Tyr Phe Gln Pro Phe Tyr Gln
            210                 215                 220

Pro Asn Glu Cys Gly Lys Ala Leu Cys Val Arg Pro Asp Val Met Glu
225                 230                 235                 240

Leu Asp Glu Leu Tyr Glu Phe Pro Gly Tyr Ser Arg Asp Pro Thr Met
                245                 250                 255

Tyr Leu Ala Leu Arg Asn Leu Ile Leu Ala Leu Trp Tyr Thr Asn Cys
            260                 265                 270

Lys Glu Ala Leu Thr Pro Gln Lys Cys Ile Pro His Ile Ile Val Arg
            275                 280                 285

Gly Leu Val Arg Ile Arg Cys Val Gln Glu Val Glu Arg Ile Leu Tyr
            290                 295                 300

Phe Met Thr Arg Lys Gly Leu Ile Asn Thr Gly Val Leu Ser Val Gly
305                 310                 315                 320

Ala Asp Gln Tyr Leu Leu Pro Lys Asp Tyr His Asn Lys Ser Val Ile
                325                 330                 335

Ile Ile Gly Ala Gly Pro Ala Gly Leu Ala Ala Ala Arg Gln Leu His
            340                 345                 350

Asn Phe Gly Ile Lys Val Thr Val Leu Glu Ala Lys Asp Arg Ile Gly
            355                 360                 365

Gly Arg Val Trp Asp Asp Lys Ser Phe Lys Gly Val Thr Val Gly Arg
            370                 375                 380

Gly Ala Gln Ile Val Asn Gly Cys Ile Asn Asn Pro Val Ala Leu Met
385                 390                 395                 400

Cys Glu Gln Leu Gly Ile Ser Met His Lys Phe Gly Glu Arg Cys Asp
                405                 410                 415

Leu Ile Gln Glu Gly Gly Arg Ile Thr Asp Pro Thr Ile Asp Lys Arg
            420                 425                 430

Met Asp Phe His Phe Asn Ala Leu Leu Asp Val Val Ser Glu Trp Arg
            435                 440                 445

Lys Asp Lys Thr Gln Leu Gln Asp Val Pro Leu Gly Glu Lys Ile Glu
            450                 455                 460

Glu Ile Tyr Lys Ala Phe Ile Lys Glu Ser Gly Ile Gln Phe Ser Glu
465                 470                 475                 480

Leu Glu Gly Gln Val Leu Gln Phe His Leu Ser Asn Leu Glu Tyr Ala
                485                 490                 495

Cys Gly Ser Asn Leu His Gln Val Ser Ala Arg Ser Trp Asp His Asn
            500                 505                 510

Glu Phe Phe Ala Gln Phe Ala Gly Asp His Thr Leu Leu Thr Pro Gly
            515                 520                 525

Tyr Ser Val Ile Ile Glu Lys Leu Ala Glu Gly Leu Asp Ile Gln Leu
            530                 535                 540

Lys Ser Pro Val Gln Cys Ile Asp Tyr Ser Gly Asp Glu Val Gln Val
545                 550                 555                 560

Thr Thr Thr Asp Gly Thr Gly Tyr Ser Ala Gln Lys Val Leu Val Thr
                565                 570                 575

Val Pro Leu Ala Leu Leu Gln Lys Gly Ala Ile Gln Phe Asn Pro Pro
            580                 585                 590
```

-continued

Leu Ser Glu Lys Lys Met Lys Ala Ile Asn Ser Leu Gly Ala Gly Ile
        595                 600                 605

Ile Glu Lys Ile Ala Leu Gln Phe Pro Tyr Arg Phe Trp Asp Ser Lys
        610                 615                 620

Val Gln Gly Ala Asp Phe Phe Gly His Val Pro Pro Ser Ala Ser Lys
625                 630                 635                 640

Arg Gly Leu Phe Ala Val Phe Tyr Asp Met Asp Pro Gln Lys Lys His
            645                 650                 655

Ser Val Leu Met Ser Val Ile Ala Gly Glu Ala Val Ala Ser Val Arg
            660                 665                 670

Thr Leu Asp Asp Lys Gln Val Leu Gln Gln Cys Met Ala Thr Leu Arg
            675                 680                 685

Glu Leu Phe Lys Glu Gln Glu Val Pro Asp Pro Thr Lys Tyr Phe Val
        690                 695                 700

Thr Arg Trp Ser Thr Asp Pro Trp Ile Gln Met Ala Tyr Ser Phe Val
705                 710                 715                 720

Lys Thr Gly Gly Ser Gly Glu Ala Tyr Asp Ile Ile Ala Glu Asp Ile
            725                 730                 735

Gln Gly Thr Val Phe Ala Gly Glu Ala Thr Asn Arg His Phe Pro
            740                 745                 750

Gln Thr Val Thr Gly Ala Tyr Leu Ser Gly Val Arg Glu Ala Ser Lys
            755                 760                 765

Ile Ala Ala Phe
        770

<210> SEQ ID NO 86
<211> LENGTH: 52
<212> TYPE: PRT
<213> ORGANISM: Homo sapiens

<400> SEQUENCE: 86

Gln Cys Leu Val Trp Val Gln Cys Ser Phe Pro Asn Cys Gly Lys Trp
1               5                   10                  15

Arg Arg Leu Cys Gly Asn Ile Asp Pro Ser Val Leu Pro Asp Asn Trp
            20                  25                  30

Ser Cys Asp Gln Asn Thr Asp Val Gln Tyr Asn Arg Cys Asp Ile Pro
        35                  40                  45

Glu Glu Thr Trp
    50

<210> SEQ ID NO 87
<211> LENGTH: 251
<212> TYPE: PRT
<213> ORGANISM: Homo sapiens

<400> SEQUENCE: 87

Ser Gly Val Glu Gly Ala Ala Phe Gln Ser Arg Leu Pro His Asp Arg
1               5                   10                  15

Met Thr Ser Gln Glu Ala Ala Cys Phe Pro Asp Ile Ile Ser Gly Pro
            20                  25                  30

Gln Gln Thr Gln Lys Val Phe Leu Phe Ile Arg Asn Arg Thr Leu Gln
        35                  40                  45

Leu Trp Leu Asp Asn Pro Lys Ile Gln Leu Thr Phe Glu Ala Thr Leu
    50                  55                  60

Gln Gln Leu Glu Ala Pro Tyr Asn Ser Asp Thr Val Leu Val His Arg
65                  70                  75                  80

-continued

```
Val His Ser Tyr Leu Glu Arg His Gly Leu Ile Asn Phe Gly Ile Tyr
            85                  90                  95

Lys Arg Ile Lys Pro Leu Pro Thr Lys Lys Thr Gly Lys Val Ile Ile
            100                 105                 110

Ile Gly Ser Gly Val Ser Gly Leu Ala Ala Arg Gln Leu Gln Ser
            115                 120                 125

Phe Gly Met Asp Val Thr Leu Leu Glu Ala Arg Asp Arg Val Gly Gly
            130                 135                 140

Arg Val Ala Thr Phe Arg Lys Gly Asn Tyr Val Ala Asp Leu Gly Ala
145                 150                 155                 160

Met Val Val Thr Gly Leu Gly Asn Pro Met Ala Val Val Ser Lys
                165                 170                 175

Gln Val Asn Met Glu Leu Ala Lys Ile Lys Gln Lys Cys Pro Leu Tyr
            180                 185                 190

Glu Ala Asn Gly Gln Ala Val Pro Lys Glu Lys Asp Glu Met Val Glu
            195                 200                 205

Gln Glu Phe Asn Arg Leu Leu Glu Ala Thr Ser Tyr Leu Ser His Gln
            210                 215                 220

Leu Asp Phe Asn Val Leu Asn Asn Lys Pro Val Ser Leu Gly Gln Ala
225                 230                 235                 240

Leu Glu Val Val Ile Gln Leu Gln Glu Lys His
                245                 250

<210> SEQ ID NO 88
<211> LENGTH: 312
<212> TYPE: PRT
<213> ORGANISM: Homo sapiens

<400> SEQUENCE: 88

Ser Asp Val Tyr Leu Ser Ser Arg Asp Arg Gln Ile Leu Asp Trp His
1               5                   10                  15

Phe Ala Asn Leu Glu Phe Ala Asn Ala Thr Pro Leu Ser Thr Leu Ser
            20                  25                  30

Leu Lys His Trp Asp Gln Asp Asp Phe Glu Phe Thr Gly Ser His
            35                  40                  45

Leu Thr Val Arg Asn Gly Tyr Ser Cys Val Pro Val Ala Leu Ala Glu
    50                  55                  60

Gly Leu Asp Ile Lys Leu Asn Thr Ala Val Arg Gln Val Arg Tyr Thr
65                  70                  75                  80

Ala Ser Gly Cys Glu Val Ile Ala Val Asn Thr Arg Ser Thr Ser Gln
            85                  90                  95

Thr Phe Ile Tyr Lys Cys Asp Ala Val Leu Cys Thr Leu Pro Leu Gly
            100                 105                 110

Val Leu Lys Gln Gln Pro Pro Ala Val Gln Phe Val Pro Pro Leu Pro
            115                 120                 125

Glu Trp Lys Thr Ser Ala Val Gln Arg Met Gly Phe Gly Asn Leu Asn
            130                 135                 140

Lys Val Val Leu Cys Phe Asp Arg Val Phe Trp Asp Pro Ser Val Asn
145                 150                 155                 160

Leu Phe Gly His Val Gly Ser Thr Thr Ala Ser Arg Gly Glu Leu Phe
                165                 170                 175

Leu Phe Trp Asn Leu Tyr Lys Ala Pro Ile Leu Leu Ala Leu Val Ala
            180                 185                 190

Gly Glu Ala Ala Gly Ile Met Glu Asn Ile Ser Asp Asp Val Ile Val
```

```
                195                 200                 205
Gly Arg Cys Leu Ala Ile Leu Lys Gly Ile Phe Gly Ser Ser Ala Val
    210                 215                 220
Pro Gln Pro Lys Glu Thr Val Val Ser Arg Trp Arg Ala Asp Pro Trp
225                 230                 235                 240
Ala Arg Gly Ser Tyr Ser Tyr Val Ala Ala Gly Ser Ser Gly Asn Asp
                245                 250                 255
Tyr Asp Leu Met Ala Gln Pro Ile Thr Pro Gly Pro Ser Ile Pro Gly
            260                 265                 270
Ala Pro Gln Pro Ile Pro Arg Leu Phe Phe Ala Gly Glu His Thr Ile
            275                 280                 285
Arg Asn Tyr Pro Ala Thr Val His Gly Ala Leu Leu Ser Gly Leu Arg
            290                 295                 300
Glu Ala Gly Arg Ile Ala Asp Gln
305                 310

<210> SEQ ID NO 89
<211> LENGTH: 457
<212> TYPE: PRT
<213> ORGANISM: Zea mays

<400> SEQUENCE: 89

Ala Thr Val Gly Pro Arg Val Ile Val Val Gly Ala Gly Met Ser Gly
1               5                   10                  15
Ile Ser Ala Ala Lys Arg Leu Ser Glu Ala Gly Ile Thr Asp Leu Leu
            20                  25                  30
Ile Leu Glu Ala Thr Asp His Ile Gly Gly Arg Met His Lys Thr Asn
        35                  40                  45
Phe Ala Gly Ile Asn Val Glu Leu Gly Ala Asn Trp Val Glu Gly Val
    50                  55                  60
Asn Gly Gly Lys Met Asn Pro Ile Trp Pro Ile Val Asn Ser Thr Leu
65                  70                  75                  80
Lys Leu Arg Asn Phe Arg Ser Asp Phe Asp Tyr Leu Ala Gln Asn Val
                85                  90                  95
Tyr Lys Glu Asp Gly Gly Val Tyr Asp Glu Asp Tyr Val Gln Lys Arg
            100                 105                 110
Ile Glu Leu Ala Asp Ser Val Glu Glu Met Gly Glu Lys Leu Ser Ala
        115                 120                 125
Thr Leu His Ala Ser Gly Arg Asp Asp Met Ser Ile Leu Ala Met Gln
    130                 135                 140
Arg Leu Asn Glu His Gln Pro Asn Gly Pro Ala Thr Pro Val Asp Met
145                 150                 155                 160
Val Val Asp Tyr Tyr Lys Phe Asp Tyr Glu Phe Ala Glu Pro Pro Arg
                165                 170                 175
Val Thr Ser Leu Gln Asn Thr Val Pro Leu Ala Thr Phe Ser Asp Phe
            180                 185                 190
Gly Asp Asp Val Tyr Phe Val Ala Asp Gln Arg Gly Tyr Glu Ala Val
        195                 200                 205
Val Tyr Tyr Leu Ala Gly Gln Tyr Leu Lys Thr Asp Asp Lys Ser Gly
    210                 215                 220
Lys Ile Val Asp Pro Arg Leu Gln Leu Asn Lys Val Val Arg Glu Ile
225                 230                 235                 240
Lys Tyr Ser Pro Gly Gly Val Thr Val Lys Thr Glu Asp Asn Ser Val
                245                 250                 255
```

```
Tyr Ser Ala Asp Tyr Val Met Val Ser Ala Ser Leu Gly Val Leu Gln
            260                 265                 270

Ser Asp Leu Ile Gln Phe Lys Pro Lys Leu Pro Thr Trp Lys Val Arg
        275                 280                 285

Ala Ile Tyr Gln Phe Asp Met Ala Val Tyr Thr Lys Ile Phe Leu Lys
    290                 295                 300

Phe Pro Arg Lys Phe Trp Pro Glu Gly Lys Gly Arg Glu Phe Phe Leu
305                 310                 315                 320

Tyr Ala Ser Ser Arg Arg Gly Tyr Tyr Gly Val Trp Gln Glu Phe Glu
                325                 330                 335

Lys Gln Tyr Pro Asp Ala Asn Val Leu Leu Val Thr Val Thr Asp Glu
            340                 345                 350

Glu Ser Arg Arg Ile Glu Gln Gln Ser Asp Glu Gln Thr Lys Ala Glu
        355                 360                 365

Ile Met Gln Val Leu Arg Lys Met Phe Pro Gly Lys Asp Val Pro Asp
    370                 375                 380

Ala Thr Asp Ile Leu Val Pro Arg Trp Trp Ser Asp Arg Phe Tyr Lys
385                 390                 395                 400

Gly Thr Phe Ser Asn Trp Pro Val Gly Val Asn Arg Tyr Glu Tyr Asp
                405                 410                 415

Gln Leu Arg Ala Pro Val Gly Arg Val Tyr Phe Thr Gly Glu His Thr
            420                 425                 430

Ser Glu His Tyr Asn Gly Tyr Val His Gly Ala Tyr Leu Ser Gly Ile
        435                 440                 445

Asp Ser Ala Glu Ile Leu Ile Asn Cys
    450                 455

<210> SEQ ID NO 90
<211> LENGTH: 453
<212> TYPE: PRT
<213> ORGANISM: Homo sapiens

<400> SEQUENCE: 90

Met Ser Asn Lys Cys Asp Val Val Val Gly Gly Gly Ile Ser Gly
1               5                   10                  15

Met Ala Ala Ala Lys Leu Leu His Asp Ser Gly Leu Asn Val Val Val
                20                  25                  30

Leu Glu Ala Arg Asp Arg Val Gly Gly Arg Thr Tyr Thr Leu Arg Asn
            35                  40                  45

Gln Lys Val Lys Tyr Val Asp Leu Gly Gly Ser Tyr Val Gly Pro Thr
        50                  55                  60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                85                  90                  95

Tyr Pro Phe Arg Gly Pro Phe Pro Pro Val Trp Asn Pro Ile Thr Tyr
            100                 105                 110

Leu Asp His Asn Asn Phe Trp Arg Thr Met Asp Asp Met Gly Arg Glu
        115                 120                 125

Ile Pro Ser Asp Ala Pro Trp Lys Ala Pro Leu Ala Glu Glu Trp Asp
    130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175
```

```
Thr His Glu Val Ser Ala Leu Trp Phe Leu Trp Tyr Val Lys Gln Cys
            180                 185                 190

Gly Gly Thr Arg Ile Ile Ser Thr Thr Asn Gly Gly Gln Glu Arg
            195                 200             205

Lys Phe Val Gly Gly Ser Gly Gln Val Ser Glu Arg Ile Met Asp Leu
210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
            260                 265                 270

His Phe Asn Pro Pro Leu Pro Met Met Arg Asn Gln Met Ile Thr Arg
            275                 280                 285

Val Pro Leu Gly Ser Val Ile Lys Cys Ile Val Tyr Tyr Lys Glu Pro
        290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
            340                 345                 350

Ala Arg Leu Thr Lys Glu Glu Arg Leu Lys Lys Leu Cys Glu Leu Tyr
            355                 360                 365

Ala Lys Val Leu Gly Ser Leu Glu Ala Leu Glu Pro Val His Tyr Glu
            370                 375                 380

Glu Lys Asn Trp Cys Glu Glu Gln Tyr Ser Gly Gly Cys Tyr Thr Thr
385                 390                 395                 400

Tyr Phe Pro Pro Gly Ile Leu Thr Gln Tyr Gly Arg Val Leu Arg Gln
                405                 410                 415

Pro Val Asp Arg Ile Tyr Phe Ala Gly Thr Glu Thr Ala Thr His Trp
            420                 425                 430

Ser Gly Tyr Met Glu Gly Ala Val Glu Ala Gly Glu Arg Ala Ala Arg
            435                 440                 445

Glu Ile Leu His Ala
    450

<210> SEQ ID NO 91
<211> LENGTH: 150
<212> TYPE: PRT
<213> ORGANISM: Homo sapiens

<400> SEQUENCE: 91

Met Ala Ala Val Ser Leu Arg Leu Gly Asp Leu Val Trp Gly Lys Leu
1               5                   10                  15

Gly Arg Tyr Pro Pro Trp Pro Gly Lys Ile Val Asn Pro Pro Lys Asp
            20                  25                  30

Leu Lys Lys Pro Arg Gly Lys Glu Cys Phe Phe Val Lys Phe Phe Gly
        35                  40                  45

Thr Glu Asp His Ala Trp Ile Lys Val Glu Gln Leu Lys Pro Tyr His
    50                  55                  60

Ala His Lys Glu Glu Met Ile Lys Ile Asn Lys Gly Lys Arg Phe Gln
65                  70                  75                  80

Gln Ala Val Asp Ala Val Glu Glu Phe Leu Arg Arg Ala Lys Gly Lys
```

-continued

```
                85                  90                  95
Asp Gln Thr Ser Ser His Asn Ser Ser Asp Asp Lys Asn Arg Arg Asn
            100                 105                 110

Ser Ser Glu Glu Arg Ser Arg Pro Asn Ser Gly Asp Glu Lys Arg Lys
        115                 120                 125

Leu Ser Leu Ser Glu Gly Lys Val Lys Lys Asn Met Gly Glu Gly Lys
        130                 135                 140

Lys Arg Val Ser Ser Gly
145             150
```

PEPTIDES USEFUL FOR MODULATING HISTONE DEMETHYLASE FUNCTION

CROSS-REFERENCE TO RELATED APPLICATIONS

This application is a National Phase Entry Application under 35 U.S.C. §371 of International Application No. PCT/US2013/076903 filed Dec. 20, 2013, and claims benefit under 35 U.S.C. §119(e) of U.S. Provisional Application No. 61/740,181 filed Dec. 20, 2012, the contents of which are incorporated herein by reference in their entireties.

GOVERNMENT SUPPORT

This invention was made with Government support under grant No. 5R01GM078458 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Dec. 20, 2013, is named 043214-076011-PCT_SL.txt and is 47,781 bytes in size.

FIELD OF THE INVENTION

The present invention relates to the field of therapeutic peptides, specifically peptides that can modulate the function of histone demethylases, and methods of using the same. The invention also provides novel peptide binding site and antibodies directed to the binding site. Methods of using the peptides and antibodies to treat disease are also provided.

BACKGROUND

Since the discovery of the first histone lysine specific demethylase LSD1/KDM1a, histone lysine demethylation has emerged as an epigenetic paradigm (Shi et al., 2004). So far, over 20 histone lysine demethylases (KDMs) have been characterized, belonging to either the FAD-dependent LSD or the $Fe^{2+}$ and α-ketoglutarate-dependent Jumonji C-terminal domain (JmjC) family (Allis et al., 2007; Bernstein et al., 2007; Chen et al., 2006b; Klose et al., 2006; Kubicek and Jenuwein, 2004; Rice and Allis, 2001; Ruthenburg et al., 2007). Genetic, biochemical and functional studies further indicate that these KDMs play a role in a wide range of biological processes, including gene expression, cell growth, differentiation, development and disease pathogenesis (Bhaumik et al., 2007; Egger et al., 2004; Esteller, 2008; Nottke et al., 2009; Shi, 2007). Abrogated expression or enzymatic activity of histone demethylases has been implicated in human diseases such as cancer (Chi et al., 2010; Esteller, 2008; Smith et al., 2007). Therefore, deciphering the regulatory mechanisms of histone demethylases is important for understanding their biological and pathophysiological functions (Chen et al., 2007; Chen et al., 2006b; Horton et al., 2010; Shi, 2007).

For example it is important to understand how the activity of KDMs is regulated (Chen et al., 2007; Chen et al., 2006b; Horton et al., 2010; Lan et al., 2008; Wilson, 2007). It has been found that many KDMs, while active on synthetic peptides or core histone substrates, exhibit very weak or no detectable activity on nucleosomal substrates in vitro. However, when transfected into cells robust activity on chromatin can be detected, suggesting the existence of additional cofactors required for full activity (Shi et al., 2004; Tahiliani et al., 2007).

We, and others, have identified CoREST as a cofactor required for LSD1/KDM1a action on nucleosomal substrates (Lee et al., 2005; Shi et al., 2005), representing the first breakthrough toward understanding how KDM activity is regulated. However, the molecular details underlying the cofactor-enhanced demethylase activity of LSD1 remain elusive (Forneris et al., 2007; Yang et al., 2006). Moreover, the cofactor activity of CoREST is highly specific, only facilitating demethylation of nucleosomal substrates by LSD1 but not any other KDMs. Further investigation is required to determine if cofactor-modulation is a general mechanism for the regulation of KDM functions. In particular, there are two areas to be addressed: first, whether different cofactors exist for other histone demethylases; and second, the molecular mechanism(s) employed by such cofactors to facilitate histone demethylase activity.

Answers to these questions would provide novel ways of treating diseases associated with defects resulting in dysfunction of these mechanisms.

SUMMARY OF THE INVENTION

We have now discovered short peptides derived from NPAC/GLYR1 that can modulate LSD2/KDM1b enzymatic activity and biological function in vivo. To our knowledge, the ability of NPAC regulating LSD2 function has not been previously known. Modulation of the LSD2 enzymatic activity and biological function can be used in treatment of diseases, such as diseases involved in cell proliferation, like cancer. LSD2 is also known to be involved in oocytogenesis. Accordingly, the peptides of the invention also have function in reproductive biology. For example, the peptides are also useful to treat infertility caused by the LDS2 activity problems by stimulating LSD2 activity. The isolated peptides of the invention, as well as shRNA, siRNA, and antibodies based on the key interacting portions of NPAC and LSD2 are useful for treatment of diseases resulting from too much cell proliferation, such as cancer.

LSD2/AOF1/KDM1b is a histone demethylase, demethylating mono- and di-methylated H3K4 and H3K9. LSD2 regulates gene transcription and DNA methylation, and plays important role in development. Evidence suggest it plays a role in human diseases including cancer. NPAC/GLYR1 is a histone code reader and it specifically and directly interacts with LSD2, and is responsible for LSD2 genomic targeting in human genome.

Specifically, the invention provides peptides that can stimulate LSD2 demethylase activity in vitro and in vivo and block the interaction between LSD2 and NPAC. Peptides blocking the interaction between LSD2 and NPAC can inhibit the function of LSD2 in vivo.

In our examples we show, that expression of the peptides in vivo can down regulate of the expression of cyclines that are LSD2 target genes in breast cancer cells. These genes regulate breast cancer cell growth. We have observed that depletion of either LSD2 and NPAC inhibits the expression of cyclines and inhibit breast cancer cell proliferations and/or growth.

Accordingly, we provide methods for inhibiting and/or reducing cancer cell growth and/or proliferation, such as breast cancer cell growth, comprising administering to a patient with cancer one or more of the peptides of the invention that inhibit LSD2. Similarly, other diseases where methylation plays a pathologic role, can be treated with the peptides of the invention. In some aspects of all the embodiments of the invention, a cell is first determined to have overexpression of LSD2 and/or NPAC and if such overexpression is detected then inhibiting and/or reducing the cell growth and/or proliferation by administering a peptide, siRNA, shRNA and/or antibody as described herein.

In some aspects of all the methods of the invention, the cancer cell growth and/or proliferation is inhibited using an antibody recognizing these peptide to block LSD2 and NPAC interaction, and/or the interaction of LSD2 and histone H3.

We also provide the crystal structure of LSD2, and LSD2 in complex with NPAC and histone peptide (its substrate). Thus, we have identified the binding pocket in LSD2 accommodating NPAC and histone peptides. The binding pocket can be used in methods for drug design or screening drugs that can inhibit the binding of NPAC to LSD2.

BRIEF DESCRIPTION OF THE DRAWINGS

FIG. 1A depicts a schematic of NPAC domain structure. AT, AT-hook motif. PWWP, Pro-Trp-Trp-Pro domain (SEQ ID NO: 63). FIG. 1B demonstrates that LSD2 in the NPAC complex can efficiently demethylate nucleosomal H3K4me2. Tandem affinity purified NPAC and LSD2 complexes were incubated with nucleosomes purified from HeLa, and analyzed by immunoblot using indicated antibodies. FIG. 1C demonstrates that addition of recombinant NPAC can improve H3K4 demethylase activity of the LSD2 complex. FIG. 1D demonstrates that recombinant NPAC stimulates LSD2 nucleosomal H3K4 demethylation in a dose-dependent manner. The amount of LSD2 enzyme and NPAC cofactor proteins used in each reaction is indicated. Demethylation was assessed by Immunoblot using indicated antibodies. Significantly larger amounts of His-LSD2 are required for efficient demethylation of nucleosomes (See FIG. 7A). FIG. 1E demonstrates that NPAC stimulates H3K4 demethylation mediated by LSD2 in cells Immuno-fluorescence staining of U2OS transiently transfected with LSD2 alone or in combination with NPAC. Representatives with similar levels of GFP-LSD2 are shown. See also FIGS. 7A-7D.

FIG. 2A depicts a schematic representation of the wild-type and deletion mutants of NPAC. DH, dehydrogenase domain; black box, AT-hook motif. FIG. 2A discloses "PWWP" as SEQ ID NO: 63. FIG. 2B demonstrates nucleosome demethylation assays examining cofactor activities of NPAC mutants. Equal amounts of LSD2 were used in nucleosome demethylation reactions 2-11, in combination with various GST-tagged NPAC truncation proteins indicated above. GST was included as a negative control. FIG. 2C demonstrates that the linker region of NPAC can stimulate LSD2 histone demethylase activity towards short H3K4me2 peptides. Molecular masses corresponding to mono- and dimethylated H3K4 peptides (residues 1-21) are denoted as me1 and me2, respectively. FIG. 2D demonstrates that the linker region of NPAC is sufficient for LSD2 binding. Purified GST and GST tagged wild-type and mutant NPAC proteins were used for GST pulldown of purified His-LSD2. Pulldown complexes were separated by SDS-PAGE and visualized by coomassie blue staining Asterisk, GST-fusion protein.

FIG. 3A depicts a comparison of the domain structures of human LSD2 and LSD1. Numbers indicate residue positions at the boundaries of each domain. The unpredicted, novel zinc finger domain (ZF) is shown, CW-type zinc finger (Zf-CW), linker region, SWIRM domain, amine oxidase domain (AO), N-terminal flexible regions, and the tower domain of LSD1 are shown. FIGS. 3B-3D depict the crystal structures of LSD2 (3B), NPAC-LSD2 heterodimer (3C), and the ternary complex of LSD2-NPAC-H3 peptide (3D). Disordered regions are shown in dashed lines, and FAD in stick representation. Three zinc atoms are shown as grey balls. N- and C-termini of LSD2 are indicated. NPAC and H3K4M peptide are indicated and shown in ribbon representation. See also FIGS. 8A-8B, 9A-9C, and Table 3.

FIG. 4A depicts a structural overlay of LSD2 and LSD1. FIG. 4B depicts the structure of the N-terminal zinc finger of LSD2. Two zinc ions (grey balls) are coordinated with a $Cys_4His_2Cys_2$ motif with the indicated residues shown in stick representation. This novel zinc finger domain bears little resemblance to known zinc finger structures. FIG. 4C depicts the structure of the CW-type zinc finger of LSD2. Residues involved in zinc coordination are labeled and shown in stick representation. The disordered region is indicated by a dotted line. FIG. 4D depicts superimposed structures of the SWIRM domains of LSD2 and LSD1. The extended loop and α9-helix in LSD2 SWIRM domain are denoted. The side chains of unconserved residues are presented in stick presentation. FIG. 4E demonstrates that mutation of the extended loop in LSD2 SWIRM domain impairs its histone demethylase activity. MALDI-TOF mass spectrometry analyses of the demethylation of H3K4me2 peptides incubated with indicated proteins. LSD2.WT, wild-type LSD2. LSD2.M, an LSD2 mutant replacing YQPNEC (SEQ ID NO: 64) 273-278 with a flexible linker GSGSGS (SEQ ID NO: 65). See also FIGS. 10A-10F and Table 3.

FIGS. 5A-5I demonstrate that a dodecapeptide of NPAC interacts with LSD2. FIGS. 5A-5B demonstrate that accommodation of NPAC residues in a hydrophobic pocket between the AO and SWIRM domains of LSD2. Surface rendering and ribbon representation of LSD2 is shown in (FIG. 5A) and (FIG. 5B), respectively. FIG. 5B discloses SEQ ID NO: 51. Critical residues involved in interaction are shown in stick representation from LSD2 AO domain, from LSD2 SWIRM domain, and from NPAC. FIG. 5C depicts a structural superimposition of the NPAC binding site of LSD2 and the corresponding regions of LSD1. The LSD2 structures are nearly identical with or without NPAC binding. FIG. 5D depicts a schematic of deletion mutants of the NPAC linker region. The box marks the position of NPAC residues 214-225. FIG. 5D discloses SEQ ID NOS 63 and 76, respectively, in order of appearance. FIG. 5E depicts examination of LSD2 binding of NPAC deletion mutants by GST-pull down. His-LSD2 in pulldown products were separated by SDS-PAGE and visualized by coomassie blue staining FIG. 5F depicts immunoblot analyses of nucleosome demethylation assays of NPAC mutants described in FIG. 5D using indicated antibodies. FIG. 5G depicts partial sequences (SEQ ID NOS 1 and 77-79, respectively, in order of appearance) of NPAC mutations (residues 188-252) disrupting the potential NPAC binding site for LSD2 interaction. FIG. 5H depicts GST-pulldown analysis of LSD2 binding by NPAC mutants in FIG. 5G. Coomassie blue staining of His-LSD2 in input and GST-pulldown complexes is shown. The results indicate that NPAC residues 219-223 are the key residues for LSD2 interactions. See also FIG. 6G. FIG. 5I depicts immunoblot analyses of nucleosome demethylation assays of NPAC mutants described in FIG. 5G using indicated antibodies.

FIGS. 6A-6H demonstrate that the NPAC dodecapeptide stimulates LSD2 histone demethylase activity by assisting enzyme-substrate interaction. FIGS. 6A-6B depict a close-up view of the interplay of LSD2, NPAC and H3K4M peptide in the co-crystal structure. Surface rendering and ribbon representation of LSD2 is shown in FIG. 6A and FIG. 6B, respectively. H3K4M peptide (histone H3 residues 1-21, with Lys4 replaced with a Met) and NPAC (residues 214-225) are shown in ribbon representation. Critical residues involved in H3 peptide interaction are shown in stick representation. Hydrogen bonds are indicated by dashed lines. FIG. 6C demonstrates that H3L20 makes a new contact with the NPAC-LSD2 complex, with its side chain inserted in a hydrophobic patch formed by NPAC F217 and LSD2 residues. FIG. 6D depicts sequences (SEQ ID NOS 1 and 80-82, respectively, in order of appearance) of NPAC dodecapeptides with mutations disrupting the potential interaction of NPAC with H3K4M peptide in the LSD2-NPAC-H3K4M peptide ternary complex. FIG. 6E demonstrates that NPAC F217 is essential for its cofactor activity. Immunoblots of nucleosome demethylation assays are shown. FIG. 6F demonstrates that the wild-type NPAC dodecapeptide, but not the F217A mutant, can stimulate LSD2-mediated demethylation of H3K4me2 peptides. FIG. 6G demonstrates that mutations of D214, H216 and F217 of NPAC do not affect LSD2 binding. Isothermal Titration Calorimetry enthalpy plots of wild-type and mutant NPAC dodecapeptide binding to LSD2. Indicated NPAC peptides were injected into LSD2 containing cuvettes. FIG. 6H depicts Isothermal Titration Calorimetry enthalpy plots of the binding of the H3K4M peptide to LSD2, and LSD2 in complex with either wild-type (WT) or F217A (M6) NPAC peptides (residues 214-225). H3K4M peptide (residues 1-21) was injected into cuvettes containing indicated combination of LSD2 and NPAC peptides. See also FIGS. 11A-11B, 12A-12F and Tables 4 and 5.

FIG. 7A depicts the determination of the threshold dosage of purified LSD2 required for nucleosomal H3K4 demethylation. 2 μg of nucleosomes purified from HeLa were incubated with various amount of His-LSD2 proteins for 2 hours at 30° C. The demethylation reactions were analyzed by immunoblotting using indicated antibodies. 0.5 μg of His-LSD2 showed no obvious demethylase activity under the experimental conditions, and was used in all nucleosome demethylation assays to the examination of the cofactor activities of wild-type and mutant NPAC proteins and peptides unless otherwise stated. FIG. 7B demonstrates that NPAC has no stimulatory effect on LSD1-mediated nucleosome demethylation. 2 μg LSD1 in combination with 5 μg purified NPAC or CoREST protein was used for histone demethylase assays. Even though LSD1 effectively demethylated H3K4me2 of bulk histone substrates (compare lane 6 & 7), nucleosomal demethylation activity was only observed in the presence of CoREST (compare lane 5 to lane 1). Both full-length (wt) and the linker region (residues 152-268) of NPAC failed to stimulate LSD1 demethylation of nucleosomes (compare lane 3-4 to lane 2). FIG. 7C demonstrates that NPAC stimulates LSD2 H3K4me1 demethylase activity in vivo Immunofluorescence analyses of H3K4me1 demethylation in cells expressing LSD2 alone or in combination with full-length NPAC. Transfected cells are marked by arrows; cells shown significant reduction of H3K4me1 are marked by dotted circles. Ectopic expression of LSD2 alone shows weak demethylation of H3K4me1. In contrast, coexpression of LSD2 and NPAC induces obvious global decrease of H3K4me1. Ectopic expression of NPAC alone did not induce detectable changes in H3K4me1/2 levels, possibly due to the limited amount of endogenous LSD2 in cells (data not shown). FIG. 7D depicts immunofluorescence analyses of H3K9me2 demethylation in cells coexpressing LSD2 and full-length NPAC. No H3K9me2 demethylation activity was observed in cells expressing either LSD2 alone (data not shown), or coexpressing LSD2 and NPAC.

FIG. 8A discloses SEQ ID NO: 83 and FIG. 8B discloses SEQ ID NO: 1.

FIG. 9A depicts structural superimposition of LSD2 alone and the ternary complex of LSD2-NPAC-H3K4M peptide shown in ribbon representation. NPAC and H3K4M peptide are shown. The structures of LSD2 are nearly identical. FIG. 9B depicts the structure of the LSD2 catalytic site in the ternary complex of LSD2, NPAC and H3K4M peptide. LSD2 is shown in ribbon representation and FAD in stick representation. K4M and K9 of H3 peptide, and LSD2 catalytic residue K661 are shown in stick representation. Distances are given in angstroms. The distance between K9 and FAD is 13.96 angstrom, disfavoring H3K9 demethylation by LSD2 with or without NPAC binding. FIG. 9C depicts mass spectrometry analyses of LSD2 demethylase activity on H3K9me2 peptides. A high concentration of wild-type LSD2 (1.2 μM) was incubated with biotinylated H3K9me2 peptide of indicated length, and no demethylase activity was detected. Biotinylation of H3K9me2 peptides at the C-terminus does not affect the interaction between LSD2 and substrate (data not shown). Histone demethylation assays using nucleosome or bulk histone substrates also failed to detect any H3K9me2 demethylase activity of human LSD2, in the presence or absence of NPAC protein (data not shown).

FIG. 10A depicts structural superimposition of the AO domains of LSD2 and LSD1, shown in ribbon representation. FIG. 10B depicts a close-up view of the substrate binding site of LSD2, with the H3K4M peptide. FIG. 10B discloses SEQ ID NO: 84. FIG. 10C depicts a close-up view of the substrate binding site of LSD1, with the H3K4M peptide shown. FAD coenzyme and residues involved in interactions are shown in stick representation. Hydrogen bonds and salt bridge network are shown as dashed lines. Residues contacting the N-terminus of H3K4M peptide are highly conserved in both enzymes, indicating similar mechanisms of substrate recognition. FIG.

10D depicts a structural superimposition of the Zf-CW domains of LSD2 and ZCWPW1 (2RR4.PDB, in complex with histone H3K4me3 peptide) (He et al., 2010). The SWIRM domain of LSD2 is shown. Histone H3K4me3 peptide bound to the Zf-CW domain of ZCWPW1 is shown. FIG. 10E depicts a close-up view of the interaction between H3K4me3 peptide and a hydrophobic pocket in the Zf-CW domain of ZCWPW1, formed by three tryptophan residues shown in stick representation. FIG. 10F depicts a close-up view of the interaction between the SWIRM and Zf-CW domains in LSD2 structure. LSD2 Zf-CW domain superimposes with that of ZCWPW1, with a similar hydrophobic patch formed by W139, W150 and V193. This hydrophobic patch is filled with the side chain of residues L340 and I343 in the adjacent SWIRM domain. Thus LSD2 Zf-CW is unlikely to interact with other proteins or histone modifications on this surface unless significant conformational change occurs.

FIG. 11A depicts a sequence alignment of human LSD1 (SEQ ID NOS 87 and 88, respectively, in order of appearance), LSD2 (SEQ ID NO: 85), MAO (SEQ ID NO: 90) and Maize PAO (SEQ ID NO: 89). The Zf-CW domain of LSD2 (SEQ ID NO: 86) is aligned with that of human ZCWPW1. Identical and highly conserved residues are highlighted in dark grey; conserved residues in light grey. Secondary structural elements of LSD2 are indicated above the sequences. Residues that are involved in zinc coordination are connected by solid lines. Residues that are involved in interactions with the H3K4M peptide and NPAC in the co-crystal structure are indicated by triangles and squares, respectively. Notably, many residues in the α9-helix and the extended loop in LSD2 SWIRM domain make contacts with NPAC and the C-terminal tail of H3K4M peptide, and are significantly different from LSD1. FIG. 11B depicts a Ligplot of the interaction of the H3K4M peptide with LSD2 and NPAC in co-crystals of the ternary complex. The carbon, oxygen, and nitrogen atoms are colored in black, mottled, and white, respectively. Lengths of hydrogen bond (dashed lines) are given in angstroms. Internal hydrogen bonds are not shown. The N-terminus of H3K4M peptide interacts with the AO domain of LSD2, while the C-terminal tail of H3K4M peptide interacts with the LSD2 SWIRM domain and NPAC residues 214-217. FIG. 11B discloses SEQ ID NO: 83.

FIGS. 12A-12B demonstrate LSD2 demethylation and NPAC cofactor activity on H3K4me2 peptide 1-21 (FIG. 12A) and 1-15 (FIG. 12B) 50 µM H3K4me2 peptides (residues 1-21 in FIG. 12A and residues 1-15 in FIG. 12B) were incubated with 0.15 µM or 1.2 µM purified LSD2 (residues 51-822) as indicated in 50 mM Tris-HCl, pH 8.5, 50 mM KCl, 5 mM MgCl$_2$, 5% glycerol at 37° C. for 30 min, in the presence or absence of NPAC protein (residues 152-252). Demethylation products were analyzed by MALDI-TOF mass spectrometry. 0.15 µM LSD2 can efficiently demethylate the longer H3K4me2 peptide (1-21), but has no detectable activity on the shorter histone peptide (1-15), demethylation of which requires high concentration (1.2 µM) of LSD2. In comparison, while NPAC protein showed robust cofactor activity using the longer H3K4me2 peptide (1-21) as expected, no stimulation effect was observed for the shorter H3K4me2 peptide (1-15) even in the presence of high concentration of LSD2. It indicates the importance of histone residue 16-21 to LSD2 enzymatic activity and NPAC cofactor activity, supporting our model that NPAC assists enzyme-substrate interactions by creating a new binding site for H3 L20 in the LSD2-NPAC complex. FIG. 12C depicts LSD2 demethylation and NPAC cofactor activity on longer H3K4me2 peptide (1-44). 2 µg H3K4me2 peptide (1-44) were incubated with 0.8 µg GST-LSD2 (1-822) and 2 µg wild-type or F217A full-length GST-NPAC proteins in 100 µl demethylation buffer (50 mM Tris-HCl pH 8.1, 1 mM NAD$^+$, 0.1 Unit formaldehyde dehydrogenase) at 30° C. for 2 hours. LSD2 alone can efficiently demethylate di-methyl H3K4 of the long peptides, converting large majority of the substrate to H3K4me1. Wild-type NPAC protein can efficiently stimulate LSD2 demethylation, producing unmethylated H3K4. F217A mutation impairs NPAC cofactor activity as expected, showing little stimulatory effect if any. To compare demethylation efficiency, 1.2 µg bio-H3K4me2 peptide (H3 residue 1-21, equal molar ratio to 2 ug H3K4me2 1-44 peptide in above assays) was demethylated by LSD2 under identical conditions (bottom panel). Significantly fewer H3K4me2 peptides (1-21) were converted to H3K4me1. The result suggests that H3 residues 22-44 may make additional contacts with LSD2 enzyme and are important for H3K4 demethylation efficiency. FIG. 12D demonstrates that F217A mutation significantly impaired the cofactor activity of full-length NPAC on nucleosomes. No obvious stimulatory activity of full-length NPAC F217A mutant was detected in nucleosome demethylation assays using a threshold amount of LSD2, which showed no obvious demethylation activity by LSD2 itself. The cofactor activity of wild-type NPAC was readily detected under the same conditions. FIG. 12E demonstrates that full-length NPAC F217A protein retains residue cofactor activity to H3K4 nucleosome demethylation mediated by LSD2. Stimulatory activity of full-length F217A mutant was observed in lane 4 and 9, where more NPAC protein and LSD2 enzymes were used than in FIG. 12D as indicated. Importantly, the demethylation of nucleosomal H3K4me2 was much more efficient in the presence of wild-type NPAC under same conditions (comparing lane 3 verse 4, and 8 verse 9). It is noted that no obvious cofactor effect of F217A peptide or linker regions was detected in nucleosome and peptide demethylation assays (FIG. 6E and data not shown). FIG. 12F depicts Coomassie staining of NPAC proteins used in histone demethylase assays. GST-NPAC.d1-6 were shown in FIG. 2D. FIG. 12F discloses "His6" as SEQ ID NO: 75.

FIG. 13A depicts a schematic of NPAC domain structure. AT, AT-hook motif. Figure discloses "PWWP" as SEQ ID NO: 63. FIG. 13B demonstrates that NPAC is a specific component of the LSD2 complex Immunoblot analyses of tandem affinity purified (TAP) LSD2 and LSD1 complexes using denoted antibodies. LSD2 and LSD1 bait proteins were tagged with FLAG-HA and were detected by immunoblot using anti-HA antibody. FIG. 13C demonstrates that LSD2 specifically associates with the NPAC complex, but not CtBP Immunoblot analyses of TAP NPAC and CtBP complexes using denoted antibodies. FIG. 13D demonstrates that NPAC directly interacts with LSD2. GST and GST-LSD2 were used to pulldown recombinant His-NPAC purified from E. coli. Pulldown complexes were separated by SDS-PAGE and visualized by coomassie blue staining Asterisk, non-specific protein. FIG. 13E demonstrates that NPAC directly binds to nucleosomes. GST and GST-NPAC were used to pulldown nucleosomes purified from HeLa. Coomassie blue staining of histones in pulldown products is shown. FIG. 13F demonstrates that NPAC bridges the association of LSD2 and nucleosomes in vitro. GST-LSD2 recombinant protein was used to pull down nucleosomes in the presence or absence of His-NPAC. Pulldown complexes were resolved by SDS-PAGE and stained by coomassie blue. Asterisk, full-length protein. FIG. 13G demonstrates that overexpression of NPAC can target LSD2 to chromatin in vivo. Immunofluorescence staining of FLAG:HA-NPAC and GFP-LSD2, either ectopically expressed alone or in combination, at metaphase of cell cycle.

FIGS. 14A-14C demonstrate that NPAC selectively binds to nucleosomal H3K36me3. FIG. 14A demonstrates selective association of NPAC with modification-specific nucleosomes. Immunoblot analyses of input and nucleosomes bound to GST or GST-NPAC using indicated modification-specific anti-histone antibodies. FIG. 14B demonstrates that NPAC.d1 (residues 1-150) is required and sufficient for its interaction with nucleosomes. Schematic of NPAC deletion mutants are shown above. GST tagged proteins and pull-down nucleosomes were resolved on SDS-PAGE and visualized by coomassie blue staining. Asterisk, full-length protein. FIG. 14B discloses "PWWP" as SEQ ID NO: 63. FIG. 14C demonstrates that NPAC.d1 specifically binds to H3K36me3 nucleosomes. MLA nucleosomes with indicated modifications were pulled down by GST-tagged NPAC.d1. Input and bound nucleosomes were analyzed by immunoblot using anti-H3 antibody. Pulldown efficiency relative to unmodified nucleosomes (wild-type) was quantified by densitometry analysis (right panel). $K_c$ indicates the lysine analogue.

FIGS. 15A-15F demonstrate that DNA binding by the NPAC PWWP domain (SEQ ID NO: 63) is important for NPAC-nucleosome interaction. FIG. 15A depicts the predicted secondary structure of NPAC.d1. Residue numbers and secondary structure elements are indicated. Positively charged residues are colored in red. FIG. 15A discloses SEQ ID NO: 91. FIG. 15B depicts a ribbon representation of a model of the NPAC PWWP domain (SEQ ID NO: 63). Histone H3K36me3 and aromatic cage residues of NPAC are shown in sticks. FIG. 15C depicts electrostatic surface representation of the NPAC PWWP domain (SEQ ID NO: 63). The side chain of H3K36me3 is shown as in FIG. 15B. Potential binding sites for histones and nucleosomal DNA are indicated. FIG. 15D depicts a schematic of NPAC truncation proteins. FIG. 15D discloses "PWWP" as SEQ ID NO: 63. FIG. 15E demonstrates that intact NPAC PWWP domain (SEQ ID NO: 63) is required for DNA binding. GST-pulldown analyses of DNA binding by NPAC truncation proteins described in FIG. 15D. Ethidium bromide staining of input and pulldown DNA is shown. FIG. 15F demonstrates competitive inhibition of the interaction between NPAC.d5 and nucleosomes by free DNA. Equal amount of GST-NPAC.d5 is used to pulldown nucleosomes in the presence of increasing amount of free double-strand DNA. Coomassie blue staining of pulldown complexes is shown.

FIG. 16A demonstrates that NPAC is enriched at coding regions. Representative ChIP-chip profiles are shown. Bars, MAT score of NPAC ChIP-chip signals. Gene structures are shown below, with short vertical bars representing exons. Arrow marks direction of transcription. FIG. 16A discloses "PWWP" as SEQ ID NO: 63. FIG. 16B demonstrates genome-wide distribution of NPAC binding sites on human chromosome 3, 21, 22, and X. FIG. 16C depicts the genome-wide correlation of NPAC and LSD2 chromatin association. FIG. 16D depicts average NPAC ChIP-chip profile on active and repressed genes, the expression levels of which fall in the top 10% or bottom 10% of the 4270 genes on the array. Genes within each category were aligned at transcription start and termination sites (TSS and TTS), and Meta-gene region was generated by resizing gene body regions to 3000 bp in length. 1000 bp regions, in actual distance, outside gene boundaries were also examined. The average MAT score is presented. FIG. 16E depicts the average gene profile of H3K36me3. Published ChIP-seq data were analyzed and presented as in FIG. 16D. FIG. 16F demonstrates that NPAC binding profile mimics H3K36me3 profile and differs from H3K79me3. ChIP was performed using indicated antibodies. Enrichment relative to input was quantified by qPCR and presented in arbitrary units. X-axis denotes the distance qPCR amplicon to TSS. Gene structure of HUWE1 is shown above. FIG. 16G demonstrates that LSD2 binds to the coding region of HUWE1, colocalizing with NPAC. Anti-FLAG ChIP was performed on HeLa cells stably expressing 3× FLAG tagged LSD2 (3Fg-LSD2) and vector-transduced cells (mock). Data are presented as fold enrichment relative to mock. FIG. 16H demonstrates that NPAC binds to coding regions but not at the promoters of multiple target genes. ChIP was performed as in FIG. 16F. Error bars, standard deviation of duplicates.

FIGS. 17A-17H demonstrate that H3K36me3 recruits NPAC, which in turn, recruits LSD2 to coding regions. FIG. 17A demonstrates specific depletion of SETD2 by shRNA. Relative mRNA expression was quantified by qRT-PCR and normalized with RPL13. Error bars, standard deviation of duplicates. FIG. 17B demonstrate that depletion of SETD2 reduces global H3K36me3 levels, and does not affect H3K4me2 or the expression of NPAC Immunoblot of whole cell lysate harvested 72 hours post treatment using indicated antibodies. FIG. 17C depicts ChIP analysis of H3K36me3 level changes on indicated genes upon SETD2 depletion. qPCR primers denoted on X-axis are specific to coding regions, unless specified otherwise. Pro, promoter. Data are presented as enrichment relative to input. Error bar, standard deviation of duplicates from representative experiments. FIG. 17D demonstrates that NPAC binding at coding regions is reduced upon SETD2 depletion, coinciding with the reduction of H3K36me3. Anti-NPAC specific antibody was used from ChIP. Data are presented as in FIG. 17C. Error bars, standard deviation of duplicates from representative experiments. FIG. 17E demonstrates that shRNA effectively depletes NPAC, but does not affect LSD2 expression. Immunoblot of whole cell lysate is shown. FIG. 17F demonstrates that depletion of NPAC diminishes LSD2 binding at coding regions. Anti-FLAG ChIP was performed on HeLa cells stably expressing 3× FLAG-LSD2 after treated with either control or NPAC shRNA for 4 days. Data are presented as fold enrichment compared to mock as in FIG. 4G. Error bars, standard deviation of duplicates from representative experiments. FIG. 17G demonstrates that H3K4me2 levels at coding regions are elevated after NPAC depletion. Quantitative ChIP data are presented as enrichment relative to input. Error bars, SEM of triplicates from representative experiments. *, p<0.05; , p<0.01. FIG. 17H** demonstrates that NPAC depletion results in down-regulation of a subset of NPAC-LSD2 associated genes. qRT-PCR data are normalized with GAPDH and presented as abundance relative to control shRNA treated HeLa. Error bars, SEM of biological triplicates. *, p<0.05.

FIGS. 18A-18B demonstrate NPAC is a nuclear protein stably associated with chromatin in vivo. FIG. 18A demonstrates cellular localization of NPAC at different stages of the cell cycle. Immunofluorescence staining of HeLa transiently transfected with FLAG:HA-NPAC. Green, anti-HA staining of NPAC; red, H3K4me2; blue, DAPI DNA counterstain. Arrow, transfected cell. A similar cellular distribution pattern is observed for endogenous NPAC by immunofluorescence staining using an anti-NPAC antibody (data not shown). FIG. 18B demonstrates that NPAC associates with nucleosomes in vivo. As outlined in the left panel, nuclei purified from HeLa cells stably expressing FLAG:HA-NPAC were digested by micrococcal nuclease for indicated time. The digestion reaction was stopped by adding EDTA to 5 mM. Soluble and chromatin fractions were separated by centrifugation at 8000×g for 5 minutes at 4° C. The soluble fraction of each digestion was analyzed for nucleosomal DNA visualized by ethidium staining of the agarose gel (bottom right), and also for FLAG:HA-NPAC protein by immunoblot using an anti-FLAG antibody (top right). N, total nuclear protein. Mono-, di- and oligo-nucleosomal DNA is indicated.

FIG. 19A depicts electrostatic surface representation of the structures of PWWP domains (SEQ ID NO: 63). Patches of positively charged residues are observed on the surface of a few human PWWP domains (SEQ ID NO: 63) with available structures (Wu et al., 2011). The surface electrostatic potential of the PWWP domain (SEQ ID NO: 63) of HGDF and mouse DNMT3B have been previously reported (Lukasik et al., 2006; Qiu et al., 2002). FIG. 19B depicts electrophoresis mobility shift assays detecting DNA binding of various PWWP domains (SEQ ID NO: 63). Protein-DNA complexes were resolved by electrophoresis. Retarded and free DNA detected by SYBR green staining was shown. We confirm DNA binding of DNMT3B PWWP domain (SEQ ID NO: 63), and also detect DNA binding of the PWWP domains (SEQ ID NO: 63) of confirmed and putative H3K36me3 readers, such as DNMT3A, WHSC1 and WHSCL1. FIG. 19C demonstrates that an intact NPAC PWWP domain (SEQ ID NO: 63) is required for nucleosome binding. GST-tagged NPAC truncation proteins (schematic shown in FIG. 15D) were used to pull down nucleosomes purified from HeLa cells. Histones of input and precipitated nucleosomes were resolved by SDS-PAGE and stained by coomassie blue. *, non-specific band.

FIG. 20A demonstrates that NPAC and LSD2 associate with a common set of genes. NPAC and LSD2 peaks were identified by ChIP-chip analysis of human chromosomes 21, 22, 3 and X using a tiling array (Human Genome Tiling 2.0 Array, Affymetrix). 192 common genes identified in the Ensembl GRCh37.p2 database represent 61% of NPAC-associated genes and 40% of LSD2 target genes. FIG. 20B depicts genome-wide colocalization of NPAC with LSD2, H3K36me3, H3K9me3 and H3K27me3. Hatched lines, permuted model of each modification. Approximately 60% of NPAC peaks are located within 500 bp from known H3K36me3 sites in the human genome, and about 40% in close vicinity of a LSD2 peak, demonstrating tight genome-wide association of NPAC with H3K36me3 and LSD2. In contrast, NPAC does not correlate with H3K9me3 and H3K27me3 having an anti-colocalization for each mark, with $p<10^{-16}$. FIGS. 20C-20D demonstrate NPAC distribution correlates with H3K36me3, but differs from H3K79me3 and H3K4me2 within the coding regions of LSD2 associated genes. ChIP data are presented as enrichment relative to input in arbitrary units as in FIG. 16F. Enrichment of LSD2 binding at the coding regions of DNAJB11 and CCNL1, which mimics the pattern of NPAC and H3K36me3, has been reported.

FIG. 23A demonstrates that LSD2 is located at 6p22 in human genome, a hot spot for translocation. FIG. 23B depicts the results of microarray analyses comparing the expression of LSD2 expression in breast cancer and normal tissues. LSD2 is overexpressed in certain types of breast cancer. *, p<0.05. FIG. 23C depicts QRT-PCR confirmation of LSD2 overexpression in basal-like breast cancer. FIG. 23D demonstrates that depletion of LSD2 by shRNA significantly reduces anchor-free growth of MCF7 and MDA-MB-231 in soft agar assays.

FIG. 24A demonstrates that depletion of NPAC by shRNA reduces anchor-free growth of MCF7 and MDA-MB-231 in soft agar assays, the phenotype of LSD2 depletion. FIG. 24B demonstrates that depletion of either NPAC or LSD2 down regulates CCND1 and CCDE1 expression. FIG. 24C demonstrates that NPAC directly associates with the coding region of CCND1. FIG. 24D demonstrates that NPAC depletion reduces LSD2 association with CCND1. FIG. 24E demonstrates that NPAC depletion causes increase of H3K4me2 levels at LSD2 binding site.

FIG. 25A depicts a schematic LSD2-NPAC interaction at target genes. NPAC tightly associates with specific loci in human genome via its PWWP domain (SEQ ID NO: 63). The linker region of NPAC, located between the PWWP (SEQ ID NO: 63) and dehydrogenase (DH) domains, interacts with LSD2, thus recruits LSD2 to specific loci (left panel). Point mutations of the LSD2 binding motif in NPAC prevents NPAC-LSD2 interaction, hence the recruitment of LSD2 (middle panel). A short peptide bearing the LSD2 binding motif can competitively inhibit NPAC-LSD2 interaction, hence the recruitment of LSD2 (right panel). FIG. 25B demonstrates that ectopic expression of wild-type, but not the mutant NPAC can prevent the down regulation of CCND1 and CCNE1 caused by endogenous NPAC depletion. FIG. 25C demonstrates that ectopic expression of NPAC.214-215.F217A peptide down regulates CCND1 and CCNE1 expression.

DETAILED DESCRIPTION OF THE INVENTION

Figure 1A:
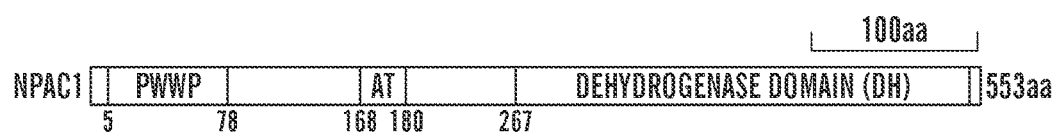
FIGS. 1A-1E demonstrate that NPAC is a cofactor of LSD2 positively modulating its H3K4 demethylase activity in vitro and in vivo.

The invention is based, at least in part, in our discovery of the specific region in NPAC that interacts with LSD2 and that the inhibition of this interaction inhibits and/or reduces cell growth and/or proliferation, e.g. of a cancer cell. Specifically, we have demonstrates that breast cancer growth (e.g. both ER-positive (MCF7) and ER-negative (MDA- MB-231) metastatic lines), can be inhibited using inhibitors of the NPAC/LSD2 interaction, such as the peptides and antibodies described herein. We provide novel peptides and antibodies that can be used to regulate action of LSD2 by inhibiting and/or reducing its interaction with NPAC.

We provide data to show that depletion of LSD2 and NPAC significantly reduces the growth of MDA-MB-231, which is a triple negative breast cancer cell line and a commonly used model for drug resistant breast cancers. LSD2/KDM1b/AOF1 is the only mammalian homolog of LSD1 and possesses similar histone H3K4 demethylase activity (Ciccone et al., 2009; Fang et al., 2010; Yang et al., 2010). However, LSD2 is a component of a different cellular complex and has distinctive functions from LSD1 (Ciccone et al., 2009; Fang et al., 2010; van Essen et al., 2010). Genetic studies indicate that LSD2 is required for the homeostasis of global H3K4 methylation in mouse oocytes and regulates parental gene imprinting (Ciccone et al., 2009). In somatic tissue, LSD2 seems to play an important role in active gene transcription. LSD2 is reported to be a potential H3K9 demethylase and is required for controlling NF-κB induced gene activation by demethylating H3K9 at promoters (van Essen et al., 2010). We demonstrate herein that LSD2 is an active H3K4 demethylase that specifically associates with the coding region of target genes. Removal of endogenous LSD2 promotes an increase in H3K4me2 levels and a concurrent decrease in H3K9me2 levels, specifically at coding regions but not at the corresponding promoters, and results in down regulation of gene transcription (Fang et al., 2010). These genetic and functional studies suggest that LSD2 is an important epigenetic regulator involved in diverse biological processes. For example, LSD2 has been implicated in oocytogenesis. Accordingly, in some aspects, described herein is a method of modulating oocytogenesis by administering a peptide, nucleic acid, and/or antibody as described herein to inhibit the interaction of NPAC and LSD2 and/or to inhibit the enzymatic activity of LSD2.

In one aspect, described herein is an isolated peptide consisting of an isolated NPAC-derived peptide consisting of any one or a combination of amino acid sequences as set forth in Table 6. In one aspect, described herein is isolated peptide consisting essentially of an isolated NPAC-derived peptide consisting of any one or a combination of amino acid sequences as set forth in Table 6. In some embodiments, the NPAC peptide can consist of the amino acid sequence of SEQ ID NO: 001. In some embodiments, the NPAC peptide can consist of the amino acid sequence of SEQ ID NO: 002. In some embodiments, the NPAC peptide can comprise the amino acid sequence of SEQ ID NO: 001. In some embodiments, the NPAC peptide can comprise the amino acid sequence of SEQ ID NO: 002.

TABLE 6

| SEQ ID NO: | Amino Acid Sequence |
|---|---|
| 001 | DPHFHHFLLSQT |
| 002 | FHHFLLS |
| 003 | DADPHFHHFLLSQTEK |
| 004 | DADPHFHHFLLSQTE |
| 005 | DADPHFHHFLLSQT |
| 006 | DADPHFHHFLLSQ |
| 007 | DADPHFHHFLLS |
| 008 | ADPHFHHFLLSQTEK |
| 009 | ADPHFHHFLLSQTE |
| 010 | ADPHFHHFLLSQ |
| 011 | ADPHFHHFLLS |
| 012 | DPHFHHFLLSQTEK |
| 013 | DPHFHHFLLSQTE |
| 014 | DPHFHHFLLSQT |
| 015 | DPHFHHFLLSQ |
| 016 | DPHFHHFLLS |
| 017 | PHFHHFLLSQTEK |
| 018 | PHFHHFLLSQTE |
| 019 | PHFHHFLLSQT |
| 020 | PHFHHFLLSQ |
| 021 | PHFHHFLLS |
| 022 | HFHHFLLSQTEK |
| 023 | HFHHFLLSQTE |
| 024 | HFHHFLLSQT |
| 025 | HFHHFLLSQ |
| 026 | HFHHFLLS |
| 027 | FHHFLLSQTEK |
| 028 | FHHFLLSQTE |
| 029 | FHHFLLSQT |
| 030 | FHHFLLSQ |
| 031 | DADPHFHHFLLSQTEK |
| 032 | ADPHFHHFLLSQTEK |
| 033 | DPHFHHFLLSQTEK |
| 034 | PHFHHFLLSQTEK |
| 035 | HFHHFLLSQTEK |
| 036 | FHHFLLSQTEK |
| 037 | DADPHFHHFLLSQTE |
| 038 | ADPHFHHFLLSQTE |
| 039 | DPHFHHFLLSQTE |
| 040 | PHFHHFLLSQTE |
| 041 | HFHHFLLSQTE |
| 042 | FHHFLLSQTE |
| 043 | DADPHFHHFLLSQT |
| 044 | ADPHFHHFLLSQT |
| 045 | DPHFHHFLLSQT |

TABLE 6-continued

| SEQ ID NO: | Amino Acid Sequence |
|---|---|
| 046 | PHFHHFLLSQT |
| 047 | HFHHFLLSQT |
| 048 | FHHFLLSQT |
| 049 | DADPHFHHFLLSQ |
| 050 | ADPHFHHFLLSQ |
| 051 | DPHFHHFLLSQ |
| 052 | PHFHHFLLSQ |
| 053 | HFHHFLLSQ |
| 054 | FHHFLLSQ |
| 055 | DADPHFHHFLLS |
| 056 | ADPHFHHFLLS |
| 057 | DPHFHHFLLS |
| 058 | PHFHHFLLS |
| 059 | HFHHFLLS |

SEQ ID NO: 003 consists of amino acids 212 to 227 of wild-type NPAC. SEQ ID NO: 001 consists of amino acids 214-225 of wild-type NPAC.

In some embodiments, the isolated peptide described herein can comprise a mutation and/or modification. In some embodiments, an isolated peptide as described herein can be an analog, derivative, variant, conservative substitution variant, or functional fragment of the amino acid sequences described above herein. Variants of the isolated peptides described herein (e.g. SEQ ID NOs: 001-0059) can be obtained by mutations of native nucleotide or amino acid sequences, for example SEQ ID NO: 001 or a nucleotide sequence encoding a peptide comprising SEQ ID NO:001. A "variant," as referred to herein, is a polypeptide substantially homologous to an isolated peptide described herein (e.g. SEQ ID NOs: 001-59), but which has an amino acid sequence different from that of an isolated peptide described herein because of one or a plurality of deletions, insertions or substitutions. A homolog of an isolated peptide as described herein can also comprise amino acid sequences that are homologous to the regions of NPAC which the isolated peptides described herein were derived (e.g. amino acids 212-227 of NPAC).

The variant amino acid or DNA sequence preferably is at least 60%, at least 70%, at least 80%, at least 90%, at least 91%, at least 92%, at least 93%, at least 94%, at least 95%, at least 96%, at least 97%, at least 98%, at least 99%, or more, identical to the sequence from which it is derived (referred to herein as an "original" sequence). The degree of homology (percent identity) between an original and a mutant sequence can be determined, for example, by comparing the two sequences using freely available computer programs commonly employed for this purpose on the world wide web. The variant amino acid or DNA sequence preferably is at least 60%, at least 70%, at least 80%, at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp.

Alterations of the original amino acid sequence can be accomplished by any of a number of known techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, an isolated peptide as described herein can be chemically synthesized and mutations can be incorporated as part of the chemical synthesis process.

In the co-crystal structure of the ternery complex of LSD2-NPAC-H3 peptide described herein, NPAC residue F217 makes hydrophobic interaction with H3L20 to assist enzyme-substrate interaction; NPAC residues 220, 221 and 222 are buried in a hydrophobic cleft in LSD2, making hydrophobic interactions with LSD2. Accordingly, in some embodiments, replacing any of these residues with a non-hydrophobic residue can disrupt the function of NPAC and inhibit LSD2 enzymatic activity.

In some embodiments, a fragment of NPAC with substitution of NPAC F217 can inhibit LSD2 activity. In some embodiments, modified NPAC protein comprising one or more mutations and/or variants shown in Table 7 can inhibit LSD2 activity.

In some embodiments, the isolated peptide described herein comprises at least one mutation selected from the group consisting of: a substitution of residue 217 of NPAC with alanine, -glycine, serine, threonine, histidine, lysine, asparagine, aspartic acid, glutamic acid or glutamine; a substitution of residue 219 of NPAC with alanine, glycine or serine; a substitution of residue 223 of NPAC with alanine or glycine; a substitution of any of residues 220-222 of NPAC with alanine, glycine or serine; a deletion of any of amino acids 219-223 of NPAC; deletion of any of amino acids 223-225; and any combination thereof. In some embodiments, the isolated peptide described herein comprises at least one mutation selected from the group consisting of: a substitution of residue 217 of NPAC with alanine, glycine, or serine; a substitution of residue 219 of NPAC with alanine, glycine or serine; a substitution of residue 223 of NPAC with alanine or glycine; a substitution of any of residues 220-222 of NPAC with alanine, glycine or serine; a deletion of any of amino acids 219-223 of NPAC; deletion of any of amino acids 223-225; and any combination thereof. In some embodiments, the isolated peptide described herein comprises at least one mutation selected from the group consisting of: a substitution of NPAC histidine 219 with alanine; a substitution of NPAC serine 223 with alanine; a substitution of residues 220-222 of NPAC with alanines; a deletion of amino acids 219-223 of NPAC;

deletion of amino acids 223-225; and any combination thereof. Exemplary mutations and possible combinations thereof are shown in Table 7. In some embodiments, an isolated peptide can comprise an amino acid sequence of Table 6 modified with one or more of the mutations shown in Table 7. In some aspects of all the embodiments of the invention, the isolated peptide comprises at least 2, 3, or 4 mutations selected from the muations set forth above. In some embodiments, described herein is an isolated peptide comprising a substitution of residue 217 of NPAC with alanine, glycine, serine, threonine, histidine, lysine, asparagine, aspartic acid, glutamic acid or glutamine.

In one aspect, described herein is a modified NPAC or a fragment thereof comprising at least one mutation selected from: a substitution of residue 217 of NPAC with alanine, glycine, serine, threonine, histidine, lysine, asparagine, aspartic acid, glutamic acid or glutamine; a substitution of residue 219 of NPAC with alanine, glycine or serine; a substitution of residue 223 of NPAC with alanine or glycine; a substitution of any of residues 220-222 of NPAC with alanine, glycine or serine; a deletion of any of amino acids 219-223 of NPAC; deletion of any of amino acids 223-225; and any combination thereof. In some embodiments, described herein is a modified NPAC or a fragment thereof comprising at least one mutation selected from: a substitution of residue 217 of NPAC with alanine, glycine, or serine; a substitution of residue 219 of NPAC with alanine, glycine or serine; a substitution of residue 223 of NPAC with alanine or glycine; a substitution of any of residues 220-222 of NPAC with alanine, glycine or serine; a deletion of any of amino acids 219-223 of NPAC; deletion of any of amino acids 223-225; and any combination thereof. In some embodiments, described herein is a modified NPAC or a fragment thereof comprising at least one mutation selected from: a substitution of NPAC histidine 219 with alanine; a substitution of NPAC serine 223 with alanine; a substitution of residues 220-222 of NPAC with alanines; a deletion of amino acids 219-223 of NPAC; deletion of amino acids 223-225; deletion of amino acids and any combination thereof. In some embodiments, described herein is a modified NPAC or a fragment thereof comprising a substitution of residue 217 of NPAC with alanine, glycine, serine, threonine, histidine, lysine, asparagine, aspartic acid, glutamic acid or glutamine.

As regards mutations to residues 217, 220, 221, or 222 of the polypeptides described herein in, substitutions of non-hydrophobic residues are preferred.

Table 7 shows mutations and variants contemplated by the invention. These mutations are particularly useful when made to NPAC with a sequence of SEQ ID NO: 61. The mutations may also be made to any of the peptides in Table 6, wherein peptides with mutations that do not affect the interaction of the peptide with LSD2 are useful in the methods of the invention. For example, we have shown that all the F217 substitutions are functional. Also, full-length NPAC protein with any of the mutations of Table 7 can inhibit cancer cell growth by deplacing enodenous NPAC from the genome and disrupting LSD2 recruitment and function. Table 7 "X"s mark possible dual mutation combinations. A single peptide can comprise one or more of the mutations indicated in Table 7, e.g two, three, four, or more mutations. A single modified NPAC polypeptide or fragment thereof can comprise one or more of the indicated mutations, e.g two, three, four, or more.

TABLE 7

| | F217A | F217G | F217S | F217T | F217H | F217L | F217N | F217D | F217E | F217Q | H219A | H219G | H219S |
|---|---|---|---|---|---|---|---|---|---|---|---|---|---|
| F217A | | | | | | | | | | | X | X | X |
| F217G | | | | | | | | | | | X | X | X |
| F217S | | | | | | | | | | | X | X | X |
| F217T | | | | | | | | | | | X | X | X |
| F217H | | | | | | | | | | | X | X | X |
| F217L | | | | | | | | | | | X | X | X |
| F217N | | | | | | | | | | | X | X | X |
| F217D | | | | | | | | | | | X | X | X |
| F217E | | | | | | | | | | | X | X | X |
| F217Q | | | | | | | | | | | X | X | X |
| H219A | X | X | X | X | X | X | X | X | X | X | | | |
| H219G | X | X | X | X | X | X | X | X | X | X | | | |
| H219S | X | X | X | X | X | X | X | X | X | X | | | |
| S223G | X | X | X | X | X | X | X | X | X | X | X | X | X |
| S223A | X | X | X | X | X | X | X | X | X | X | X | X | X |
| F220A | X | X | X | X | X | X | X | X | X | X | X | X | X |
| F220S | X | X | X | X | X | X | X | X | X | X | X | X | X |
| L221A | X | X | X | X | X | X | X | X | X | X | X | X | X |
| L221S | X | X | X | X | X | X | X | X | X | X | X | X | X |
| L222A | X | X | X | X | X | X | X | X | X | X | X | X | X |
| L222S | X | X | X | X | X | X | X | X | X | X | X | X | X |
| delH219 | X | X | X | X | X | X | X | X | X | X | | | |
| delF220 | X | X | X | X | X | X | X | X | X | X | X | X | X |
| delL221 | X | X | X | X | X | X | X | X | X | X | X | X | X |
| delA222 | X | X | X | X | X | X | X | X | X | X | X | X | X |
| delS223 | X | X | X | X | X | X | X | X | X | X | X | X | X |
| delH219-S223 | X | X | X | X | X | X | X | X | X | X | | | |
| delQ224 | X | X | X | X | X | X | X | X | X | X | X | X | X |
| delT225 | X | X | X | X | X | X | X | X | X | X | X | X | X |
| delS223-T225 | X | X | X | X | X | X | X | X | X | X | X | X | X |

| | S223G | S223A | F220A | F220S | L221A | L221S | L222A | L222S | delH219 |
|---|---|---|---|---|---|---|---|---|---|
| F217A | X | X | X | X | X | X | X | X | X |
| F217G | X | X | X | X | X | X | X | X | X |

TABLE 7-continued

| | | | | | | | | | |
|---|---|---|---|---|---|---|---|---|---|
| F217S | X | X | X | X | X | X | X | X | X |
| F217T | X | X | X | X | X | X | X | X | X |
| F217H | X | X | X | X | X | X | X | X | X |
| F217L | X | X | X | X | X | X | X | X | X |
| F217N | X | X | X | X | X | X | X | X | X |
| F217D | X | X | X | X | X | X | X | X | X |
| F217E | X | X | X | X | X | X | X | X | X |
| F217Q | X | X | X | X | X | X | X | X | X |
| H219A | X | X | X | X | X | X | X | X | |
| H219G | X | X | X | X | X | X | X | X | |
| H219S | X | X | X | X | X | X | X | X | |
| S223G | | | X | X | X | X | X | X | X |
| S223A | | | X | X | X | X | X | X | X |
| F220A | X | X | | | X | X | X | X | X |
| F220S | X | X | | | X | X | X | X | X |
| L221A | X | X | X | X | | | X | X | X |
| L221S | X | X | X | X | | | X | X | X |
| L222A | X | X | X | X | X | X | | | X |
| L222S | X | X | X | X | X | X | | | X |
| delH219 | | X | X | X | X | X | X | X | |
| delF220 | X | X | | | X | X | X | X | X |
| delL221 | | | X | X | | | X | X | X |
| delA222 | X | X | X | X | X | X | | | X |
| delS223 | | X | X | X | X | X | X | X | X |
| delH219-S223 | | | | | | | | | |
| delQ224 | X | X | X | X | X | X | X | X | X |
| delT225 | X | X | X | X | X | X | X | X | X |
| delS223-T225 | | X | X | X | X | X | X | X | X |

| | delF220 | delL221 | delA222 | delS223 | delH219-S223 | delQ224 | delT225 | delS223-T225 |
|---|---|---|---|---|---|---|---|---|
| F217A | X | X | X | X | X | X | X | X |
| F217G | X | X | X | X | X | X | X | X |
| F217S | X | X | X | X | X | X | X | X |
| F217T | X | X | X | X | X | X | X | X |
| F217H | X | X | X | X | X | X | X | X |
| F217L | X | X | X | X | X | X | X | X |
| F217N | X | X | X | X | X | X | X | X |
| F217D | X | X | X | X | X | X | X | X |
| F217E | X | X | X | X | X | X | X | X |
| F217Q | X | X | X | X | X | X | X | X |
| H219A | X | X | X | X | | X | X | X |
| H219G | X | X | X | X | | X | X | X |
| H219S | X | X | X | X | | X | X | X |
| S223G | X | X | X | | | X | X | |
| S223A | X | X | X | | | X | X | |
| F220A | | X | X | X | | X | X | X |
| F220S | | X | X | X | | X | X | X |
| L221A | X | | X | X | | X | X | X |
| L221S | X | | X | X | | X | X | X |
| L222A | X | X | | X | | X | X | X |
| L222S | X | X | | X | | X | X | X |
| delH219 | X | X | X | X | | X | X | X |
| delF220 | | X | X | X | | X | X | X |
| delL221 | X | | X | X | | X | X | X |
| delA222 | X | X | | X | | X | X | X |
| delS223 | X | X | X | | | X | X | |
| delH219-S223 | | | | | | X | X | X |
| delQ224 | X | X | X | X | X | | X | |
| delT225 | X | X | X | X | X | X | | |
| delS223-T225 | X | X | X | | X | | | |

Other variants can comprise conservatively substituted sequences, meaning that one or more amino acid residues of an original peptide are replaced by different residues, and that the conservatively substituted peptide retains a desired biological activity, i.e., the ability to inhibit the interaction of LSD2 and NPAC that is essentially equivalent to that of the original peptide. Examples of conservative substitutions include substitution of amino acids that do not alter the secondary and/or tertiary structure of SEQ ID NOs: 001-059, substitutions that do not change the overall or local hydrophobic character, substitutions that do not change the overall or local charge, substitutions by residues of equivalent sidechain size, or substitutions by sidechains with similar reactive groups.

Other examples involve substitution of amino acids that have not been evolutionarily conserved in the parent sequence across species. Advantageously, in some embodiments, these conserved amino acids and structures are not altered when generating conservatively substituted sequences. In some embodiments, if altered, amino acids found at equivalent positions in other NPAC polypeptides are substituted.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar sidechain volume are well known. Isolated peptides comprising conservative amino acid substitutions can be tested in any one of the assays described herein to confirm that a desired activity, e.g. inhibiting LSD2 and NPAC is retained, as determined by the assays described elsewhere herein.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

Particularly preferred conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

Any cysteine residue not involved in maintaining the proper conformation of the isolated peptide as described herein can also be substituted, generally with serine, to improve the oxidative stability of the molecule and prevent aberrant crosslinking. Conversely, cysteine bond(s) can be added to the isolated peptide as described herein to improve its stability or facilitate multimerization.

In some embodiments, an isolated peptide as described herein can comprise the amino acid sequence of a homologous NPAC gene corresponding to the amino acids of SEQ ID NOs: 001-059. One of ordinary skill in the art is familiar with how to align the amino acid sequences of SEQ ID NOs: 001-059 with known homologous genes or with non-human polypeptide sequences directly or indirectly (e.g. deduced from nucleotide sequences). By way of non-limiting example, the isolated peptides described herein can be aligned with homologous peptides using amino acid alignment programs freely available for that purpose on the world wide wide, e.g. BLAST. These homologous peptides may comprise naturally-occurring variants of the isolated peptides described herein (e.g. SEQ ID NOs. 001-059), that is, the homologous peptides may comprise substitutions, insertions or deletions relative to peptides comprising the amino acid sequences of SEQ ID NOs: 001-059. Homologous peptides can be of any biological origin. By way of non-limiting example, NPAC polypeptide sequences are known for human (NCBI Gene ID No: 84656), mouse (NCBI Gene ID No: 74022); cow (NCBI Gene ID NO: 539636); and rat (NCBI Gene ID No: 360477).

As used herein, a "functional fragment" is a fragment or segment of a peptide comprising at least 5 amino acids and which can inhibit the interaction of NPAC and LSD2 according to the assays described below herein. A functional fragment can comprise conservative substitutions of the sequences disclosed herein so long as they preserve the function of inhibiting the interaction between LSD2 and NPAC. This can be tested by detecting an inhibition of at least 50% of that of the parent (e.g. original) version of the peptide. For example, methods for detecting the demethylation resulting from the interaction of LSD2 and NPAC are described elsewhere herein.

To enhance stability, bioavailability, and/or delivery of the peptides into the cells, the peptides can be modified. For example, in some embodiments, an isolated peptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, an isolated peptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an isolated peptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, an isolated peptide can be modified, e.g. a moiety can be added to one or more of the amino acids comprising the peptide. In some embodiments, an isolated peptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, an isolated peptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties.

An isolated peptide as described herein can be coupled and or connected to a second functional molecule, peptide and/or polypeptide. In some embodiments, an isolated peptide as described herein is coupled to a targeting molecule. In some embodiments, an isolated peptide as described herein is coupled to a targeting molecule by expressing the peptide and the targeting molecule as a fusion peptide, optionally with a peptide linker sequence interposed between them. As used herein a "targeting molecule" can be any molecule, e.g. a peptide, antibody or fragment thereof, antigen, targeted liposome, or a small molecule that can bind to or be bound by a specific cell or tissue type. By way of non-limiting example, if it is desired to target an isolated peptide as described herein to the lung (e.g. to treat a lung cancer), an isolated peptide comprising the amino acid sequence of SEQ ID NO: 001 could be coupled to an antibody or fragment thereof which is specific for lung cells or tissue, e.g. an antibody or antibody fragment as described in US Patent Publication 2005/0287066. The addition of an antibody to an isolated peptide as described herein permits the peptide to accumulate additively at the desired target site, e.g. the tumor microenvironment.

In some embodiments, an isolated peptide as described herein can be a fusion peptide or polypeptide. A fusion polypeptide can comprise a peptide linker domain interposed between the first domain of the peptide comprising an amino acid sequence of SEQ ID NOs: 001-059 or derivativatives, variants, functional fragments, prodrug, or analog thereof as described herein and at least a second domain of the fusion peptide. The first peptide domain can be the N-terminal domain or the C-terminal domain or an internal sequence in the case where the partner domain forms after fragment complementation of constituent parts. Methods of synthesizing or producing a fusion protein are well known to those of ordinary skill in the art.

In some embodiments, an isolated peptide as described herein can be a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), which are incorporated by reference herein in their entireties.

In some embodiments, an isolated peptide as described herein can be a pharmaceutically acceptable solvate. The term "solvate" refers to an isolated peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

In some embodiments, an isolated peptide as described herein can be in a non-crystalline, i.e. amorphous solid form.

In one aspect, described herein is a vector comprising a nucleic acid encoding a peptide as described herein. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. Many vectors useful for transferring exogenous genes into target mammalian cells are available. The vectors can be episomal, e.g., plasmids, virus derived vectors such cytomegalovirus, adenovirus, etc., or can be integrated into the target cell genome, through homologous recombination or random integration, e.g., retrovirus derived vectors such MMLV, HIV-1, ALV, etc. Many viral vectors are known in the art and can be used as carriers of a nucleic acid modulatory compound into the cell. For example, constructs containing the nucleic acid encoding a polypeptide can be integrated and packaged into non-replicating, defective viral genomes like Adenovirus, Adeno-associated virus (AAV), or Herpes simplex virus (HSV) or others, including retroviral and lentiviral vectors, for infection or transduction into cells. Alternatively, the construct can be incorporated into vectors capable of episomal replication, e.g. EPV and EBV vectors. The nucleic acid incorporated into the vector can be operatively linked to an expression control sequence such that the expression control sequence controls and regulates the transcription and translation of that polynucleotide sequence.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector can comprise additional elements, for example, the expression vector can have two replication systems, thus allowing it to be maintained in two organisms, for example in human cells for expression and in a prokaryotic host for cloning and amplification.

The term "transfection" as used herein to methods, such as chemical methods, to introduce exogenous nucleic acids, such as the nucleic acid sequences encoding a peptide as described herein into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to those that use cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

As used herein, the term "viral vector" refers to a nucleic acid vector construct that includes at least one element of viral origin and has the capacity to be packaged into a viral vector particle. The viral vector can contain the nucleic acid encoding a peptide as described herein in place of non-essential viral genes. The vector and/or particle can be utilized for the purpose of transferring any nucleic acids into cells either in vitro or in vivo. Numerous forms of viral vectors are known in the art. The term "replication incompetent" when used in reference to a viral vector means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins for packaging the virus) and viral particles cannot be formed in the patient's cells. The term "transduction" as used herein refers to the use of viral particles or viruses to introduce exogenous nucleic acids into a cell.

Retroviruses, such as lentiviruses, provide a convenient platform for delivery of nucleic acid sequences encoding an agent of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety.

In some embodiments, a nucleotide sequence of interest is inserted into an adenovirus-based expression vector. Unlike retroviruses, which integrate into the host genome, adenoviruses persist extrachromosomally thus minimizing the risks associated with insertional mutagenesis (Haj-Ahmad and Graham (1986) J. Virol. 57:267-74; Bett et al. (1993) J.

Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76). Adenoviral vectors have several advantages in gene therapy. They infect a wide variety of cells, have a broad host-range, exhibit high efficiencies of infectivity, direct expression of heterologous sequences at high levels, and achieve long-term expression of those sequences in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. For all these reasons vectors derived from human adenoviruses, in which at least the E1 region has been deleted and replaced by a gene of interest, have been used extensively for gene therapy experiments in the preclinical and clinical phase. Adenoviral vectors for use with the compositions and methods described herein can be derived from any of the various adenoviral serotypes, including, without limitation, any of the over 40 serotype strains of adenovirus, such as serotypes 2, 5, 12, 40, and 41. The adenoviral vectors of used in the methods described herein are generally replication-deficient and contain the sequence of interest under the control of a suitable promoter. For example, U.S. Pat. No. 6,048,551, incorporated herein by reference in its entirety, describes replication-deficient adenoviral vectors that include a human gene under the control of the Rous Sarcoma Virus (RSV) promoter. Other recombinant adenoviruses of various serotypes, and comprising different promoter systems, can be created by those skilled in the art. See, e.g., U.S. Pat. No. 6,306,652, incorporated herein by reference in its entirety. Other useful adenovirus-based vectors for delivery of nucleic acid sequences include, but are not limited to "minimal" adenovirus vectors as described in U.S. Pat. No. 6,306,652, which retain at least a portion of the viral genome required for encapsidation (the encapsidation signal), as well as at least one copy of at least a functional part or a derivative of the ITR; and the "gutless" (helper-dependent) adenovirus in which the vast majority of the viral genome has been removed and which produce essentially no viral proteins, such vectors can permit gene expression to persist for over a year after a single administration (Wu et al. (2001) Anesthes. 94:1119-32; Parks (2000) Clin. Genet. 58:1-11; Tsai et al. (2000) Curr. Opin. Mol. Ther. 2:515-23).

In some embodiments, a nucleotide sequence encoding a peptide as described herein is inserted into an adeno-associated virus-based expression vector. AAV is a parvovirus which belongs to the genus Dependovirus and has several features not found in other viruses. AAV can infect a wide range of host cells, including non-dividing cells. AAV can infect cells from different species. AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions, facilitating production, storage and transportation. AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus. Adeno-associated virus (AAV) has been used with success in gene therapy. AAV has been engineered to deliver genes of interest by deleting the internal nonrepeating portion of the AAV genome (i.e., the rep and cap genes) and inserting a heterologous sequence (in this case, the sequence encoding the agent) between the ITRs. The heterologous sequence is typically functionally linked to a heterologous promoter (constitutive, cell-specific, or inducible) capable of driving expression in the patient's target cells under appropriate conditions. Recombinant AAV virions comprising a nucleic acid sequence encoding an agent of interest can be produced using a variety of art-recognized techniques, as described in U.S. Pat. Nos. 5,139,941; 5,622,856; 5,139,941; 6,001,650; and 6,004,797, the contents of each of which are incorporated by reference herein in their entireties. Vectors and cell lines necessary for preparing helper virus-free rAAV stocks are commercially available as the AAV Helper-Free System (Catalog No. 240071) (Agilent Technologies, Santa Clara, Calif.).

Additional viral vectors useful for delivering nucleic acid molecules encoding a peptide as described herein include those derived from the pox family of viruses, including vaccinia virus and avian poxvirus. Alternatively, avipoxviruses, such as the fowlpox and canarypox viruses, can be used to deliver the genes. The use of avipox vectors in cells of human and other mammalian species is advantageous with regard to safety because members of the avipox genus can only productively replicate in susceptible avian species. Methods for producing recombinant avipoxviruses are known in the art and employ genetic recombination, see, e.g., WO 91/12882; WO 89/03429; and WO 92/03545.

Molecular conjugate vectors, such as the adenovirus chimeric vectors, can also be used for delivery of sequence encoding a peptide as described herein (Michael et al. (1993) J. Biol. Chem. 268:6866-69 and Wagner et al. (1992) Proc. Natl. Acad. Sci. USA 89:6099-6103). Members of the Alphavirus genus, for example the Sindbis and Semliki Forest viruses, can also be used as viral vectors for delivering a nucleic acid sequence (See, e.g., Dubensky et al. (1996) J. Virol. 70:508-19; WO 95/07995; WO 96/17072).

In some embodiments, the vector further comprises a signal peptide operably linked to the peptide. Signal peptides are terminally (usually N-terminally) located peptide sequences that provide for passage of the protein into or through a membrane. Different signal peptides can be of use in different applications. For example, as regards a cellular system for the production of isolated peptides as described herein, a secretory signal peptide can permit increased yields and ease of purification. As a further example, as regards cells which produce peptides as described herein and which are administered for therapeutic purposes to a subject, multiple signal peptides, e.g. a peptide signaling for secretion from the first cell, a peptide signaling for internalization by a second cell, and a final peptide signaling for nuclear localization can increase the amount of peptide reaching the target environment. As a further example, as regards, e.g. gene therapy applications, a peptide signaling for nuclear localization can increase the amount of peptide reaching the target environment. Signal peptides are known in the art. Non-limiting examples of nuclear localization signal (NLS)

peptides for use in mammalian cells include; the SV40 large T-antigen NLS (PKKKRKV) (SEQ ID NO: 66); the nucleoplasmin NLS (KR[PAATKKAGQA]KKKK (SEQ ID NO: 67); the K-K/R-X-K/R consensus NLS; and PY-NLSs (see, e.g. Dingwall et al. J Cell Biol 188 107:841-9 and Makkerh et al. Curr Biol. 1996 6:1025-7; both of which are incorporated by reference herein in their entireties, for further discussion). Non-limiting examples of secretion signal peptides for use in mammalian cells include human albumin signal peptide (MKWVTFISLLFLFSSAYS) (SEQ ID NO: 68); human chymotrypsin signal peptide (MAFL-WLLSCWALLGTTGF) (SEQ ID NO: 69); human interleukin-2 signal peptide (MQLLSCIALILALV) (SEQ ID NO: 70); human trypsinogen-2 signal peptide (MNLLLILT-FVAAAVA) (SEQ ID NO: 71); and sequences which include a coding region for a signal for precursor cleavage by signal peptidase, furin or other prohormone convertases (e.g., PC3). For example, a signal (peptide) sequence which is cleaved by furin (also known as PACE, see U.S. Pat. No. 5,460,950), other subtilisins (including PC2, PC1/PC3, PACE4, PC4, PC5/PC6, LPC/PC7IPC8/SPC7 and SKI-I; Nakayama, Biochem. J., 327:625-635 (1997)); enterokinase (see U.S. Pat. No. 5,270,181) or chymotrypsin can be introduced into the signal (peptide) sequence as defined herein. Additional signal peptides are known in the art and the choice of signal peptide can be influenced by the cell type, growth conditions, and the desired destination of the peptide.

In one aspect, described herein is a cell expressing a vector comprising a nucleic acid encoding a peptide as described herein. In some embodiments, the cell expressing a vector as described herein is a cell suitable for the production of polypeptides. A cell suitable for the production of polypeptides can be a prokaryotic or eukaryotic cell, e.g. bacteria, virus, yeast, fungi, mammalian cells, insect cells, plant cells, and the like. By way of non-limiting example, cells for the production of proteins are commercially available, e.g. bacterial cells (BL21 derived cells—Cat. No. 60401-1, Lucigen; Middleton, Wis. and mammalian cells (293 F cells—Cat. No. 11625-019, Invitrogen; Grand Island, N.Y.).

Recombinant molecules, e.g. vectors as described herein, can be introduced into cells via transformation, particularly transduction, conjugation, lipofection, protoplast fusion, mobilization, particle bombardment, electroporation (Neumann et al., "Gene Transfer into Mouse Lyoma Cells by Electroporation in High Electric Fields," *EMBO J.* 1(7):841-845 (1982); Wong et al., "Electric Field Mediated Gene Transfer," *Biochem Biophys Res Commun* 107(2):584-587 (1982); Potter et al., "Enhancer-dependent Expression of Human Kappa Immunoglobulin Genes Introduced into Mouse pre-B Lymphocytes by Electroporation," *Proc. Natl. Acad. Sci. USA* 81(22):7161-7165 (1984), which are hereby incorporated by reference in their entirety), polyethylene glycol-mediated DNA uptake (Joseph Sambrook & David W. Russell, Molecular Cloning: A Laboratory Manual cp. 16 (2d ed. 1989), which is hereby incorporated by reference in its entirety), or fusion of protoplasts with other entities (e.g., minicells, cells, lysosomes, or other fusible lipid-surfaced bodies that contain the chimeric gene) (Fraley et al., "Liposome-mediated Delivery of Tobacco Mosaic Virus RNA into Tobacco Protoplasts: A Sensitive Assay for Monitoring Liposome-protoplast Interactions," *Proc. Natl. Acad. Sci. USA*, 79(6):1859-1863 (1982), which is hereby incorporated by reference in its entirety). The host cell is then cultured in a suitable medium, and under conditions suitable for expression of the protein or polypeptide of interest. After cultivation, the cell is disrupted by physical or chemical means, and the protein or polypeptide purified from the resultant crude extract. Alternatively, cultivation may include conditions in which the protein or polypeptide is secreted into the growth medium of the recombinant host cell, and the protein or polypeptide is isolated from the growth medium. Alternative methods may be used as suitable.

The peptides can also be attached to adjuvants. The term "adjuvant" refers to a compound or mixture that enhances the immune response and/or promotes the proper rate of absorption following inoculation, and, as used herein, encompasses any uptake-facilitating agent. Non-limiting examples of adjuvants include, chemokines (e.g., defensins, HCC-1, HCC4, MCP-1, MCP-3, MCP4, MIP-1α, MIP-1β, MIP-1δ, MIP-3α, MIP-2, RANTES); other ligands of chemokine receptors (e.g., CCR1, CCR-2, CCR-5, CCR6, CXCR-1); cytokines (e.g., IL-1β, IL-2, IL-4, IL-5, IL-6, IL-7, IL-8, IL-10, IL-12, IL-13, IL-15, IL-17 (A-F), IL-18; IFNα, IFN-γ; TNF-α; GM-CSF); TGF)-β; FLT-3 ligand; CD40 ligand; other ligands of receptors for those cytokines; Th1 cytokines including, without limitation, IFN-γ, IL-2, IL-12, IL-18, and TNF; Th2 cytokines including, without limitation, IL-4, IL-5, IL-10, and IL-13; and Th17 cytokines including, without limitation, IL-17 (A through F), IL-23, TGF-β and IL-6; immunostimulatory CpG motifs in bacterial DNA or oligonucleotides; derivatives of lipopolysaccharides such as monophosphoryl lipid A (MPL); muramyl dipeptide (MDP) and derivatives thereof (e.g., murabutide, threonyl-MDP, muramyl tripeptide, N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alani-ne-2-(1'-2'-dipalmitoyl-sn-glycero-3hydroxyphosphoryloxy)-ethylamine (CGP 19835A, referred to as MTP-PE)); MF59 (see Int'l Publication No. WO 90/14837); poly[di (carboxylatophenoxy)phosphazene] (PCPP polymer; Virus Research Institute, USA); RIBI (GSK), which contains three components extracted from bacteria, monophosphoryl lipid A, trehalose dimycolate and cell wall skeleton (MPL+TDM+CWS) in a 2% squalene/Tween 80 emulsion; OM-174 (a glucosamine disaccharide related to lipid A; OM Pharma SA, Meyrin, Switzerland); heat shock proteins and derivatives thereof; Leishmania homologs of elF4a and derivatives thereof; bacterial ADP-ribosylating exotoxins and derivatives thereof (e.g., genetic mutants, A and/or B subunit-containing fragments, chemically toxoided versions); chemical conjugates or genetic recombinants containing bacterial ADP-ribosylating exotoxins or derivatives thereof; C3d tandem array; lipid A and derivatives thereof (e.g., monophosphoryl or diphosphoryl lipid A, lipid A analogs, AGP, AS02, AS04, DC-Chol, Detox, OM-174); ISCOMS and saponins (e.g., Quil A, QS-21, Stimulon® (Cambridge Bioscience, Worcester, Mass.)); squalene; superantigens; or salts (e.g., aluminum hydroxide or phosphate, calcium phosphate). See also Nohria et al. *Biotherapy*, 7:261-269, 1994; Richards et al., in *Vaccine Design*, Eds. Powell et al., Plenum Press, 1995; and Pashine et al., *Nature Medicine*, 11:S63-S68, 4/2005) for other useful adjuvants. Further examples of adjuvants can include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co-polymer (CytRx, Atlanta Ga.), QS-21 (Cambridge Biotech Inc., Cambridge Mass.), and SAF-M (Chiron, Emeryville Calif.), AMPHIGEN® adjuvant, saponin, Quil A or other saponin fraction, monophosphoryl lipid A, and Avridine lipid-amine adjuvant, and METASTIM®. Other suitable adjuvants can include, for example, surface active substances such as lysolecithin, pluronic polyols, polyanions, peptides, oil or hydrocarbon emulsions, keyhole limpet hemocyanins, dinitrophenol, and others.

In some embodiments, the cell producing the peptide as described herein can be administered to a subject, e.g. for the treatment of cancer.

In some embodiments, the cell expressing a vector encoding a peptide as described herein can be a cell of a subject, e.g. a subject administered gene therapy for the treatment of cancer. Vectors for gene therapy can comprise viral or non-viral vectors as described elsewhere herein.

In one aspect, described herein is a method of modulating LSD2 enzymatic activity comprising administering to a cell an isolated peptide as described herein. In some embodiments, administering can comprise contacting the cell with an isolated peptide as described herein and/or a vector comprising a nucleic acid encoding a peptide as described herein.

In one aspect, described herein is a method of inhibiting and/or reducing cyclin D1 and cyclin E1 function in a cell comprising the step of administering to the cell an agent capable of inhibiting the interaction between LSD2 and NPAC. In some embodiments, the agent is an isolated peptide as described herein and/or a vector encoding an isolated peptide as described herein. In some embodiments, the vector encodes an isolated peptide as described herein operably linked to a signal peptide. In some embodiments, the agent is an LSD2 shRNA. In some embodiments, the agent is an antibody that specifically binds to a peptide consisting of an amino acid sequence selected from Table 6. In some embodiments, the agent is an antibody that specifically binds to NPAC peptides consisting of amino acids 214-225 (e.g. a peptide having the amino acid sequence of SEQ ID NO: 001). In some embodiments, the agent is an antibody that specifically binds to LSD2 peptide consisting of amino acids 220-300.

In some embodiments, the cell administered an agent capable of inhibiting the interaction between LSD2 and NPAC is a cancer cell. In some embodiments, the cancer is selected from the group consisting of: breast cancer, bladder cancer, AML, colorectal cancer, CML, endometrial cancer, glioma, pancreatic cancer, melanoma, small cell lung cancer, non-small cell lung cancer, prostate cancer, or thyroid cancer. The inhibition of the interaction between LSD2 and NPAC can be determined, e.g. by detecting a decrease in the ability of NPAC to stimulate LSD2-mediated nucleosomal demethylation. A non-limiting example of such an assay is as follows: briefly, purified 0.5 μg full-length His-LSD2 and 1 μg NPAC protein or peptides are incubated with 50 μM H3K4me2 peptides (residues 1-21) in 50 mM Tris-HCl, pH 8.5, 50 mM KCl, 5 mM $MgCl_2$, 5% glycerol at 37° C. for 30 min. The products are analyzed by SDS-PAGE electrophoresis and immunoblot using methylation specific anti-histone H3 antibodies as previously described (Shi et al. 2004). Similar assays (e.g. in the presence or absence of an NPAC protein or peptide) can be used to determine if an agent can modulate LSD2 enzymatic activity.

In one aspect, the methods described herein relate to a method of treating cancer by administering to the subject an isolated peptide or a vector encoding the isolated peptide as described herein. In some embodiments, the peptide comprises a signal peptide. In some embodiments, the subject is administered a cell comprising the vector. In some embodiments, the subject is administered the vector, e.g. gene therapy. In some embodiments, the subject is administered an isolated peptide. Methods of delivering peptides is known in the art. By way of non-limiting example, a fusion peptide comprising a peptide sequence as described herein and anthrax protective antigen, TAT peptide, transportan, VP22, or polyarginine can more readily enter a cell. For further discussion of peptide delivery systems, see, e.g. Jones et al. Br J Pharmacol 2005 145:1093-1102; and Torchillin. Drug Discovery Today Tech 2009; which are incorporated by reference herein in their entireties. In some embodiments, a fusion peptide comprising an isolated peptide sequence as described herein can additionally comprise the peptide sequence RKKRRQRRR (SEQ ID NO: 060). This short peptide is derived from HIV TAT protein, and can increase the delivery of a large variety of cargoes, including peptides, proteins, and nucleic acids, into cells. (For further discussion see, e.g. Ruben et al. J. Virol. 63 (1989) 1-8; Fawell et al. Proc. Natl. Acad. Sci. U.S.A. 91 (1994) 664-668; Vives et al. J. Biol. Chem. 272 (1997) 16010-16017; and Futaki et al. J. Biol. Chem. 276 (2001) 5836-5840: each of which is incorporated by reference herein in its entirety.

In some embodiments, the method of treatment comprises inhibiting and/or reducing cyclin D1 and cyclin E1 function in a cell obtained from a subject and assaying the cell from the subject for increased demethylation; wherein and if increased demethylation is detected in the cell then the subject is administered an agent capable of inhibiting the interaction of NPAC and LSD2. In some embodiment, the agent comprises an isolated peptide or a vector encoding the isolated peptide. In some embodiments, the peptide comprises a signal peptide. In some embodiments, the increased demethylation is assayed using an immunoblot assay, e.g. as described elsewhere herein. In some embodiments, the agent comprises an NPAC shRNA. In some embodiments, the agent comprises an LSD2 shRNA. In some embodiments, the agent comprises an NPAC shRNA. In some embodiments, the agent comprises an NPAC siRNA. In some embodiments, the agent comprises an LSD2 siRNA. In some embodiments, the agent comprises an antibody or antibody reagent that specifically binds to a peptide consisting of an amino acid sequence selected from Table 6. In some embodiments, the antibody or antibody reagent specifically binds to a NPAC peptide consisting of amino acids 214-225 of NPAC. In some embodiments, the agent comprises an antibody or antibody reagent that specifically binds to LSD2 peptide consisting of amino acids 220-300.

In one aspect, described here is an antibody or antibody reagent that specifically binds to a peptide consisting of an amino acid sequence selected from Table 6. In some embodiments, the antibody or antibody reagent specifically binds to a NPAC peptide consisting of amino acids 214-225 of NPAC.

The region of LSD2 comprising amino acid residues 220-300, as demonstrated herein, interacts with the histone tail and is important for LSD2 enzymatic activity. Unlike the catalytic site, which is buried and inaccessible, the region comprising amino acids 220-300 is solvent exposed as shown in the crystal structures herein. Therefore, an antibody that binds to and inhibits this region can inhibit the enzymatic action of LSD2.

Accordingly, in one aspect, described herein is an antibody or antibody reagent that specifically binds to LSD2 peptide consisting of amino acids 220-300, e.g. that inhibits the interaction of LSD2 and NPAC.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeable herein are used herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

A further kind of antibody reagent is an intrabody i.e. an intracellular antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Intrabodies work within the cell and bind intracellular protein. Intrabodies can include whole antibodies or antibody binding fragments thereof, e.g. single Fv, Fab and F(ab)'2, etc. Methods for intrabody production are well known to those of skill in the art, e.g. as described in WO 2002/086096. Antibodies will usually bind with at least a KD of about 1 mM, more usually at least about 300 μM, typically at least about 10 μM, more typically at least about 30 μM, preferably at least about 10 μM, and more preferably at least about 3 μM or better.).

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Avidity is the measure of the strength of binding between an antigen-binding molecule (such as an antibody reagent described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody reagent described herein) will bind to their cognate or specific antigen with a dissociation constant ($K_D$ of $10^{-5}$ to $10^{-12}$ moles/liter or less, and preferably $10^{31\ 7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g. specific) are typically in the range of $10^{-10}$ M (0.1 nM) to $10^{-5}$ M (10000 nM). The stronger an interaction is, the lower is its $K_D$. Preferably, a binding site on an antibody reagent described herein will bind to the desired antigen with an affinity less than 500 nM, preferably less than 200 nM, more preferably less than 10 nM, such as less than 500 pM. Specific binding of an antibody reagent to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an agent (e.g. an antibody reagent) described herein to bind to a target, such a peptide consisting of, e.g. the amino acid sequence of SEQ ID NO; 001, with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if an agent described herein binds to a first peptide consisting of an amino acid sequence of SEQ ID NO: 001 with a $K_D$ of $10^{-5}$ M or lower, but not to another randomly selected peptide, then the agent is said to specifically bind the first peptide. Specific binding can be influenced by, for example, the affinity and avidity of the agent and the concentration of the agent. The person of ordinary skill in the art can determine appropriate conditions under which the agents described herein selectively bind the targets using any suitable methods, such as titration of an agent in a suitable cell and/or peptide binding assay.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode a monoclonal antibody molecule or antigen binding region thereof. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of skill. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli.*, for example. Other gene expression elements useful for the expression of cDNA encoding antibodies or antigen-binding portions thereof include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983) Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody, antigen-binding portion thereof, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding fragment thereof, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, or antigen-binding portion thereof as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled chimeric, humanized, or composite human antibodies, portions and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or peptides described herein, E. coli K12 strains such as E. coli W3110 (ATCC 27325), Bacillus species, enterobacteria such as Salmonella typhimurium or Serratia marcescens, and various Pseudomonas species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Exemplary eukaryotic cells that can be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, one or more antibodies or antibody reagent thereof as described herein can be produced in vivo in an animal that has been engineered or transfected with one or more nucleic acid molecules encoding the polypeptides, according to any suitable method.

In some embodiments, an antibody or antibody reagent thereof as described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned H and L chain genes in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies or antigen-binding portions thereof. The co-expression can occur by using either the same or different plasmids in the same host. Genes for both H and L chains or portions thereof can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies, antigen-binding portions thereof and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to susb-cellular plastids, or limited to seeds (endosperms). See, e.g., U.S. Patent Pub. No. 2003/0167531; U.S. Pat. No. 6,080,560; U.S. Pat. No. 6,512,162; WO 0129242. Several plant-derived antibodies have reached advanced stages of development, including clinical trials (see, e.g., Biolex, N.C.).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. No. 5,585,089; U.S. Pat. No. 6,835,823; U.S. Pat. No. 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Alternatively, techniques described for the production of single chain antibodies (see, e.g. U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (see, e.g. Skerra et al., Science 242:1038-1041 (1988); which is incorporated by reference herein in its entirety).

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Mammalian cells are a preferred host for expressing nucleotide segments encoding immunoglobulins or fragments thereof. See Winnacker, From Genes to Clones, (VCH Publishers, NY, 1987), which is incorporated herein by reference in its entirety. A number of suitable host cell lines capable of secreting intact heterologous proteins have been developed in the art, and include CHO cell lines, various COS cell lines, HeLa cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," *Immunol Rev* 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. See Co et al., "Chimeric and Humanized Antibodies with Specificity for the CD33 Antigen," *J Immunol* 148:1149 (1992), which is incorporated herein by reference in its entirety. Alternatively, antibody coding sequences can be incorporated in transgenes for introduction into the genome of a transgenic animal and subsequent expression in the milk of the transgenic animal (e.g., according to methods described in U.S. Pat. No. 5,741,957, U.S. Pat. No. 5,304, 489, U.S. Pat. No. 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in is entirety). For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982), which is incorporated herein by reference in its entirety).

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, and the like. See generally, Vols. I & II Immunol Meth. (Lefkovits & Pernis, eds., Acad. Press, NY, 1979 and 1981).

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to the epitope comprising the amino acid sequence of SEQ ID NO: 1.

In one aspect, described herein is a pharmaceutical composition comprising an isolated peptide as described herein and a pharmaceutically acceptable carrier. In one aspect, described herein is a pharmaceutical composition comprising a modified NPAC polypeptide and/or fragment thereof as described herein and a pharmaceutically acceptable carrier. In one aspect, described herein is a pharmaceutical composition comprising a vector as described herein and a pharmaceutically acceptable carrier. In one aspect, described herein is a pharmaceutical composition comprising a cell as described herein and a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL;

(22) $C_2$-$C_{12}$ alcohols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an isolated peptide as described herein.

In some embodiments, the pharmaceutical composition as described herein, e.g. one comprising an isolated peptide as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of compositions as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agent as disclosed herein can also be incorporated into the parenteral dosage forms of the disclosure, including conventional and controlled-release parenteral dosage forms.

Pharmaceutical compositions as described herein, e.g. those comprising an isolated peptide as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In some embodiments, a pharmaceutical composition as described herein can be administered in a liposome formulation. As used herein, "lipid vesicle" or "liposome" refers to vesicles surrounded by a bilayer formed of lipid components usually including lipids optionally in combination with non-lipidic components. The interior of a vesicle is generally aqueous. One major type of liposomal composition not generally found in nature includes phospholipids other than naturally-derived phosphatidylcholine. Neutral lipid vesicle compositions, for example, can be formed from dimyristoyl phosphatidylcholine (DMPC) or dipalmitoyl phosphatidylcholine (DPPC). Anionic lipid vesicle compositions generally are formed from dimyristoyl phosphatidylglycerol. Another type of liposomal composition is formed from phosphatidylcholine (PC) such as, for example, soybean PC, and egg PC. Another type is formed from mixtures of phospholipid and/or phosphatidylcholine and/or cholesterol. Lipids for lipid vesicle or liposome formation are known in the art or described herein below. Liposomes are formed by the self-assembly of phospholipid molecules in an aqueous environment. The amphipathic phospholipid molecules form a closed bilayer sphere in an attempt to shield their hydrophilic groups from the aqueous environment, while still maintaining contact with the aqueous phase via the hydrophilic head group. The resulting closed sphere can encapsulate aqueous soluble drugs or agents within the bilayer membrane. Non-limiting examples of liposome compositions include those described U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gbizon A, et al. "Sterically stabilized liposomes. Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556 each of which is incorporated herein by reference in its entirety.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the compositions described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation or radiation therapy. Further, the methods of treatment can further include the use of surgical treatments.

In some embodiments, the methods described herein relate to treating a subject having or diagnosed as having cancer with a composition as described herein, e.g. an isolated peptide or antibody as described herein. Subjects having cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer or exposure to risk factors for cancer (e.g. smoking or radiation) can also aid in determining if a subject is likely to have cancer or in making a diagnosis of cancer.

The compositions and methods described herein can be administered to a subject having or diagnosed as having cancer. In some embodiments, the methods described herein comprise administering an effective amount of a composition described herein, e.g. peptides and/or antibodies as described herein to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to effect a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor size, among others. The dosage can be determined by a physician and adjusted, as necessary, to suit observed effects of the treatment.

In certain embodiments, an effective dose of a composition as described herein can be administered to a patient once. In certain embodiments, an effective dose of a composition can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor size by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to an agent. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of an agent described herein, according to the methods described herein depend upon, for example, the form of the agent, its potency, and the extent to which symptoms, markers, or indicators of a condition described herein are desired to be reduced, for example the percentage reduction desired for tumor size is desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy in, e.g. the treatment of a condition described herein, or to induce a response as described herein can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. a decrease in tumor size). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. tumor size and/or mortalit.

In vitro and animal model assays are provided herein which allow the assessment of a given dose. By way of non-limiting example, the effects of a dose of a composition as described herein can be assessed by administering the composition to a mouse with ectopic tumor.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level.

"Complete inhibition" is a 100% inhibition as compared to a reference level. In the context of a marker or symptom is meant a statistically significant decrease in such level. The decrease can be, for example, at least 10%, at least 20%, at least 30%, at least 40% or more, and is preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, *canine* species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g. cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA. As used herein, the term "RNAi" refers to any type of interfering RNA, including but are not limited to RNAi, siRNA, shRNA, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" and "RNA interfering" with respect to an agent of the technology described herein, are used interchangeably herein.

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow. RNAi may be delivered with the help of nanoparticles as described for example in Schiffelers and Storm, Expert Opin Drug Deliv. 2006 May; 3(3):445-54 or liposomes (e.g. Hughes et al., Methods Mol Biol. 2010; 605: 445-59).

As used herein a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

The term "agent" refers generally to any entity which is normally not present or not present at the levels being administered to a cell, tissue or subject. An agent can be selected from a group comprising: polynucleotides; polypeptides; small molecules; antibodies; or functional fragments thereof. A polynucleotide can be RNA or DNA, and can be single or double stranded, and can be selected from a group comprising: nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid (DNA or RNA), small molecule, aptamer, protein, peptide, antibody, polypeptide comprising an epitope-binding fragment of an antibody, antibody fragment, peptide-nucleic acid (PNA), locked nucleic acid (LNA), small organic or inorganic molecules; saccharide; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or mammalian cells or tissues; naturally occurring or synthetic compositions; peptides; aptamers; and antibodies, or fragments thereof. An agent can be applied to the media, where it contacts the cell and induces its effects. Alternatively, an agent can be intracellular as a result of, e.g. introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the terms "treat" "treatment" "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention is further illustrated by the following examples, which should not be construed as further limiting.

Some embodiments of the technology described herein can be defined according to any of the following numbered paragraphs:

1. An isolated peptide consisting of an NPAC peptide consisting of an amino acid sequence of Table 6.
2. An isolated peptide consisting essentially of an NPAC peptide consisting of an amino acid sequence of Table 6.
3. The isolated peptide of paragraphs 1 and 2 comprising at least one mutation selected from: a substitution of residue 217 of NPAC with alanine, glycine, serine, threonine, histidine, lysine, asparagine, aspartic acid, glutamic acid or glutamine; a substitution of residue 219 of NPAC with alanine, glycine or serine; a substitution of residue 223 of NPAC with alanine or glycine; a substitution of any of residues 220-222 of NPAC with alanine, glycine or serine; a deletion of any of amino acids 219-223 of NPAC; deletion of any of amino acids 223-225; and any combination thereof.
4. A modified NPAC or a fragment thereof comprising at least one mutation selected from: a substitution of residue 217 of NPAC with alanine, glycine, serine, threonine, histidine, lysine, asparagine, aspartic acid, glutamic acid or glutamine; a substitution of residue 219 of NPAC with alanine, glycine or serine; a substitution of residue 223 of NPAC with alanine or glycine; a substitution of any of residues 220-222 of NPAC with alanine, glycine or serine; a deletion of any of amino acids 219-223 of NPAC; deletion of any of amino acids 223-225; and any combination thereof.
5. A vector comprising a nucleic acid encoding the peptide of paragraphs 1-4.
6. The vector of paragraph 5 further comprising a signal peptide operably linked to the peptide.
7. The vector of paragraph 6 wherein the signal peptide comprises a nuclear localization signal.
8. A cell expressing the vector of any of paragraphs 5-7.
9. A method of modulating LSD2 enzymatic activity comprising administering to a cell an isolated peptide of paragraphs 1-4.
10. A method of inhibiting/reducing cyclin D1 and cyclin E1 function in a cell comprising the step of administering to the cell an agent capable of inhibiting the interaction between LSD2 and NPAC.
11. The method of paragraph 10, wherein the cell is a cancer cell obtained from a subject and further comprising a step of assaying the cancer cell from the subject for increased demethylation, and if increased demethylation is detected in the cancer cell then administering to the subject the agent capable of inhibiting the interaction between LSD2 and NPAC.

12. The method of any of paragraphs 10-11, wherein the agent is the isolated peptide of paragraphs 1-4 or a vector encoding the isolated peptide of paragraph 1-4 operably linked to a signal peptide.

13. The method of any of paragraphs 10-11, wherein the agent is an LSD2 shRNA.

14. The method of any of paragraphs 10-11, wherein the agent is an antibody that specifically binds to NPAC peptides consisting of amino acids 214-225.

15. The method of any of paragraphs 10-11, wherein the agent is an antibody that specifically binds to LSD2 peptides consisting of amino acids 220-300.

16. The method of any one of the paragraphs 10-15, wherein the cell is a cancer cell.

17. The method of any of paragraphs 11-16, wherein the increased demethylation is assayed using an immunoblot assay.

18. The method of any of paragraphs 11-17, wherein the cancer is breast cancer, bladder cancer, AML, colorectal cancer, CML, endometrial cancer, glioma, pancreatic cancer, melanoma, small cell lung cancer, non-small cell lung cancer, prostate cancer, or thyroid cancer.

19. A pharmaceutical composition comprising the peptide of paragraphs 1-3, the modified NPAC or a fragment thereof of paragraph 4, the vector of paragraphs 5-7, or the cell of paragraph 8, or the antibody of paragraphs 20-23, and a pharmaceutically acceptable carrier.

20. An antibody that specifically binds to NPAC peptide consisting of amino acids 214-225 of NPAC.

21. An antibody that specifically binds to LSD2 peptide consisting of amino acids 220-300.

22. The antibody of any of paragraphs 20-21 wherein the antibody is a monoclonal antibody.

23. The antibody of any of paragraphs 20-22 wherein the antibody is an intrabody.

24. A composition comprising a peptide of any of paragraphs 1-3, wherein the peptide is pegylated.

25. The composition of paragraph 24, further comprising a carrier.

26. The composition of paragraph 25, wherein the carrier is a pharmaceutically acceptable carrier.

27. The use of a composition comprising the peptide of paragraphs 1-3, the modified NPAC or a fragment thereof of paragraph 4, the vector of paragraphs 5-7, or the cell of paragraph 8, or the antibody of paragraphs 20-23 to treat cancer, the method comprising administering the composition to a subject in need of treatment for cancer.

28. The use of paragraph 27, wherein a cancer cell from the subject is first determined to have an increased level of demethylation.

29. The use of any of paragraphs 27-28, wherein the cancer is breast cancer, bladder cancer, AML, colorectal cancer, CML, endometrial cancer, glioma, pancreatic cancer, melanoma, small cell lung cancer, non-small cell lung cancer, prostate cancer, or thyroid cancer

EXAMPLES

Example 1

Dynamic regulation of histone methylation represents a fundamental epigenetic mechanism underlying eukaryotic gene regulation. Yet little is known about how the catalytic activities of histone demethylases are regulated. Here, we identify and characterize NPAC/GLYR1 as an LSD2/KDM1b-specific cofactor that stimulates H3K4me1/2 demethylation. We determine the crystal structures of LSD2 alone, and LSD2 in complex with the NPAC linker region in the absence or presence of histone H3 peptide, at 2.9, 2.0 and 2.25 angstrom resolution, respectively. These crystal structures and further biochemical characterization define a dodecapeptide of NPAC (residues 214-225) as the minimal functional unit for its cofactor activity and provide structural determinants and a molecular mechanism underlying the intrinsic cofactor activity of NPAC in stimulating LSD2-catalyzed H3K4me1/2 demethylation. Thus, these findings establish a new model for how a cofactor directly regulates histone demethylation and will have significant impact on our understanding of catalytic activity-based epigenetic regulation.

Identifying NPAC as a novel LSD2 cofactor stimulating H3K4 demethylation. Structure determination of LSD2 alone or in complex with NPAC and histone H3 peptide. Defining the key NPAC residues essential for its intrinsic LSD2 cofactor activity. Establishing a new molecular model for how a cofactor regulates histone demethylation Introduction Since the discovery of the first histone lysine specific demethylase LSD1/KDM1a, histone lysine demethylation has emerged as an epigenetic paradigm (Shi et al., 2004). So far, over 20 histone lysine demethylases (KDMs) have been characterized, belonging to either the FAD-dependent LSD family or the $Fe^{2-}$ and α-ketoglutarate-dependent Jumonji C-terminal domain (JmjC) family (Allis et al., 2007; Bernstein et al., 2007; Chen et al., 2006b; Tsukada et al., 2006; Rice and Allis, 2001; Ruthenburg et al., 2007). Genetic, biochemical and functional studies further indicate that these KDMs play crucial roles in a wide range of biological processes, including gene expression, cell growth, differentiation, development and disease pathogenesis (Bhaumik et al., 2007; Egger et al., 2004; Esteller, 2008; Nottke et al., 2009; Shi, 2007).

A key question remains in the mechanistic understanding of how the enzymatic activities of KDMs is precisely regulated (Chen et al., 2006b; Horton et al., 2010; Lan et al., 2008; Wilson, 2007). It has been found that many KDMs, while being active on synthetic peptides or core histone substrates, exhibit very weak or no detectable activity on nucleosomal substrates in vitro. When transfected into cells however, robust activity on chromatin can be detected, suggesting the existence of additional cofactors required for full activity (Shi et al., 2004; Tahiliani et al., 2007). We, and others, have identified CoREST as a cofactor required for LSD1 action on nucleosomal substrates (Lee et al., 2005; Shi et al., 2005), representing the first breakthrough toward understanding how KDM activity is regulated. However, the molecular details underlying the cofactor-enhanced demethylase activity of LSD1 remain elusive (Forneris et al., 2007; Yang et al., 2006). Moreover, the cofactor activity of CoREST is highly specific, only facilitating demethylation of nucleosomal substrates by LSD1 but not any other KDMs. Further investigation is required to determine if cofactor-modulation is a general mechanism for the regulation of KDM functions. In particular, there are two areas to be addressed: first, whether different cofactors exist for other histone demethylases; and second, the molecular mechanism(s) employed by such cofactors to facilitate histone demethylase activity.

LSD2/KDM1b/AOF1 is the only mammalian homolog of LSD1 and possesses similar histone H3K4 demethylase activity (Ciccone et al., 2009; Fang et al., 2010; Yang et al., 2010). However, LSD2 is a component of a different cellular complex and has distinctive functions from LSD1 (Ciccone et al., 2009; Fang et al., 2010; van Essen et al., 2010). Genetic studies indicate that LSD2 is required for the homeostasis of global H3K4 methylation in mouse oocytes and regulates parental gene imprinting (Ciccone et al., 2009). In somatic tissue, LSD2 seems to play an important role in active gene transcription. LSD2 is reported to be a potential H3K9 demethylase and is required for controlling NF-κB induced gene activation by demethylating H3K9 at promoters (van Essen et al., 2010). On the other hand, we show that LSD2 is an active H3K4 demethylase that specifically associates with the coding region of target genes. Removal of endogenous LSD2 promotes an increase in H3K4me2 levels and a concurrent decrease in H3K9me2 levels specifically at coding regions but not at the corresponding promoters, and results in down regulation of gene transcription (Fang et al., 2010). These genetic and functional studies suggest that LSD2 is an important epigenetic regulator involved in diverse biological processes. How LSD2 activity is targeted to various functional sites and whether its activity is regulated by specific cofactors remain unknown.

Here, we report a novel cofactor of LSD2, NPAC/GLYR1, which positively regulates H3K4me2/1 specific histone demethylase activity of LSD2. NPAC, a putative H3K36me3 reader (Vermeulen et al., 2010), is a previously uncharacterized integral component of the LSD2 histone demethylase complex (Fang et al., 2010). We show that NPAC directly interacts with LSD2 and positively regulates its H3K4 demethylation activity both in vitro and in vivo. To understand the precise molecular mechanism of NPAC in regulating LSD2 enzymatic activity, we determined the crystal structures of LSD2, LSD2 in complex with NPAC, and the ternary complex of LSD2-NPAC-H3 peptide. The structural studies, together with molecular and biochemical characterization, illustrate a new molecular model of cofactor-mediated regulation of the catalytic activity of a histone demethylase.

Results

NPAC is a Cofactor of LSD2 Positively Regulating its H3K4 Histone Demethylase Activity.

NPAC/GLYR1 (protein ID: Q49A26) contains multiple functional domains, including a PWWP (Pro-Trp-Trp-Pro) domain (SEQ ID NO: 63), an AT-hook motif and a dehydrogenase domain (FIG. 1A). The presence of a dehydrogenase domain within NPAC was particularly intriguing since CtBP, a well-known corepressor and component of the LSD1 complex, also possesses a dehydrogenase domain (Chinnadurai, 2007; Shi et al., 2003). The potential analogy of NPAC/LSD2 to CtBP/LSD1 prompted us to focus on understanding the activity of NPAC in relation to LSD2 function. However, unlike CtBP, attempts to identify the intrinsic enzymatic activity of NPAC as a potential dehydrogenase using either recombinant NPAC protein purified from E. coli or the NPAC complex purified from HeLa cells by tandem affinity purification (TAP) were unsuccessful (data not shown).

Figure 1B:
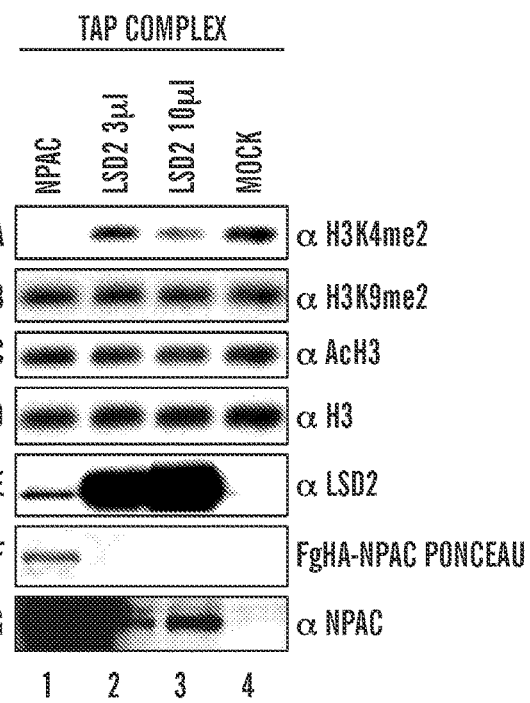
Figure 1C:
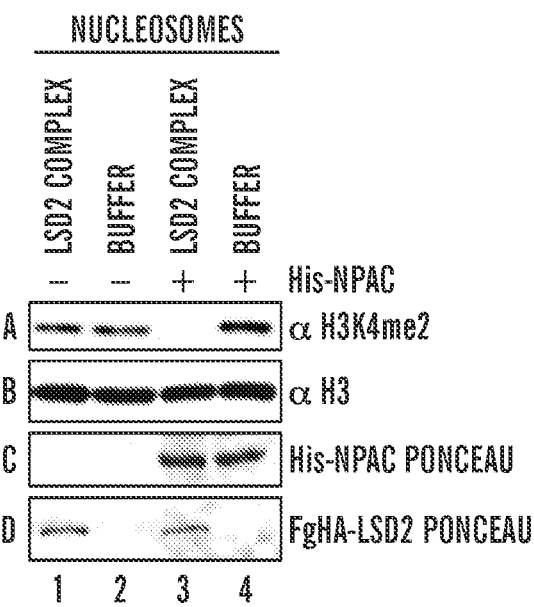

While excluding any intrinsic histone demethylase activity of recombinant NPAC, we observed that the NPAC complex purified from HeLa by TAP has robust H3K4me2 demethylase activity toward nucleosomes (FIG. 1B, lane 1). The H3K4 demethylase activity of the NPAC complex is likely attributed to endogenous LSD2, since LSD2 is the only histone demethylase detected in the complex by mass spectrometry (data not shown). Paradoxically, while the H3K4 demethylase activity is higher, the relative amount of LSD2 in the NPAC complex is significantly lower than that of the LSD2 complex, in which a small amount of endogenous NPAC is co-purified with LSD2 (FIG. 1B, panel g). Addition of purified recombinant NPAC to the LSD2 complex significantly improves nucleosomal demethylation (FIG. 1C). These observations suggest that NPAC may positively regulate LSD2 histone demethylase activity on nucleosomes, similar to the cofactor activity of CoREST for LSD1 (Lee et al., 2005; Shi et al., 2005).

Figure 1D:
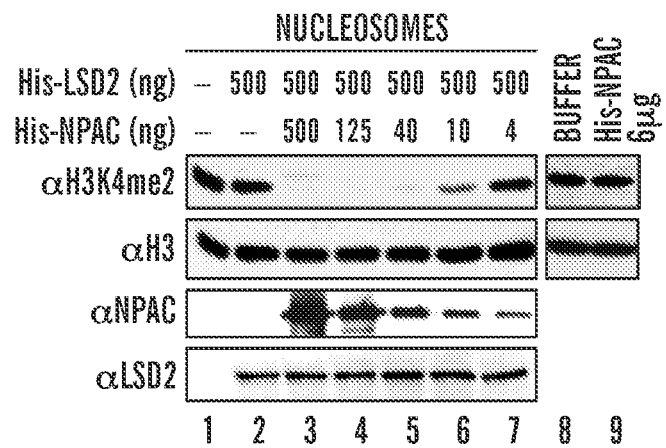
Figure 7A:
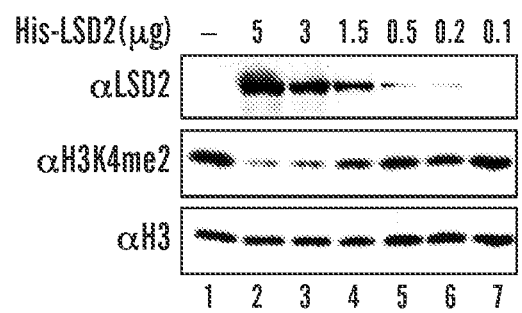
FIGS. 7A-7D demonstrate that NPAC cofactor activity is specific for H3K4 demethylation by LSD2.
Figure 7B:
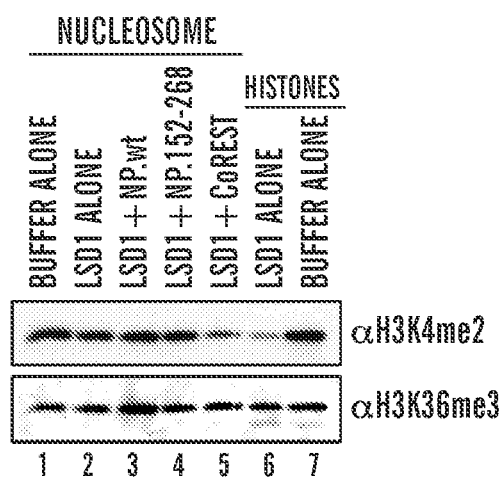

To directly validate its cofactor activity, we investigated whether NPAC alone is sufficient to enhance the activity of recombinant LSD2 in vitro. We have previously reported that unlike LSD1, recombinant LSD2 can demethylate nucleosomal H3K4me2 at a high dosage (Fang et al., 2010). Therefore, to measure the stimulatory effect of NPAC on nucleosomal substrates, we titrated down the amount of recombinant 6×his tagged LSD2 ("6×his" disclosed as SEQ ID NO: 75) (His-LSD2) until no obvious histone demethylase activity was detected (FIG. 7A, lane 5). Using this threshold dosage of His-LSD2, we performed nucleosome demethylation assays with increasing amounts of recombinant His-NPAC, which stimulated LSD2 activity in a dose-dependent manner (FIG. 1D). In contrast, NPAC has no stimulatory effect on nucleosome demethylation by LSD1 (FIG. 7B), and NPAC itself possesses no demethylase activity (FIG. 1D, lane 9).

Figure 1E:
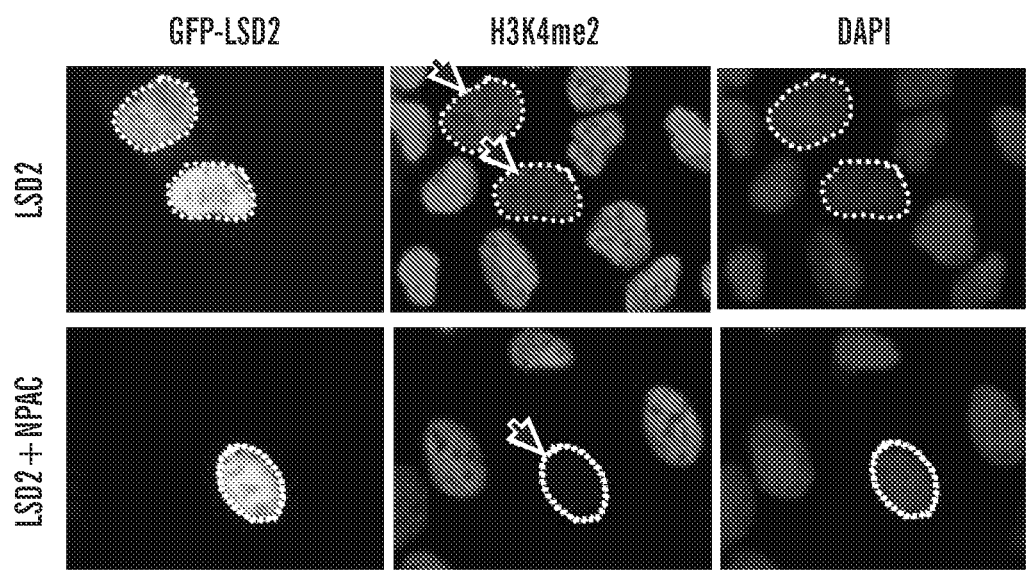
Figure 7C:
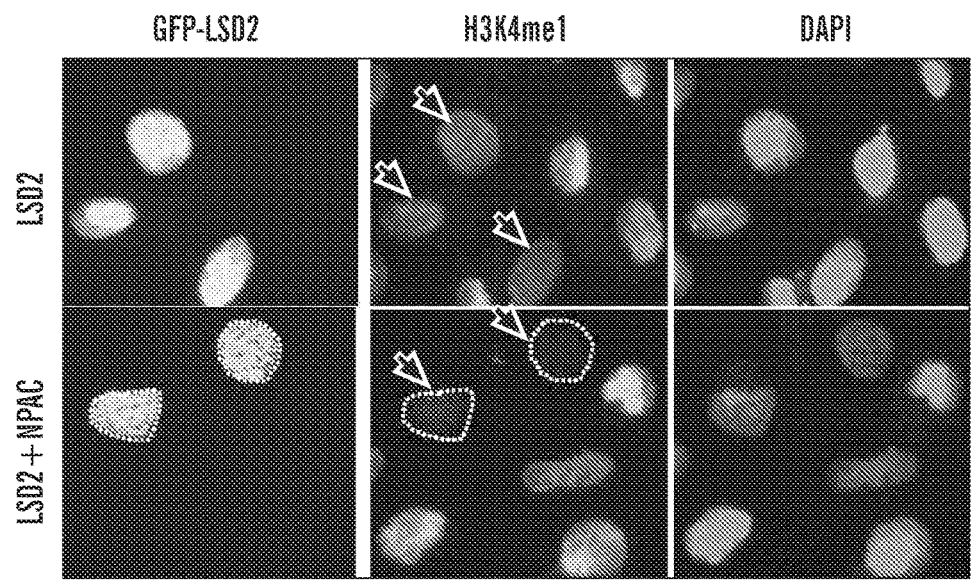
Figure 7D:
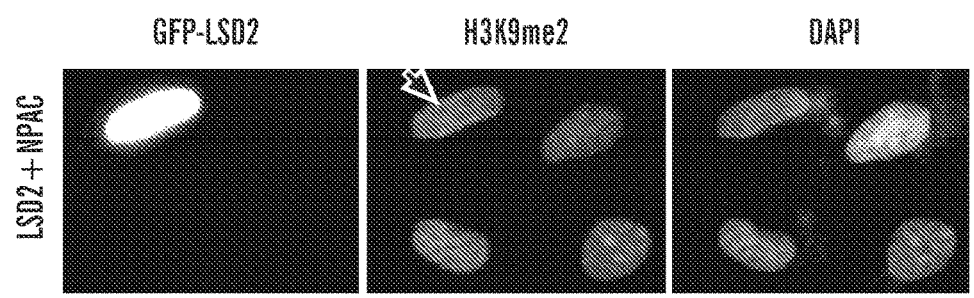

To further validate NPAC cofactor function in vivo, we coexpressed NPAC and LSD2 and observed much more pronounced depletion of di- and mono-methylated H3K4 in cells than expressing LSD2 alone (FIGS. 1E and 7C). Coexpression of NPAC does not change the substrate specificity of LSD2, since H3K9me2 and other histone marks examined showed no detectable changes (FIG. 7D and data not shown). Taken together, both in vitro and in vivo data suggest that NPAC is a specific cofactor for LSD2, positively regulating its H3K4 specific histone demethylase activity.

The Linker Region of NPAC is Sufficient for Cofactor Activity and LSD2 Interaction.

Figure 2A:
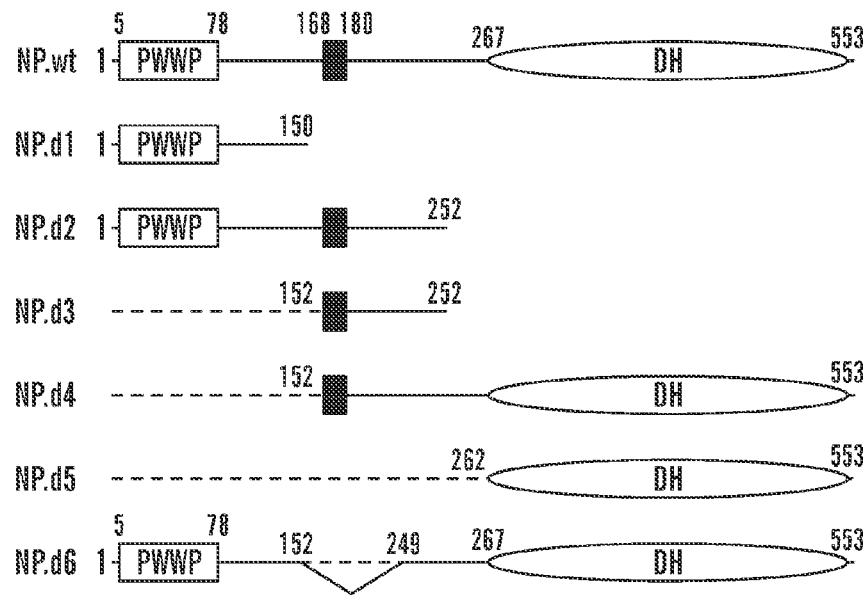
FIGS. 2A-2D demonstrate that the linker region of NPAC is sufficient for its cofactor activity and LSD2 interaction.
Figure 2B:
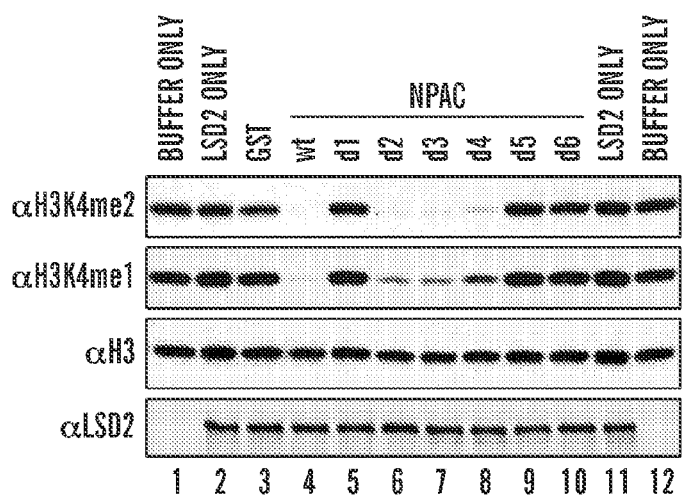
Figure 2C:
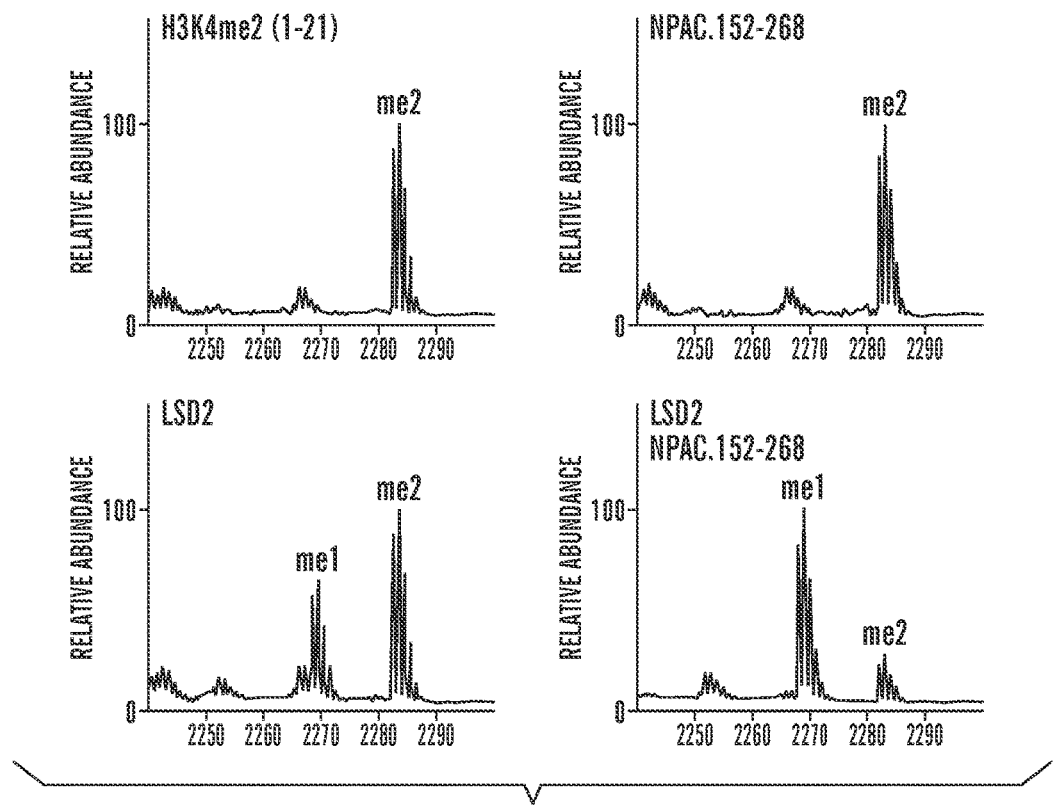

To identify the functional domain responsible for NPAC cofactor activity, we generated NPAC deletion mutants (FIG. 2A) and examined their ability to facilitate LSD2 activity on nucleosome substrates. Neither the PWWP domain (SEQ ID NO: 63) (NP.d1, residues 1-150) nor the dehydrogenase domain (NP.d5, residues 262-553) stimulated LSD2 (FIG. 2B, lane 5 and 9 compared to lane 2 and 11). In contrast, truncation proteins containing the linker region, NP.d2 (residues 1-252), NP.d3 (residues 152-252) and NP.d4 (residues 152-553), significantly enhance LSD2 demethylase activity (lane 6-8), while deletion of the linker region (residues 152-252) abolishes cofactor activity (NP.d6, lane 10). Furthermore, the linker region of NPAC exhibits strong cofactor activity for LSD2 even when a synthetic H3K4me2 peptide (residues 1-21) is used as the substrate (FIG. 2C).

Figure 2D:
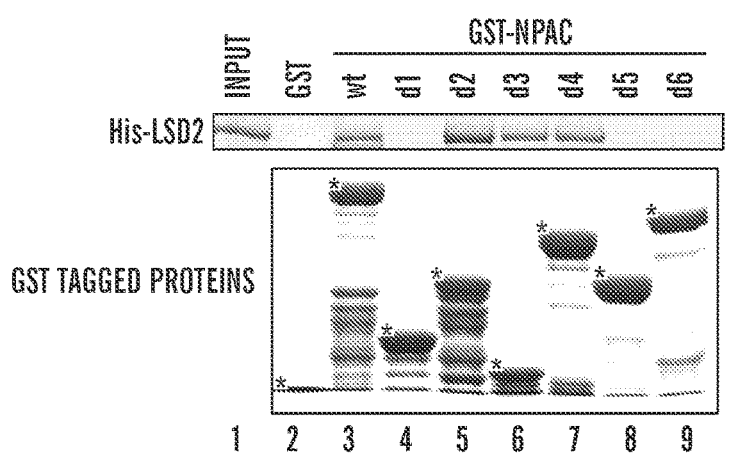

Examining the same NPAC mutants using GST-pulldown assays, we further show that truncation proteins possessing strong cofactor activity (NP.d2, NP.d3 and NP.d4) are also capable of directly interacting with LSD2 (FIG. 2D). Neither the PWWP domain (SEQ ID NO: 63) (NP.d1) nor the dehydrogenase domain (NP.d5) interacts with LSD2 (lane 4 and 8, respectively), and removal of either domain (NP.d4, NP.d2) does not adversely affect LSD2 binding (lane 7 and 5, compare to lane 3). Removing the linker region (NP.d6) abolishes NPAC-LSD2 interaction (lane 9).

Taken together, we conclude that the linker region of NPAC is responsible for LSD2 interaction as well as cofactor activity. It has been proposed that CoREST stimulates LSD1 histone demethylase activity on nucleosomes by assisting in docking of LSD1-CoREST to nucleosomal substrates via its DNA-binding SANT2 domain (Yang et al., 2006). In contrast, the linker region of NPAC facilitates LSD2 enzymatic activity, regardless of whether the substrate is chromatin, nucleosome or a modified short histone peptide, and the nucleosome-binding PWWP domain (SEQ ID NO: 63) of NPAC is dispensable for its cofactor activity. These observations indicate a novel mechanism for the direct action of a cofactor on histone demethylation, primarily involving the histone tail.

The Crystal Structures of LSD2, LSD2-NPAC and the Ternary Complex of LSD2-NPAC-H3 Peptide.

Figure 8A:
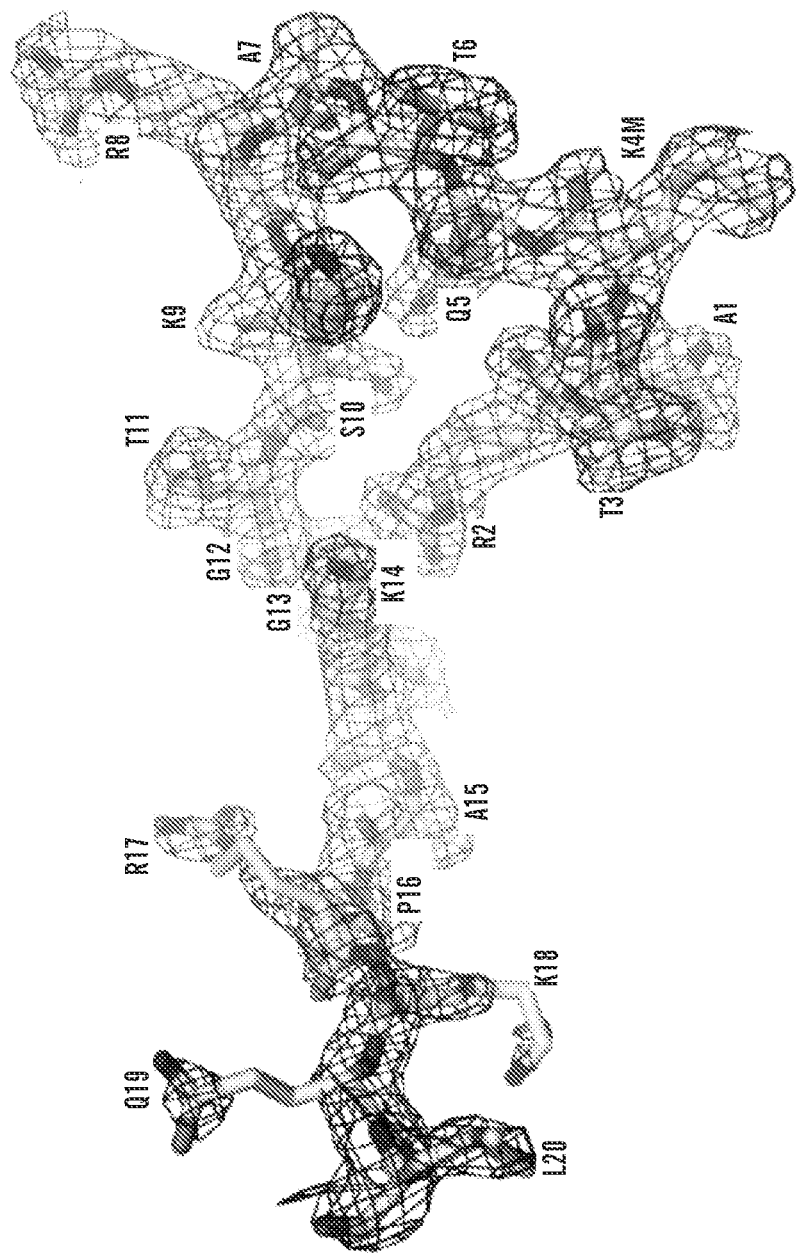
FIGS. 8A-8B depict electron density maps of the H3K4M peptide and NPAC in the co-crystal structure of LSD2-NPAC-H3K4M peptide ternary complex are shown in stick representation in FIG. 8A and FIG. 8B, respectively. The map is calculated at 2.25 Å and contoured at 0.8. Residue L20 of the H3K4M peptide are clearly covered by electron density, indicating that this critical residue making contact with the LSD2-NPAC complex was built correctly in the structural model. The linker region of NPAC (residues 152-268) was used for co-crystallization studies. Residues 214-225 of NPAC display nice electron density and can be unambiguously identified, while other residues are disordered and not found in the co-crystal structure.
Figure 8B:
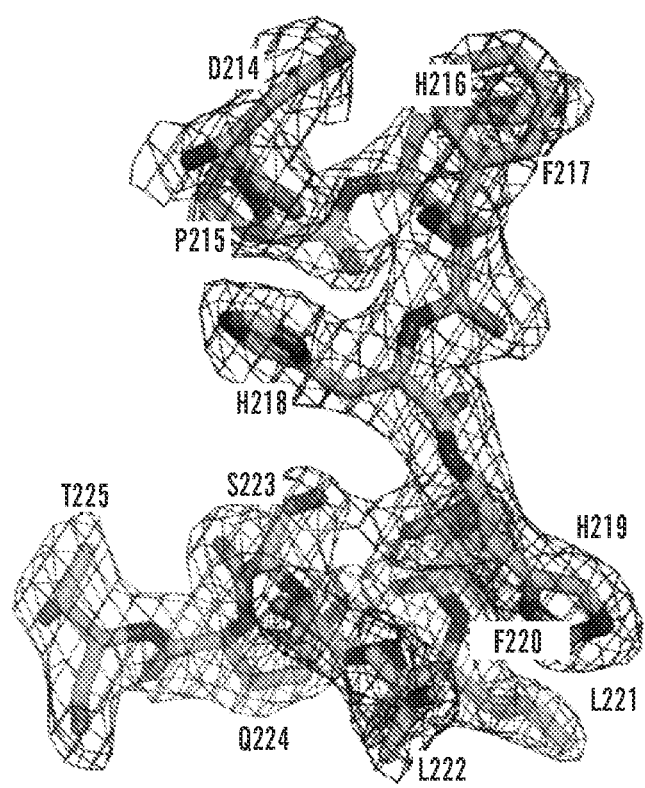

To understand the structural basis for LSD2 function and its regulation by NPAC, we solved the LSD2 crystal structure using a truncated protein (residues 51-822) purified to homogeneity, and the co-crystal structures of LSD2 in complex with the NPAC linker region (amino acids 152-268) in the presence and absence of H3K4M peptides (Histone H3 residues 1-21, replacing K4 with a methionine to mimic the H3K4me2 substrate of LSD2) (Forneris et al., 2007). Resolutions of the refined models were 2.9 Å, 2.25 Å and 2.0 Å, respectively (Table 1, Table 2 and FIGS. 8A-8B).

Figure 3A:
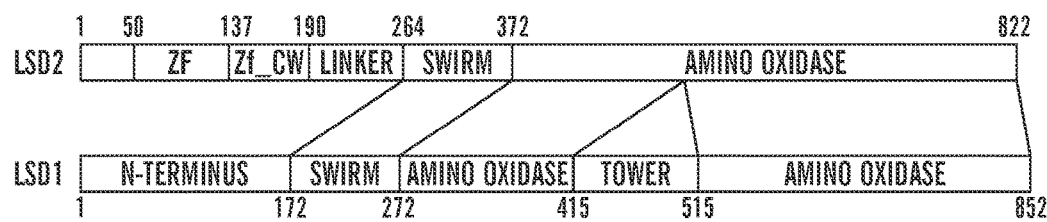
FIGS. 3A-3D demonstrate that binding of NPAC does not induce significant conformational changes in LSD2.
Figure 3B:
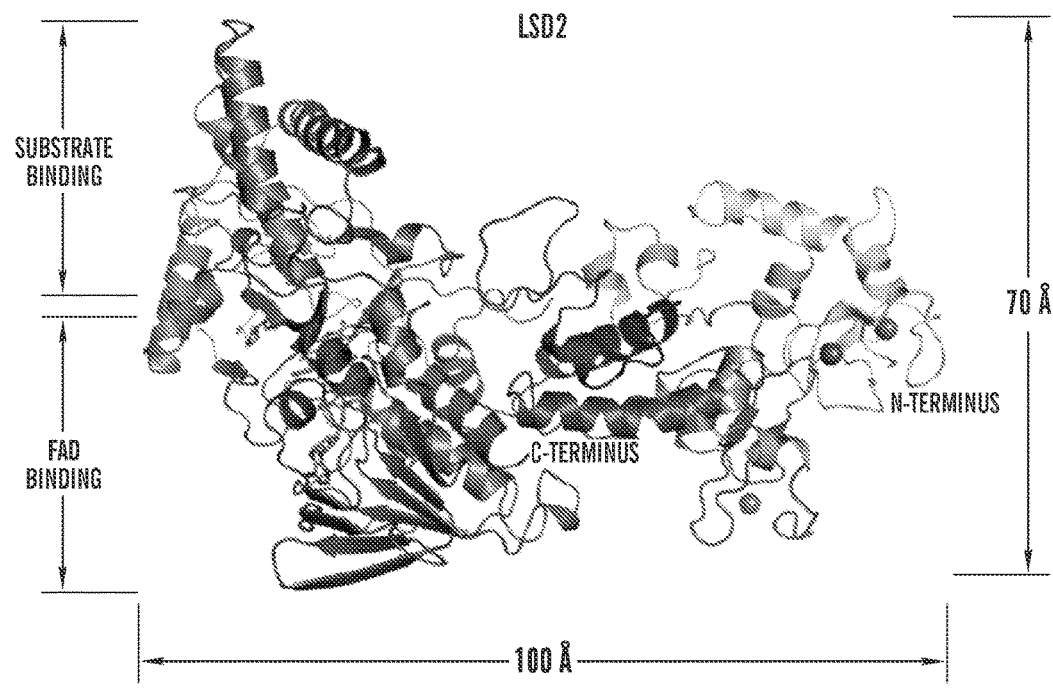
Figure 3C:
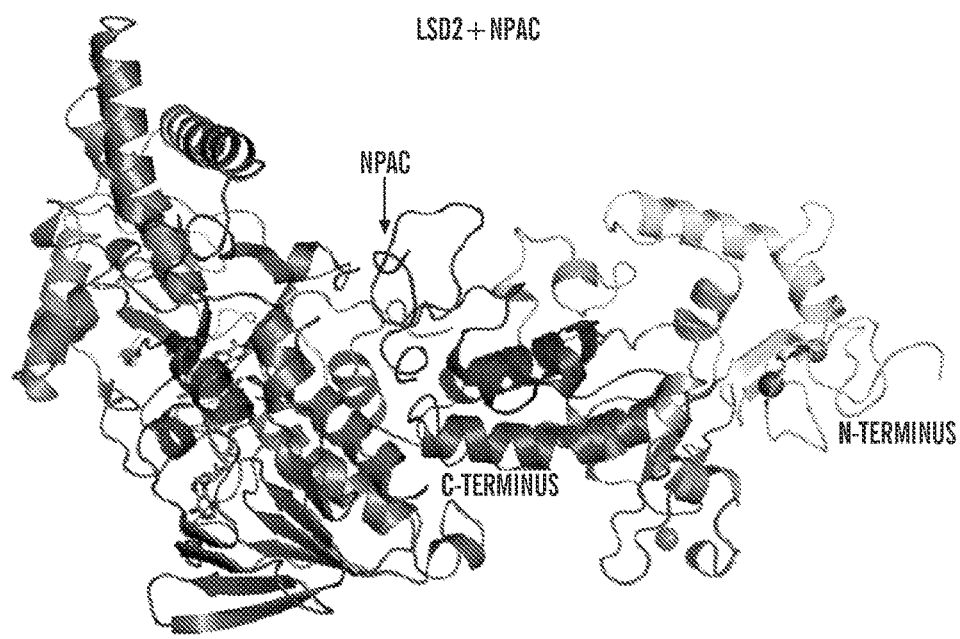
Figure 3D:
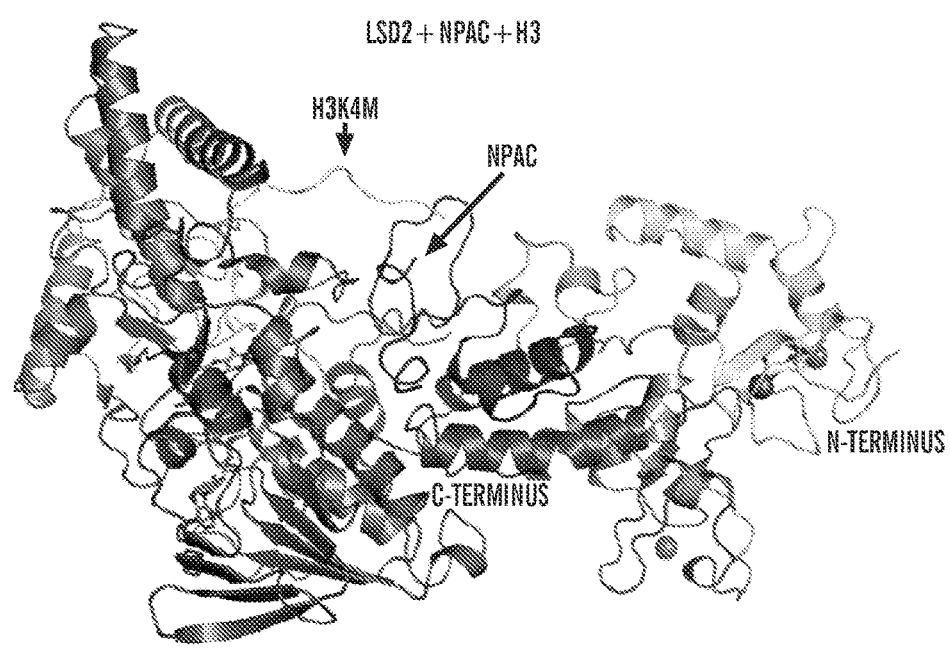
Figure 9A:
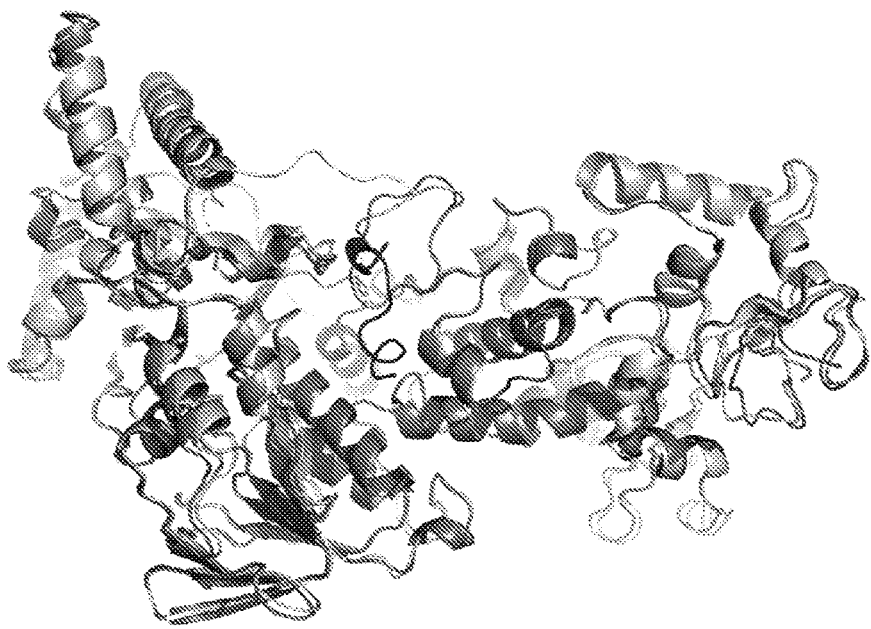
FIGS. 9A-9C depict analysis of the interaction between LSD2 and H3K4M peptide.
Figure 9B:
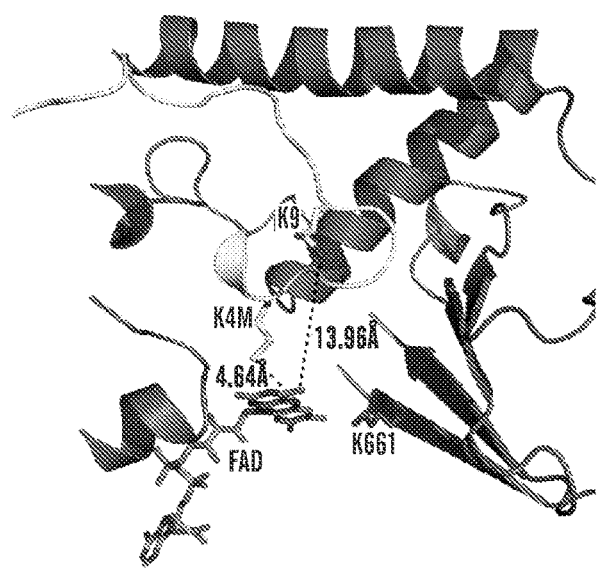
Figure 9C:
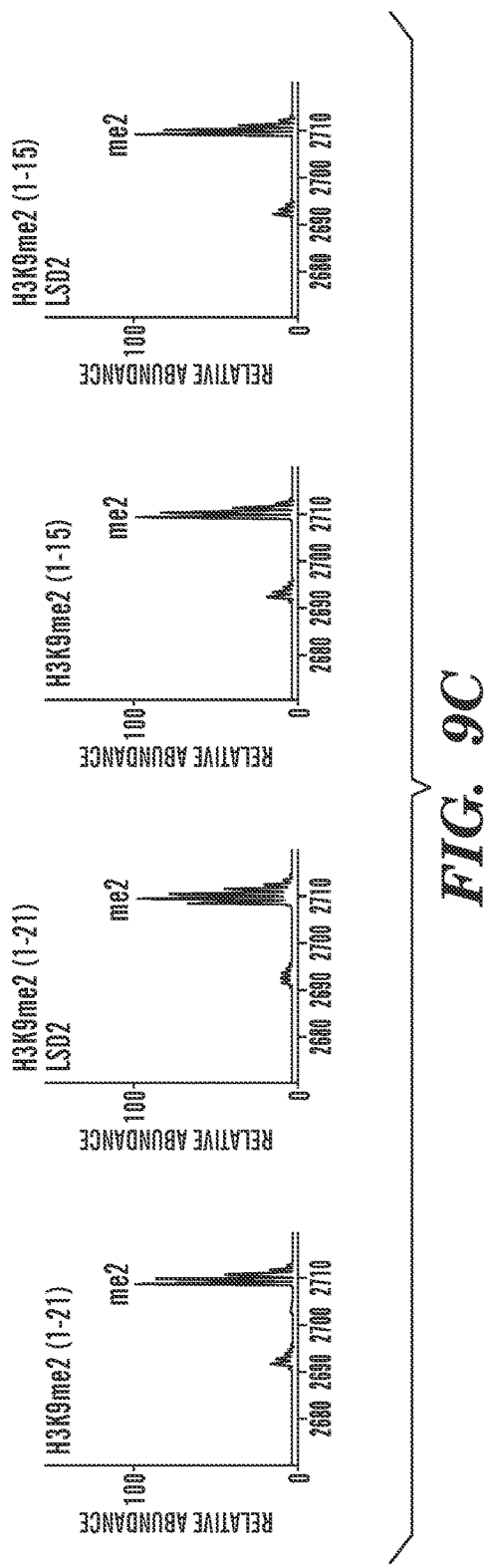

The structure of LSD2 adopts a compact rod shape and is comprised of four recognizable domains: a novel, unpredicted zinc finger domain with two zinc atoms coordinated by a $Cys_4His_2Cys_2$ motif (ZF, lime), a CW-type zinc finger domain with one zinc atom coordinated by four cysteines (Zf-CW, purple), a SWIRM domain (red) and an amine oxidase domain (AO, green) (FIG. 3A-3B). Compared to the structure of LSD2 alone, the co-crystal structures show that NPAC binding does not significantly alter the overall structure of LSD2 or induce conformational changes in the catalytic domain. Similarly, the inclusion of histone H3K4M peptide does not lead to significant conformational changes in the LSD2-NPAC complex (FIGS. 3C-3D, 9A and Table 3). This suggests that unlike regulators of the SET1 family histone methyltransferases (Dou et al., 2006; Southall et al., 2009), NPAC does not employ an allosteric mechanism to facilitate LSD2 enzymatic activity or switch LSD2 substrate specificity (FIG. 9B-9C).

The LSD2 Structure Reveals Common and Distinct Features from LSD1.

Figure 10A:
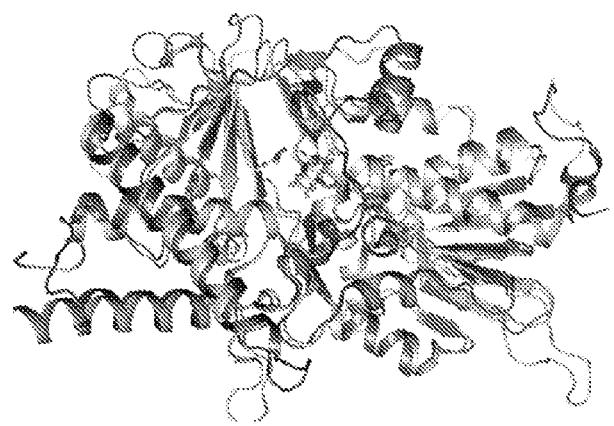
FIGS. 10A-10F depict a comparison of the catalytic domains of LSD2 and LSD1 (FIGS. 10A-10C) and a comparison of Zf-CW domains of LSD2 and ZCWPW1 that binds to H3K4me3 (FIGS. 10D-10F).
Figure 10B:
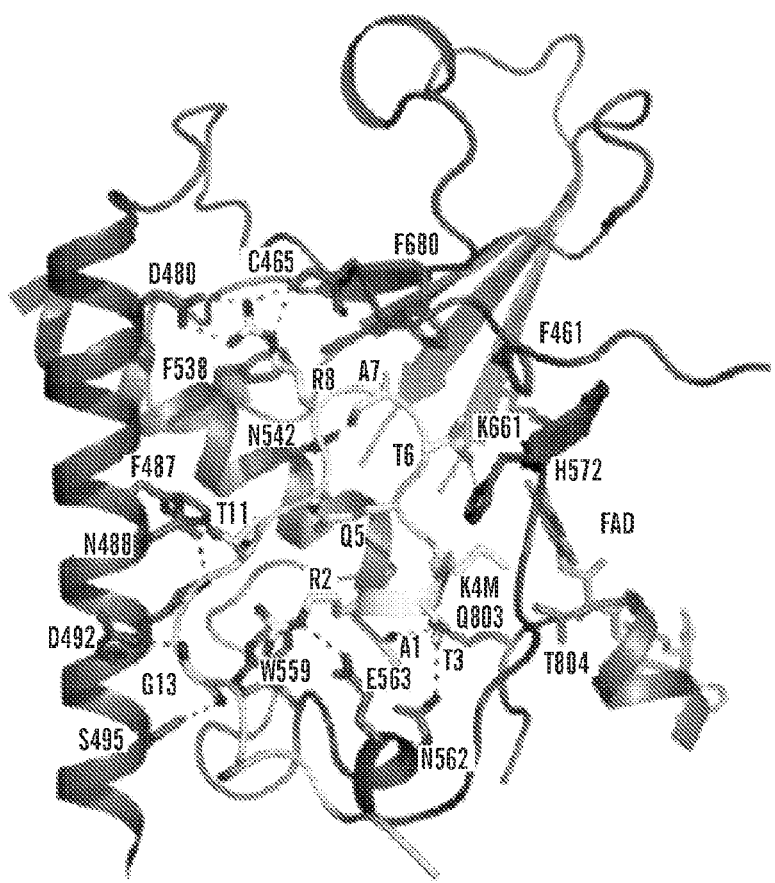
Figure 10C:
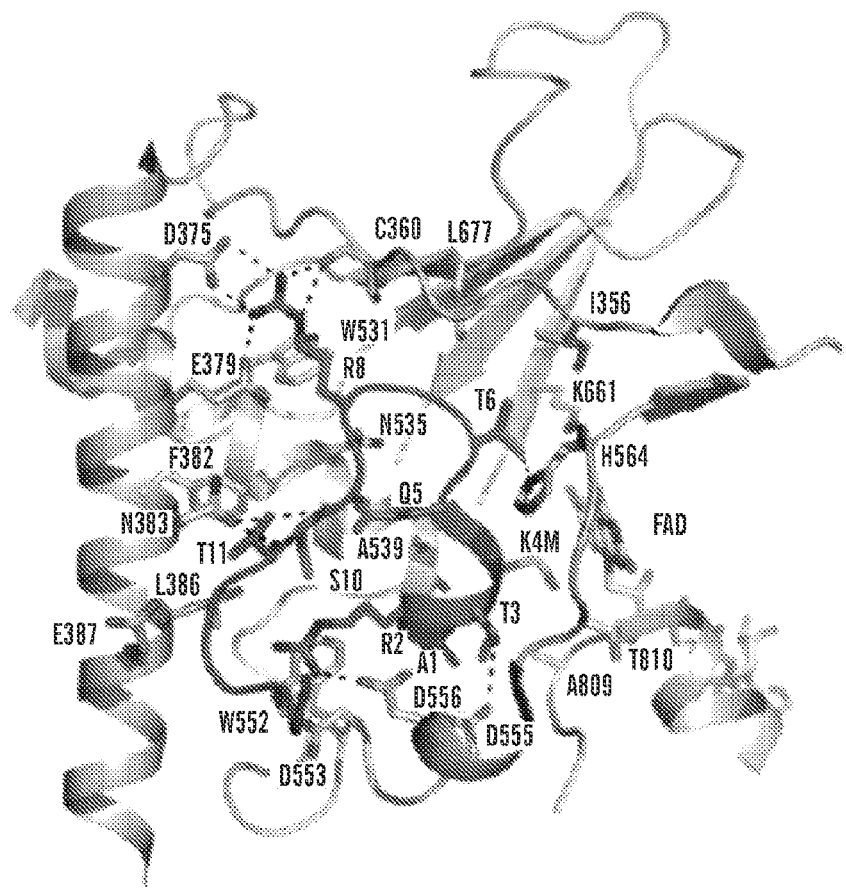

LSD2 and LSD1 share significant similarities in the AO catalytic domain (Chen et al., 2006a; Forneris et al., 2007; Stavropoulos et al., 2006; Yang et al., 2006). The overall folding and positions of the catalytic residue K661 and residues coordinating the FAD coenzyme are well conserved, creating indistinguishable catalytic cavities (FIG. 10A-10C), consistent with their similar substrate specificities (Ciccone et al., 2009; Fang et al., 2010; Shi et al., 2004; Yang et al., 2010). However, the crystal structure reveals several distinctive structural features of LSD2, which may significantly influence its intrinsic histone demethylase activity and explain differing regulatory mechanisms.

Figure 4A:
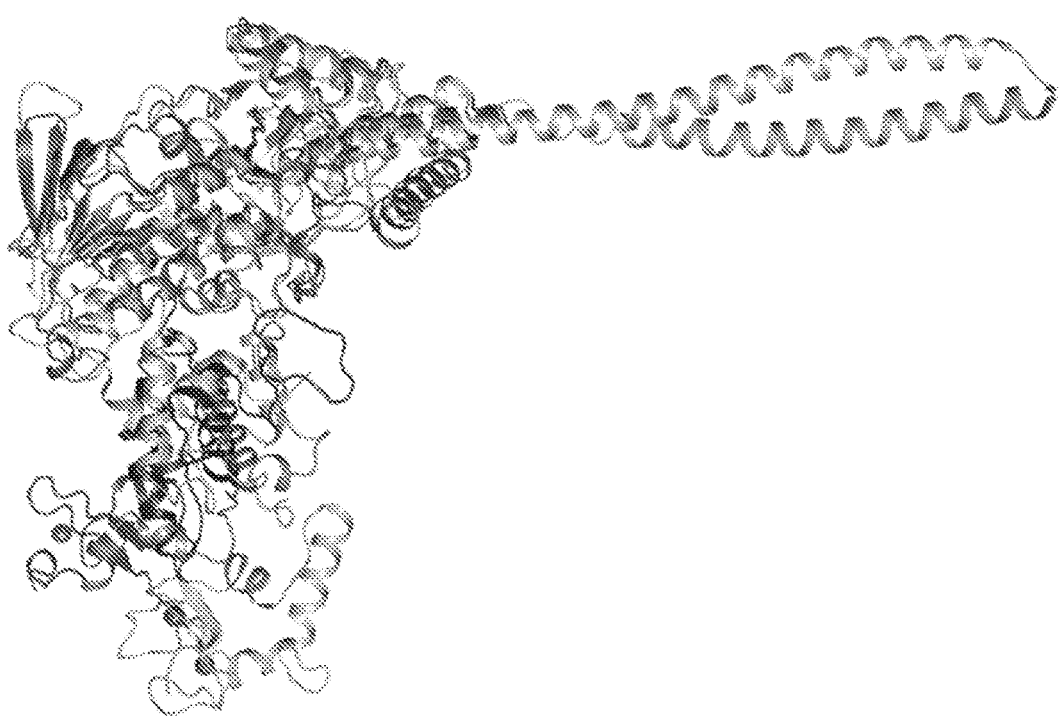
FIGS. 4A-4E demonstrate that LSD2 exhibits common and distinctive structural features compared to LSD1.
Figure 4B:
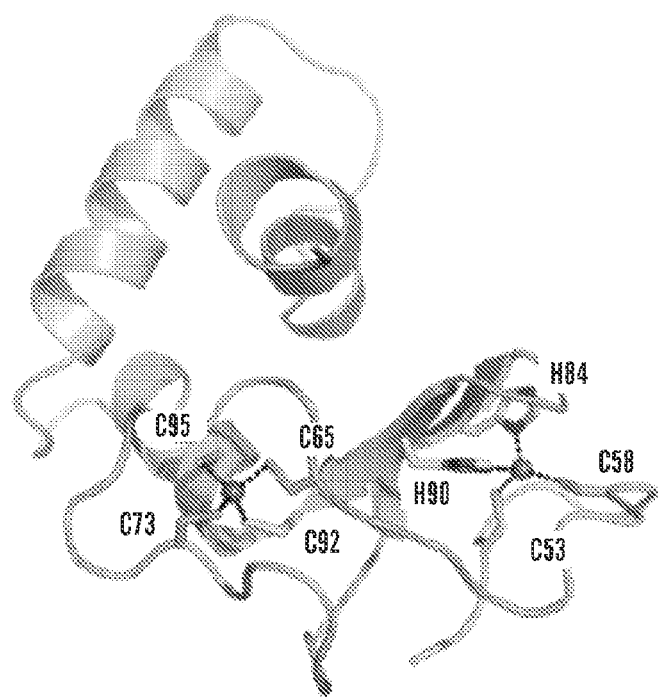
Figure 4C:
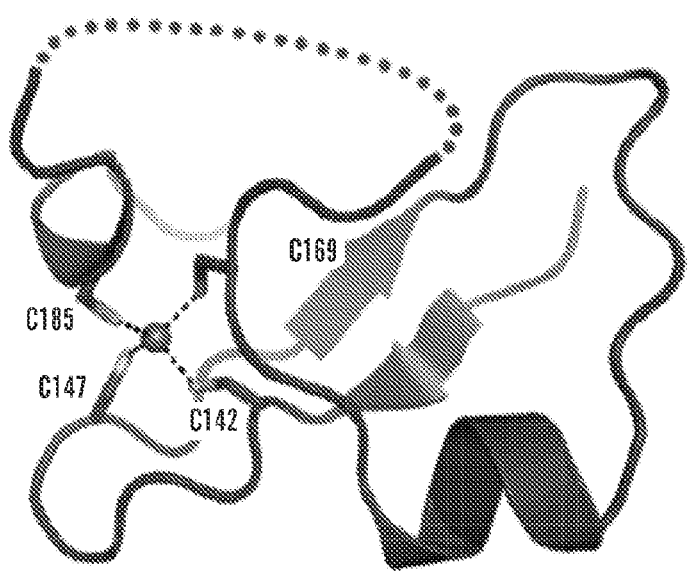
Figure 4D:
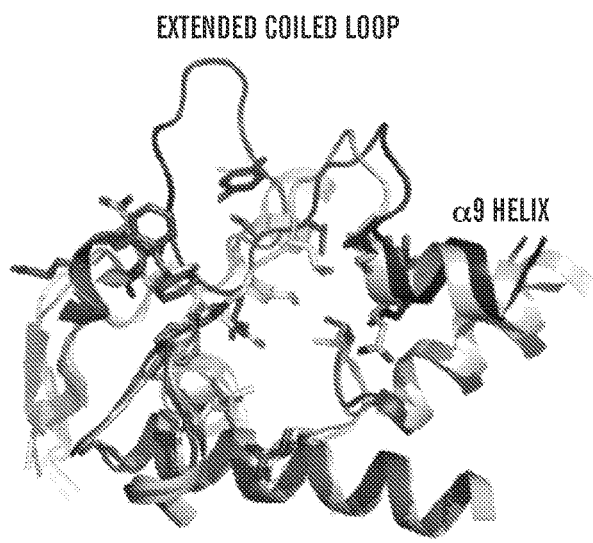
Figure 4E:
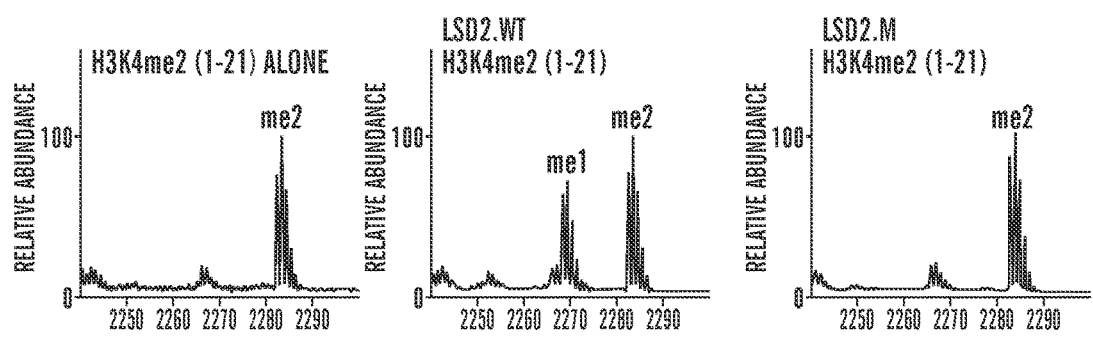
Figure 10D:
Figure 10E:
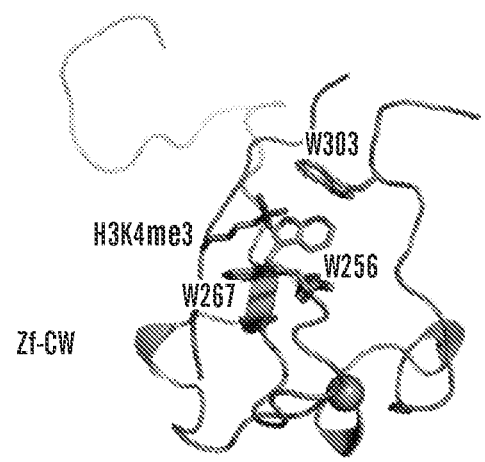
Figure 10F:
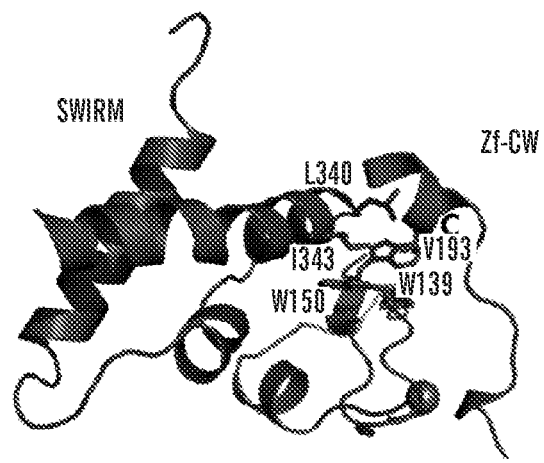

The most striking structural difference between LSD2 and LSD1 is the "tower domain," which is present in the LSD1 AO domain but absent in LSD2 (FIG. 4A). The tower domain of LSD1 is the binding site for CoREST. The lack of a tower domain in LSD2 inherently necessitates an alternate mechanism for LSD2-cofactor interaction. Another distinction is that the two zinc finger domains present in LSD2 are absent in LSD1 (FIG. 4B-4C). The first zinc finger of LSD2 bares little sequence or structural similarity to $Cys_4His_2Cys_2$-type or other types of zinc fingers in the Protein Data Bank. Notably, the Zf-CW domain of LSD2 superimposes with that of ZCWPW1 (FIG. 10D), a specific reader of tri-methyl H3K4 (FIG. S4E) (He et al., 2010). However, the hydrophobic pocket in the LSD2 Zf-CW domain is filled with the side chain of residues L340 and 1343 in the adjacent SWIRM domain (FIG. 10F). Thus, it is unlikely to interact with other proteins or histone modifications on this surface unless significant conformational change occurs. In LSD2, the two zinc fingers wrap around the SWIRM domain and together form a globular structure that contacts the AO domain. Though the molecular function of these zinc fingers is unclear and warrants future investigation, both are required for LSD2 histone demethylase activity (Fang et al., 2010; Yang et al., 2010). These zinc fingers may play a structural role in stabilizing the conformation of the AO and SWIRM domains. In comparison, the N-terminal region of LSD1 is unstructured, and dispensable for LSD1 activity (Shi et al., 2004). Finally, despite some similarities, a significant difference in the LSD2 SWIRM domain is an extended coiled loop connected to the α9-helix, whereas the corresponding region in LSD1 is a short α-helix (FIG. 4D). This extended loop and the α9-helix are adjacent to the AO domain, suggesting a possible function in LSD2 enzymatic activity. Indeed, replacing the extended coil loop (residues 273-278) with a flexible peptide sequence (GSGSGS) (SEQ ID NO: 65) significantly impaired its enzymatic activity in histone peptide demethylation assays (FIG. 4E).

A Dodecapeptide of NPAC Interacts with LSD2.

Figure 5A:
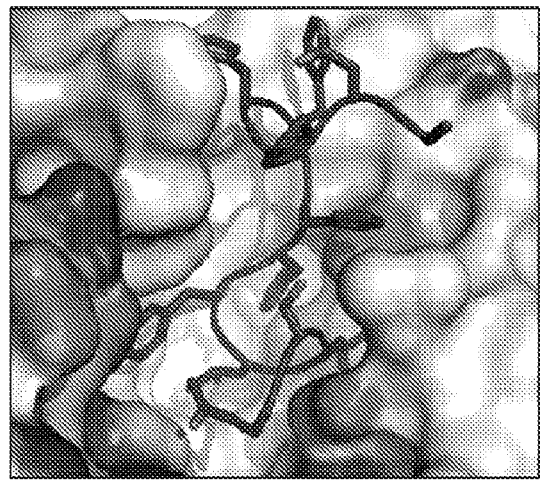
Figure 5B:
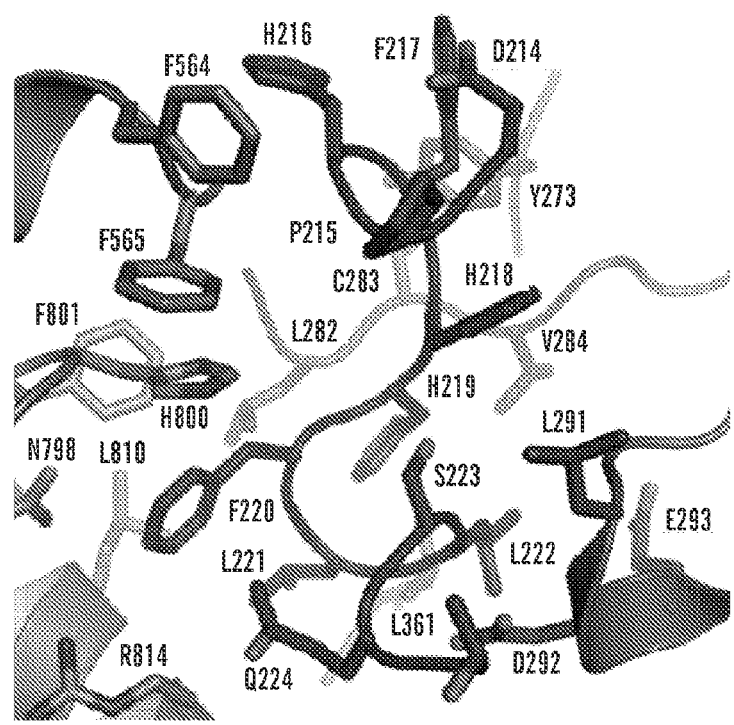
Figure 5C:
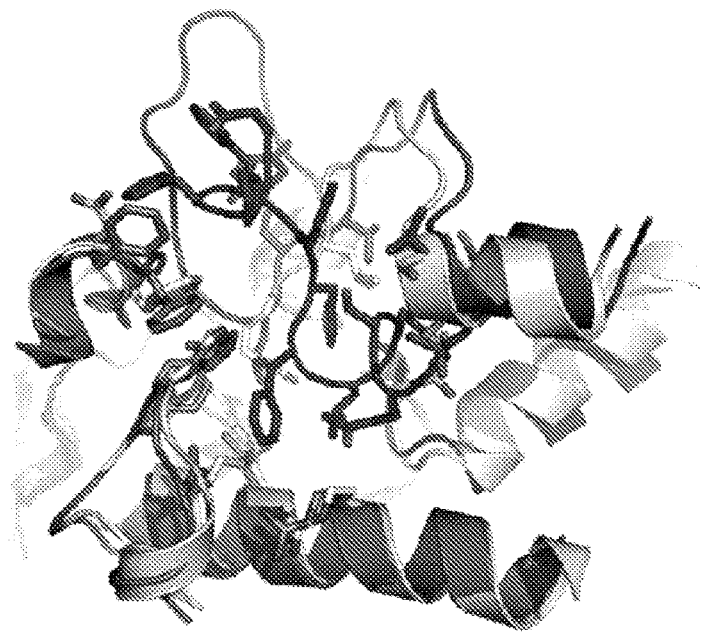

In the co-crystal structures, we unambiguously identified a dodecapeptide of NPAC (residues 214-225) (FIG. 8B), while other residues of NPAC were not built into the final model due to lack of electron density. This short NPAC peptide binds to LSD2 in a deep hydrophobic groove located between the AO and SWIRM domains, close to its catalytic site (FIG. 5A). Specifically, residues H219, F220, L221 and L222 of NPAC are deeply buried in the hydrophobic patch formed by residues L282, V284, L291, L361, F801 and L810 of LSD2 (FIG. 5B). Residues 214-217 of NPAC are projected away from this hydrophobic patch and make little contact with LSD2. Notably, LSD2 residues L282, V284 and L291 are located in the α9-helix and upstream coiled loop of LSD2 SWIRM domain, which is one of the structural differences from LSD1 (FIGS. 5C and 11A) and their conformation is nearly identical to the structure of LSD2 alone (FIGS. 4D and 9A).

Figure 5D:
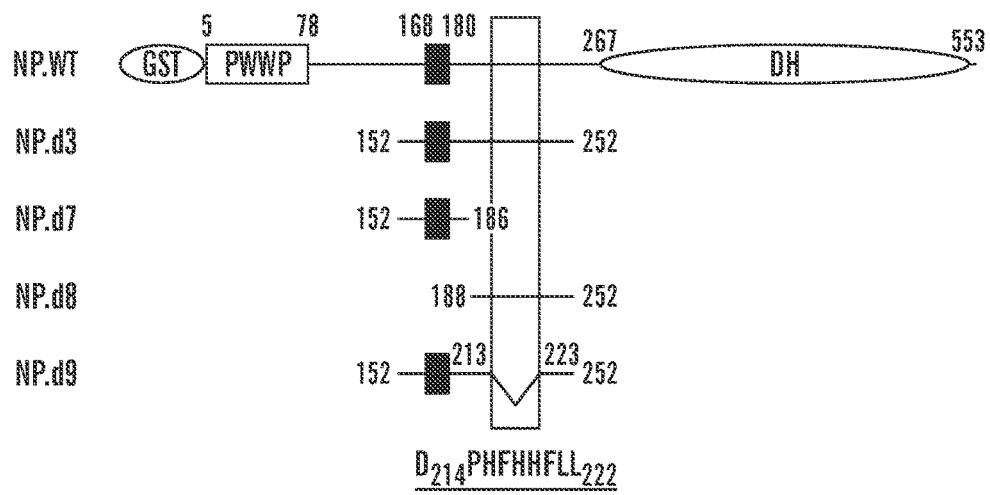

To validate the importance of the dodecapeptide for NPAC/LSD2 interaction, we designed truncation mutants in the NPAC linker region (NP.d7-9, schematic shown in FIG. 5D) and examined their ability to interact with LSD2 (FIG. 5E). As expected, deletion of amino acids 214-222 from NP.d3 (NP.d9) completely abolishes LSD2 binding (lane 6). NP.d8 (residues 188-252, lane 5), but not NP.d7 (residues 152-186, containing the AT hook motif, lane 4), is sufficient for LSD2 interaction. Consistent with the results from these binding assays, NP.d8, but not NP.d7 or NP.d9, significantly enhances LSD2 histone demethylase activity on nucleosomal substrates (FIG. 5F). The co-crystal structures predict that residues H219, F220, L221 and L222 of NPAC comprise the major binding sites for LSD2. Indeed, point mutation and deletion of these critical residues within NPAC 188-252 (NP.M1-3, partial sequences shown in FIG. 5G) result in loss of LSD2 binding (FIG. 5H), as well as loss of the ability to stimulate LSD2 activity (FIG. 5I). Collectively, these results confirm the structural predictions and identify the key residues of NPAC to interact with LSD2 that are important for NPAC cofactor activity.

Interplay Among Enzyme, Cofactor and Substrate.

Figure 6A:
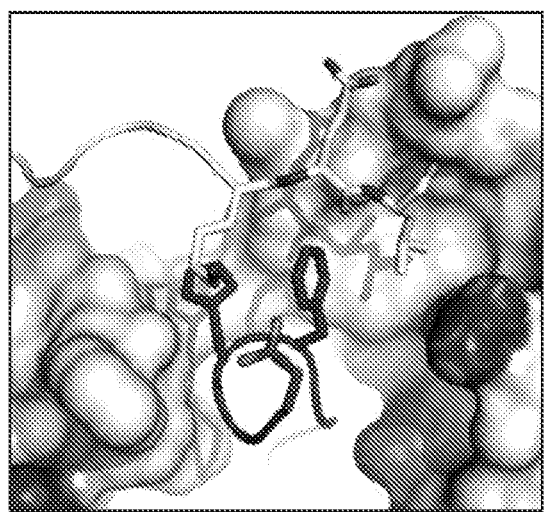
Figure 6B:
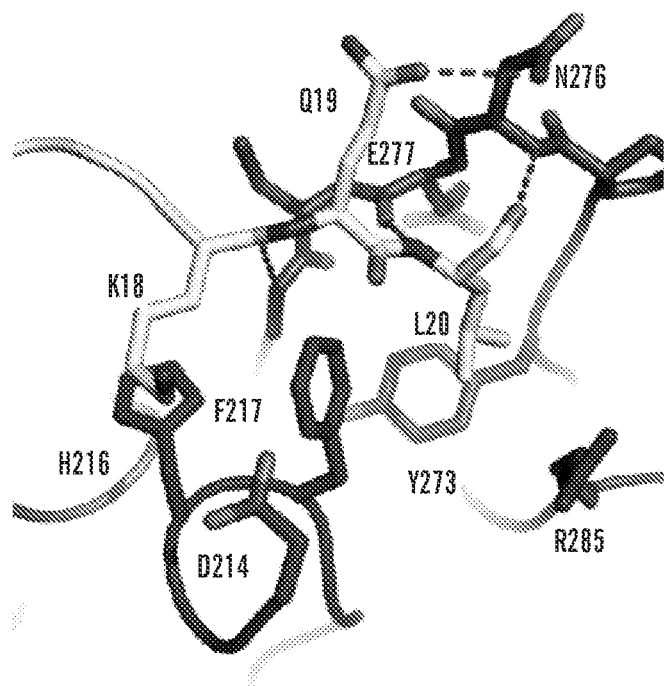
Figure 11A:
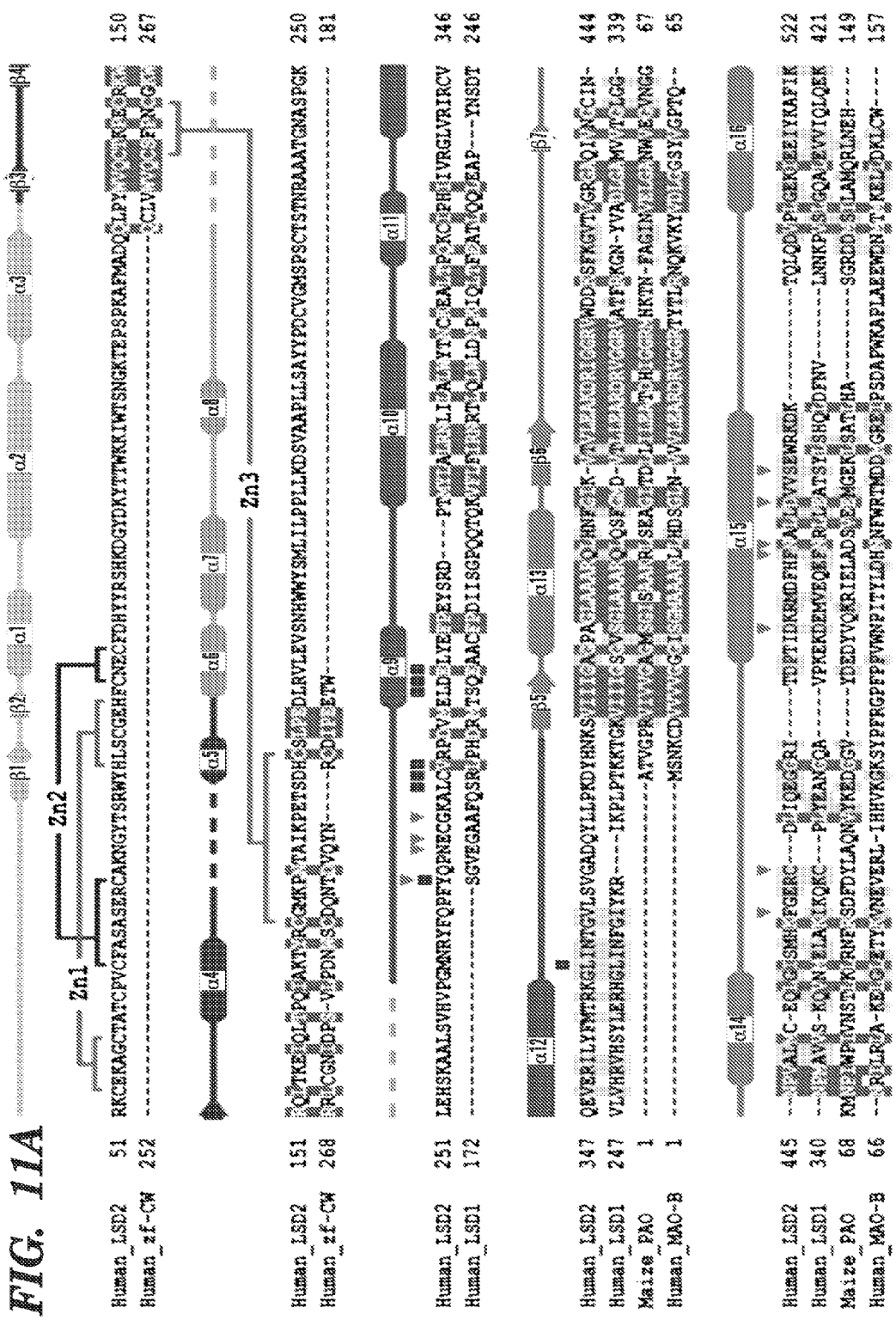
FIGS. 11A-11B depict the structure of LSD2 and residues interacting with NPAC and Histone H3.
Figure 11A:
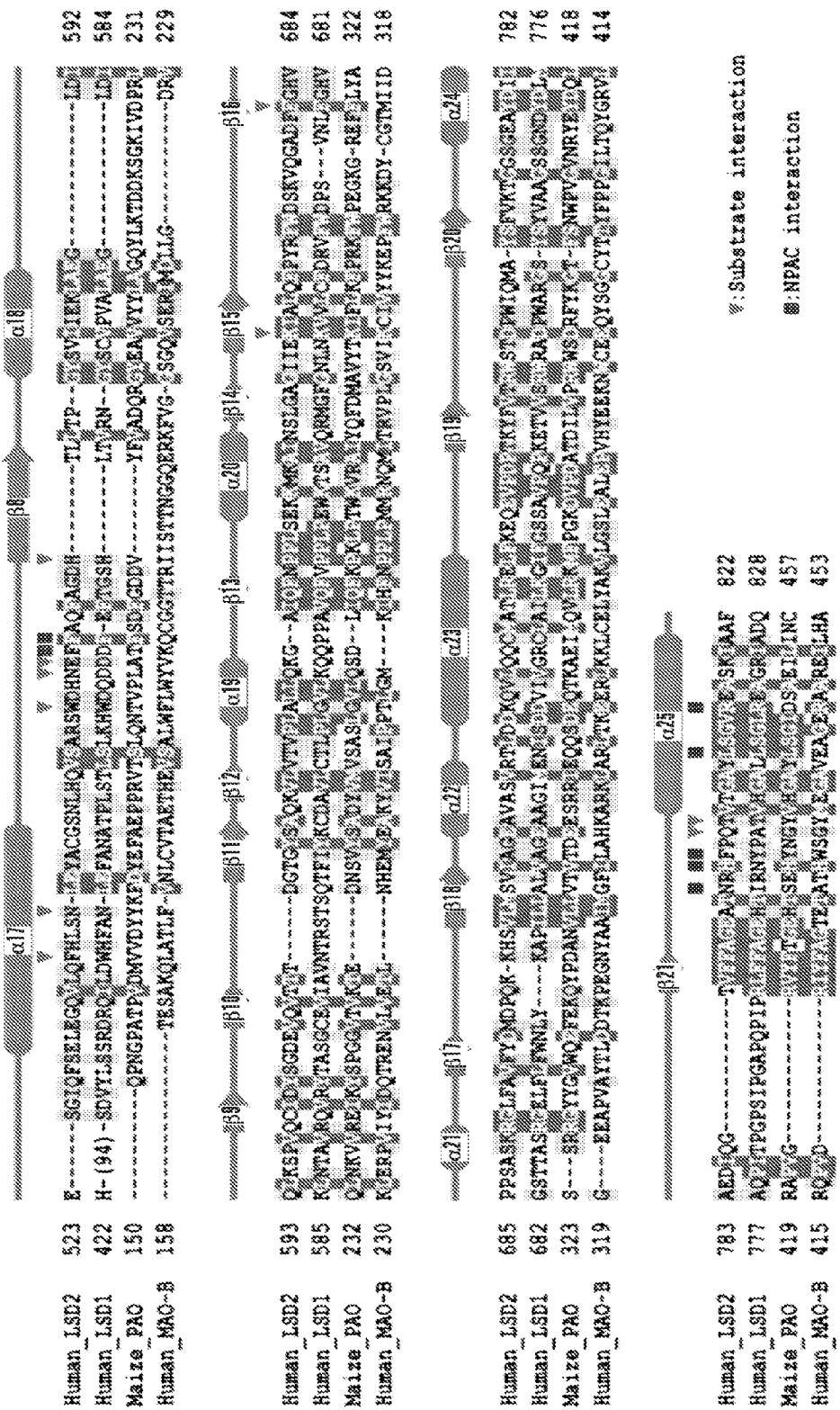
Figure 11B:
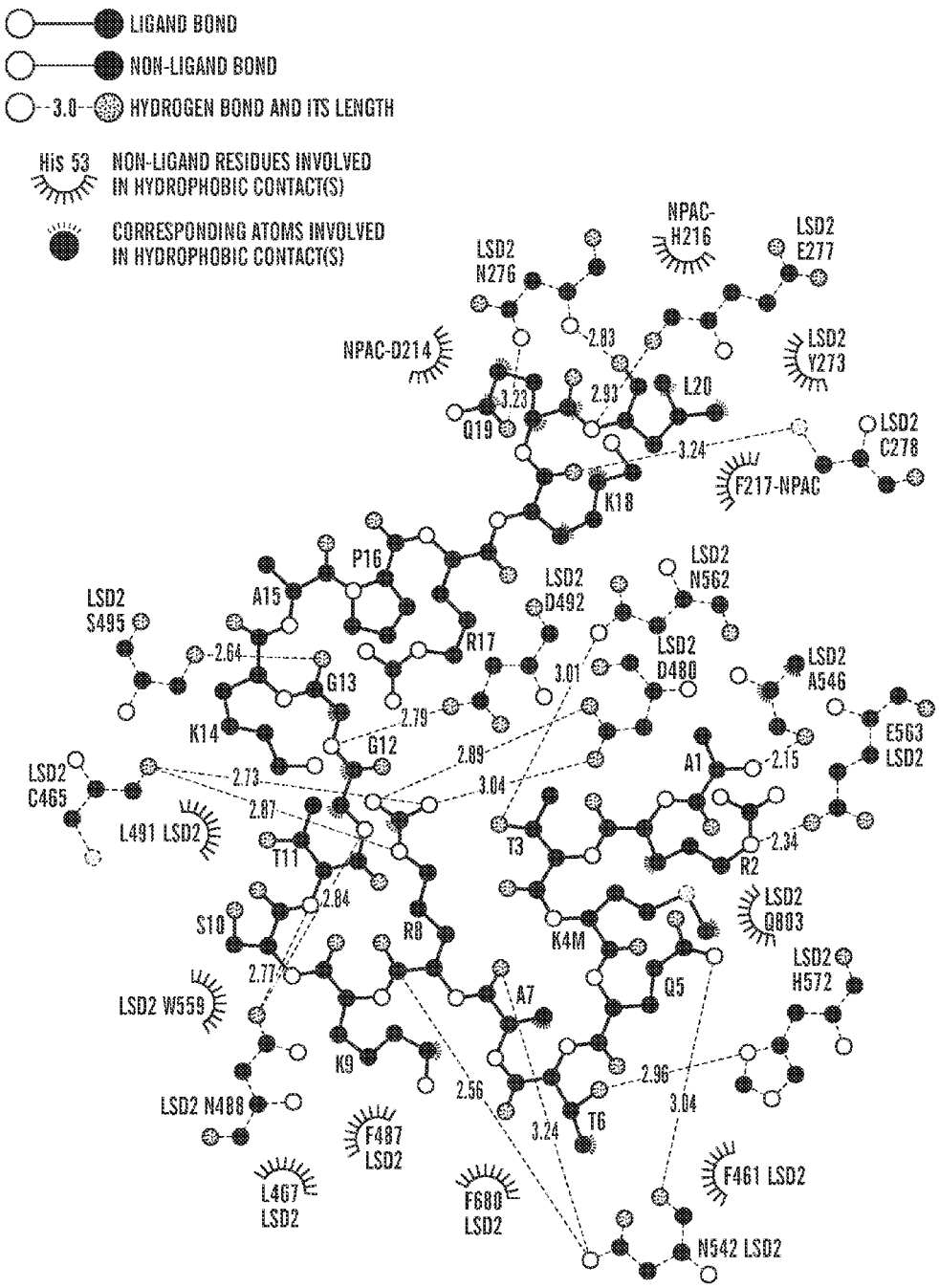

Despite similar interactions observed between the N-terminus of the H3 peptide with the catalytic cavity of LSD2 and LSD1 (FIG. 10A-10C), the co-crystal structure of the LSD2-NPAC-H3 peptide complex reveals additional, unique interactions among enzyme, cofactor and substrate (summarized in FIG. 11A-11B). A network of hydrogen bonds is formed between the main chains of K18, L20 of H3K4M peptide and G279, E277, N276 of LSD2, and between the side chains of H3Q19 and N276 of LSD2 (FIG. 6A-6B). These interactions are unique to LSD2, not observed in the co-crystal structure of LSD1, CoREST and the H3K4M peptide, in which only residues 1-16 of histone H3 are visible (Forneris et al., 2007). Without wishing to be bound by theory, we speculate that the interactions between H3 substrate and LSD2 residues in the extended loop may explain why this region is important for its enzymatic activity (FIG. 4E).

The structure of the ternary complex also reveals a unique interaction of H3 peptide with the LSD2-NPAC complex. NPAC F217, together with LSD2 residues Y273, E277 and 8285, creates a new hydrophobic patch in the LSD2-NPAC complex that accommodates the side chain of H3L20 (FIG. 6C), suggesting a stronger substrate interaction compared to LSD2 alone. In the co-crystal structure, the side chain of H3K18 is in close proximity to D214 and H216 of NPAC, suggesting potential contacts. However, the electron density of the side chain of H3K18 is poor (FIG. 8A), suggesting a flexible conformation and weak interactions involving H3K18 side chain. Taken together, these structural analyses suggest that the dodecapeptide (NPAC residues 214-225) is likely the minimal functional unit for NPAC cofactor activity. While the residues H219, F220, L221 and L222 of NPAC comprise the major binding sites for LSD2 and are responsible for LSD2 and NPAC interaction, NPAC residue F217 likely directly contributes to the cofactor activity of NPAC by stabilizing the enzyme-substrate complex.

F217 of NPAC Stabilizes Enzyme-Substrate Interaction and is Essential for Cofactor Activity.

Figure 6F:
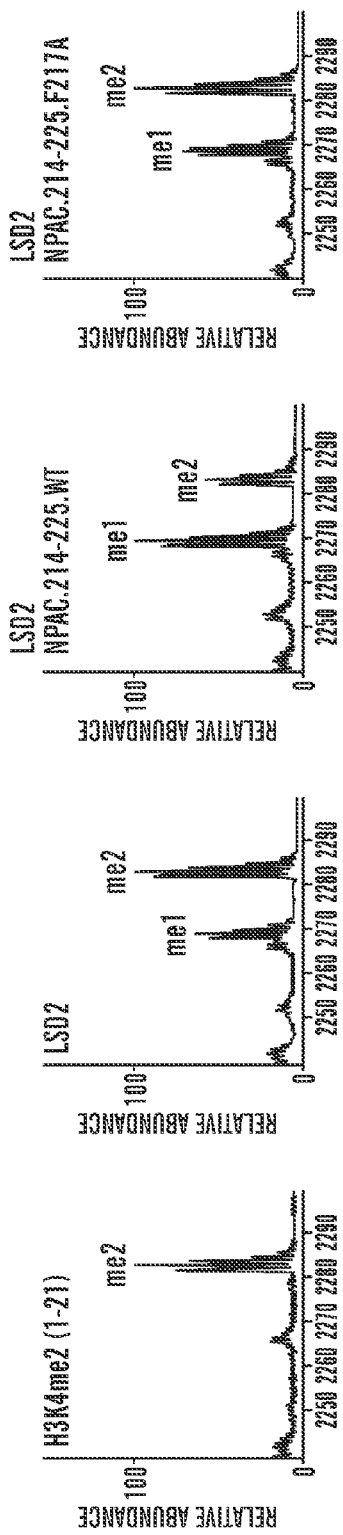

To determine if the dodecapeptide (NPAC residues 214-225) is the minimal functional unit for NPAC cofactor activity and whether F217 plays a critical role, we synthesized the wild-type and mutant dodecapeptides and examined their cofactor activities (NP.M4-6, sequences shown in FIG. 6D). As expected, wild-type NPAC peptide is sufficient to enhance LSD2 activity in nucleosome demethylation assays (FIG. 6E, comparing lane 3 to lane 2); while the F217A single mutation (NP.M6) abolishes cofactor activity (lane 6). In contrast, mutations of D214 and H216 (NP.M4 and NP.M5) have a marginal effect on cofactor activity (comparing lane 4-5 to lane 6), consistent with the structural predictions that neither residues makes important contacts with LSD2 or H3 peptide. These results were further confirmed in demethylation assays using H3K4me2 peptide substrate (residues 1-21)(FIG. 6F).

Figure 12A:
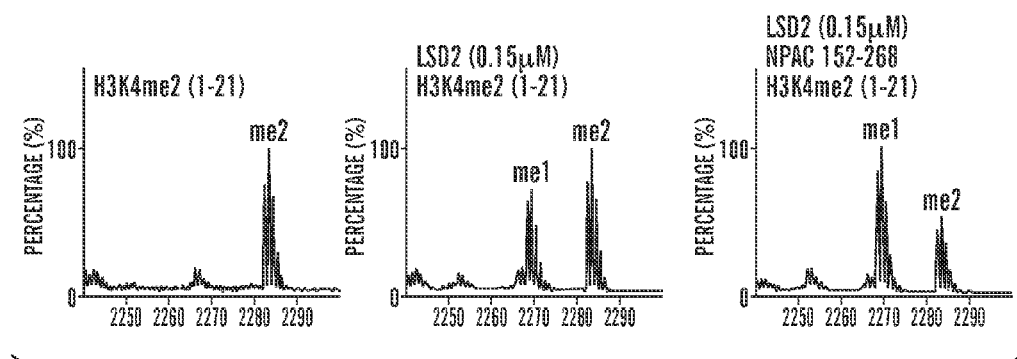
FIGS. 12A-12F depict analysis of LSD2 demethylation activity and mutational analysis.
Figure 12B:
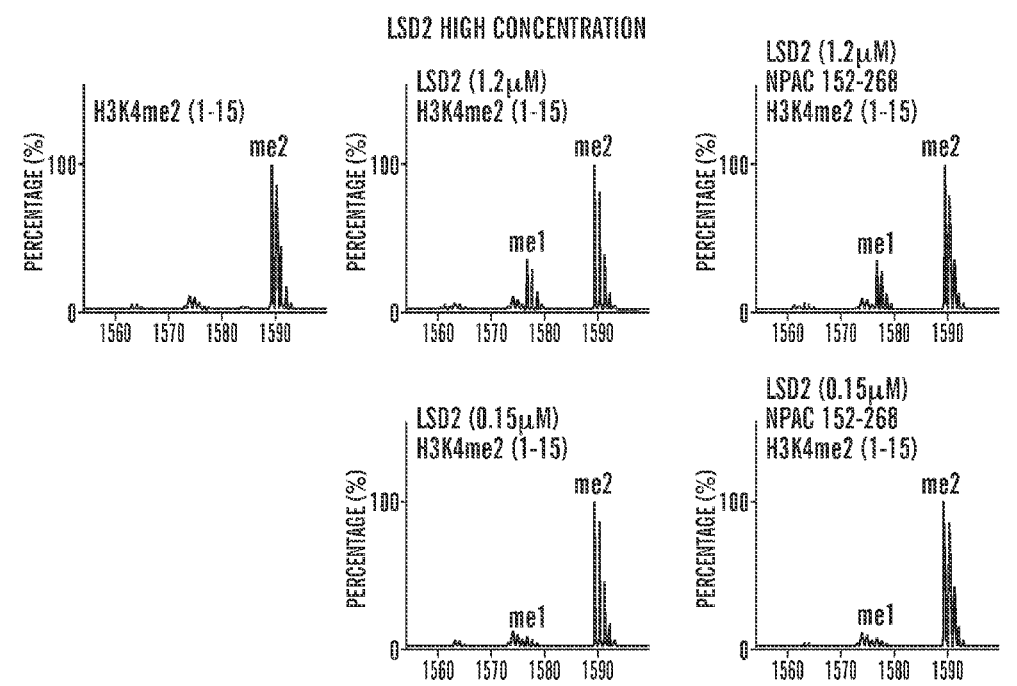

We did not detect NPAC cofactor activity when a shorter H3K4me2 peptide (residues 1-15) was used, even though weak demethylation activity of this substrate was detected using a high concentration of LSD2 (FIG. 12A-12B). The result supports our model that H3L20 is important for NPAC cofactor activity by making contact with the LSD2-NPAC complex. The significant differences between H3K4me2 peptides 1-15 and 1-21 suggest that the length of the H3 peptide may affect LSD2 enzymatic activity, thus potentially influencing NPAC cofactor activity. To investigate this further, we synthesized a longer H3K4me2 peptide (H3 residues 1-44). The longer peptide seems to be a better substrate for LSD2. Under identical conditions, LSD2 demethylated a large majority of the longer H3K4me2 peptide (1-44), producing H3K4me1 and also H3K4me0 products; while only around 30% of H3K4me2 of the short peptide (1-21) were converted to H3K4me1. These observations indicate that H3 residues 16-44 may interact with LSD2 outside its catalytic cavity, and these interactions significantly influence H3K4 demethylation efficiency. Notably, the wild-type NPAC protein can robustly stimulate LSD2 demethylation of the longer peptide (1-44), and the cofactor activity of F217A NPAC mutant was very weak or undetectable (FIG. S6C).

Figure 12C:
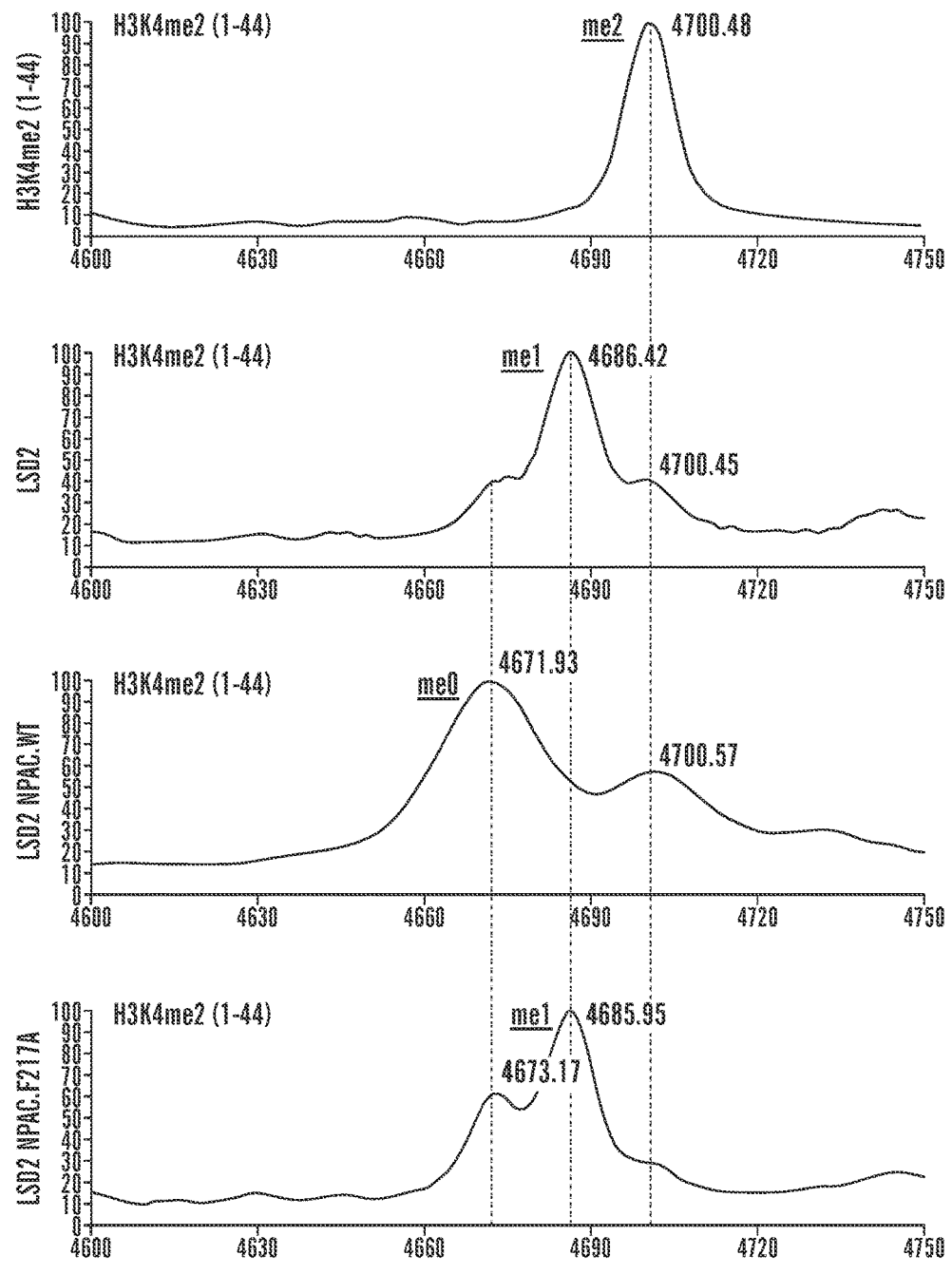
Figure 12C:
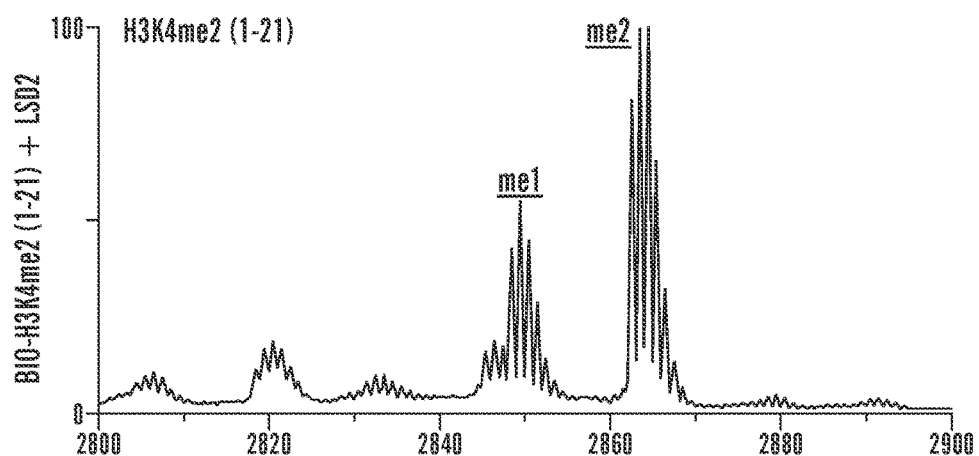
Figure 12D:
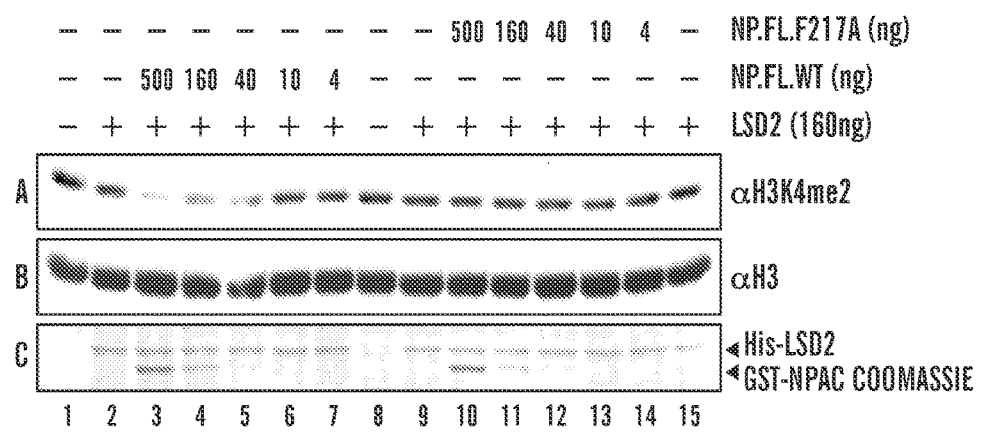
Figure 12E:
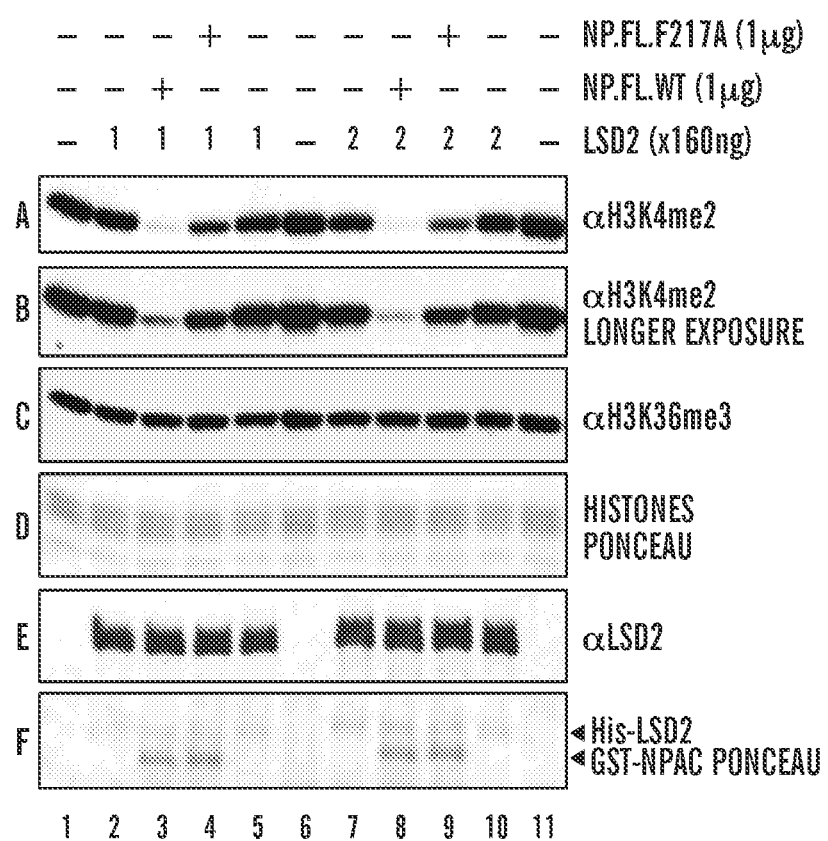
Figure 12F:
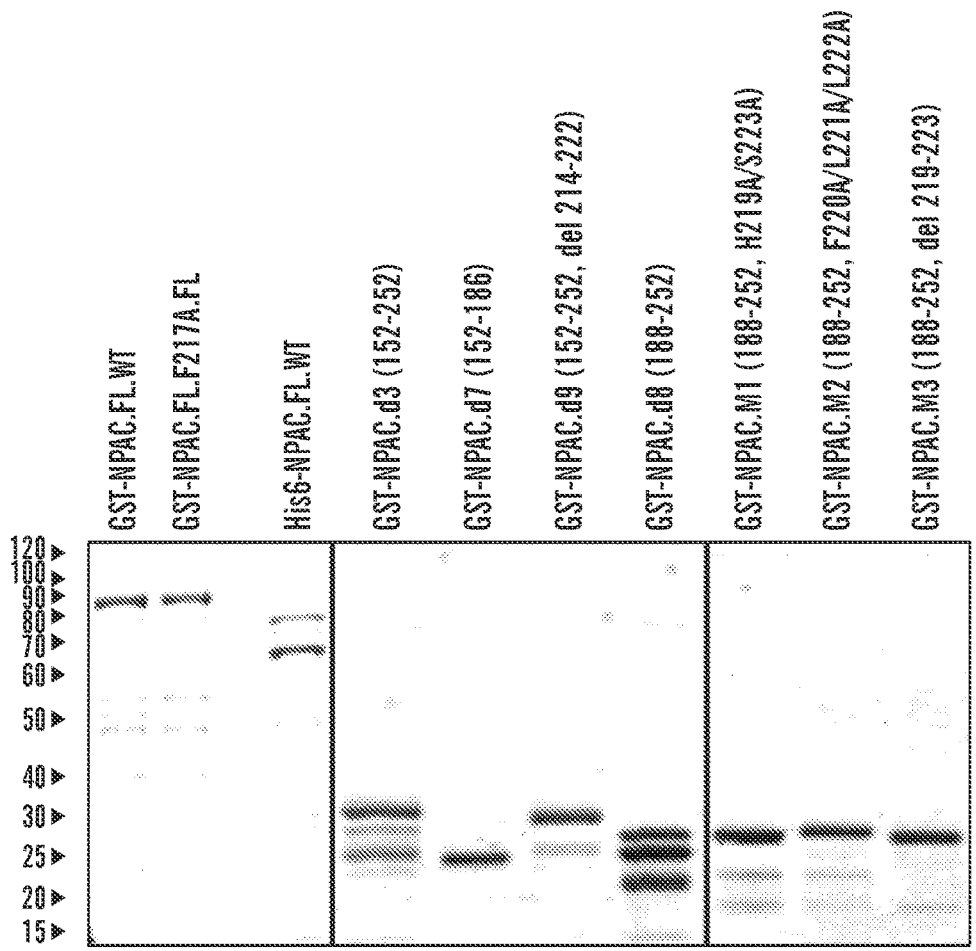

To further characterize the importance of NPAC F217 for cofactor activity, we compared full-length wild-type and F217A NPAC protein in nucleosome demethylation assays. Using a threshold amount of LSD2 where no obvious nucleosome demethylase activity was observed (FIG. 12D, lane 2 and 9), we didn't detect cofactor activity of F217A mutant, while wild-type NPAC showed robust activity (FIG. 12D, lane 10-14). However, residual stimulatory activity of full-length NPAC F217A protein was detected when more NPAC and LSD2 proteins were used (FIG. 12E, panel a, lane 4 and 9). Wild-type NPAC clearly has far superior cofactor activity than F217A mutant (FIGS. 12D and 12E panel b, comparing lanes 3 verse 4, and 8 verse 9). This demonstrates the central role of F217 in NPAC cofactor activity, and emphasizes the importance of the interactions of H3 tail along the surface of LSD2 enzyme to demethylase activity.

To investigate the functional role of NPAC F217 in its cofactor activity, we first examined the effect of F217A mutation on LSD2 binding. Isothermal Titration Calorimetry (ITC) studies showed that wild-type, F217A and D214A/H216A/F217A triple mutant peptides bind to LSD2 equally well, with a Kd of 0.92±0.08 µM, 0.93±0.07 µM and 0.99±0.08 µM, respectively (FIG. 6G and Table 4). Thus, the side chains of NPAC residues F217, D214 and H216 are not involved in LSD2 interaction, consistent with the structural predictions. Importantly, the result demonstrates that the inactivation of NPAC F217A mutant is not due to compromised LSD2 interaction.

Next we investigated the effect of wild-type and mutant NPAC dodecapeptides on LSD2-H3K4M peptide binding by ITC. Shown in FIG. 6H, H3K4M peptide has a higher affinity to the LSD2-NPAC complex (blue line) than to LSD2 alone (red line). Importantly, the F217A mutation (NP.M6) significantly diminishes the ability of NPAC to stabilize the interaction between LSD2 and the H3K4M peptide (green line). Wild-type NPAC peptide has no appreciable affinity to H3K4M peptide (cyan line). The thermodynamic features of these interactions are summarized in Table 5. Taken together, these results confirm that NPAC residue F217 directly contributes to the cofactor activity of NPAC by stabilizing the enzyme-substrate complex.

Discussion

The present study identifies NPAC/GLYR1 as a novel cofactor specific for LSD2/KDM1b histone demethylase. Structural and biochemical studies determine the minimal functional segment of NPAC (a dodecapeptide, residues 214-225) responsible for its cofactor activity. NPAC residues 219-223 interact directly with LSD2. This interaction aligns NPAC residue F217 with the hydrophobic patch on the surface of LSD2, creating a new binding pocket that accommodates the side chain of L20 on histone H3. As a result, NPAC stabilizes the interaction between LSD2 and histone H3 substrates, facilitating H3K4 demethylation.

This study thus provides a detailed molecular model precisely illustrating the mechanism of cofactor-assisted histone demethylation.

Histone demethylases may associate with transcriptional factors or chromatin binding proteins, and sometimes may themselves contain chromatin-binding modules. All of these present important mechanisms in targeting histone demethylases to specific loci, perceivably increased local enzyme concentration facilitating histone demethylation. The proposed mechanism for LSD1 cofactor CoREST fits this model (Yang et al., 2006). As a putative H3K36me3 binding protein, NPAC may also play an important role in targeting LSD2 in the human genome. However, independent of its PWWP (SEQ ID NO: 63) chromatin-binding module, a NPAC dodecapeptide (residues 214-225) shows robust cofactor activity, stimulating LSD2 demethylation of both nucleosomes and synthetic histone peptides. Thus, we show for the first time a cofactor activity independent of the targeting effect, challenging the dogma of histone demethylase regulation.

Our finding answers an intriguing question: what happens beyond tethering a histone demethylase to nucleosomes? Without wishing to be bound by theory, we propose that the interactions of H3 tail with LSD2 outside of its catalytic cavity play an important role in regulating histone demethylation efficiency. Structural and biochemical data indicate that NPAC cofactor activity is centered on residue F217 and its ability to assist LSD2 interacting with histone H3 Leu20. The effect of this single interaction on LSD2 activity is striking considering the extensive interactions already in place, particularly between histone H3 residues 1-16 and the LSD2 catalytic domain (FIG. 11B). It indicates that even weak interactions of the H3 tail along the surface of the enzyme can be important. Indeed, we observe that LSD2 prefers longer H3K4me2 peptides (FIG. 12A-12C). LSD1 is inactive to H3K4me1 peptide 1-16 but can demethylate peptides 1-21 and 1-30 with similar efficiency (Forneris et al., 2005). Thus, H3 residues 17-21 are important for LSD1 demethylase activity even though the interaction is not stable enough to be observed in the co-crystal structure (Forneris et al., 2007; Yang et al., 2006). Without wishing to be bound by theory, we speculate that stabilizing the interaction between H3 tail and histone demethylases, either by protein factors similar to NPAC or by additional histone modifications on the H3 tail, may present an important mechanism in regulating histone demethylase activity.

Though CoREST may contribute to cofactor activity through a docking mechanism, there are at least two pieces of evidence indicating additional mechanisms exist. We and others have shown that the CoREST linker region without the two SANT domains retains significant cofactor activity for LSD1 (Lee et al., 2005; Shi et al., 2005). Moreover, Forneris and colleagues showed that CoREST-bound LSD1 exhibits a 2-fold increase in catalytic rate using H3K4me2 peptide substrate (residues 1-21) (Forneris et al., 2007).

Findings described herein have significantly advanced our current understanding of cofactor-mediated regulation of histone lysine demethylases in many other aspects. Our findings indicate that the regulation of the enzymatic activity by associated cofactors is likely a general mechanism underlying the regulation of KDM function. Also, the high selectivity of cofactors for histone demethylases, with each cofactor preferentially and specifically regulating its associated KDM but not the others, may have significant biological implications by defining their specific functional loci in the genome. While the present study does not exclude the possibility that one common cofactor may work for several KDMs under certain circumstances, it is also possible that each KDM may have more than one cofactor to regulate its diverse functions in distinctive biological processes. For example, in addition to CoREST, LSD1 is regulated by several associating factors including BHC80 (Lan et al., 2007), MTA-2 (Wang et al., 2009) and nuclear receptors such as estrogen and androgen receptors (Metzger et al., 2005; Nair et al., 2010).

Of particular note, our biochemical and structural analyses described herein suggest that NPAC facilitates H3K4 specific demethylase activity of LSD2 but does not promote switching to H3K9 demethylase activity. Similar to LSD1, the co-crystal structure reveals extensive interactions between the histone H3 tail and the enzyme. The side chain of H3K4M fits nicely in the catalytic site, consistent with the robust H3K4 demethylation activity. In contrast, the side chain of H3K9 is distant from the FAD N5 atom, making LSD2 unfavorable as a potential H3K9me1/2 demethylase (FIG. 9B-9C). However, mouse LSD2 has been reported to possess H3K9 demethylase activity (van Essen et al., 2010). Thus, it remains unclear how LSD2, and arguably also LSD1, may demethylate H3K9. Binding of NPAC does not induce significant conformational changes to allow the switch of LSD2 substrate selectivity (H3K4 verse H3K9, FIG. 9A-9C). However, we do not exclude the possibility that binding of a yet unidentified cofactor to LSD2 may significantly change its conformation enabling H3K9 demethylation.

Finally, the findings from the present study have significant biological, clinical and therapeutic implications. Abrogated expression or enzymatic activity of histone demethylases has been strongly implicated in human diseases such as cancer (Chi et al., 2010; Esteller, 2008; Smith et al., 2007). Our study provides a new tool for the rational design of specific inhibitors or activators of histone demethylases based on their selective interaction with corresponding cofactors. This is significant, since most current LSD inhibitors effectively inhibit both LSD1 and LSD2 indiscriminately, not surprising given their nearly indistinguishable catalytic domains (Binda et al., 2010; Stavropoulos and Hoelz, 2007).

Experimental Procedures

Crystallization and Data Collection.

All crystals were grown using the hanging-drop vapor diffusion method. LSD2 (residues 51-822) and NPAC (residues 152-268) were used. LSD2 used for crystallization of the enzyme alone contains N-terminal extra residues (PLG-SEFKGLRRR) (SEQ ID NO: 72), while LSD2 used for other crystallization contains extra residues (GPGS) (SEQ ID NO: 73) result from 3C cleavage. The H3 peptide used for crystallization is ARTMQTARKSTGGKAPRKQLA (SEQ ID NO: 74) (H3K4M). Crystals of LSD2 alone were grown in the condition with reservoir containing 7% PEG 8000, 200 mM NaCl, 100 mM $Na_2HPO_4/KH_2PO_4$ (pH 6.0) at 18° C. The LSD2-NPAC complex was grown in the condition with buffer consisting of 10% PEG 3350, 20 mM citric acid, and 30 mM Bis-tris propane at 4° C. The LSD2-NPAC-H3K4M complex was crystallized in two forms. One belongs to space group $P2_1$ in the condition of reservoir containing 10% PEG 3350, 20 mM citric acid, and 30 mM Bis-tris propane and the other belongs to space group $P3_221$ in the condition of reservoir containing 10% PEG 3350, 100 mM $NH_4I$, 100 mM MES (pH 6.2) at 4° C. (Table 1 and Table 2). All crystals were slowly equilibrated with a cryoprotectant buffer containing reservoir buffer plus 15% glycerol (v/v) and were flash frozen in a cold nitrogen stream at −173° C. All crystals were examined on X8 Proteum system (Bruker AXS) and data sets were collected on beamline BL17U at Shanghai Synchrotron Radiation Facility (Shanghai, China). All data were processed using the program HKL2000 (Otwinowski and Minor, 1997)

Structure Determination.

The structure of LSD2 alone was determined by molecular replacement using the LSD1 structure (2V1D.PDB) as a searching model (Forneris et al., 2007) in $P2_12_12_1$ form. The crystals contain two molecules in one asymmetric unit. Rotation and translation function searches were performed with the program PHASER (McCoy et al., 2005). The structure of LSD2-NPAC and LSD2-NPAC-H3K4M were determined by difference Fourier method and the models were manually built with COOT (Emsley and Cowtan, 2004). All refinements were performed using the refinement module phenix.refine of PHENIX package (Adams et al., 2002). The model quality was checked with the PROCHECK program (Laskowski et al., 1993), which showed good stereochemistry according to the Ramachandran plot for all structures. The structure similarity search was performed with DALI Server (Holm et al., 2008) and structure superimposition was performed with COOT (Emsley and Cowtan, 2004). Even though the $Cys_4His_2Cys_2$ motif of LSD2 Zf domain (residues 51-137) resembles AN1-type zinc fingers, its structure bears little similarity to AN1-Zfs or other zinc fingers in PDB database. All structure figures were generated by PyMol (DeLano). Statistics of structure determination and refinement are summarized in Table 1 and Table 2.

Histone Demethylase Activity Assays.

Histone peptides are purchased from Millipore, or custom synthesized. The purity of all peptides are >95% as determined by HPLC and mass spectrometry. In vitro histone demethylase activity assays were performed as described (Shi et al., 2004). Briefly, purified LSD2 and NPAC derived peptides or proteins were incubated with 50 μM H3K4me2 peptides (residues 1-21) in 50 mM Tris-HCl, pH 8.5, 50 mM KCl, 5 mM $MgCl_2$, 5% glycerol at 37° C. for 30 min. The products were desalted through a C18 Ziptip (Millipore) and analyzed on a MALDI-TOF micro MX mass spectrometer (ABI 4700, Applied Biosystems). The laser intensity was kept constant for all of the samples. All MS data were processed using Data Explorer 4.5 (Applied Biosystems). Both full-length and truncational LSD2 (residues 51-822) were used for histone peptide demethylation assays and similar results were obtained.

For nucleosome demethylation assays, typically 0.5 μg full-length His-LSD2, 1 μg NPAC protein or peptides, and 2 μg nucleosomes purified from HeLa were used, and demethylation efficiency was analyzed by SDS-PAGE electrophoresis and immunoblot using methylation specific anti-histone H3 antibodies as previously described (Shi et al. 2004).

ACCESSION NUMBERS. The atomic coordinates of the structures in this work have been deposited in the Protein Data Bank with accession codes 4GU1 for LSD2, 4GUT for LSD2-NPAC, 4GUR for LSD2-NPAC-H3 (1-21) (Space Group $p2_1$) and 4GUS for LSD2-NPAC-H3(1-21) (Space Group $p3_221$).

REFERENCES

Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002). PHENIX: building new software for automated crystallographic structure determination. Acta Cryst. 58, 1948-1954.

Allis, C. D., Berger, S. L., Cote, J., Dent, S., Jenuwien, T., Kouzarides, T., Pillus, L., Reinberg, D., Shi, Y., Shiekhattar, R., et al. (2007). New nomenclature for chromatin-modifying enzymes. Cell 131, 633-636.

Bernstein, B. E., Meissner, A., and Lander, E. S. (2007). The mammalian epigenome. Cell 128, 669-681.

Bhaumik, S. R., Smith, E., and Shilatifard, A. (2007). Covalent modifications of histones during development and disease pathogenesis. Nat. Struct. Mol. Biol. 14, 1008-1016.

Binda, C., Valente, S., Romanenghi, M., Pilotto, S., Cirilli, R., Karytinos, A., Ciossani, G., Botrugno, O. A., Forneris, F., Tardugno, M., et al. (2010). Biochemical, structural, and biological evaluation of tranylcypromine derivatives as inhibitors of histone demethylases LSD1 and LSD2. J. Ame. Chem. Soc. 132, 6827-6833.

Chen, Y., Yang, Y., Wang, F., Wan, K., Yamane, K., Zhang, Y., and Lei, M. (2006a). Crystal structure of human histone lysine-specific demethylase 1 (LSD1). Proc Natl Acad Sci USA 103, 13956-13961.

Chen, Z., Zang, J., Whetstine, J., Hong, X., Davrazou, F., Kutateladze, T. G., Simpson, M., Mao, Q., Pan, C. H., Dai, S., et al. (2006b). Structural insights into histone demethylation by JMJD2 family members. Cell 125, 691-702.

Chi, P., Allis, C. D., and Wang, G. G. (2010). Covalent histone modifications—miswritten, misinterpreted and mis-erased in human cancers. Nat Rev Cancer 10, 457-469.

Chinnadurai, G. (2007). Transcriptional regulation by C-terminal binding proteins. Int. J. Biochem. Cell Biol. 39, 1593-1607.

Ciccone, D. N., Su, H., Hevi, S., Gay, F., Lei, H., Bajko, J., Xu, G., Li, E., and Chen, T. (2009). KDM1B is a histone H3K4 demethylase required to establish maternal genomic imprints. Nature 461, 415-418.

DeLano, W. L. The PyMOL Molecular Graphics System (2002). Available on the World Wide Web at pymol.org.

Dou, Y., Milne, T. A., Ruthenburg, A. J., Lee, S., Lee, J. W., Verdine, G. L., Allis, C. D., and Roeder, R. G. (2006). Regulation of MLL1 H3K4 methyltransferase activity by its core components. Nat. Struct. Mol. Biol 13, 713-719.

Egger, G., Liang, G., Aparicio, A., and Jones, P. A. (2004). Epigenetics in human disease and prospects for epigenetic therapy. Nature 429, 457-463.

Emsley, P., and Cowtan, K. (2004). Coot: model-building tools for molecular graphics. Acta Crystallogr. D Biol Crystallogr. 60, 2126-2132.

Esteller, M. (2008). Epigenetics in cancer. N. Engl. J. Med. 358, 1148-1159.

Fang, R., Barbera, A. J., Xu, Y., Rutenberg, M., Leonor, T., Bi, Q., Lan, F., Mei, P., Yuan, G. C., Lian, C., et al. (2010).

Human LSD2/KDM1b/AOF1 regulates gene transcription by modulating intragenic H3K4me2 methylation. Mol. Cell 39, 222-233.

Forneris, F., Binda, C., Adamo, A., Battaglioli, E., and Mattevi, A. (2007). Structural basis of LSD1-CoREST selectivity in histone H3 recognition. J. Biol. Chem. 282, 20070-20074.

Forneris, F., Binda, C., Vanoni, M. A., Battaglioli, E., and Mattevi, A. (2005). Human histone demethylase LSD1 reads the histone code. J. Biol. Chem. 280, 41360-41365.

He, F., Umehara, T., Saito, K., Harada, T., Watanabe, S., Yabuki, T., Kigawa, T., Takahashi, M., Kuwasako, K., Tsuda, K., et al. (2010). Structural insight into the zinc finger CW domain as a histone modification reader. Structure 18, 1127-1139.

Holm, L., Kaariainen, S., Rosenstrom, P., and Schenkel, A. (2008). Searching protein structure databases with Dali-Lite v.3. Bioinformatics 24, 2780-2781.

Horton, J. R., Upadhyay, A. K., Qi, H. H., Zhang, X., Shi, Y., and Cheng, X. (2010). Enzymatic and structural insights for substrate specificity of a family of jumonji histone lysine demethylases. Nat. Struct. Mol. Biol. 17, 38-43.

Lan, F., Collins, R. E., De Cegli, R., Alpatov, R., Horton, J. R., Shi, X., Gozani, O., Cheng, X., and Shi, Y. (2007). Recognition of unmethylated histone H3 lysine 4 links BHC80 to LSD1-mediated gene repression. Nature 448, 718-722.

Lan, F., Nottke, A. C., and Shi, Y. (2008). Mechanisms involved in the regulation of histone lysine demethylases. Curr. Opin. Cell Biol. 20, 316-325.

Laskowski, R. A., MacArthur, M. W., Moss, D. S., and Thornton, J. M. (1993). PROCHECK: a program to check the stereochemical quality of protein structures. J. Appl. Crystallogr. 26, 283-291.

Lee, M. G., Wynder, C., Cooch, N., and Shiekhattar, R. (2005). An essential role for CoREST in nucleosomal histone 3 lysine 4 demethylation. Nature 437, 432-435.

McCoy, A. J., Grosse-Kunstleve, R. W., Storoni, L. C., and Read, R. J. (2005). Likelihood-enhanced fast translation functions. Acta Crystallogr. D Biol. Crystallogr. 61, 458-464.

Metzger, E., Wissmann, M., Yin, N., Muller, J. M., Schneider, R., Peters, A. H., Gunther, T., Buettner, R., and Schule, R. (2005). LSD1 demethylates repressive histone marks to promote androgen-receptor-dependent transcription. Nature 437, 436-439.

Nair, S. S., Nair, B. C., Cortez, V., Chakravarty, D., Metzger, E., Schule, R., Brann, D. W., Tekmal, R. R., and Vadlamudi, R. K. (2010). PELP1 is a reader of histone H3 methylation that facilitates oestrogen receptor-alpha target gene activation by regulating lysine demethylase 1 specificity. EMBO Rep. 11, 438-444.

Nottke, A., Colaiacovo, M. P., and Shi, Y. (2009). Developmental roles of the histone lysine demethylases. Development 136, 879-889.

Otwinowski, Z., and Minor, W. (1997). Processing of X-ray Diffraction Data Collected in Oscillation Mode. Methods Enzymol 276, 307-326.

Rice, J. C., and Allis, C. D. (2001). Histone methylation versus histone acetylation: new insights into epigenetic regulation. Curr. Opin. Cell Biol. 13, 263-273.

Ruthenburg, A. J., Allis, C. D., and Wysocka, J. (2007). Methylation of lysine 4 on histone H3: intricacy of writing and reading a single epigenetic mark. Mol. Cell 25, 15-30.

Shi, Y. (2007). Histone lysine demethylases: emerging roles in development, physiology and disease. Nat. Rew. Genet. 8, 829-833.

Shi, Y., Lan, F., Matson, C., Mulligan, P., Whetstine, J. R., Cole, P. A., and Casero, R. A. (2004). Histone demethylation mediated by the nuclear amine oxidase homolog LSD1. Cell 119, 941-953.

Shi, Y., Sawada, J., Sui, G., Affar el, B., Whetstine, J. R., Lan, F., Ogawa, H., Luke, M. P., and Nakatani, Y. (2003). Coordinated histone modifications mediated by a CtBP co-repressor complex. Nature 422, 735-738.

Shi, Y. J., Matson, C., Lan, F., Iwase, S., Baba, T., and Shi, Y. (2005). Regulation of LSD1 Histone Demethylase Activity by Its Associated Factors. Mol. Cell 19, 857-864.

Smith, L. T., Otterson, G. A., and Plass, C. (2007). Unraveling the epigenetic code of cancer for therapy. Trends. Genet. 23, 449-456.

Southall, S. M., Wong, P. S., Odho, Z., Roe, S. M., and Wilson, J. R. (2009). Structural basis for the requirement of additional factors for MLL1 SET domain activity and recognition of epigenetic marks. Mol. Cell 33, 181-191.

Stavropoulos, P., Blobel, G., and Hoelz, A. (2006). Crystal structure and mechanism of human lysine-specific demethylase-1. Nat. Struc. Mol. Biol. 13, 626-632.

Stavropoulos, P., and Hoelz, A. (2007). Lysine-specific demethylase 1 as a potential therapeutic target. Expert Opin. Ther. Targets 11, 809-820.

Tahiliani, M., Mei, P., Fang, R., Leonor, T., Rutenberg, M., Shimizu, F., Li, J., Rao, A., and Shi, Y. (2007). The histone H3K4 demethylase SMCX links REST target genes to X-linked mental retardation. Nature 447, 601-605.

Tsukada, Y., Fang, J., Erdjument-Bromage, H., Warren, M. E., Borchers, C. H., Tempst, P., Zhang, Y. (2006) Histone demethylation by a family of JmjC domain-containing protiens. Nature 439, 811-816.

van Essen, D., Zhu, Y., and Saccani, S. (2010). A feedforward circuit controlling inducible NF-kappaB target gene activation by promoter histone demethylation. Mol. Cell 39, 750-760.

Vermeulen, M., Eberl, H. C., Matarese, F., Marks, H., Denissov, S., Butter, F., Lee, K. K., Olsen, J. V., Hyman, A. A., Stunnenberg, H. G., and Mann, M. (2010). Quantitative interaction proteomics and genome-wide profiling of epigenetic histone marks and their readers. Cell 142, 967-980.

Wang, Y., Zhang, H., Chen, Y., Sun, Y., Yang, F., Yu, W., Liang, J., Sun, L., Yang, X., Shi, L., et al. (2009). LSD1 is a subunit of the NuRD complex and targets the metastasis programs in breast cancer. Cell 138, 660-672.

Wilson, J. R. (2007). Targeting the JMJD2A histone lysine demethylase. Nat. Struc. Mol. Biol. 14, 682-684.

Xiao, B., Jing, C., Wilson, J. R., Walker, P. A., Vasisht, N., Kelly, G., Howell, S., Taylor, I. A., Blackburn, G. M., and Gamblin, S. J. (2003). Structure and catalytic mechanism of the human histone methyltransferase SETT/9. Nature 421, 652-656.

Yang, M., Gocke, C. B., Luo, X., Borek, D., Tomchick, D. R., Machius, M., Otwinowski, Z., and Yu, H. (2006). Structural basis for CoREST-dependent demethylation of nucleosomes by the human LSD1 histone demethylase. Mol. Cell 23, 377-387.

Yang, Z., Jiang, J., Stewart, D. M., Qi, S., Yamane, K., Li, J., Zhang, Y., and Wong, J. (2010). AOF1 is a histone H3K4 demethylase possessing demethylase activity-independent repression function. Cell Res. 20, 276-287.

Supplemental Experimental Procedures
Protein Purification.

cDNA of full-length human NPAC (NM_032569) were amplified from HeLa by RT-PCR. All constructs were generated using PCR-based cloning strategy and all mutants were generated using Quick-Change Site-Directed Mutagenesis Kit (Stratagene) and verified by DNA sequencing. For crystallography, the linker region of human NPAC (residues 152-268) were subcloned into a pGEX-6P-1 derivative encoding a His6 tag (SEQ ID NO: 75) upstream of a GST tag, then transformed in Escherichia coli strain BL21(DE3) and were induced for over-expression at 15° C. His6-tagged (SEQ ID NO: 75) proteins were purified by Nickel Nitrilotriacetic Acid affinity chromatography followed by 3C protease cleavage. Additional NPAC mutants and full-length protein were subcloned into pGEX-4T-1, expressed and purified from BL21(DE3) using glutathione agarose beads (Sigma-Aldrich). His6 tagged (SEQ ID NO: 75) full-length NPAC were expressed from pET-14b and purified from E. coli.

Human LSD2 (residues 51-822) was subcloned into a pFastBacl derivative encoding a His6 tag (SEQ ID NO: 75) and a 3C protease cleavage site. Recombinant LSD2 was expressed in Sf9 insect cells using the Bac-to-Bac baculoviral system (Invitrogen). LSD2 used for crystallization of the enzyme alone contains N-terminal extra residues (PLG-SEFKGLRRR) (SEQ ID NO: 72), while LSD2 used for other crystallization contain extra residues (GPGS) (SEQ ID NO: 73) result from 3C cleavage. The proteins were purified to homogeneity using anion exchange and gel filtration chromatography. The purified LSD2 were concentrated and used for crystallization and isothermal titration calorimetry (ITC). The LSD2-NPAC complex for crystallization was prepared by directly mixing equal molar LSD2 and NPAC. Full-length human LSD2 were expressed and purified as previously described (Fang et al., 2010)

Isothermal Titration Calorimetry (ITC) Binding Study.

ITC binding study was performed using ITC-200 microcalorimeter (MicroCal, GE health care), where 0.4 mM H3K4M peptide (residues 1-21) was titrated into the Calorimetric cell containing 0.029 mM LSD2 (residues 51-822) or LSD2-NPAC complex at 15° C. To study the interaction between LSD2 and NPAC peptides, 3 mM wild-type or mutant NPAC peptides (residues 214-225) was injected into the cell containing 0.2 mM LSD2 (residues 51-822). All proteins and peptides were prepared in 10 mM HEPES, pH 8.0, and 0.1 M NaCl. The data were fitted by software Origin 7.0.

Examine NPAC-LSD2 Interaction by GST-Pulldown.

5-10 m GST or GST-NPAC fusion proteins were bound to glutathione agarose, and were incubated with 2 μg full-length His-LSD2 overnight in 50 mM NaPO$_4$ pH 7.4, 150 mM NaCl, 0.5% NP-40, 5% glycerol, 10 μM ZnSO$_4$, 1 mM MgCl$_2$, 1 mM DTT, 0.1 mM PMSF at 4° C. After washed 4 times with same buffer at 4° C., glutathione agarose beads were boiled in 1×SDS sample loading buffer. Elute was resolved on a 15% SDS-PAGE gel and stained by coomassie blue.

TABLE 1

Crystallographic data and structure refinement statistics

| Crystal (PDB access number) | LSD2 (4GU1) | LSD2-NPAC (4GUT) | LSD2-NPAC-H3K4M (4GUS)[c] |
|---|---|---|---|
| Data collection | | | |
| Wavelength (Å) | 0.97947 | 0.97916 | 1.00001 |
| Resolution (Å) | 50.00-2.90 (3.00-2.90) | 50.00-2.00 (2.07-2.00) | 50.00-2.25 (2.33-2.25) |
| Space group | P2$_1$2$_1$2$_1$ | P2$_1$ | P3$_2$21 |
| Cell parameters (Å, °) | a = 89.2 | a = 62.0 | a = 101.1 |
| | b = 89.2 | b = 89.8 | b = 101.1 |
| | c = 342.5 | c = 86.7 | c = 177.4 |
| | | β = 105.0° | γ = 120.0° |
| Completeness (%) | 99.5 (98.2) | 95.2 (75.9) | 99.9 (100.0) |
| Rmerge (%) | 12.4 (67.0) | 7.6 (34.6) | 8.1 (65.3) |
| I/σ (I) | 17.4 (2.5) | 23.5 (3.6) | 24.6 (3.6) |
| Redundancy | 13.5 (8.6) | 6.8 (5.0) | 10.6 (10.6) |
| No. of all reflections | 785,997 (48,478) | 402,920 (23,610) | 548,052 (54,314) |
| No. of unique reflections | 58,222 (5,637) | 59,253 (4,722) | 51,703 (5,124) |
| Refinement statistics | | | |
| Resolution (Å)[a] | 50.00-2.90 (3.00-2.90) | 50.00-2.00 (2.07-2.00) | 50.00-2.25 (2.33-2.25) |
| Rwork/Rfree (%)[b] | 18.50/22.79 | 19.60/20.72 | 20.71/23.70 |
| Deviation from identity | | | |
| Bonds, (Å) | 0.011 | 0.011 | 0.008 |
| Angles (°) | 1.342 | 1.147 | 1.039 |
| Average B factor (Å2) | 83.438 | 39.159 | 44.413 |
| Ramachandran plot statistics | | | |
| Most favored regions (%) | 85.8 | 91.3 | 88.2 |
| Allowed regions (%) | 13.8 | 8.4 | 11.5 |
| Generously allowed regions (%) | 0.1 | 0 | 0 |
| Disallowed regions (%)[d] | 0.3 | 0.3 | 0.3 |

[a] The values for the data in the highest resolution shell are shown in parentheses.
[b] Rfree = ΣTest||Fobs| − |Fcalc||/ΣTest |Fobs|, where Test is a test set of about 5% of the total reflections randomly chosen and set aside prior to refinement for the complex.
[c] The LSD2-NPAC-H3K4M structure was also determined in the P2$_1$ crystal form, which is similar to the structure in P3$_2$21 form (Table 2 and Table 3).
[d] Residues Q803 and K75 of LSD2 lie in disallowed regions, and both residues locate at turn regions.

The main chain of LSD2 Q803 interacts with FAD and the side chain forms a hydrogen bond with the residue A546 and S768. These strong interactions together lead to a restrained conformation of Q803 of LSD2. A hydrogen bond interaction is formed between LSD2 residues A74 and G77, which possible distorts K75 and causes it to lie in a disallowed region.

TABLE 2

Crystallographic data and structure refinement statistics of the LSD2-NPAC-H3K4M structure in P2$_1$ form, related to Table 1

| Crystal | LSD2-NPAC-H3K4M (4GUR)* |
|---|---|
| Data Collection | |
| Wavelength (Å) | 0.97908 |
| Resolution (Å) | 50.00-2.50 (2.59-2.50) |
| Space group | P2$_1$ |
| Cell parameters (Å, °) | a = 62.2, b = 89.0, c = 88.8, β = 103.3° |
| Completeness (%) | 94.5 (96.9) |
| Rmerge (%) † | 7.4 (45.8) |
| I/σ (I) | 15.7 (2.5) |
| Redundancy | 3.8 (3.6) |
| No. of all reflections | 116,622 (11,286) |
| No. of unique reflections | 30,690 (3,135) |
| Refinement statistics | |
| Resolution (Å) | 50.00-2.50 (2.59-2.50) |
| Rwork/Rfree (%) | 18.79/20.45 |
| Deviation from identity | |
| Bonds, (Å) | 0.012 |
| Angles, (°) | 1.372 |
| Average B factor, (Å2) | 51.685 |

TABLE 2-continued

Crystallographic data and structure refinement statistics of the LSD2-NPAC-H3K4M structure in P2$_1$ form, related to Table 1

| Crystal | LSD2-NPAC-H3K4M (4GUR)* |
|---|---|
| Ramachandran plot statistics | |
| Most favored regions (%) | 88.1 |
| Allowed regions (%) | 11.6 |
| Generously allowed regions (%) | 0 |
| Disallowed regions (%) | 0.3 |

*We have determined two LSD2-NPAC-H3K4M structures in two crystal forms, one belongs to the P2$_1$ (2.5 Å resolution) and the other belongs to the P3$_2$21 (2.25 Å resolution, Table 1) space group. The two structures are nearly identical with a largest root mean square deviation (RMSD) of 0.321 Å for 687 Cα atoms. The major difference is that LSD2 residues 171-182 in the co-crystal structure from the P2$_1$ form were not built into the final model due to lacking electron density; while in the structure from the P3$_2$21 form, the corresponding loop region was stabilized by crystal packing and thus was built into the final model. Another difference is that residues 213-224 and residues 214-225 of NPAC were built according to the electron density in the crystal forms of P2$_1$ and P3$_2$21, respectively. Taking into consideration resolution and quality of final models, the structure from the P3$_2$21 form was used for all structural descriptions and comparisons.

TABLE 3

Summary of root-mean-squared deviation (RMSD) of structural comparisons, related to FIGS. 3 and 4.

| Structures compared | RMSD (Å) (atom number) | RMSD (Å) (Cα number) |
|---|---|---|
| LSD2 alone vs LSD2-NPAC | 1.089 (5317) | 0.915 (679) |
| LSD2-NPAC vs LSD2-NPAC-H3 | 0.634 (5350) | 0.531 (678) |
| LSD2-NPAC-H3K4 (P2$_1$ vs P3$_2$21) | 0.306 (5626) | 0.321 (687) |
| The AO domains of LSD1 and LSD2 | 2.199 (2501) | 2.055 (385) |
| The SWIRM domains of LSD1 and LSD2 | 1.089 (398) | 0.833 (58) |
| Zf-CW domains of LSD2 and ZCWPW1 | 1.954 (272) | 2.098 (41) |

TABLE 4

ITC-derived thermodynamic parameters and affinities of the binding of wild-type and mutant NPAC peptides with LSD2 [a], related to FIG. 6

| ID | 1 | 2 | 3 |
|---|---|---|---|
| Protein in the syringe [b] | NPAC.214-225.WT | NPAC.214-225.M6 (F217A) | NPAC.214-225.M8 (D214A/H216A/F217A) |
| Temperature (° C.) | 15 | 15 | 15 |
| Binding ratio | 1.06 ± 0.01 | 1.10 ± 0.01 | 1.09 ± 0.01 |
| Kd (μM) | 0.92 ± 0.08 | 0.93 ± 0.07 | 0.99 ± 0.08 |
| Δ H (cal/mol) | −8482 ± 121 | −8182 ± 97 | −8288 ± 101 |
| Δ S (cal/mol/deg) | −1.82 | −0.783 | −1.3 |

[a] ITC enthalpy plots are shown in FIG. 6G.
[b] 3 mM wild-type or mutant NPAC peptides (residues 214-225) were injected into the calorimetric cell containing 0.2 mM LSD2 for ITC binding studies.

TABLE 5

ITC-derived thermodynamic parameters and affinities of the binding of H3K4M peptide with LSD2, or LSD2 in complex with wild-type or mutant NPAC peptides [a], related to FIG. 6

| ID | 1 | 2 | 3 | 4 |
|---|---|---|---|---|
| Protein in cell [b] | NPAC214-225.WT | LSD2 | LSD2 and NPAC.214-225. WT[a] | LSD2 and NPAC.214-225.F217A |
| Concentration (mM) | 0.029 | 0.029 | 0.029/0.029 [c] | 0.029/0.029 [c] |
| Temperature (° C.) | 15 | 15 | 15 | 15 |
| Binding ratio | N.D. [d] | 1.07 ± 0.01 | 0.94 ± 0.01 | 0.86 ± 0.01 |
| Kd (μM) | N.D. [d] | 0.99 ± 0.06 | 0.68 ± 0.07 | 0.89 ± 0.06 |

TABLE 5-continued

ITC-derived thermodynamic parameters and affinities of the
binding of H3K4M peptide with LSD2, or LSD2 in complex with wild-
type or mutant NPAC peptides [a], related to FIG. 6

| ID | 1 | 2 | 3 | 4 |
|---|---|---|---|---|
| Δ H (cal/mol) | N.D. [d] | −5619 ± 45 | −1.147E4 ± 134 | −3938 ± 37 |
| Δ S (cal/mol/deg) | N.D. [d] | 7.98 | −11.6 | 14 |

Figure 6H:
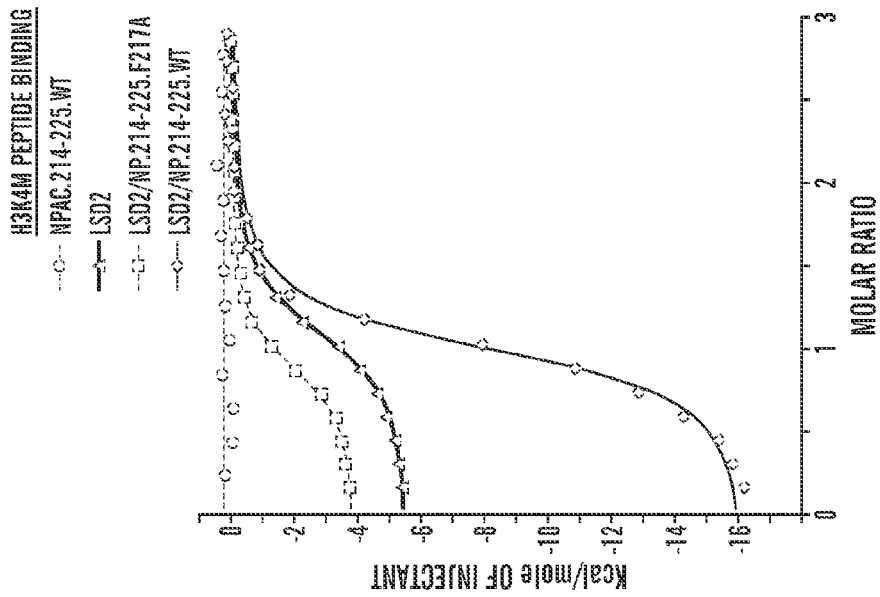
Figure 6G:
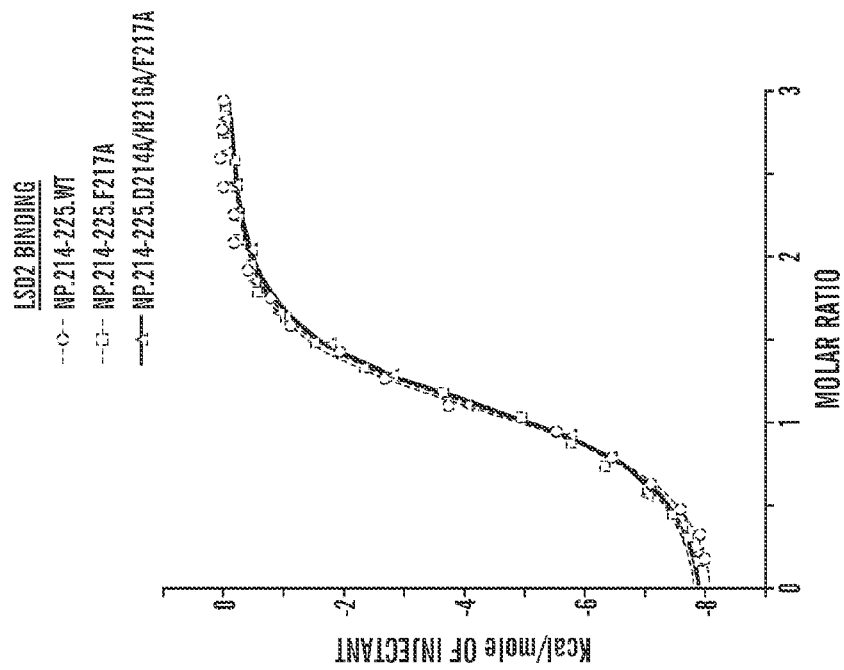

[a] ITC enthalpy plots were shown in FIG. 6H
[b] 0.4 mM H3K4M peptide in syringe was injected into the calorimetric cell containing indicated proteins and peptides for ITC binding studies.
[c] LSD2 protein and NPAC peptides were pre-mixed at 1:1 molar ratio at 0.029 mM.
[d] N.D., not detected. No binding was detected between wild-type NPAC peptide (NPAC.214-225.WT) and H3K4M peptide.

Example 2

Productive transcription of eukaryotic genes is an essential cellular process that involves RNA polymerase II (Pol II) and dynamic remodeling of nucleosomes. Increasing evidence suggests that specific histone modifications play key roles in governing this nuclear process. The histone demethylase, LSD2/KDM1b, functions in active gene transcription by maintaining a repressive epigenetic code at the gene body of actively transcribed genes. However, the molecular mechanism for specifically targeting LSD2 to these loci is unknown. Here we identify a PWWP (Pro-Trp-Trp-Pro) (SEQ ID NO: 63) domain-containing protein NPAC/GLYR1 as an integral component of the LSD2 complex that directly associates with LSD2 in vitro and genome-wide. We show that NPAC requires nucleosomal conformation for stable and specific binding to H3K36me3, and consequently directs of LSD2 to efficiently demethylate H3K4me2 at coding regions of actively transcribed genes. Interfering with components of this histone code-reader-effector regulatory pathway perturbs co-transcriptional histone modifications and results in reduced mRNA production. These results indicate that NPAC not only specifically recognizes nucleosomal H3K36me3 but also coordinates the action of the LSD2 complex to govern the co-transcriptional histone modifications at the gene body, thereby providing a new layer of epigenetic control underlying effective mRNA production in eukaryotic cells.

Introduction

The interplay and dynamics of histone modifications, including acetylation, methylation, phosphorylation, and ubiquitination, are essential for regulating the structure and diverse functions of chromatin in eukaryotes, and play important roles in cell growth, survival and differentiation, embryonic development, and their related pathologies, including oncogenic transformation (Bernstein et al., 2007; Cheung et al., 2000; Esteller, 2008; Groth et al., 2007; Khorasanizadeh, 2004; Meissner, 2010; Turner, 2002). Mono-, di- and tri-methylation of the s-amine group of lysines at different residue positions of histones are the most common yet complex histone modifications in the epigenome. Cooperating with other types of histone modifications, they control chromatin structure and function, ultimately leading to variable biological outcomes (Berger, 2007; Grewal and Rice, 2004; Kouzarides, 2002; Martin and Zhang, 2005; Ruthenburg et al., 2007; Shi, 2007). In recent years, much progress has been made in identifying the distinctive distribution of histone methylation marks across different functional elements in the genome. However, we have gained limited insight into the questions of how specific histone methylation patterns are established and maintained; and how they contribute to gene regulation and other biological processes.

Methylation of histone H3 lysine 4, tri- and di-methylation in particular, is generally considered a mark for euchromatin and gene activation. In yeast, H3K4me3 peaks at the transcriptional start sites (TSS), marking all active gene promoters. Di-methylation of H3K4 covers the coding region of actively transcribed genes, and peaks in the middle of the open reading frames (ORFs), while mono-methylated H3K4 peaks at the 3'-end of ORFs (Pokholok et al., 2005). The distribution of H3K4 methylation in mammals is similar to yeast, in term of the progressive change from tri-methylation to mono-methylation of H3K4 moving from the TSS into the coding regions of actively transcribed genes. However, in mammals, both H3K4me3 and H3K4me2 levels rapidly decrease within the coding regions, with narrower peaks of H3K4me3 compared to H3K4me2 (Barski et al., 2007; Bernstein et al., 2005; Birney et al., 2007).

In addition to H3K4 methylation, other histone modifications distinguish the coding regions and promoters of active genes in both yeast and mammals. The consensus is that histone acetylation also marks the TSS and is progressively lost, while H2B monoubiquitilation, H3K79me2/3 and H3K36me3 are enriched within the coding region (Guenther et al., 2007; Lee et al., 2007; Rando and Chang, 2009; Schones and Zhao, 2008). Notably, histone modifications decorating a promoter and the TSS are mostly absent in the coding region, and vice versa, despite the close spatial and functional link between these regions.

The mechanism underlying the establishment and maintenance of distinctive histone codes at the TSS and coding regions has been elucidated in great detail in yeast. It has been shown that histone methylation is closely linked to RNA Pol II, and is established by the step-wise recruitment of various histone methyltransferases at different stages of gene transcription (Buratowski and Kim, 2010; Hampsey and Reinberg, 2003). Meanwhile, there is an active mechanism preventing spread of the "promoter histone code" into the coding region. The HDACs-containing Set3C complex is recruited by Set3 binding to di-methylated H3K4 (Kim and Buratowski, 2009), and the Rpd3S complex is recruited downstream by Eaf3 bound to H3K36me3, together leading to hypoacetylation at coding regions (Carrozza et al., 2005; Keogh et al., 2005). Similar mechanisms are likely shared with mammals. However, given the subtle differences in the histone codes of active genes as well as the much more complicated structure of mammalian genes comparing to yeast, additional mechanisms are likely to be revealed in mammals.

We have reported that human LSD2/KDM1b/AOF1, an H3K4 specific histone demethylase, positively contributes to optimal gene transcription. LSD2 preferentially associates with the coding regions of actively transcribed genes, and maintains a repressive chromatin structure by actively demethylating H3K4 and keeping H3K9 methylation at high levels via its association with G9a histone methyltransferase (Fang et al., 2010). Other biological functions of LSD2 have been reported. In developing oocytes, mouse LSD2 is required for de novo DNA methylation of a subset of maternally imprinted genes (Ciccone et al., 2009). In mouse dendritic cells, LSD2 is important for the activation of NF-κB target genes, functioning as an H3K9me2 demethylase recruited to gene promoters by NF-κB (van Essen et al., 2010). The various roles of LSD2 in gene transcription are likely a consequence of the distinctive regulatory elements that it associates with under different cellular and gene context. Thus, how LSD2 is targeted to specific loci is a fundamental yet unresolved question that is absolutely essential for understanding its diverse biological functions that have not been fully characterized.

Here we report that NPAC/GLYR1/NP60 is an integral component of the LSD2 complex, directly interacting with LSD2. We demonstrate for the first time that NPAC is a bonafide reader of H3K36me3 that requires a nucleosomal context for its function. ChIP-chip analysis and in vivo studies indicate that NPAC is responsible for targeting LSD2 to H3K36me3 enriched coding regions to modulate active gene transcription. Thus, the close partnership between histone code reader NPAC and epigenetic modifier LSD2 not only defines the functional landscape of the H3K4me2 demethylase activity, but also the dynamic interplay of histone modifications after elongating Pol II.

Results

NPAC is a Specific Component of the LSD2 Complex, Directly Interacting with LSD2.

Figure 13A:
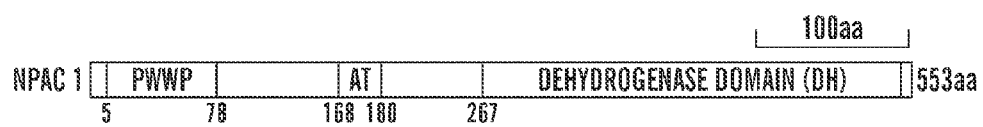
FIGS. 13A-13G demonstrate that NPAC is a multi-domain protein that interacts with LSD2 and nucleosomes.

We have reported the LSD2-containing complex with a protein composition that is strikingly different from the LSD1 complex (Fang et al., 2010). Given the correlation of LSD2 binding and H3K36me3 at the coding region of actively transcribed genes, we were interested to investigate the function of potential H3K36me3 readers in targeting LSD2 to its specific functional loci. Three putative H3K36me3 readers—NSD3 H3K36 methyltransferase, DNA mismatch repair protein MSH6 and NPAC were identified in the LSD2 complex (Fang et al., 2010). Of particular interest is NPAC, a largely uncharacterized protein of 553 amino acids (also named NP60, n-PAC, GLYR1, protein ID: Q49A26) (Fu et al., 2006). The NPAC sequence revealed several functional domains, including a PWWP (Pro-Trp-Trp-Pro) (SEQ ID NO: 63) domain, an AT-hook motif, and an NAD-binding dehydrogenase domain (DH) that belongs to the dehydrogenase family of 3-hydroxyisobutyrate and related beta-hydroxyacids dehydrogenases (FIG. 13A).

Figure 13B:
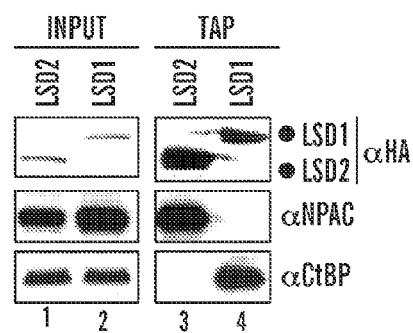
Figure 13C:
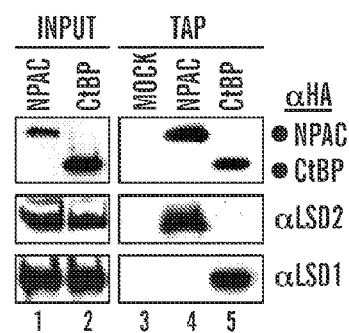
Figure 13D:
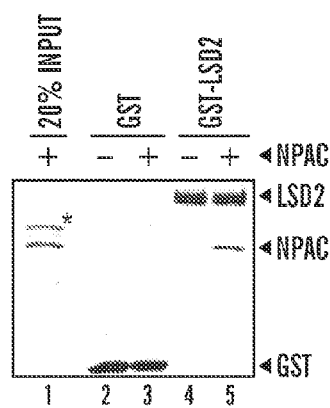

Immunoblot analyses of the LSD2 and LSD1 complexes purified using identical procedures indicate that NPAC is specifically associated with the LSD2 complex; whereas CtBP, a well known corepressor and component of the LSD1 complex, is not presented in the LSD2 complex (FIG. 13B). Likewise, endogenous LSD2 was detected in tandem affinity purified (TAP) NPAC complex, but not in the CtBP complex, and endogenous LSD1 was detected in the CtBP complex, but not the NPAC complex (FIG. 13C). Furthermore, we detected a direct interaction between LSD2 and NPAC through GST pulldown experiments using recombinant purified GST-LSD2 and His-NPAC proteins (FIG. 13D). These results indicate that LSD2 and NPAC specifically and directly interact with each other and are both integral to a complex distinct from that of LSD1.

NPAC is a Nucleosome-Binding Protein Recruiting LSD2 to Chromosomes.

Figure 13E:
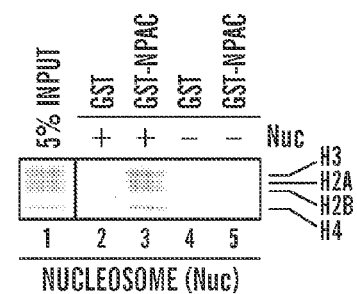

Determining how histone demethylases are specifically targeted to their functional sites is a key step in understanding their biological function and mechanism of action. Having demonstrated that NPAC directly interacts with LSD2, we next investigated whether NPAC is a nucleosome-binding protein that can bridge the association of LSD2 and nucleosomes, and hence promote LSD2 binding to chromatin in cells. We first investigated NPAC chromatin-association in vivo Immunofluorescence staining of either endogenous or ectopically expressed FLAG-HA tagged NPAC both indicate that NPAC is a nuclear protein associated with chromatin at all stages of the cell cycle (FIG. 18A and data not shown). Consistent with the tight NPAC-chromatin association observed during cell division, NPAC mostly associates with the nuclear pellet after salt extraction (data not shown). However, NPAC can be released into solution by micrococcal nuclease digestion, concomitant with the release of nucleosomes (FIG. 18B). Furthermore, in vitro GST pulldown assays show that NPAC binds strongly with purified nucleosomes (FIG. 13E). Thus, these studies validate NPAC as a chromatin-associated factor that stably associates with nucleosomes in vivo and in vitro.

Figure 13F:
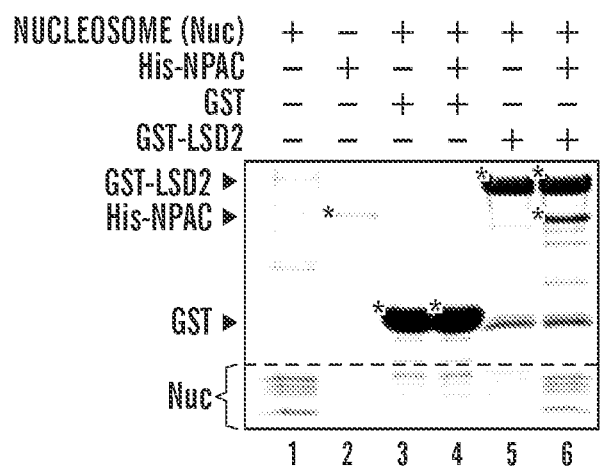
Figure 13G:
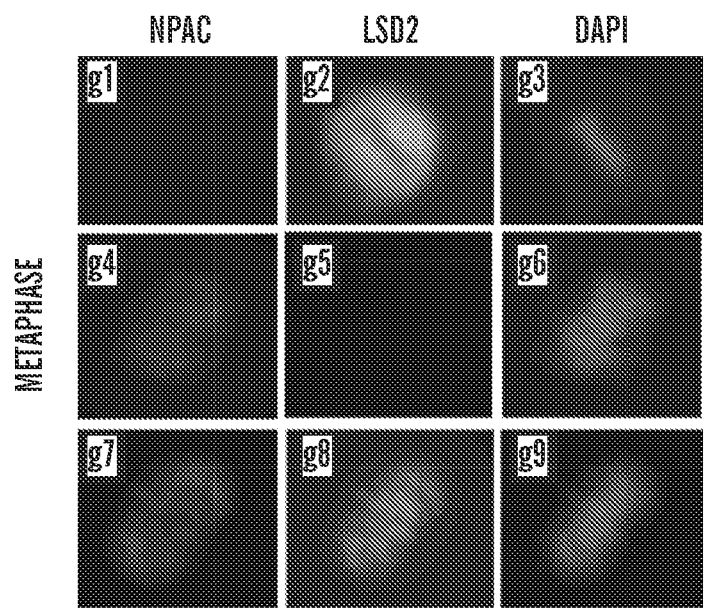

We next examined if NPAC, LSD2 and nucleosomes form stable complexes in vitro. GST pulldown analyses show that while LSD2 alone does not stably associate with nucleosomes (FIG. 13F, lane 5), GST-LSD2 is able to pull down nucleosomes in the presence of recombinant NPAC (FIG. 13F, lane 6). The result from in vitro assays was further validated in cells. GFP-LSD2 expressed alone exhibits a diffuse distribution at metaphase and is mostly excluded from the condensed chromosomes (FIG. 13G: g1-3). In comparison, NPAC alone localizes exclusively to chromatin (FIG. 13G: g4-6). After coexpression with NPAC, GFP-LSD2 is observed decorating mitotic chromatin (FIG. 13G: g7-9), in stark contrast to the diffuse staining of GFP-LSD2 alone during mitosis (FIG. 13G: g1-3). Collectively, these data indicates that NPAC is able to directly bind to both LSD2 and nucleosomes, therefore target LSD2 to nucleosomes and chromosomes in vitro and in vivo.

The Specific Recognition of H3K36Me3 by the NPAC PWWP (SEQ ID NO: 63) Domain Requires Nucleosomal Conformation.

The PWWP (SEQ ID NO: 63) domains of several chromatin-associating proteins have been reported to recognize specific histone modifications (Dhayalan et al., 2010; Vezzoli et al., 2010; Wu et al., 2011). Using a highly sensitive proteomic technique, SILAC, Vermeulen and colleagues identified NPAC as a putative H3K36me3 reader (Vermeulen et al., 2010). However, the selective binding of NPAC to H3K36me3 was not fully characterized. In fact, we failed to detect selective NPAC binding to histone peptides bearing H3K36me3 or other modifications using either GST-pulldown or Isothermal Titration Calorimetry (ITC) (data not shown). This may be due to limitations of these techniques in detecting low affinity interactions. However, given the close proximity of H3K36 to the nucleosome core (Luger et al., 1997), it is also plausible that NPAC requires a nucleosomal conformation for optimal binding of the histone modification (Levy and Gozani, 2010).

Figure 14A:
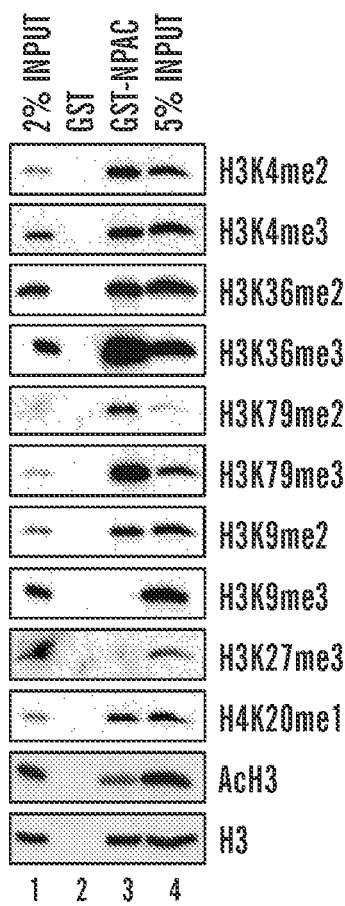

To test this, we first examined whether NPAC could selectively bind to H3K36me3 or other modification-enriched nucleosomes. We used GST-NPAC to pull down nucleosomes purified from HeLa cells and examined the specific histone modifications of bound nucleosomes. Nucleosomes associated with NPAC were significantly enriched in H3K36me3 and H3K79me3/2 marks, while H3K4me2 appeared to be slightly enriched (FIG. 14A). In contrast, H3K9me3 and H3K27me3, both heterochromatin marks, were markedly depleted. Interestingly, acetylated nucleosomes also seem to be depleted from NPAC-associating nucleosomes. Other modifications examined, including H3K4me3, H3K36me2, H3K9me2 and H4K20me1, did not show obvious enrichment or depletion in the NPAC-associated nucleosomes. Taken together, these results indicate that NPAC can recognize a specific histone code in vitro in the nucleosomal context, preferentially binding to H3K36me3 and perhaps H3K79me3.

To identify the functional domain required for NPAC-nucleosome interaction, we examined a panel of NPAC truncation proteins for nucleosome binding (FIG. 14B). NPAC.d1 (residues 1-150) and NPAC.d2 (residues 1-250) both showed strong binding to nucleosomes (FIG. 14B, lane 3 and 4), comparable to full-length NPAC (lane 2). NPAC.d3 (residue 81-553) and NPAC.d4 (residue 181-553), which remove the PWWP (SEQ ID NO: 63) domain alone or together with the AT-hook motif, both abolish the ability to interact with nucleosomes. Thus, the N-terminal region of NPAC, residues 1-150 containing the PWWP (SEQ ID NO: 63) domain, is sufficient for nucleosome interaction; while both the AT hook and dehydrogenase domains of NPAC are not required.

Figure 14C:
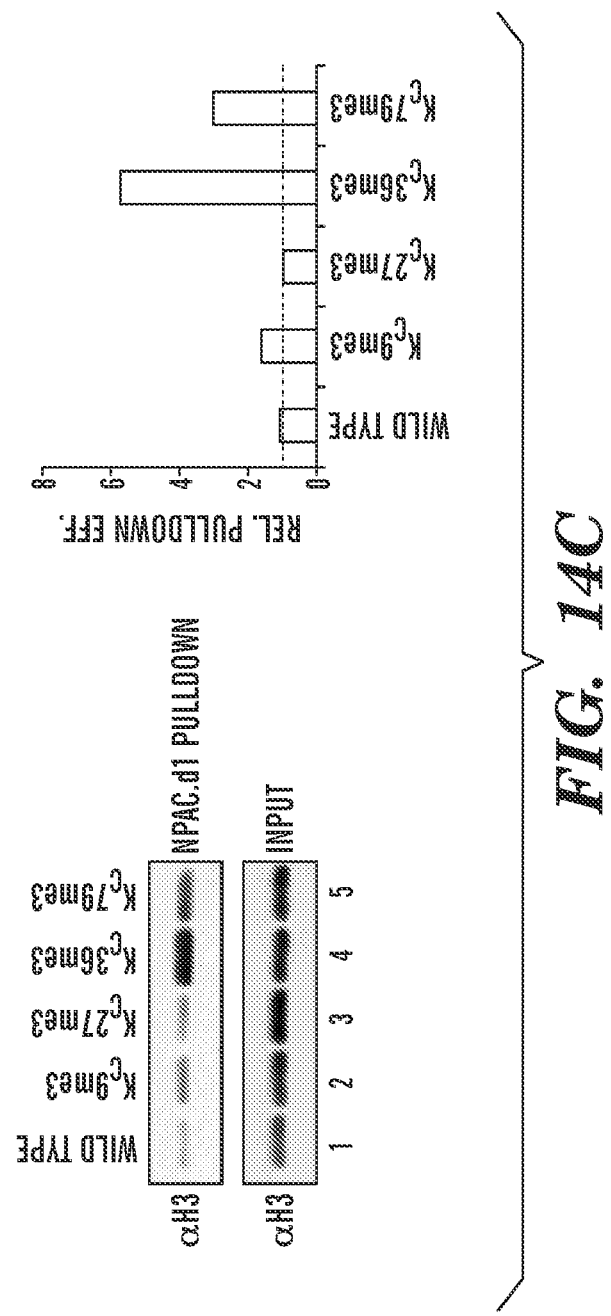

We next examined whether NPAC.d1 is sufficient to mediate modification-specific interaction with nucleosomes. We generated recombinant nucleosomes with site-specific methylation using Methyl-Lysine Analog (MLA) technology (Simon et al., 2007). We examined $H3K_c36me3$, $H3K_c79me3$, $H3K_c9me3$ or $H3K_c27me3$ MLA nucleosomes ($K_c$ indicates the lysine analogue), representing the most enriched (H3K36me3, H3K79me3) or most depleted (H3K9me3, H3K27me3) histone modifications in NPAC precipitated nucleosomes. NPAC.d1 consistently shows the highest binding affinity for $H3K_c36me3$ nucleosomes over $H3K_c79me3$, though the latter shows higher affinity than unmodified nucleosomes or nucleosomes modified with $H3K_c9me3$ or $H3K_c27me3$ (FIG. 14C).

Together, these data establish the PWWP domain of NPAC as an H3K36me3 specific histone code reader in the context of nucleosomes. Furthermore, the stable and selective interaction of NPAC with nucleosomal H3K36me3, not observed with modified histone peptides, suggests that a stable interaction with nucleosome may require NPAC binding to both modified histones and DNA. The interaction of NPAC with DNA may in turn, strengthen the specific binding of H3K36me3 by NPAC.

DNA Binding Ability of the NPAC PWWP (SEQ ID NO: 63) Domain is Required for NPAC-Nucleosome Interaction.

Figure 15D:
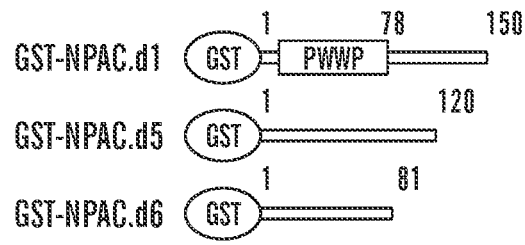
Figure 19A:
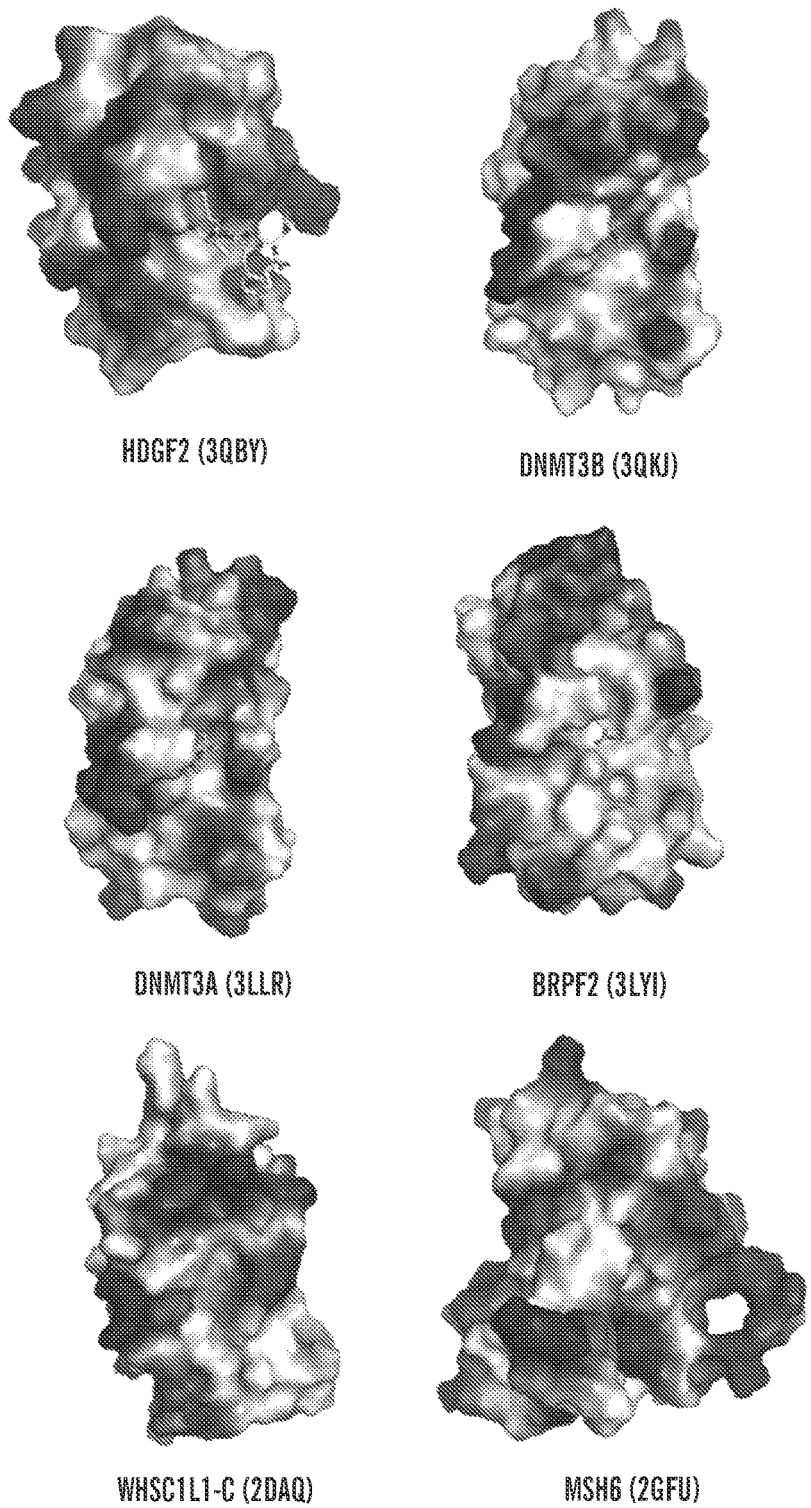
FIGS. 19A-19C demonstrate structures and DNA/nucleosome binding of various PWWP domains (SEQ ID NO: 63).

PWWP (SEQ ID NO: 63) domain-containing proteins have also been reported to bind DNA (Lukasik et al., 2006; Qiu et al., 2002). The secondary structure of the NPAC PWWP (SEQ ID NO: 63) domain is predicted to be composed of four β-strands and two α-helixes (FIG. 15A). We made a 3D structure model for the NPAC PWWP (SEQ ID NO: 63) domain based on the crystal structure of human DNMT3B (Wu et al., 2011) using the FFAS server (Jaroszewski et al., 2011). The simulated structure shows that the NPAC PWWP (SEQ ID NO: 63) domain harbors an aromatic cage formed by Y19, W22, F46 and L16. Presumably, NPAC employs this aromatic cage to bind the tri-methyl lysine of H3K36me3 (FIG. 15B), like other Royal family members (Adams-Cioaba and Min, 2009; Taverna et al., 2007). Many positively charged residues in the putative PWWP (SEQ ID NO: 63) domain of NPAC are predicted to be solvent exposed and an elongated positively charged surface is formed adjacent to the H3K36me3 binding pocket, similar to the PWWP (SEQ ID NO: 63) domains of HDGF and DNMT3b (Lukasik et al., 2006; Qiu et al., 2002; Yang and Everett, 2007). In both proteins, the PWWP domains non-specifically make multiple, extensive contacts with negatively charged DNA. Similar positively charged surfaces are identified in nearly all reported PWWP (SEQ ID NO: 63) structures (FIG. 19A). Collectively, the structural model predicts that the NPAC PWWP (SEQ ID NO: 63) domain is capable of binding to H3K36me3, at the same time, also interacting with nucleosomal DNA.

Figure 15E:
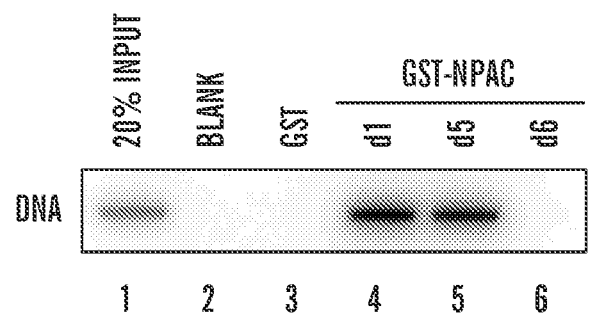
Figure 15F:
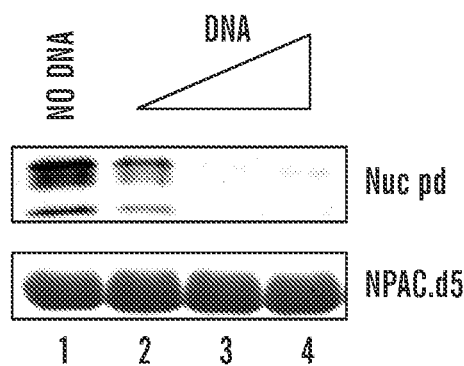
Figure 19B:
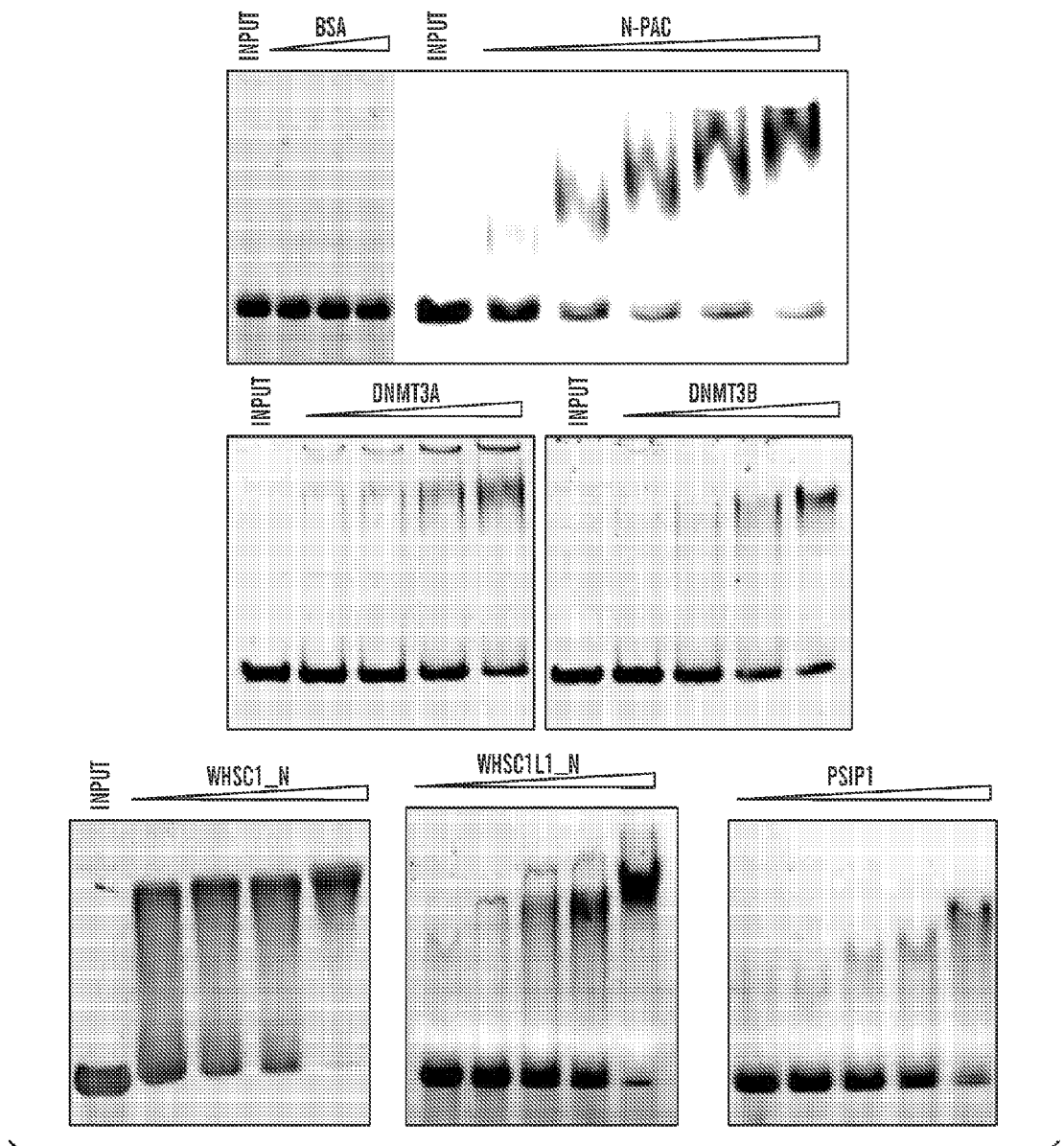

To validate this model, we designed two additional truncation proteins of NPAC (schematics shown in FIG. 15D) and tested their DNA binding ability by GST-pulldown. As expected, NPAC.d1 can bind to double strand DNA (FIG. 15E, lane 4). NPAC.d5 (residues 1-120) removes a significant portion of the unstructured, positively charged tail in NPAC.d1, but still pulls down DNA nearly as efficiently as NPAC.d1 (FIG. 15E, lane 5). In contrast, NPAC.d6 (residues 1-81) is unable to interact with DNA (FIG. 15E, lane 6). NPAC.d6 (residues 1-81) deletes a portion of the α2-helix of the PWWP (SEQ ID NO: 63) domain, thus likely disrupts the correct folding of the PWWP (SEQ ID NO: 63) domain as suggested by the predicted structure. Taken together, these data suggest that the PWWP (SEQ ID NO: 63) domain of NPAC is capable of binding DNA and the intact PWWP (SEQ ID NO: 63) domain is required for efficient DNA binding. Additionally, we detected DNA binding of several putative and confirmed H3K36me3 readers (FIG. 19B), suggesting that nucleosomal DNA binding is likely a common feature of the PWWP-domain (SEQ ID NO: 63) containing H3K36me3 readers.

Figure 19C:
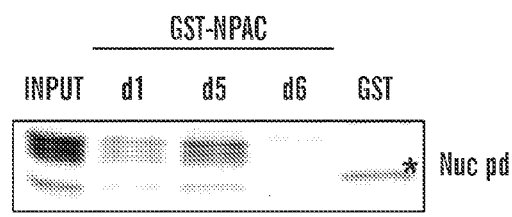

To investigate the importance of DNA binding to NPAC-nucleosome interaction, we tested whether free DNA can competitively block the interaction between NPAC and nucleosomes. In GST-pulldown experiments, NPAC.d6, which is unable to bind DNA, also failed to interact with nucleosomes; while NPAC.d5 can readily do so (FIG. 19C). Addition of increasing amount of double strand DNA compromised the nucleosome binding ability of NPAC.d5 in a dose dependent manner (FIG. 15E).

The competition assay suggests that DNA binding is important for the stable interaction of the NPAC PWWP (SEQ ID NO: 63) domain and nucleosomes. Furthermore, these observations support our model that both nucleosomal DNA and H3K36me3 may synergistically contribute to the stable and selective interaction between NPAC and the modified nucleosome, thus providing a plausible explanation for why the PWWP (SEQ ID NO: 63) domain requires a nucleosomal context for efficient and specific interaction with H3K36me3.

The Genome-Wide Binding of NPAC Correlates with LSD2 and H3K36Me3.

Figure 16A:
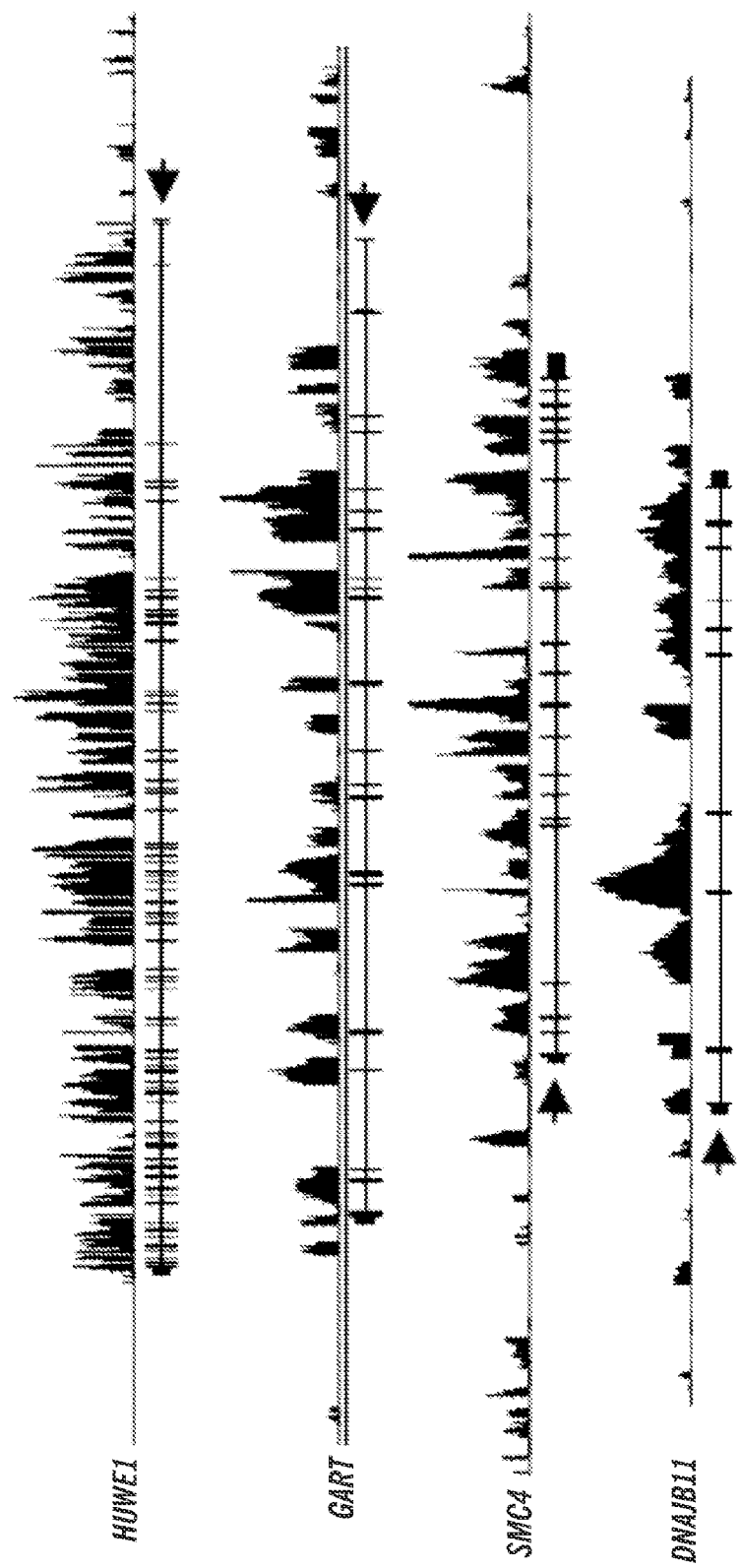
FIGS. 16A-16H demonstrate that NPAC is enriched within the coding regions of active genes, correlating with the genome-wide distribution of LSD2 and H3K36me3.
Figure 16B:
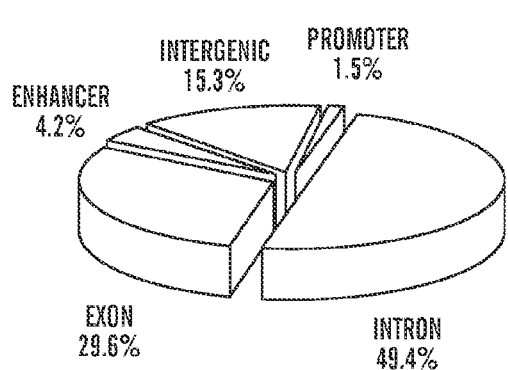
Figure 16C:
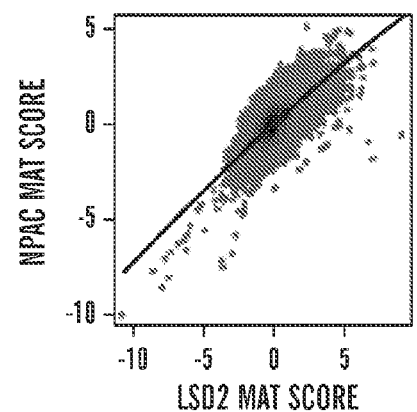
Figure 20A:
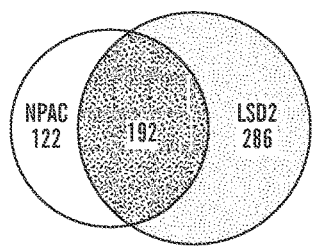
FIGS. 20A-20D demonstrate that NPAC binding colocalizes with LSD2 and H3K36me3, but its distribution differs from that of H3K79me3 and H3K4me2.

The ability of NPAC to interact with LSD2 and nucleosomal H3K36me3 indicates that NPAC may target LSD2 to loci that are enriched with H3K36me3 modifications in vivo. To test this hypothesis, we examined the genome-wide profile of NPAC binding on human chromosomes 3, 21, 22 and X using ChIP-chip analysis as previously carried out for LSD2 (Fang et al., 2010). More than 500 peaks (P<0.0001) were identified using the MAT algorithm (Model-based Analysis of Tiling-array) (Johnson et al., 2006). Notably, we observed that the majority of NPAC peaks are associated with coding regions, downstream of the transcription start sites (TSS) (FIG. 16A). Statistical analysis of the global distribution of NPAC-associated peaks revealed that NPAC chromatin binding is indeed enriched at coding regions, with 29.6% of NPAC located at exons and 49.4% located within introns (FIG. 16B). In comparison, exons and introns account for 1.7% and 39.8%, respectively, of the genome present on the tiling array. The enrichment of NPAC at exons and introns is highly significant, both with p values <$10^{-27}$. A small percentage of NPAC was found at gene promoters and enhancers (1.5% and 4.2%, respectively), while 15.3% of NPAC is located within distal intergenic regions. NPAC peaks were associated with 326 genes on the array, 192 (61%) of which are also known LSD2 targets (FIG. 20A). In addition, the genome-wide correlation of NPAC and LSD2 is 0.68, indicating that NPAC and LSD2 are tightly associated in vivo (FIG. 16C).

Figure 16D:
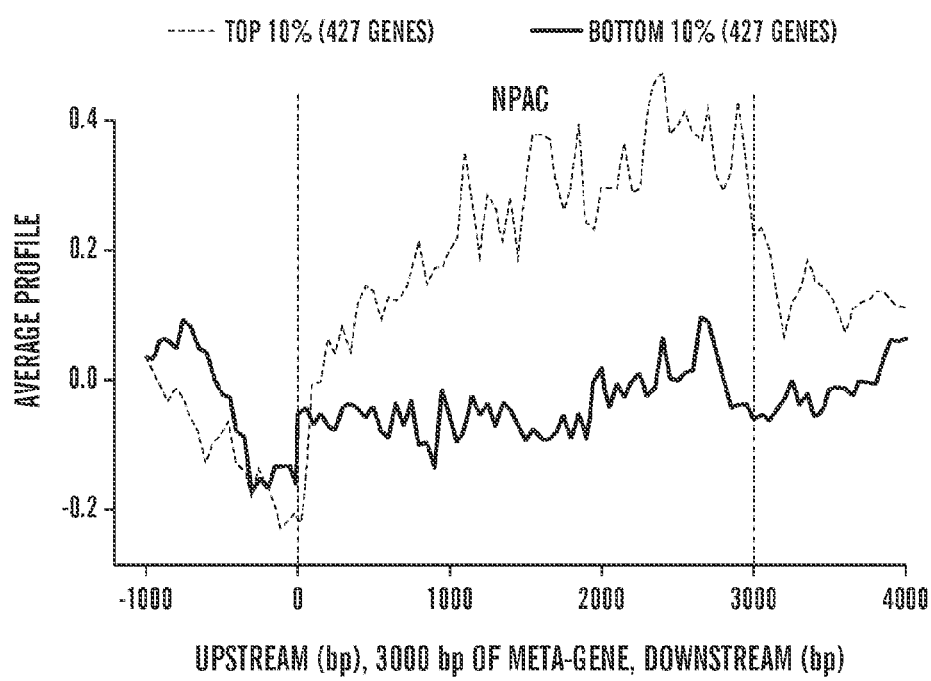
Figure 16E:
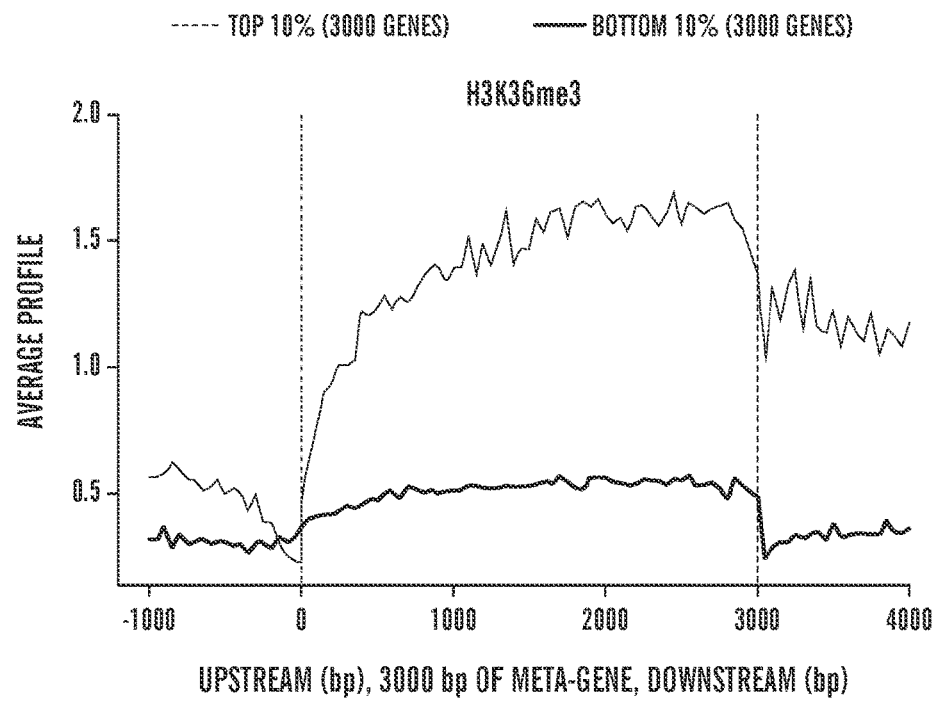
Figure 20B:
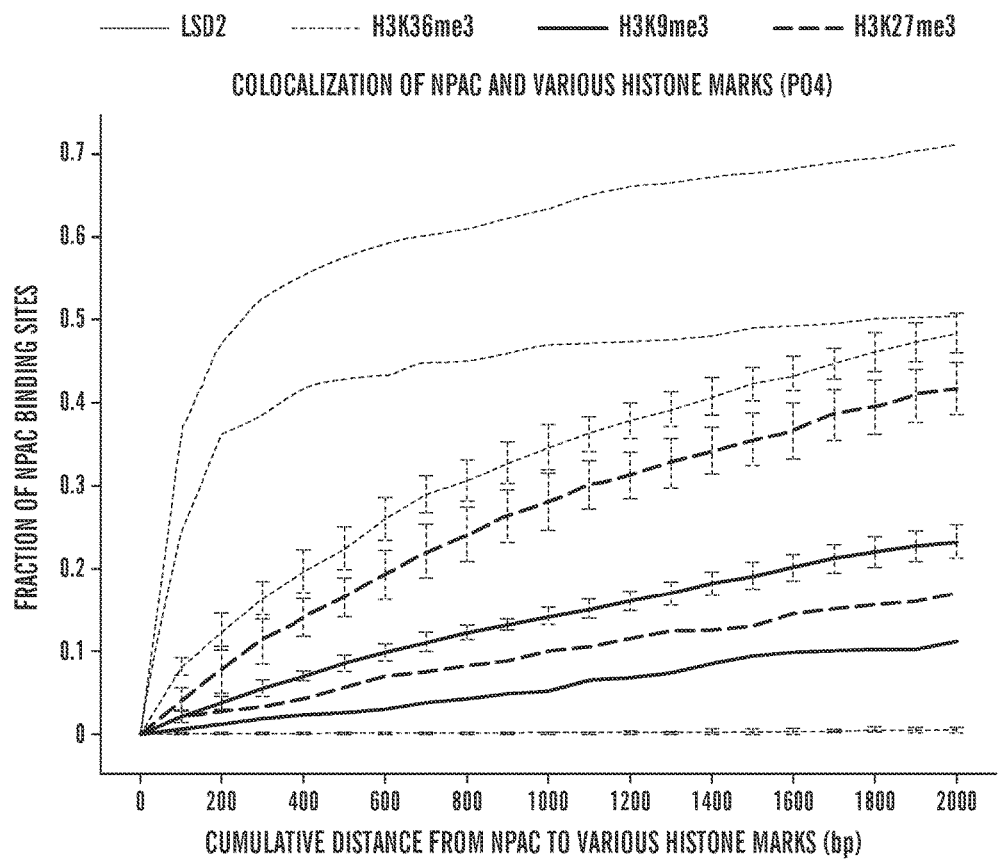

To uncover a potential role of NPAC in regulating gene expression, we next analyzed the correlation between NPAC occupancy and gene expression status. Comparison of highly expressed (top 10%) versus repressed (bottom 10%) genes in the array revealed significantly higher average NPAC ChIP-chip signals on the gene body of highly expressed genes (FIG. 16D, red line) than on repressed genes (FIG. 16D, blue line). We also observed a clear reduction in NPAC signal at the transcription start sites, regardless of the gene expression status. These observations indicate that NPAC is mainly associated with the coding region of actively transcribed genes, consistent with the genome-wide distribution pattern of LSD2 (Fang et al., 2010). In addition, the NPAC distribution pattern is nearly identical to that of H3K36me3 (FIG. 16E). NPAC peaks are in close proximity to H3K36me3 signals and are distant from H3K9me3 and H3K27me3 marks (FIG. 20B), further demonstrating a genome-wide correlation consistent with the selective binding of NPAC to H3K36me3 marks.

Figure 16F:
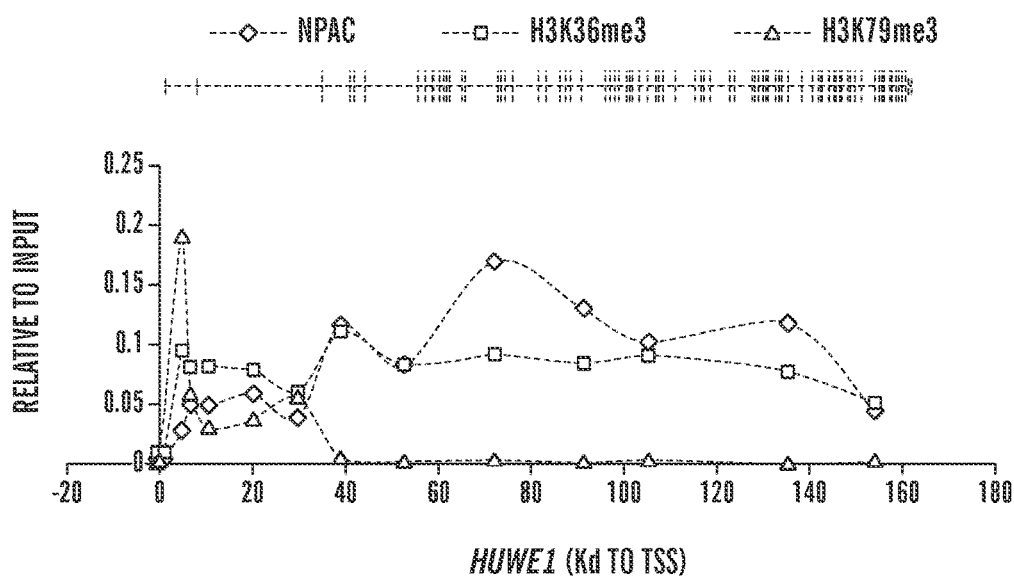
Figure 16G:
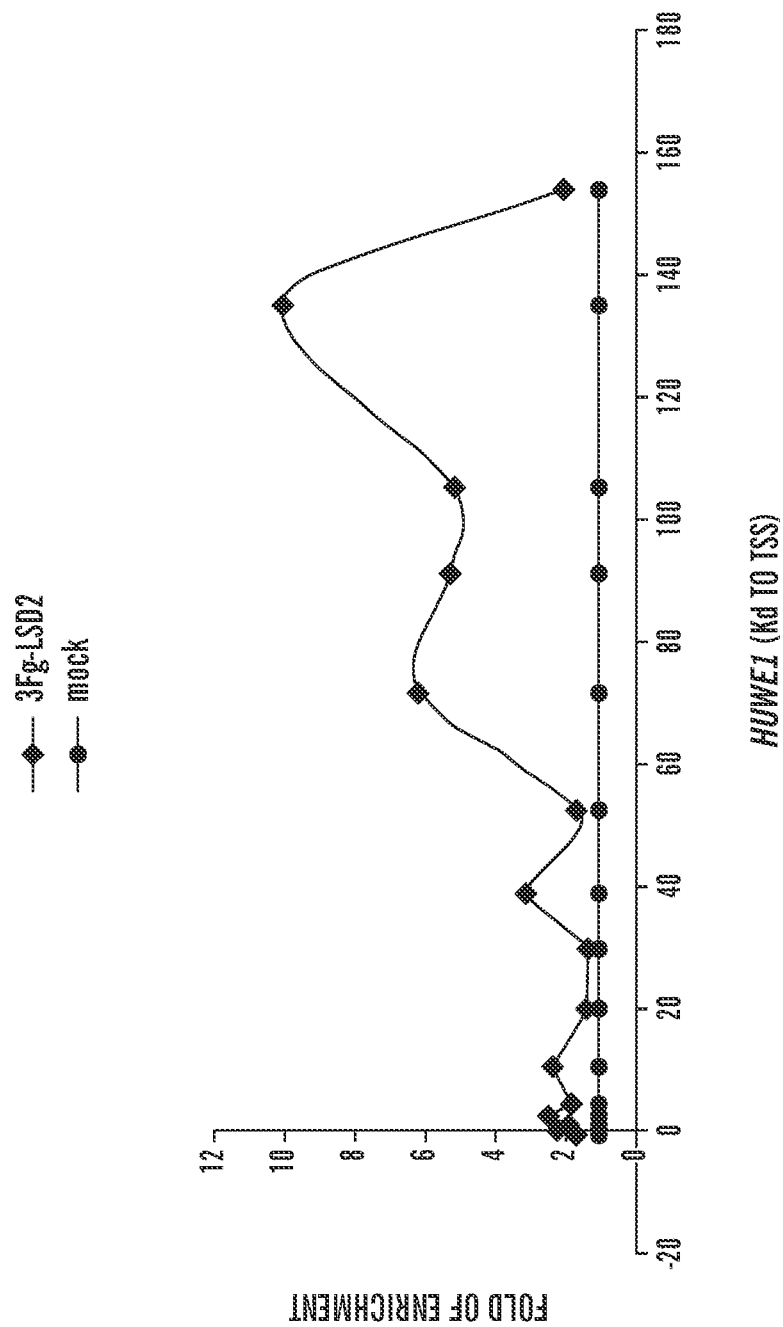
Figure 16H:
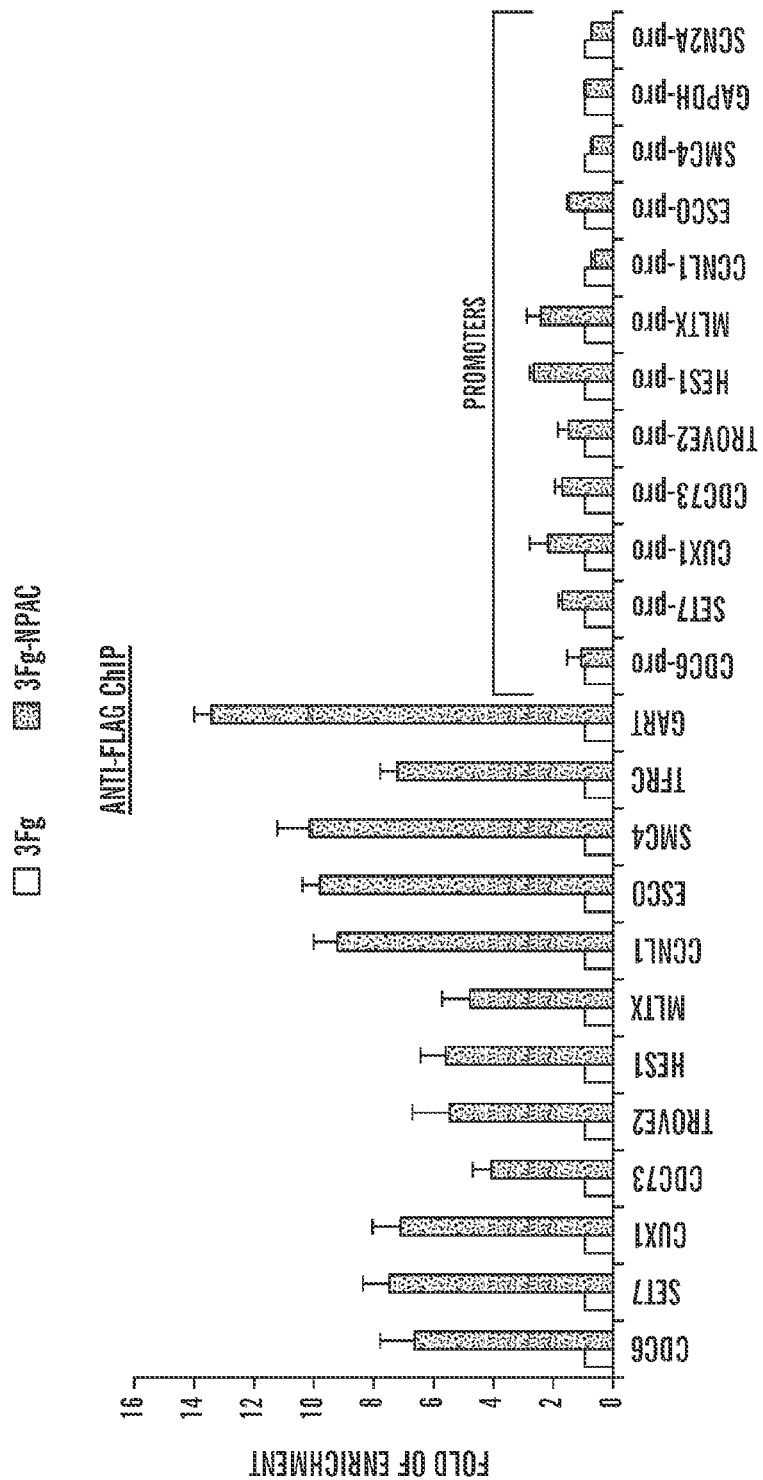
Figure 20C:
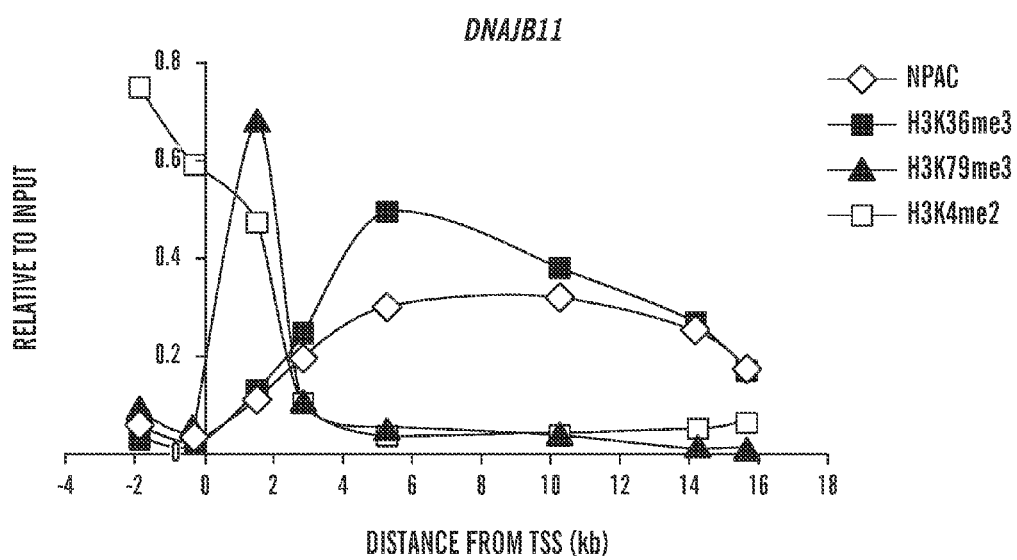
Figure 20D:
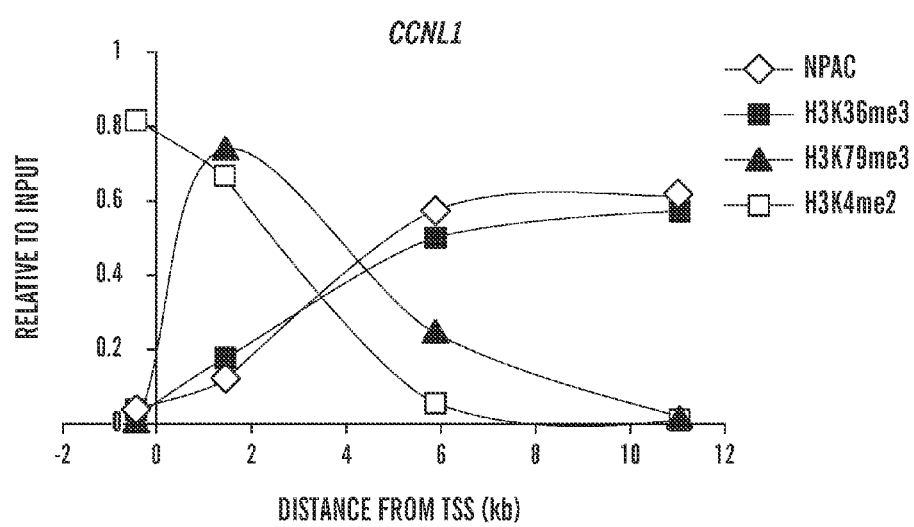

To confirm the above results, we use conventional ChIP analyses to examine NPAC binding, LSD2 co-occupancy, and histone modification profiles of candidate genes. As a representative example shown in FIG. 16F, NPAC binding tightly correlates with H3K36me3 levels within the HUWE1 gene; both NPAC and H3K36me3 levels were attenuated around the TSS (−0.7~1.0 kb), but were significantly increased within the open reading frame further downstream (FIG. 16F, blue and red lines, respectively). The pattern of NPAC binding at HUWE1 is distinct from H3K79me3, another active mark within the coding regions of actively transcribed genes (FIG. 16F, green line), further supporting that NPAC is an H3K36me3 specific reader despite of the moderate binding to H3K79me3 observed in vitro. Strong LSD2 binding was detected in the coding region of HUWE1, concordant with NPAC enrichment and consistent with the genome-wide correlation of NPAC and LSD2 (FIG. 16G). Similar correlations were also observed on DNAJB11 and CCNL1, two previously reported LSD2 target genes (FIG. 20C-20D) (Fang et al., 2010). Finally, to further confirm that this NPAC binding profile represents a general phenomenon, we tested NPAC binding on a number of additional genes identified by NPAC ChIP-chip analysis. In all cases, NPAC showed selective association with intragenic regions and not promoters (FIG. 16H). Collectively, these data indicate that NPAC specifically co-localizes with H3K36me3 marks in the gene body. In addition, NPAC and LSD2 co-occupy, thus potentially co-regulate a group of common target genes that are actively transcribed in vivo.

H3K36Me3 Regulates NPAC Chromatin Association In Vivo.

Figure 17A:
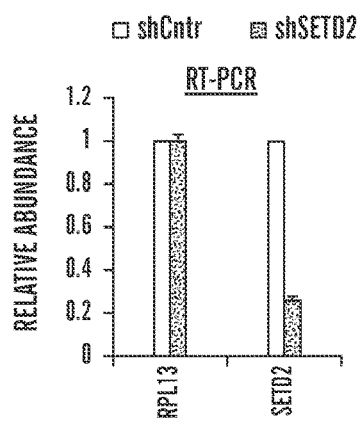
Figure 17B:
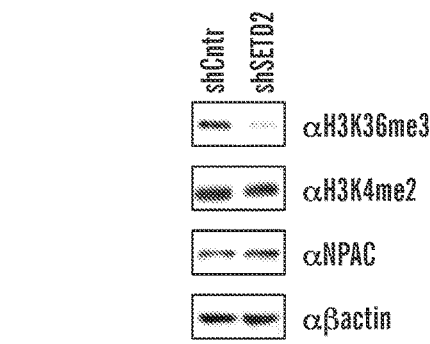
Figure 17C:
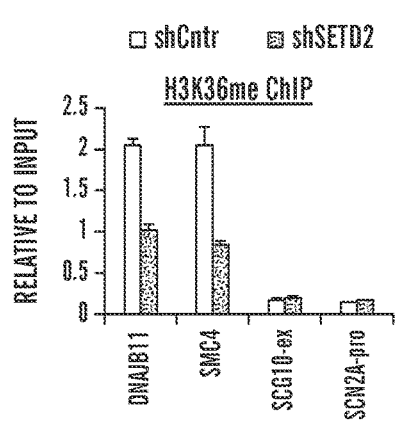
Figure 17D:
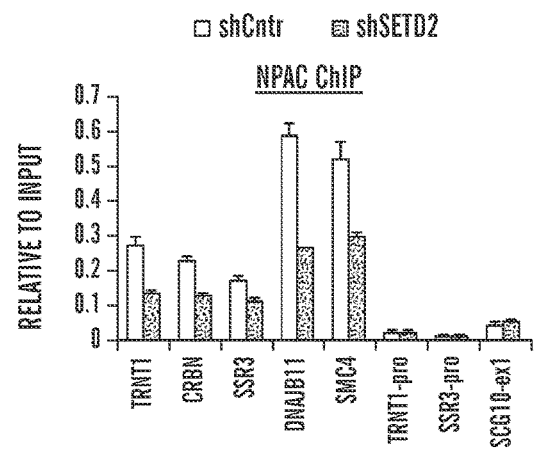

We next investigated if NPAC association with actively transcribed genes is H3K36me3 dependent in vivo. It has been reported that SETD2 mediates genome-wide H3K36 tri-methylation, but is not required for mono- and di-methylation of H3K36 (Edmunds et al., 2008). Using lentiviral shRNA, we depleted SETD2 mRNA levels in HeLa cells by about 70% (FIG. 17A) and detected a significant reduction in global H3K36me3 by immunoblot analyses (FIG. 17B). Concomitant with its diminished global levels, H3K36me3 levels were reduced by about 50% within coding regions of actively transcribed genes such as DNAJB11 and SMC4, but not at SCG10 and SCN2A, two repressed genes showing background levels of H3K36me3 ChIP signals (FIG. 17C). Significantly, a marked reduction of NPAC binding was observed at the coding regions of these active genes and several others tested (FIG. 17D). Importantly, NPAC expression was not affected by SETD2 shRNA (FIG. 17B). These results indicate that NPAC chromatin association not only correlates with but also depends upon H3K36me3 modification for genomic localization in vivo.

NPAC is Responsible for Recruiting LSD2 to Specific Loci to Modulate Active Gene Transcription.

Figure 17E:
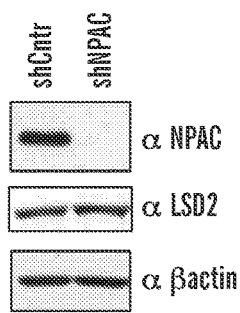
Figure 17F:
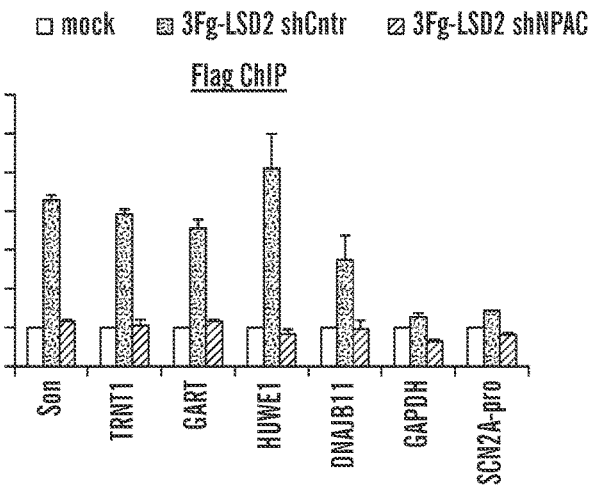
Figure 21:
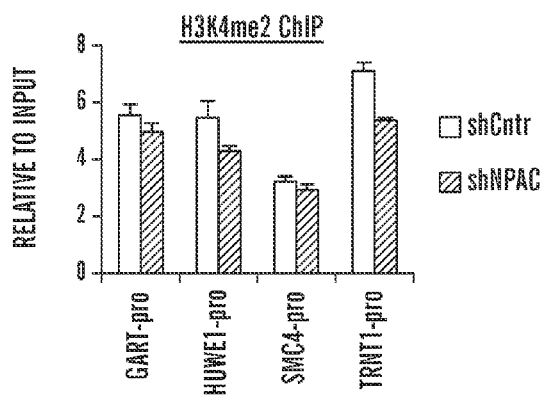
FIG. 21 demonstrates that NPAC depletion does not induce an increase in H3K4me2 levels at the promoters of its target genes. Quantitative ChIP was performed using anti-H3K4me2 antibody on HeLa cells treated with either control or NPAC shRNA for four days. Data are presented as enrichment relative to input as in FIG. 17G. Error bars, SEM of triplicates from representative experiments.

The direct interaction between LSD2 and the histone code reader NPAC (FIGS. 13A-13G) and their genome-wide correlation suggest that NPAC may play an important role in LSD2 targeting in the human genome. To test this, we depleted NPAC using shRNA and examined LSD2 chromatin association by ChIP. Lentiviral NPAC shRNA effectively reduced NPAC protein expression more than 90% compared to control shRNA (FIG. 17E). NPAC shRNA treatment had no obvious effect on LSD2 expression (FIG. 17E), yet LSD2 binding at the coding region of several LSD2-NPAC common targets was reduced to near basal levels upon NPAC depletion (FIG. 17F). Furthermore, upon NPAC depletion, quantitative ChIP analysis detected a consistent increase in H3K4me2 at coding regions of LSD2-NPAC common targets (FIG. 17G), but not at the corresponding promoters (FIG. 21), similar to our observations in LSD2 depleted cells (Fang et al., 2010). We also observed a consistent downregulation of a subset of NPAC-LSD2 associated genes after NPAC depletion (FIG. 17H). Together, these in vivo functional analyses indicate that NPAC not only colocalizes with LSD2, but also co-regulates the expression of their common target genes.

Discussion

Together, these biochemical and functional analyses support our hypothesis that H3K36me3 plays a critical role in recruiting NPAC to actively transcribed regions, which, in turn, recruits LSD2 and likely other associated epigenetic regulators, to modulate the local chromatin structure and histone modifications important for active gene transcription, thus revealed a new layer of epigenetic regulation underlying the dynamics of coordinated co-transcriptional histone modification during transcriptional elongation. The interaction between NPAC and LSD2 is essential for their function in transcription regulation, and represents an opportunity for modulating the co-regulated biological and pathophysiological functions of LSD2 and NPAC.

The regulation of cotranscriptional histone modifications in the gene body recently emerged as a fundamental yet previously underappreciated epigenetic mechanism for gene regulation (Hampsey and Reinberg, 2003; Lee and Shilatifard, 2007; Luco et al., 2011; Sims et al., 2004). This epigenetic regulatory circuit, unlike the epigenetic regulation at promoters, is not well understood. In yeast, it is well documented that Eaf3 in the Rpd3S complex binds to H3K36me3, thus recruiting HDACs and maintaining a low level of histone acetylation at coding regions (Carrozza et al., 2005; Joshi and Struhl, 2005; Keogh et al., 2005; Li et al., 2007a; Li et al., 2007b). A similar mechanism likely exists in mammals. The mammalian Eaf3 homolog MRG15, also an H3K36me3 reader, is a core component of several HDAC complexes (Pardo et al., 2002). In addition, MRG15 is reported to associate with KDM5b/JARID1B (Xie et al., 2011) and RBP2/JARID1A (Hayakawa et al., 2007) to regulate H3K4 tri-methylation at coding regions.

The interplay between the nucleosomal H3K36me3 reader NPAC and the H3K4me2 demethylase LSD2 brings to light a new facet of the mechanism underlying the establishment, maintenance and dynamic regulation of the histone code during transcriptional elongation in mammals. At a glance, the presence of two H3K36me3 readers may seem counterproductive. However, even a small spatial and/or temporal disjunction between these two readers could prevent competition for binding to the same histone tail in vivo. Therefore, without wishing to be bound by theory, we propose that NPAC and MRG15 may work in parallel and/or complement each other in keeping a repressive chromatin structure at coding regions. While MRG15 associating complexes maintain low levels of H3K4me3 and histone acetylation, the LSD2 complex targeted by NPAC provides an additional layer of control, regulating H3K4me2 and H3K9 methylation. Together, these two potentially interconnected pathways define the histone code that locks in a repressive chromatin structure in the coding region of actively transcribed genes.

One of the significant findings from this study is that stable binding of the NPAC PWWP domain (SEQ ID NO: 63) to H3K36me3 requires a nucleosomal context. Only a few H3K36me3 readers have been reported so far, including the chromodomains of MRG15 (Zhang et al., 2006) and Eaf3 (Li et al., 2007a; Sun et al., 2008; Xu et al., 2008), the PHD fingers of EcmS and Nto1, and the PWWP domains (SEQ ID NO: 63) of DNMT3a (Dhayalan et al., 2010), BRPF1 (Vezzoli et al., 2010; Wu et al., 2011) and WHSC1 (Wu et al., 2011). These proteins show selective and weak binding to the H3K36me3 histone peptide in in vitro binding assays, typically with a Kd in the sub-millimolar to millimolar range. We found that the interaction of NPAC with H3K36me3 histone peptides is too weak to be reliably detected by conventional binding assays such as GST-pulldown and ITC. On the other hand, selective interaction with nucleosomal H3K36me3 by NPAC is readily detected. These observations support the hypothesis that nucleosomal conformation may be required for the H3K36me3 readers to stably and selectively bind the modification.

The simulated 3D model structure of the NPAC PWWP domain (SEQ ID NO: 63) indicates that the tri-methyl group of H3K36 is most likely recognized by a conserved aromatic cage similar to the other reported PWWP domain (SEQ ID NO: 63) structures (Vezzoli et al., 2010; Wu et al., 2011). Importantly, the simulated structure of the NPAC PWWP domain (SEQ ID NO: 63) also reveals an elongated, positively charged putative DNA-binding patch near the H3K36me3 binding pocket. Thus, the NPAC PWWP domain (SEQ ID NO: 63) is predicted to contain structural elements for binding to both H3K36me3 and nucleosomal DNA simultaneously. Indeed, we show that the PWWP domain (SEQ ID NO: 63) of NPAC can bind double strand DNA, and DNA binding is important for NPAC interacting with nucleosomes. Notably, though robust binding to naked double-strand DNA is observed, this alone is not expected to be sufficient for NPAC-nucleosome interaction, given the selective binding of H3K36me3 nucleosome by NPAC (FIGS. 14A-14C). Thus, while an interaction with either H3K36me3 or nucleosomal DNA alone is not sufficient, DNA binding by the NPAC PWWP domain (SEQ ID NO: 63) may play an important role in establishing the initial contact with nucleosomes, which, in turn, facilitates the adjacent conserved aromatic cage in NPAC PWWP domain (SEQ ID NO: 63) to lock in the H3K36 tri-methyl group, consequently establishing a stable and modification-specific interaction between H3K36me3 nucleosomes with NPAC.

Figure 22:
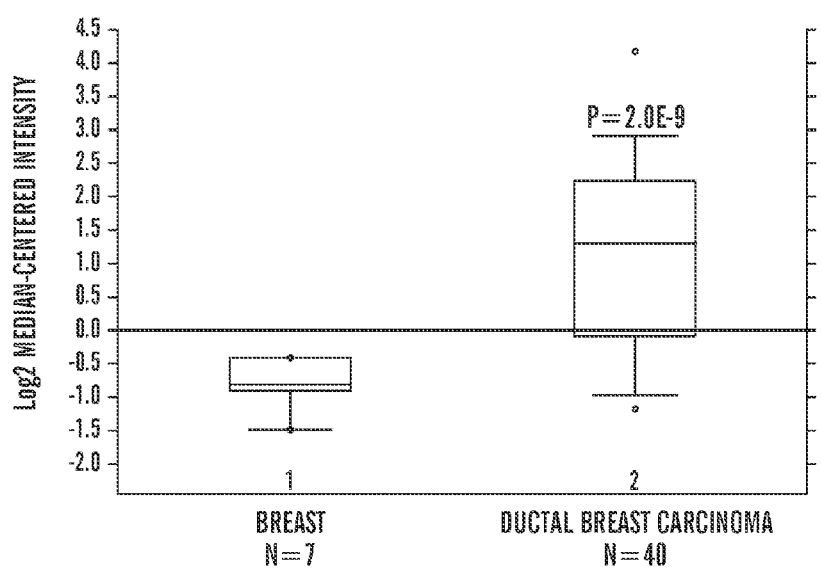
FIG. 22 demonstrates that LSD2 is overexpressed in certain type of breast cancer. The expression profiles of 7 normal breast tissues and 40 ductal breast carcinomas were analyzed by microarray (Richardson et al., 2006). Analysis of the data by Oncomine revealed that LSD2 is overexpressed by 3.9 fold in ductal breast carcinomas, with a p value of $2.0 \times 10^{-9}$.

Multiple studies in recently years have shown that histone demethylases play important roles in human diseases (Agger et al., 2008; Pedersen and Helin, 2010; Shi, 2007). Notably, there are observations suggesting a role in cancer biology for SETD2 H3K36me3 methyltransferase, LSD2 and NPAC, all three elements of the epigenetic regulator pathway elucidated here (Alhopuro et al., 2012; Duns et al., 2010; Newbold and Mokbel, 2010; Richardson et al., 2006). In particular, published expression profile analyses of breast cancer patients suggest that LSD2 is highly expressed in certain types of breast cancers, implying a function of LSD2 in breast cancer biology (FIG. 22) (Richardson et al., 2006). NPAC is one of the most frequently mutated genes in colorectal cancer patients (Alhopuro et al., 2012). Without wishing to be bound by theory, LSD2 and NPAC, preferentially enriched at exons, are likely not only important for productive gene transcription, but may also play a role in co-transcriptional mRNA splicing, both of which may have significant pathophysiological implications.

Experimental Procedures

Plasmids.

Full length human NPAC (protein ID: Q49A26) was amplified from HeLa cDNA and cloned into the XhoI and NotI sites of the pOZ-N retroviral vector and expressed as N-terminal FLAG-HA tagged protein as previously described (Shi et al., 2003). GST-NPAC cloned in pGEX-4T-1 and His6-NPAC cloned in pET-3a ("His6" disclosed as SEQ ID NO: 75) were expressed and purified from E. coli. GST and His6 tagged LSD2 proteins ("His6" disclosed as SEQ ID NO: 75) were expressed and purified from Sf9 inset cells as previously described (Fang et al., 2010).

ChIP and Tiling Array Analysis.

Tandem affinity native ChIP from HeLa stably expressing FLAG:HA-NPAC was performed as previously described (Fang et al., 2010). Briefly, native chromatin was fragmented by Micrococal nuclease digestion and sequentially immunoprecipitated using anti-FLAG and anti-HA Affinity Gel (Sigma-Aldrich). After extensive washes, FLAG and HA peptides were used for elution at each step. The final enriched DNA and input control DNA were processed for ChIP-chip analysis using Human Genome Tiling 2.0 Array (Affymetrix) per manufacture's instruction. NPAC binding sites were identified using a MAT algorithm (Model-based analysis of tiling array) (Johnson et al., 2006), with a cut-off at fold change greater than 2, and viewed using Integrated Genome Browser (Nicol et al., 2009). The profiles of histone H3K36me3 modification were generated by MACS (Zhang et al., 2008) using ChIPseq data from HeLa publicly available in the ENCODE database (Birney et al., 2007), and peaks were called with p-value of $10^{-7}$ as a cutoff.

To analysis the global distribution of NPAC peaks, enhancers were defined as ±2.5 kb from the center of the enhancer regions reported by Bing Ren and colleagues (Heintzman et al., 2009); promoters were defined as regions −2 kb to 0 kb from TSS; the coordinates of exons and introns from hg19 were downloaded from UCSC genome browser database. If a NPAC peak overlaps with more than one element, it is counted once in each category. The sum of the counts of all categories was used to calculate the percentages of the distribution of NPAC peaks.

Anti-H3K4me2 (Milipore, 07-030), anti-H3K36me3 (Abcam, ab1785), anti-H3K79me3 (Abcam, ab2621), anti-NPAC (Strategic Diagnostics Inc., 2158.00.02), anti-FLAG (Sigma-Aldrich, A2220) antibodies were used for ChIP and immunoblot as previously described (Tahiliani et al., 2007).

Nucleosome Pulldown.

Nucleosomes were purified from HeLa as previously described (Umlauf et al., 2004). To examine nucleosome binding selectivity of NPAC, 5 μg GST fusion protein bound to glutathione agarose were incubated with 20 μg nucleosomes overnight at 4° C. in nucleosome binding buffer (50 mM NaPO$_4$ pH 7.4, 200 mM NaCl, 0.5% NP-40, 5% glycerol, 10 μM ZnSO$_4$, 1 mM MgCl$_2$, 1 mM DTT, 0.1 mM PMSF). After washing 4 times with the same buffer at 4° C., the beads were boiled in 1×SDS sample loading buffer and elute was resolved by 15% SDS-PAGE for immunoblot analysis or coomassie staining.

MLA nucleosomes were reconstituted using 147 bp double-strand alpha satellite DNA and recombinant histones expressed and purified from E. coli. Tri-methylation was chemically introduced to H3K9C, H3K27C, H3K36C and H3K79C histones respectively as described (Simon et al., 2007). 2 μg MLA nucleosome was used for GST-pulldown as described above.

For free-DNA competition assays, human genomic DNA was purified from HeLa cells and fragmented to an average size around 300 bp by sonication. Equal amounts of GST-NPAC.d5 bound to glutathione beads were pre-incubated with 0, 5, 10, 25 μg genomic DNA fragments in nucleosome binding buffer for 30 minutes at room temperature, and equal amounts of nucleosomes were added and incubated overnight at 4° C. After extensive washing, GST-NPAC.d5 and bound nucleosomes were eluted by boiling in 1×SDS sample loading buffer, resolved by SDS-PAGE and stained with coomassie blue.

RNAi and qRT-PCR Analysis.

Lentiviral shRNA constructs of human NPAC and SETD2 were purchased from Open Biosystems. HeLa was infected with lentivirus expressing either control or NPAC shRNA and selected by puromycine. 72 hours post-infection, total RNA was purified using RNeazy Mini Kit (Qiagen) after on-column DNase I digestion per manufacture's instructions. 3 μg total RNA and random hexamers was used for first-strand cDNA synthesis using Superscript III First-Strand Synthesis System (Invitrogen). Real time PCR was performed using SABioscience SYBR green master mix on an IQ5 multicolor real-time PCR system (Bio-Rad). Sequence information of qRT-PCR primers are available upon request.

REFERENCES

Adams-Cioaba, M. A., and Min, J. (2009). Structure and function of histone methylation binding proteins. Biochem Cell Biol 87, 93-105.

Agger, K., Christensen, J., Cloos, P. A., and Helin, K. (2008). The emerging functions of histone demethylases. Curr Opin Genet Dev 18, 159-168.

Alhopuro, P., Sammalkorpi, H., Niittymaki, I., Bistrom, M., Raitila, A., Saharinen, J., Nousiainen, K., Lehtonen, H. J., Heliovaara, E., Puhakka, J., et al. (2012). Candidate driver genes in microsatellite-unstable colorectal cancer. Int J Cancer 130, 1558-1566.

Barski, A., Cuddapah, S., Cui, K., Roh, T. Y., Schones, D. E., Wang, Z., Wei, G., Chepelev, I., and Zhao, K. (2007). High-resolution profiling of histone methylations in the human genome. Cell 129, 823-837.

Berger, S. L. (2007). The complex language of chromatin regulation during transcription. Nature 447, 407-412.

Bernstein, B. E., Kamal, M., Lindblad-Toh, K., Bekiranov, S., Bailey, D. K., Huebert, D. J., McMahon, S., Karlsson, E. K., Kulbokas, E. J., 3rd, Gingeras, T. R., et al. (2005). Genomic maps and comparative analysis of histone modifications in human and mouse. Cell 120, 169-181.

Bernstein, B. E., Meissner, A., and Lander, E. S. (2007). The mammalian epigenome. Cell 128, 669-681.

Birney, E., Stamatoyannopoulos, J. A., Dutta, A., Guigo, R., Gingeras, T. R., Margulies, E. H., Weng, Z., Snyder, M., Dermitzakis, E. T., Thurman, R. E., et al. (2007). Identification and analysis of functional elements in 1% of the human genome by the ENCODE pilot project. Nature 447, 799-816.

Buratowski, S., and Kim, T. (2010). The role of cotranscriptional histone methylations. Cold Spring Harb Symp Quant Biol 75, 95-102.

Carrozza, M. J., Li, B., Florens, L., Suganuma, T., Swanson, S. K., Lee, K. K., Shia, W. J., Anderson, S., Yates, J., Washburn, M. P., and Workman, J. L. (2005). Histone H3 methylation by Set2 directs deacetylation of coding regions by Rpd3S to suppress spurious intragenic transcription. Cell 123, 581-592.

Cheung, P., Allis, C. D., and Sansone-Corsi, P. (2000). Signaling to chromatin through histone modifications. Cell 103, 263-271.

Ciccone, D. N., Su, H., Hevi, S., Gay, F., Lei, H., Bajko, J., Xu, G., Li, E., and Chen, T. (2009). KDM1B is a histone H3K4 demethylase required to establish maternal genomic imprints. Nature 461, 415-418.

Dhayalan, A., Rajavelu, A., Rathert, P., Tamas, R., Jurkowska, R. Z., Ragozin, S., and Jeltsch, A. (2010). The Dnmt3a PWWP domain reads histone 3 lysine 36 trimethylation and guides DNA methylation. J Biol Chem 285, 26114-26120. ("PWWP" disclosed as SEQ ID NO: 63)

Duns, G., van den Berg, E., van Duivenbode, I., Osinga, J., Hollema, H., Hofstra, R. M., and Kok, K. (2010). Histone methyltransferase gene SETD2 is a novel tumor suppressor gene in clear cell renal cell carcinoma. Cancer Res 70, 4287-4291.

Edmunds, J. W., Mahadevan, L. C., and Clayton, A. L. (2008). Dynamic histone H3 methylation during gene induction: HYPB/Setd2 mediates all H3K36 trimethylation. Embo J 27, 406-420.

Esteller, M. (2008). Epigenetics in cancer. N Engl J Med 358, 1148-1159.

Fang, R., Barbera, A. J., Xu, Y., Rutenberg, M., Leonor, T., Bi, Q., Lan, F., Mei, P., Yuan, G. C., Lian, C., et al. (2010). Human LSD2/KDM1b/AOF1 regulates gene transcription by modulating intragenic H3K4me2 methylation. Mol Cell 39, 222-233.

Fu, J., Yang, Z., Wei, J., Han, J., and Gu, J. (2006). Nuclear protein NP60 regulates p38 MAPK activity. J Cell Sci 119, 115-123.

Grewal, S. I., and Rice, J. C. (2004). Regulation of heterochromatin by histone methylation and small RNAs. Curr Opin Cell Biol 16, 230-238.

Groth, A., Rocha, W., Verreault, A., and Almouzni, G. (2007). Chromatin challenges during DNA replication and repair. Cell 128, 721-733.

Guenther, M. G., Levine, S. S., Boyer, L. A., Jaenisch, R., and Young, R. A. (2007). A chromatin landmark and transcription initiation at most promoters in human cells. Cell 130, 77-88.

Hampsey, M., and Reinberg, D. (2003). Tails of intrigue: phosphorylation of RNA polymerase II mediates histone methylation. Cell 113, 429-432.

Hayakawa, T., Ohtani, Y., Hayakawa, N., Shinmyozu, K., Saito, M., Ishikawa, F., and Nakayama, J. (2007). RBP2 is an MRG15 complex component and down-regulates intragenic histone H3 lysine 4 methylation. Genes Cells 12, 811-826.

Heintzman, N. D., Hon, G. C., Hawkins, R. D., Kheradpour, P., Stark, A., Harp, L. F., Ye, Z., Lee, L. K., Stuart, R. K., Ching, C. W., et al. (2009). Histone modifications at human enhancers reflect global cell-type-specific gene expression. Nature 459, 108-112.

Jaroszewski, L., Li, Z., Cai, X. H., Weber, C., and Godzik, A. (2011). FFAS server: novel features and applications. Nucleic Acids Res 39, W38-44.

Johnson, W. E., Li, W., Meyer, C. A., Gottardo, R., Carroll, J. S., Brown, M., and Liu, X. S. (2006). Model-based analysis of tiling-arrays for ChIP-chip. Proc Natl Acad Sci USA 103, 12457-12462.

Joshi, A. A., and Struhl, K. (2005). Eaf3 chromodomain interaction with methylated H3-K36 links histone deacetylation to Pol II elongation. Mol Cell 20, 971-978.

Keogh, M. C., Kurdistani, S. K., Morris, S. A., Ahn, S. H., Podolny, V., Collins, S. R., Schuldiner, M., Chin, K., Punna, T., Thompson, N. J., et al. (2005). Cotranscriptional set2 methylation of histone H3 lysine 36 recruits a repressive Rpd3 complex. Cell 123, 593-605.

Khorasanizadeh, S. (2004). The nucleosome: from genomic organization to genomic regulation. Cell 116, 259-272.

Kim, T., and Buratowski, S. (2009). Dimethylation of H3K4 by Set1 recruits the Set3 histone deacetylase complex to 5' transcribed regions. Cell 137, 259-272.

Kouzarides, T. (2002). Histone methylation in transcriptional control. Curr Opin Genet Dev 12, 198-209.

Lee, J. S., and Shilatifard, A. (2007). A site to remember: H3K36 methylation a mark for histone deacetylation. Mutat Res 618, 130-134.

Lee, J. S., Shukla, A., Schneider, J., Swanson, S. K., Washburn, M. P., Florens, L., Bhaumik, S. R., and Shilatifard, A. (2007). Histone crosstalk between H2B monoubiquitination and H3 methylation mediated by COMPASS. Cell 131, 1084-1096.

Levy, D., and Gozani, O. (2010). Decoding chromatin goes high tech. Cell 142, 844-846.

Li, B., Gogol, M., Carey, M., Lee, D., Seidel, C., and Workman, J. L. (2007a). Combined action of PHD and chromo domains directs the Rpd3S HDAC to transcribed chromatin. Science 316, 1050-1054.

Li, B., Gogol, M., Carey, M., Pattenden, S. G., Seidel, C., and Workman, J. L. (2007b). Infrequently transcribed long genes depend on the Set2/Rpd3S pathway for accurate transcription. Genes Dev 21, 1422-1430.

Luco, R. F., Allo, M., Schor, I. E., Kornblihtt, A. R., and Misteli, T. (2011). Epigenetics in alternative pre-mRNA splicing. Cell 144, 16-26.

Luger, K., Mader, A. W., Richmond, R. K., Sargent, D. F., and Richmond, T. J. (1997). Crystal structure of the nucleosome core particle at 2.8 A resolution. Nature 389, 251-260.

Lukasik, S. M., Cierpicki, T., Borloz, M., Grembecka, J., Everett, A., and Bushweller, J. H. (2006). High resolution structure of the HDGF PWWP domain: a potential DNA binding domain. Protein Sci 15, 314-323. ("PWWP" disclosed as SEQ ID NO: 63)

Martin, C., and Zhang, Y. (2005). The diverse functions of histone lysine methylation. Nat Rev Mol Cell Biol 6, 838-849.

Meissner, A. (2010). Epigenetic modifications in pluripotent and differentiated cells. Nat Biotechnol 28, 1079-1088.

Newbold, R. F., and Mokbel, K. (2010). Evidence for a tumour suppressor function of SETD2 in human breast cancer: a new hypothesis. Anticancer Res 30, 3309-3311.

Nicol, J. W., Helt, G. A., Blanchard, S. G., Jr., Raja, A., and Loraine, A. E. (2009). The Integrated Genome Browser: free software for distribution and exploration of genome-scale datasets. Bioinformatics 25, 2730-2731.

Pardo, P. S., Leung, J. K., Lucchesi, J. C., and Pereira-Smith, O. M. (2002). MRG15, a novel chromodomain protein, is present in two distinct multiprotein complexes involved in transcriptional activation. J Biol Chem 277, 50860-50866.

Pedersen, M. T., and Helin, K. (2010). Histone demethylases in development and disease. Trends Cell Biol 20, 662-671.

Pokholok, D. K., Harbison, C. T., Levine, S., Cole, M., Hannett, N. M., Lee, T. I., Bell, G. W., Walker, K., Rolfe, P. A., Herbolsheimer, E., et al. (2005). Genome-wide map of nucleosome acetylation and methylation in yeast. Cell 122, 517-527.

Qiu, C., Sawada, K., Zhang, X., and Cheng, X. (2002). The PWWP domain of mammalian DNA methyltransferase Dnmt3b defines a new family of DNA-binding folds. Nat Struct Biol 9, 217-224. ("PWWP" disclosed as SEQ ID NO: 63)

Rando, O. J., and Chang, H. Y. (2009). Genome-wide views of chromatin structure. Ann Rev Biochem 78, 245-271.

Richardson, A. L., Wang, Z. C., De Nicolo, A., Lu, X., Brown, M., Miron, A., Liao, X., Iglehart, J. D., Livingston, D. M., and Ganesan, S. (2006). X chromosomal abnormalities in basal-like human breast cancer. Cancer Cell 9, 121-132.

Ruthenburg, A. J., Allis, C. D., and Wysocka, J. (2007). Methylation of lysine 4 on histone H3: intricacy of writing and reading a single epigenetic mark. Mol Cell 25, 15-30.

Schones, D. E., and Zhao, K. (2008). Genome-wide approaches to studying chromatin modifications. Nature reviews 9, 179-191.

Shi, Y. (2007). Histone lysine demethylases: emerging roles in development, physiology and disease. Nature reviews 8, 829-833.

Shi, Y., Sawada, J., Sui, G., Affar el, B., Whetstine, J. R., Lan, F., Ogawa, H., Luke, M. P., and Nakatani, Y. (2003). Coordinated histone modifications mediated by a CtBP co-repressor complex. Nature 422, 735-738.

Simon, M. D., Chu, F., Racki, L. R., de la Cruz, C. C., Burlingame, A. L., Panning, B., Narlikar, G. J., and Shokat, K. M. (2007). The site-specific installation of methyl-lysine analogs into recombinant histones. Cell 128, 1003-1012.

Sims, R. J., 3rd, Belotserkovskaya, R., and Reinberg, D. (2004). Elongation by RNA polymerase II: the short and long of it. Genes Dev 18, 2437-2468.

Sun, B., Hong, J., Zhang, P., Dong, X., Shen, X., Lin, D., and Ding, J. (2008). Molecular basis of the interaction of *Saccharomyces cerevisiae* Eaf3 chromo domain with methylated H3K36. J Biol Chem 283, 36504-36512.

Tahiliani, M., Mei, P., Fang, R., Leonor, T., Rutenberg, M., Shimizu, F., Li, J., Rao, A., and Shi, Y. (2007). The histone H3K4 demethylase SMCX links REST target genes to X-linked mental retardation. Nature 447, 601-605.

Taverna, S. D., Li, H., Ruthenburg, A. J., Allis, C. D., and Patel, D. J. (2007). How chromatin-binding modules interpret histone modifications: lessons from professional pocket pickers. Nat Struct Mol Biol 14, 1025-1040.

Turner, B. M. (2002). Cellular memory and the histone code. Cell 111, 285-291.

Umlauf, D., Goto, Y., and Feil, R. (2004). Site-specific analysis of histone methylation and acetylation. Methods Mol Biol 287, 99-120.

van Essen, D., Zhu, Y., and Saccani, S. (2010). A feed-forward circuit controlling inducible NF-kappaB target gene activation by promoter histone demethylation. Mol Cell 39, 750-760.

Vermeulen, M., Eberl, H. C., Matarese, F., Marks, H., Denissov, S., Butter, F., Lee, K. K., Olsen, J. V., Hyman, A. A., Stunnenberg, H. G., and Mann, M. (2010). Quantitative interaction proteomics and genome-wide profiling of epigenetic histone marks and their readers. Cell 142, 967-980.

Vezzoli, A., Bonadies, N., Allen, M. D., Freund, S. M., Santiveri, C. M., Kvinlaug, B. T., Huntly, B. J., Gottgens, B., and Bycroft, M. (2010). Molecular basis of histone H3K36me3 recognition by the PWWP domain of Brpf1. Nat Struct Mol Biol 17, 617-619. ("PWWP" disclosed as SEQ ID NO: 63)

Wu, H., Zeng, H., Lam, R., Tempel, W., Amaya, M. F., Xu, C., Dombrovski, L., Qiu, W., Wang, Y., and Min, J. (2011). Structural and histone binding ability characterizations of human PWWP domains. PLOS one 6, e18919. ("PWWP" disclosed as SEQ ID NO: 63)

Xie, L., Pelz, C., Wang, W., Bashar, A., Varlamova, O., Shadle, S., and Impey, S. (2011). KDM5B regulates embryonic stem cell self-renewal and represses cryptic intragenic transcription. Embo J 30, 1473-1484.

Xu, C., Cui, G., Botuyan, M. V., and Mer, G. (2008). Structural basis for the recognition of methylated histone H3K36 by the Eaf3 subunit of histone deacetylase complex Rpd3S. Structure 16, 1740-1750.

Yang, J., and Everett, A. D. (2007). Hepatoma-derived growth factor binds DNA through the N-terminal PWWP domain. BMC Mol Biol 8, 101. ("PWWP" disclosed as SEQ ID NO: 63)

Zhang, P., Du, J., Sun, B., Dong, X., Xu, G., Zhou, J., Huang, Q., Liu, Q., Hao, Q., and Ding, J. (2006). Structure of human MRG15 chromo domain and its binding to Lys36-methylated histone H3. Nucleic Acids Res 34, 6621-6628.

Zhang, Y., Liu, T., Meyer, C. A., Eeckhoute, J., Johnson, D. S., Bernstein, B. E., Nusbaum, C., Myers, R. M., Brown, M., Li, W., and Liu, X. S. (2008). Model-based analysis of ChIP-Seq (MACS). Genome Biol 9, R137.

Supplemental Experimental Procedures

Tandem Affinity Purification (TAP) of Complexes.

FLAG-HA tagged bait protein was stably expressed from pOZ-N vector in a HeLa cell line as described (Shi et al., 2003). Protein complexes were purified by sequential immunoprecipitation using anti-FLAG and anti-HA Affinity Gel (Sigma-Aldrich) as previously described (Shi et al., 2003; Shi et al., 2005). FLAG or HA peptides (Sigma-Aldrich) were used for elution after each step of immunoprecipitation. HeLa-S transduced with empty pOZ-N vector was used to purify the mock complex using identical procedures.

DNA Binding Assays.

5-10 µg GST and GST-tagged NPAC truncation proteins were incubated with 1 µg linearized plasmid DNA overnight at 4° C. in 50 mM Tris pH 7.4, 200 mM NaCl, 0.2% NP-40, 1 mM $MgCl_2$, 1 mM EDTA, 1 mM DTT, 0.02 mM $ZnSO_4$. After extensive washing with the same buffer, bound DNA was eluted by incubating with 100 µl 10 mM Tris pH 8.0, 1% SDS for 15 minutes at 65° C. Pulldown DNA was purified using Qiagen PCR purification kit, resolved by agarose gel electrophoresis and stained with Ethidium Bromide.

Additionally, electrophoresis mobility shift assays were used to examine DNA binding of NPAC (residues 1-150), Human BRPF2 (residues 925-1049), DNMT3A (residues 278-427), DNMT3B (residues 206-355), PSIP1 (residues 2-101), WHSC1 (residues 208-368) and WHSC1L1 (residues 247-402). The purified PWWP domains (SEQ ID NO: 63) were incubated with a 73 bp DNA fragment derived from human α-satellite DNA (Dyer et al., 2004) in buffer containing 50 mM Tris-HCl, pH 7.5, 20 mM NaCl at room temperature for 30 minutes, except that the NPAC PWWP domain (SEQ ID NO: 63) was incubated in buffer containing 50 mM Bicine, pH 9.0, 20 mM NaCl due to its high isoelectric point. Protein-DNA complexes were analyzed on 10% TBE polyacrylmide gels (BioRad) in 0.5×TBE buffer (44.5 mM Tris, 44.5 mM boric acid, 1 mM EDTA, pH 8.4). DNA retardation was detected by staining gels with SYBR green (Sigma). The images were taken by using UVP Bioimaging System.

Micrococcal Nuclease Digestion.

Nuclei were purified from HeLa stably expressing FLAG:HA-NPAC. $2×10^7$ nuclei were digested with 0.5 units of micrococcal nuclease (Sigma-Aldrich) for 0, 0.5, 2, 5 and 10 minutes at 37° C. Digestion reactions were stopped by adding EDTA to a final concentration of 5 mM. Soluble and chromatin bound fractions were separated by centrifugation at 8000×g for 5 min at 4° C. SDS was added to half of the supernatant to a final concentration of 1% and nucleosomal DNA in the supernatant was purified using Qiagen PCR purification kit, resolved by 1% agarose gel electrophoresis and visualized by ethidium bromide staining. The remaining half of the supernatant was separated by SDS-PAGE and analyzed by anti-HA immunoblotting to compare the relative amount of FLAG:HA-NPAC in each sample.

SUPPLEMENTAL REFERENCES

Dyer, P. N., Edayathumangalam, R. S., White, C. L., Bao, Y., Chakravarthy, S., Muthurajan, U. M., and Luger, K. (2004). Reconstitution of nucleosome core particles from recombinant histones and DNA. Methods in enzymology 375, 23-44.

Lukasik, S. M., Cierpicki, T., Borloz, M., Grembecka, J., Everett, A., and Bushweller, J. H. (2006). High resolution structure of the HDGF PWWP domain: a potential DNA binding domain. Protein Sci 15, 314-323. ("PWWP" disclosed as SEQ ID NO: 63)

Qiu, C., Sawada, K., Zhang, X., and Cheng, X. (2002). The PWWP domain of mammalian DNA methyltransferase Dnmt3b defines a new family of DNA-binding folds. Nat Struct Biol 9, 217-224. ("PWWP" disclosed as SEQ ID NO: 63)

Richardson, A. L., Wang, Z. C., De Nicolo, A., Lu, X., Brown, M., Miron, A., Liao, X., Iglehart, J. D., Livingston, D. M., and Ganesan, S. (2006). X chromosomal abnormalities in basal-like human breast cancer. Cancer Cell 9, 121-132.

Shi, Y., Sawada, J., Sui, G., Affar el, B., Whetstine, J. R., Lan, F., Ogawa, H., Luke, M. P., and Nakatani, Y. (2003). Coordinated histone modifications mediated by a CtBP co-repressor complex. Nature 422, 735-738.

Shi, Y. J., Matson, C., Lan, F., Iwase, S., Baba, T., and Shi, Y. (2005). Regulation of LSD1 Histone Demethylase Activity by Its Associated Factors. Mol Cell 19, 857-864.

Wu, H., Zeng, H., Lam, R., Tempel, W., Amaya, M. F., Xu, C., Dombrovski, L., Qiu, W., Wang, Y., and Min, J. (2011). Structural and histone binding ability characterizations of human PWWP domains. PloS one 6, e18919. ("PWWP" disclosed as SEQ ID NO: 63)

Example 3

Figure 23A:
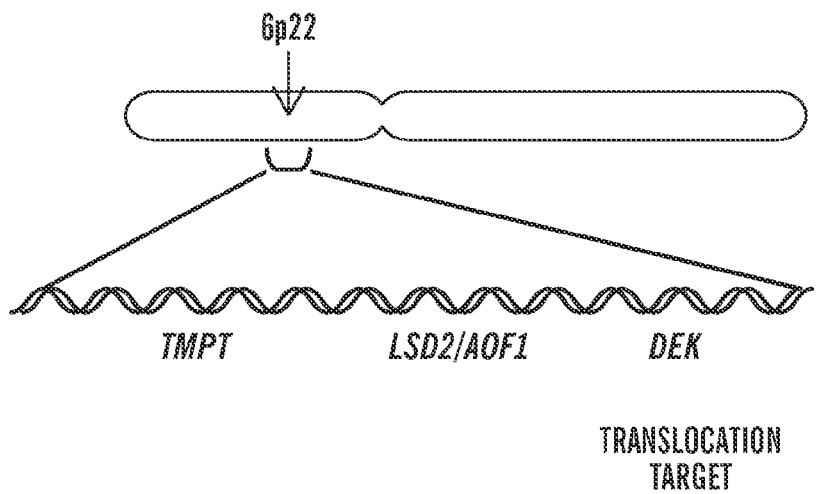
FIGS. 23A-23D demonstrate that LSD2 play a key role in breast cancer biology.
Figure 23B:
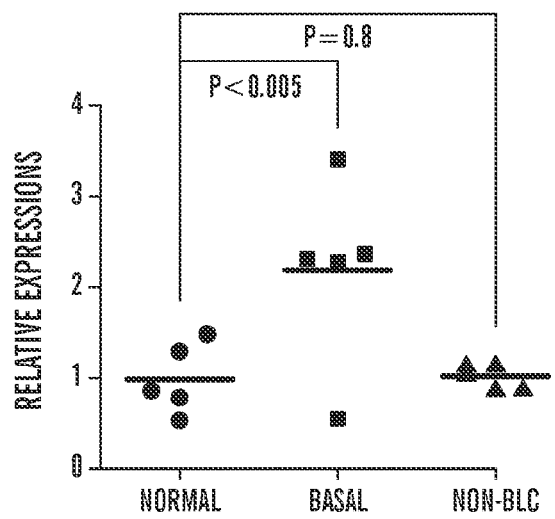
Figure 23C:
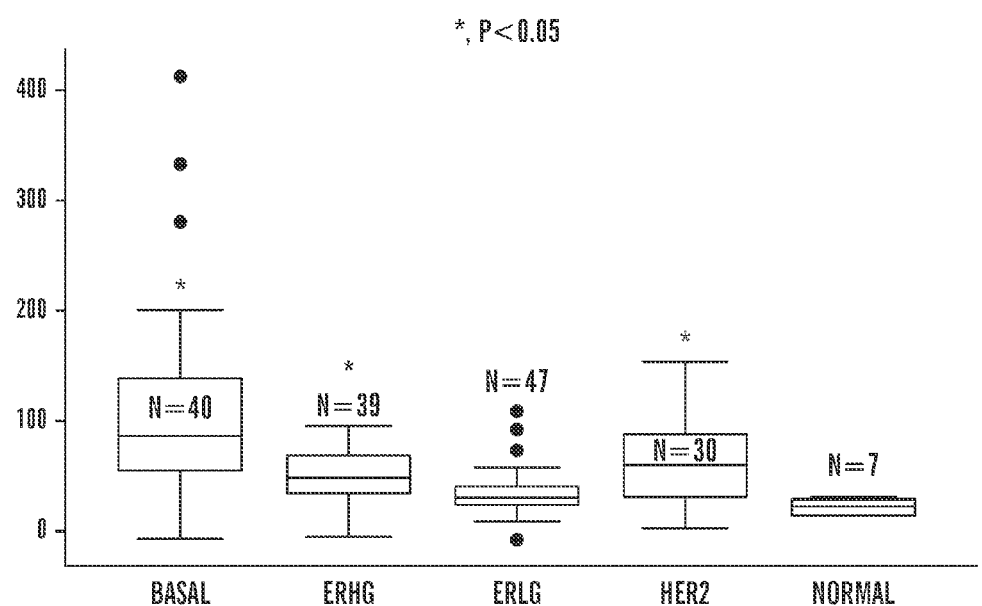
Figure 23D:
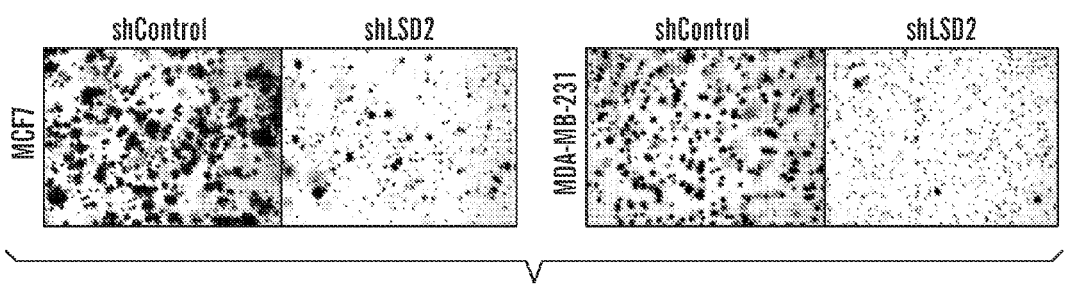

LSD2 is a novel histone demethylase, its biological function has not been fully characterized. LSD2 gene is located at 6p22, a hot spot for frequent deletion, amplification and mutation in cancers (FIG. 23A). Examination of published data of expression profile analyses of cancer specimens revealed LSD2 expression is dys-regulated in certain types of cancers, including breast cancer (Oncomine database). To examine the potential role of LSD2 in breast cancer biology, we compared LSD2 expression levels in 40 basal-like (basal), 39 $ER^+$ high grade (ERHG), 47 $ER^+$ low grade (ERLG) and 30 $HER2^+$ breast cancer specimens to 7 normal breast tissues using microarray analyses. Significant overexpression of LSD2 was observed in basal-like, $ER^+$ high grade and $HER2^+$ breast cancer patients (FIG. 23B). Overexpression of LSD2 in basal-like breast cancer is further confirmed by qRT-PCR (FIG. 23C). Together, these expression analyses suggesting a role of LSD2 in breast cancer biology, potentially functioning as an oncogene. Consistent with this hypothesis, we observed that effective LSD2 depletion by RNAi causes profound reduction of anchor-free growth of both ER-positive and ER-negative metastatic breast cancer cell lines, MCF7 and MDA-MB-231, in soft agar assays (FIG. 23D). Together, these results indicate that LSD2 plays an important role in regulating breast cancer cell growth and development.

Figure 24A:
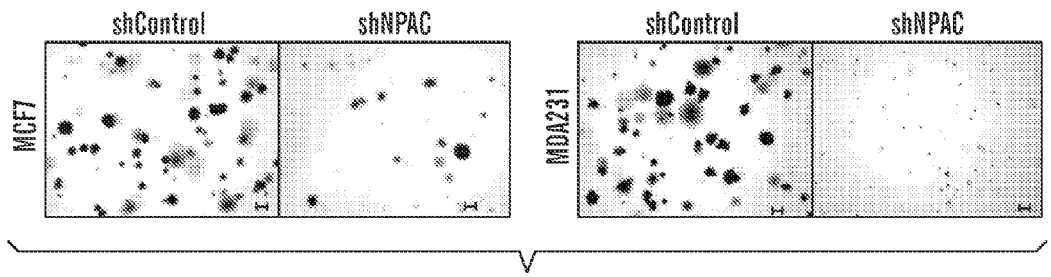
FIGS. 24A-24E demonstrate that targeted by NPAC, both LSD2 and NPAC regulate expression of cyclines.
Figure 24B:
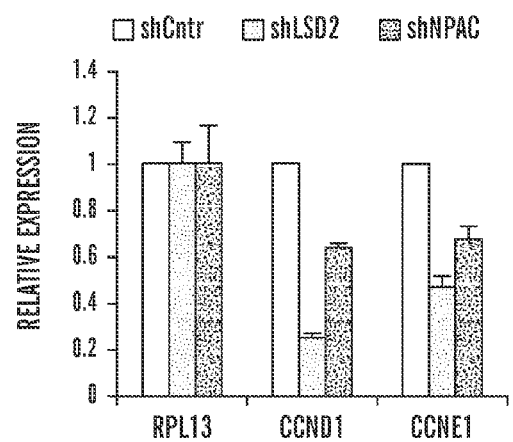
Figure 24C:
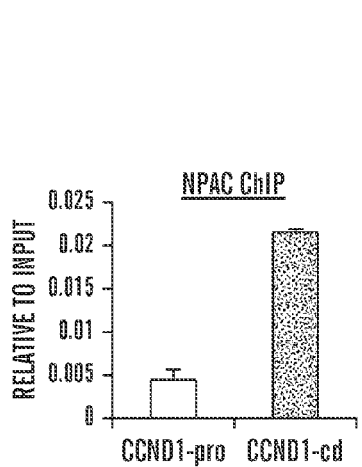
Figure 24D:
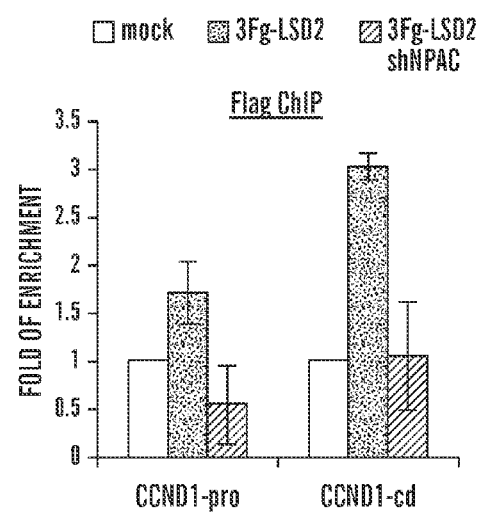
Figure 24E:
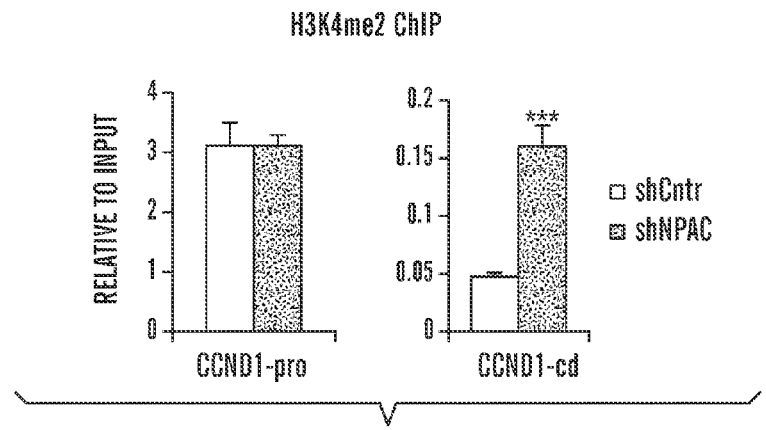

Given the ability of NPAC directly interacting with LSD2 and targeting LSD2 specific loci in human genome, we reasoned that LSD2 and NPAC may have similar functions in breast cancer, likely by co-regulating gene transcription essential for breast cancer growth and development. Indeed, depletion of NPAC by shRNA also results in reduction of anchor-free growth of MCF7 and MDA-MB-231 in soft agar assays (FIG. 24A), similar to the phenotype of LSD2 depletion. To explore the mechanism of LSD2 and NPAC function in breast cancer, we are interested to identify essential breast cancer oncogenes that are regulated by LSD2 and NPAC. After screening about 20 genes, we observed that cycline D1 and cycline E1, key regulators for breast cancer growth, are significantly down-regulated by either LSD2 or NPAC depletion (FIG. 24B). Demonstrated as a direct target of LSD2 and NPAC, we detected binding of NPAC and LSD2 at the coding region of CCND1 (FIGS. 24C and 24D). Importantly, NPAC depletion results in dissociation of LSD2 from CCND1 (FIG. 24D), and concomitant increase of H3K4 di-methylation at the loci (FIG. 24E).

Figure 25A:
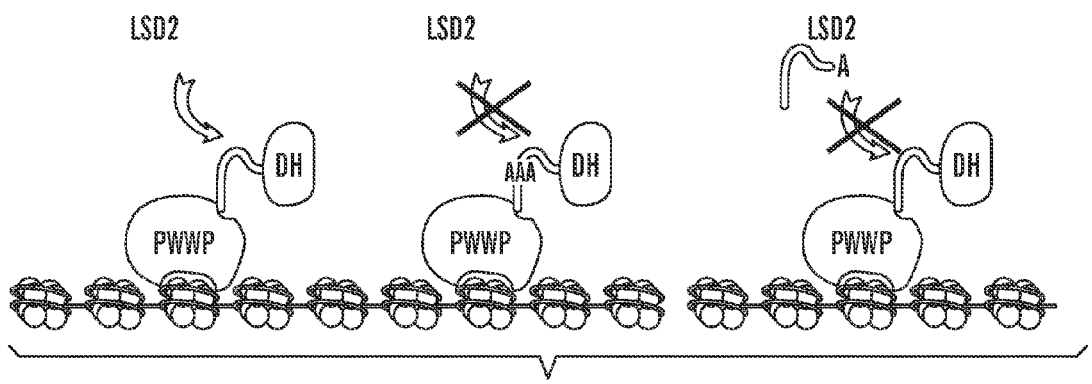
FIGS. 25A-25C demonstrate that manipulation of LSD2-NPAC interaction can regulate cycline expression.

Together, these results indicates that NPAC is responsible for recruiting LSD2 to target genes, and together LSD2 and NPAC play a key role in regulating gene expression that are important for breast cancer growth and development (FIG. 25A, left). The interaction of NPAC and LSD2 presents an opportunity for manipulating the machinery that potentially benefits breast cancer treatment.

Figure 25B:
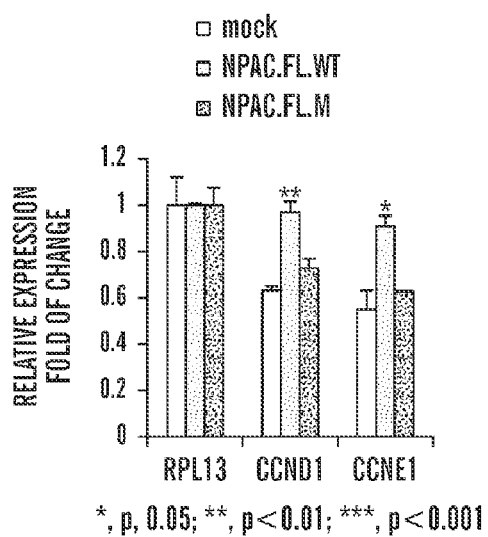

To demonstrate this concept, we examined if we can disrupt the interaction of NPAC and LSD2 to inhibit the expression of CCND1 and CCNE1. Based on the detailed interaction information revealed by our structural and biochemical studies, we introduced a triple mutant (F218A/L219A/L291A, or NP.FL.M) in the full-length NPAC that disrupts its interaction with LSD2 (FIG. 25A, middle). We first established stable MDA-MB-231 cell lines that express similar levels of the mutant or the wild-type full-length NPAC from cDNAs introduced with silent mutations and resistant to NPAC shRNA (data not shown). Ectopic expression of wild-type NPAC prevents down regulation of CCND1 and CCNE1 by NPAC shRNA (FIG. 25B). Significantly, expression of the mutant deficient in interacting LSD2 (NPAC.FL.M) failed to rescue the phenotype induced by NPAC shRNA treatment (FIG. 25B). Thus, mutation of the LSD2-interacting residues F218, L219 and L291 of NPAC can disrupt LSD2 and NPAC functions in vivo.

Figure 25C:
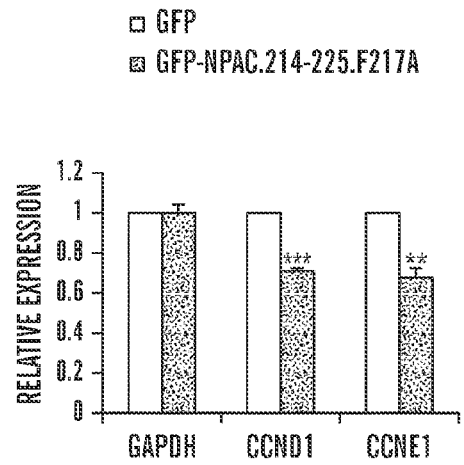

We next examined if it is possible to use a small molecule to manipulate the interaction between NPAC and LSD2, thus affecting target gene expression. We have shown that a short mutant NPAC peptide (residues 214-225) can interact with LSD2 with high affinity, however, lost its cofactor activity. NPAC214-225.F217A is expected to be able to competitive inhibit the interaction between endogenous NPAC and LSD2, without stimulating LSD2 demethylase activity (FIG. 25A, right). Overexpression of GFP-NPAC214-225.F217A consistently down regulates CCND1 and CCNE1 expression, similar to what we have observed for LSD2 depletion (FIG. 25C). Thus, unable to stimulate the histone demethylase activity of endogenous LSD2, this mutant peptide is a potent inhibitor of LSD2 function by competitively inhibiting LSD2 binding by endogenous NPAC.

Together, these in vivo functional analyses further support our hypothesis that H3K36me3 plays a critical role in recruiting NPAC to actively transcribed regions, which, in turn, recruits LSD2 and likely other associated epigenetic regulators, to modulate the local chromatin structure and modifications that are important for regulation of active gene transcription. The interaction between NPAC and LSD2 is essential for their function in transcription regulation, and represent an opportunity for modulating NPAC and LSD2 biological. This is even more significant in light of its most likely distinctive action from its homolog, KDM1a/LSD1. LSD1 is implicated in breast cancer and other cancers, yet its function in breast cancer is complex. Even though depletion of LSD1 seems to suppress cancer cell proliferation, it has also been reported to promote breast cancer metastasis.

We claim:

1. An isolated peptide, wherein the peptide consists of the amino acid sequence of an NPAC peptide consisting of SEQ ID NO: 1 with a substitution of the phenylalanine in position 4 of SEQ ID NO: 1 with alanine.

2. A vector comprising a nucleic acid encoding the peptide of claim 1.

3. The vector of claim 2 further comprising a nucleic acid encoding a signal peptide operably linked to the nucleic acid encoding the peptide.

4. The vector of claim 3 wherein the nucleic acid encoding the signal peptide comprises a nucleic acid encoding a nuclear localization signal.

5. A composition comprising the peptide of claim 1 and a carrier.

6. The composition of claim 5, wherein the carrier is a pharmaceutically acceptable carrier.

7. The composition of claim 5, wherein the peptide is pegylated.

\* \* \* \* \*